US008440808B2

(12) United States Patent
La Scola et al.

(10) Patent No.: US 8,440,808 B2
(45) Date of Patent: May 14, 2013

(54) **NUCLEIC ACID FRAGMENTS AND SPECIFIC DETECTION METHOD BY MOLECULAR IDENTIFICATION OF DIFFERENT BACTERIA SPECIES OF THE GENUS *ACINETOBACTER***

(75) Inventors: Bernard La Scola, Rousset (FR); Didier Raoult, Marseilles (FR)

(73) Assignees: Universite d'Aix-Marseille, Marseille (FR); Centre National de la Recherche Scientifique (CNRS), Paris (FR)

( * ) Notice: Subject to any disclaimer, the term of this patent is extended or adjusted under 35 U.S.C. 154(b) by 716 days.

(21) Appl. No.: 11/793,223

(22) PCT Filed: Mar. 16, 2006

(86) PCT No.: PCT/FR2006/000588
§ 371 (c)(1),
(2), (4) Date: Jun. 18, 2007

(87) PCT Pub. No.: WO2006/097636
PCT Pub. Date: Sep. 21, 2006

(65) Prior Publication Data
US 2009/0123916 A1 May 14, 2009

(30) Foreign Application Priority Data

Mar. 17, 2005 (FR) ..................... 05 02630

(51) Int. Cl.
*C07H 21/04* (2006.01)
*C12Q 1/68* (2006.01)
*C12P 19/34* (2006.01)

(52) U.S. Cl.
USPC ................. 536/24.33; 536/24.32; 435/6.12; 435/6.15; 435/91.2

(58) Field of Classification Search .................. None
See application file for complete search history.

(56) References Cited

U.S. PATENT DOCUMENTS

| 6,060,240 | A | * | 5/2000 | Kamb et al. | 506/4 |
| 6,110,680 | A | * | 8/2000 | Sutcliffe et al. | 435/6.12 |
| 6,562,958 | B1 | * | 5/2003 | Breton et al. | 536/23.7 |
| 6,727,063 | B1 | * | 4/2004 | Lander et al. | 435/6 |
| 2004/0029129 | A1 | * | 2/2004 | Wang et al. | 435/6 |
| 2009/0123916 | A1 | * | 5/2009 | La Scola et al. | 435/6 |

OTHER PUBLICATIONS

Mollet, C et al, MOlecular Microbiology, vol 26(5) pp. 1005-1011, 1997, cited on international search report.*
EMBL Accession No. ACA20939, Jun. 19, 2003 cited on Republic of France search report.*
EMBL accession No. ADA32719, Nov. 20, 2003, cited on Republic of France search report.*
Vaneechoutte, Mario et al, Applied and Environmental Microbiology, Jan. 2006, vol. 72(1), pp. 932-936, Naturally transformable *Acinetobacter* sp. Strain ADP1 belongs to the Newly Described species *Acinetobacter baylyi*.*
Barbe, Valerie et al, Nucleic acid Research, vol. 32(19), pp. 5766-5779, Oct. 28, 2004, Unique features revealed by the genome sequence of *Acinetobacter* sp. ADP1, a versatile and naturally transfomation competent bacterium, together with Supplemental content.*
La Scola et al. Journal of Clinical Microbiology (2006) 44(3): 827-832.*
Lowe et al. Nucleic Acids Research (1990) 18(7): 1757-1761.*
Database EMBL, Nov. 20, 2003, XP002342228, Database accession No. ADA32719.
Database EMBL, Jun. 19, 2003, XP002342229, Database accession No. ACA20939.
Database EMBL, Jun. 30, 2004, XP002342230, Database accession No. CR543861.
Mollet C. et al., "RPOB Sequence Analysis as a Novel Basis for Bacterial Identification", Molecular Microbiology, Blackwell Scientific, Oxford, GB, vol. 26, No. 5, 1997, pp. 1005-1011.

\* cited by examiner

*Primary Examiner* — Angela M Bertagna
(74) *Attorney, Agent, or Firm* — Oliff & Berridge, PLC

(57) ABSTRACT

RpoB gene sequences of various species of *Acinetobacter* bacteria, and a method of detection by molecular identification of various species of *Acinetobacter* bacteria using rpoB gene sequences.

22 Claims, 4 Drawing Sheets

Figure 1:
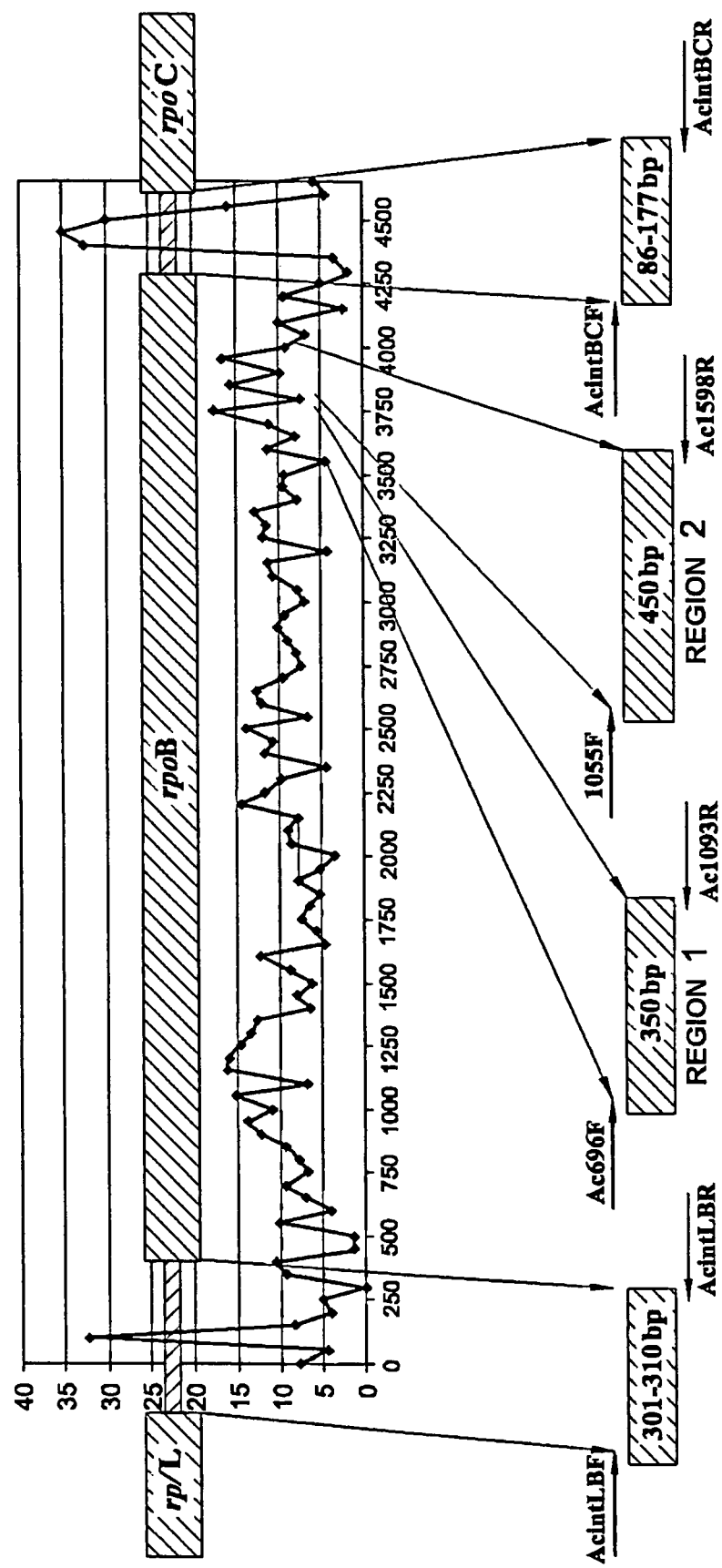

SEQUENCE LISTING

<160> NUMBER OF SEQ ID NOS: 255

<210> SEQ ID NO 1
<211> LENGTH: 22
<212> TYPE: DNA
<213> ORGANISM: Artificial sequence
<220> FEATURE:
<223> OTHER INFORMATION: Primer

<400> SEQUENCE: 1
taycgyaaag ayttgaaaga ag                                              22

<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2
cmacaccytt gttmccrtga                                                 20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gtgataarat ggcbggtcgt                                                 20

<210> SEQ ID NO 4
<211> LENGTH: 19
<212> TYPE: DNA
<213> ORGANISM: Artificial sequence
<220> FEATURE:
<223> OTHER INFORMATION: Primer

<400> SEQUENCE: 4
cgbgcrtgca tyttgtcrt                                                  19

<210> SEQ ID NO 5
<211> LENGTH: 22
<212> TYPE: DNA
<213> ORGANISM: Artificial sequence
<220> FEATURE:
<223> OTHER INFORMATION: Primer

<400> SEQUENCE: 5
gaagarctta agamdaarct tg                                              22

<210> SEQ ID NO 6
<211> LENGTH: 22
<212> TYPE: DNA
<213> ORGANISM: Artificial sequence
<220> FEATURE:
<223> OTHER INFORMATION: Primer

<400> SEQUENCE: 6
cgtttctttt cggtatatga gt                                              22

<210> SEQ ID NO 7
<211> LENGTH: 23
<212> TYPE: DNA

```
<213> ORGANISM: Artificial sequence
<220> FEATURE:
<223> OTHER INFORMATION: Primer

<400> SEQUENCE: 7
gttctttagg tatcaacatt gaa                                          23

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
gacgcaagac caatacgrat                                              20

<210> SEQ ID NO 9
<211> LENGTH: 4089
<212> TYPE: DNA
<213> ORGANISM: Acinetobacter calcoaceticus

<400> SEQUENCE: 9
atggcatact catataccga aaagaaacgg atccgtaaga attttggtaa attgccccaa    60
gtaatggaag caccgtactt actttcgatc caggtcgatt cgtatagaac gttcttgcaa   120
ggtggcaaat ctccaaaaaa ccgcgaagat atcggtctcc aagccgcatt tcgttcagtt   180
ttccctatag aaagttattc tggcaatgct gctttagaat tgttgagta tagccttggt    240 aagcctgagt ttgatgtgcg tgaatgtatt ttacgtggtt cgacttatgc ggcaccaatg   300
cgcgtaaaaa ttcgtttgat tattaaagat cgcgaaacta atctattaa agacgtacgt    360 gaacaagaag tctacatggg tgaaatgcca ctcatgacag ataatggtac ctttgtgatc   420
aatggtactg agcgtgtaat cgtatctcaa ttacaccgtt cacctggtgt gttctttgat   480
cacgataaag gcaaaacaca ttcaagtggt aaagtacttt attctgcacg tattattcct   540
taccgtggtt catggttaga ttttgaattt gatgcaaaag atttagttta tgtacgtatt   600
gaccgtcgtc gtaaattatt agcaactgtt gtgttgcgcg cattgggtta taacaatgaa   660
caaattttga atttgttcta tgaaaaagtg cctgtatatc ttgatatggg tagctatcaa   720
attgacctcg ttccagatcg tctgcgtggc gaaatggcgc aatttgatat tgcagacaat   780
gacggtaaaa tcattgttga gcaaggtaaa cgtattaatg cacgtcacgt acgtcaaatg   840
gaagcttctg gttagctaa gctatcagtt cctgatgagt acctgtatga gcgtatcact    900
gccgaagata ttactttacg taatggtgat gtgattgctg caaatacatt gttaagccat   960
gaagttatgg tgaaactggc agaaggcggt gttaaacagt tcaatatctt gtttacgaac   1020
gatattgacc gtggttcatt tgttgctgac tcattacgtg ctgacacaac atctggtcgt   1080
gaagaagcat tagttgaaat ctataaagta atgcgcccag gcgagccacc aacaaaagaa   1140
gctgctgaaa acttatttaa taacttattc ttctcttctg aacgttatga cttatctcca   1200
gtaggtcgta tgaaattcaa ccgtcgtttg ggtcgcccat acgaagttgg tactgaccag   1260
aagtcacgtg aagtagaagg tattttatcg cacgaagata tcatcgatgt attacgtaca   1320
ttagttgaaa tccgtaacgg taaaggtgaa gtcgatgata tcgatcactt gggtaaccgt   1380
cgtgtacgtt ctgttggtga atgactgaa aaccaattcc gtgttggttt ggttcgtgtt   1440
gaacgtgctg ttaagaacg tttaagccaa gcagaaacag ataatttatc tccgcaagat   1500
ctcattaacg caaaaccagt tgcagctgcg atcaaagaat ctttggttc aagccaattg   1560
```

```
tctcagttta tggatcaaaa caacccatta tctgagatta cacataagcg tcgtgtatca    1620
gcgcttggac ctggtggttt aacacgtgaa cgtgcgggct ttgaagtacg tgacgtacat    1680
caaactcact atggtcgtgt atgtccaatt gaaacgccgg aaggtccaaa cattggtttg    1740
atcaactcgc tttctgttta tgcaaaagca atgattttg  gtttcttgga aacaccttac    1800
cgtaaagtgg tagatggccg agtaactgat gctgttgaat acctttctgc tattgaagaa    1860
gtaggtactg ttattgcaca ggccgattct gcgatagata agatggtaa  cttaacagaa    1920 gattttgttt ctgttcgtca ccaaggtgac tttgtacgta tgccacctga aaaagtgacg    1980
catatggatg tatctgcaca gcaggttgta tctgtagctg catcgcttat tccattcctt    2040
gaacacgatg acgcgaaccg tgcattgatg ggttcaaaca tgcaacgtca ggcggttcct    2100
actctacgtg cggataaacc gcttgtaggt acaggtatgg aagcgaacgt tgcacgtgac    2160
tcgggcgtat gtgtgatcgc aaaccgtggt ggtgcgattg aatatgtaga tgcttctcgt    2220
atcgttattc gtgtaaacga agatgaaatg attgcaggtg aggctggtgt agatatttac    2280
aatctcatta aatatacacg ttctaaccaa aacacttgta tcaaccaaaa tattatcgtg    2340
aatttgggcg acaaagttgc tcgcggtgac atcttggcag acggtccgtc aacagatatg    2400
ggtgagcttg cgcttggtca aaacatgcgt gtagcgttca tgacgtggaa tggttacaac    2460
tacgaagact cgattttatt atctgagcgt gtacttcaag aagaccgttt aacttctatt    2520
catattcaag aattatcatg tgtagcgcgt gatactaagt taggtgcaga agaaattact    2580
gccgatattc ctaacgtagg tgaagctgca ctttctaaac ttgatgaatc tggtatcgtt    2640
tatattggtg cggaagttac tgctggtgac atccttgttg gtaaagtaac gcctaaaggt    2700
gaaactcagt taactcctga agaaaaattg cttcgtgcaa tctttggtga aaagcggct     2760 gacgttaaag actcatcttt acgtgttcca tctggtacta aaggtacagt tatcgatgtt    2820
caagtcttca cgcgtgatgg cttagagaaa gatgaccgtg cgatggcaat tgaaaaagca    2880
caacttgacg cttaccgtaa agacttgaaa gaagaataca agatctttga agaagcagct    2940
cgtgagcgtg taattcgttt gcttaacggc caagagtcta acggtggtgg ttcgactaaa    3000
cgtggcgaca agctcgttga cggtatgttg tctggtttag agcttgttga cttacttgaa    3060
atccaaccta cagatgaagc aattgctgaa cgtttatctc aaattcaagt gttcttgaaa    3120
gagaagagcg cagaaattga tgagaagttt gcagagaaga acgtaagct  ttcgactggt    3180 gatgagttaa caacaggtgt tctgaaagtt gttaaagttt acctagcagt taaacgtcgt    3240
attcagcctg gtgataaaat ggctggtcgt cacggtaaca aaggtgttgt atctaacatt    3300
ttacctgttg aagacatgcc acacgatgct aacggtgtgc cggtagatat cgtattgaac    3360
ccattgggtg taccatctcg tatgaacgtg ggtcagattc ttgagactca cttgggtatg    3420
gcagctaaag ggcttggtga taaaatcgaa aaaatgttga agaacagcg  cacagtttta    3480 gaacttcgcg aattcttaga caagatttat aacaaagtcg gcggcgagca agaagatctt    3540
gatagcttaa ctgatgctga agtcttagca cttttcaggca acttacgtgc tggtgtgcct    3600
ttagctactc ctgtatttga tggtgctgaa gaaagtcaaa ttaaagactt acttgaatta    3660
gctgatattt cgcgtactgg tcaaacagta ttgtttgatg gtcgtacggg tgaacagttt    3720
gatcgtcctg taactgtagg ttacatgtat atgctcaaat tgaaccactt ggttgatgac    3780
aaaatgcatg cgcgttcaac aggttcttac tcacttgtta ctcaacaacc gcttggtggt    3840
aaagcacaat tcgtggtca  gcgtttcggt gagatggagg tctgggcact cgaagcttac    3900
ggcgcagcat atacacttca agagatgtta actgttaagt cggatgacgt tgaaggtcgt    3960
```

```
acacgcatct ataagaatat tgtagatggt aaccattata tggatccggg tatgcctgaa    4020
tcgttcaacg tattgaccaa agagatccgt tctttaggta tcaacattga actgaaaaat    4080
ggtgactaa                                                            4089

<210> SEQ ID NO 10
<211> LENGTH: 4089
<212> TYPE: DNA
<213> ORGANISM: Acinetobacter baumannii

<400> SEQUENCE: 10
atggcatact catataccga aaagaaacgg atccgtaaga attttggtaa attgccccaa      60
gtaatggatg caccgtactt attatcgatt caggtcgatt cgtacagaac attcttgcaa     120
gatggcaaat caccaaaaaa ccgcgaagat atcggtctcc aagccgcatt tcgttcagtt     180
tttcctatcg aaagttattc tggcaatgct gctttagaat ttgttgagta tagccttggt     240
aaacctgagt cgatgtacg cgaatgtatt cttcgtggct cgacttatgc ggcaccaatg     300
cgcgttaaaa ttcgtttgat tattaaagat cgcgaaacta atcaattaa agacgtacgc     360 gaacaagaag tctatatggg tgaaattccg ctcatgactg aaaatggtac ctttgttatc     420
aacggtactg agcgtgtaat cgtatctcaa ttacaccgtt cgccaggcgt attctttgac     480
catgataaag gtaagaccca ctcaagtggt aaagtgttgt attcagcacg tatcattcct     540
taccgtggtt catggttaga cttcgaattt gatgcaaaag acttagttta cgtacgtatc     600
gaccgtcgtc gtaaattact tgctacagtt gtgttacgtg cactaggtta taacaatgaa     660
cagatcttga atttgttcta tgaaaaagta cctgtgtatc ttgacatggg tagctatcaa     720
attgaccttg tacctgagcg tttacgtggt gaaatggctc aatttgatat tactgacaat     780
gaaggtaaag tcattgttga gcaaggtaaa cgtattaatg ctcgtcacgt acgtcaaatg     840
gaagctgcag gtttaactaa gctttcagtt cctgatgaat acttatatga gcgtatcact     900
gctgaagata ttactttacg tgatggtgaa gtaattgctg caaatactct gttaagccat     960
gaagtaatgg tgaagttggc agaaggcggt gttaagcaat ttaatatctt gttcactaac    1020
gatattgacc gtggttcatt cgtagctgat acattacgtg ctgacttgac gcgtgatcgt    1080
gaagaagcat tagtagaaat ctacaaagta atgcgtccag gcgagccacc aacaaaagaa    1140
gctgctgaaa acttattcaa taacttgttc ttctcttctg aacgctatga cttatctcca    1200
gtaggtcgta tgaagttcaa ccgtcgttta ggtcgtcctt acgaagttgg tactgatcag    1260
aagtcacgcg aagttgaagg tattttatcg cacgaagata ttatcgatgt attacgtaca    1320
ttggttgaaa tccgtaacgg taaaggtgaa gtcgacgata tcgaccactt aggtaaccgt    1380
cgtgtacgtt ctgttggtga atgacagag aaccaattcc gtgtaggttt agttcgtgtt    1440
gagcgtgctg ttaaagagcg tttaagccaa gcagaaacag ataacttgtc tccacaagat    1500
ttgattaatg caaaaccagt tgctgctgca atcaaagaat tctttggttc aagccagtta    1560
tctcagttta tggaccaaaa caacccatta tctgagatta cacataaacg tcgtgtatct    1620
gcgcttggtc ctggtggttt aacacgtgaa cgtgcaggct tcgaagtacg tgacgtacac    1680
caaactcact atggtcgtgt tgtccaatt gaaactcctg aaggtccaaa cattggtttg    1740
atcaactcgc tttctgtata cgcaaaagcg aatgacttcg gtttcttgga acaccatac    1800 cgcaaagttg tagatggtcg tgtaactgat gatgttgaat atttatctgc aattgaagaa    1860
gtaggtactg ttattgcaca ggccgactct gcagtagata aagatggcaa cttaacagaa    1920
gaattcgttt ctgttcgtca tcaaggtgaa ttcgtacgta tgccgcctga aaaagtaacg    1980
```

| | |
|---|---|
| catatggacg tttctgcaca gcaggtagta tctgttgctg catcacttat tccattcctt | 2040 |
| gaacacgatg acgcaaaccg tgcgctcatg ggttcaaaca tgcaacgtca ggcagttcct | 2100 |
| actttacgtg cggataaacc gcttgtaggt acaggtatgg aagcgaacgt tgcacgtgac | 2160 |
| tctggtgtgt gtgtaatcgc aaaccgtggc ggtgtaattg aatatgtaga tgcttctcgt | 2220 |
| atcgttattc gtgtaaacga agatgaaatg gttgcaggtg aggcgggtgt agatatctat | 2280 |
| aacctcatca aatatacgcg ttcaaaccaa aatacttgta ttaaccaaaa tgttatcgtg | 2340 |
| aacttgggcg acaaagttgc tcgtggtgac atcttggcag acggtccgtc aacagacatg | 2400 |
| ggtgaacttg cgcttggtca aaacatgcgt gtagcgttca tgacatggaa tggttacaac | 2460 |
| tacgaagact cgatcttgtt atctgagcgt gtacttcaag aagaccgttt aacctctatt | 2520 |
| cacattcaag aattgtcatg tgtagcacgt gatactaagt taggtgcaga agaaattact | 2580 |
| gccgatattc ctaacgtagg tgaagctgcg ctttctaaac ttgatgaatc aggtatcgtt | 2640 |
| tatatcggtg ctgaagttac tgctggtgac atcttagttg gtaaagtaac gcctaaaggt | 2700 |
| gaaactcagt taactcctga agaaaaactg cttcgtgcaa ttttttggtga aaagcagct | 2760 |
| gacgttaaag actcatcttt acgtgttcca tctggtacta aaggtacagt tattgacgtt | 2820 |
| caagtcttca ctcgtgatgg cttagagaaa gatgaccgtg ctttagcaat tgaaaaagca | 2880 |
| cagcttgatt cttaccgtaa agacttgaaa gaagaataca agatcttcga agaagcggct | 2940 |
| cgtgagcgtg taattcgttt gcttaaaggc caagagtcta atggcggtgg ttcaactaaa | 3000 |
| cgtggtgata acttctctga agatttatta tctggtttag agcttgttga tttacttgaa | 3060 |
| attcaaccag cagatgaagc aatcgctgag cgtttaactc aaattcaagt gttcttgaaa | 3120 |
| gagaagagcg cagaaatcga tgagaaattc gctgagaaga acgtaagct tgccacaggt | 3180 |
| gatgaattaa cgactggcgt attaaaagtt gttaaggttt acttagctgt taaacgtcgt | 3240 |
| attcagcctg gtgataagat ggctggtcgt cacggtaaca agggtgttgt atctaacatc | 3300 |
| ttacctgttg aagacatgcc acatgatgct aacggtgtgc cggtagatat cgtattgaac | 3360 |
| ccgctgggtg taccatctcg tatgaacgtg ggtcagattc tagagactca cttgggtatg | 3420 |
| gcggctaaag gcttggtga caaaatcgaa aaaatgttga agaacaacg tacagttta | 3480 |
| gaactgcgcg aattcttaga caagatttat aacaaagtcg gcggtgagca agaagatctt | 3540 |
| gatagcttga ctgatgaaga aattctagcg cttgcaggta acttgcgtgc gggtgtgcct | 3600 |
| ttagctactc ctgtatttga tggtgctgaa gaaagtcaaa ttaaagactt acttgaattg | 3660 |
| gctgacattt cacgtacggg tcaaacagta ttgtttgacg gacgtacagg tgaacagttt | 3720 |
| gaccgtccag taactgttgg ttacatgtac atgcttaaat tgaaccactt ggttgatgac | 3780 |
| aagatgcatg cgcgttcaac tggttcttac tcacttgtta cacaacaacc gcttggtggt | 3840 |
| aaagcacaat tcggtggtca gcgtttcggt gagatggaag tgtgggcact tgaagcatac | 3900 |
| ggtgcagcat atacactcca agaaatgctt acagtgaagt cggatgatgt tgaaggccgt | 3960 |
| actcgcatct ataagaatat tgtagatggt aaccattata tggatccggg tatgcctgaa | 4020 |
| tcgttcaacg tattgaccaa agagatccgt tctttaggta tcaacattga actaaaaaat | 4080 |
| ggtgactaa | 4089 |

```
<210> SEQ ID NO 11
<211> LENGTH: 4089
<212> TYPE: DNA
<213> ORGANISM: Acinetobacter sp.

<400> SEQUENCE: 11
```

```
atggcatact catataccga aaagaaacgg atccgtaaga attttggtaa attgccccaa      60
gtaatggatg caccgtactt actatcgatt caggtcgatt cgtacagaac attcttgcaa     120
gatggcaaaa ctccaaaaaa ccgcgaagat atcggtctcc aagccgcatt tcgttcagtt     180
tttcctatcg aaagttattc tggcaatgct gctttagaat tgttgagta tagccttggt      240 aaacctgagt tcgatgtacg cgaatgtatt cttcgtggtt cgacttatgc ggcaccaatg     300
cgcgttaaaa ttcgtttgat tattaaagat cgcgaaacta atcaattaa agacgtacga      360 gaacaagaag tctatatggg tgaaattcca ctcatgactg aaaacggtac attcgtcatt     420
aatggtactg agcgtgtaat cgtatctcaa ttacatcgtt caccaggcgt tttctttgat     480
cacgataaag gtaaaaccca ctcaagtggt aaagtgttgt attcagcacg tatcattcct     540
taccgtggtt catggttaga cttcgaattt gatgcaaaag acttagttta cgtacgtatt     600
gaccgtcgtc gtaaattact tgctactgtt gtgttacgtg cactaggtta taacaacgaa     660
caaatcttga atttgttcta tgaaaaagta cctgtgtatc ttgacatggg cagttaccag     720
attgacctag tacctgaacg tttacgtggg gaaatggctc aatttgatat tgctgacaat     780
gacggtaaag ttattgttga gcaaggtaaa cgtattaatg ctcgtcatgt acgtcaaatg     840
gaagctgctg gtttaacaaa actttcagtt cctgatgaat acttatatga gcgtatcact     900
gctgaaaata ttactttgcg tgatggtgaa gtaattgctg cgaatacttt gttaagccat     960
gaagttatgg tgaagttggc agaaggtggt gttaaacagt tcaatatctt gtttacgaac    1020
gatattgacc gtggttcgtt tgttgctgac acattacgtg cagatacaac agctggccgt    1080
gaagaagcat tagttgaaat ttataaagta atgcgtccag gcgagccgcc aacaaaagaa    1140
gctgctgaaa acttattcaa taacttattc ttctcttctg agcgttatga cttatctcca    1200
gtaggtcgta tgaagttcaa ccgtcgtttg ggtcgtccat acgaagttgg tactgaccag    1260
aagtcacgtg aagtagaagg tatttttatcg cacgaagata tcattgatgt attacgtaca    1320
ttagttgaaa tccgtaacgg taaaggtgaa gtcgacgata tcgatcactt gggtaaccgt    1380
cgtgtacgtt ctgttggtga atgactgaa accaattcc gtgttggttt ggtacgtgtt     1440
gaacgtgctg ttaagaacg tttaagccaa gcagaaacag ataacttgtc tccacaagat    1500
ctaattaacg ctaaaccagt tgcagctgca atcaaagaat tctttggttc aagccaatta    1560
tctcagttca tggaccaaaa caacccatta tctgagatta cgcataagcg tcgtgtatca    1620
gcgcttgggc ctggtggttt aacacgtgaa cgtgcgggct ttgaagtacg tgacgtacat    1680
caaactcact atggtcgtgt atgtccaatt gaaacgccgg aaggtccaaa cattggtttg    1740
atcaactcgc tttctgtata tgcaaaagca aatgacttcg gtttcttgga aacaccttac    1800
cgtaaagtag tagatggtcg agtaactgat gcagttgaat accttttctgc gattgaagaa    1860 gtaggtactg ttattgcaca ggccgattct gcagtagata agatggcaa cctaacagaa    1920 gagtttgttt ctgttcgtca tcaaggtgaa ttcgtacgta tgccacctga aaaagtgacg    1980
catatggacg tttctgctca gcaagttgta tctgttgctg catcacttat tccattcctt    2040
gaacacgatg acgcgaaccg tgcgcttatg ggttcaaaca tgcaacgtca ggcagttcct    2100
actctacgtg cggataaacc gcttgtaggt acaggtatgg aagcgaacgt tgcacgtgac    2160
tcaggtgtgt gtgtgatcgc aaaccgtggt ggtgcaattg aatacgtaga tgcttctcgt    2220
atcgttattc gtgtaaacga agatgaaatg atcgctggtg aggcgggtgt agatatctac    2280
aacctcatta aatatacgcg ttctaaccag aacacttgta tcaaccaaaa tattatcgtg    2340
aatttgggcg acaaagttgc tcgcggtgat atcttggcag acggtccgtc tacagatatg    2400
```

-continued

```
ggtgagcttg cgcttggtca aaacatgcgc gttgcgttca tgacttggaa tggttacaac    2460
tatgaagact cgatcttatt atctgagcgc gtacttcaag aagaccgttt aacttctatt    2520
catattcaag aattatcttg tgtagcgcgt gatactaagt taggtgcaga agaaattact    2580
gccgatattc ctaacgttgg tgaagctgca ctttctaaac ttgatgagtc aggtatcgtt    2640
tatatcggtg ctgaagttac agcaggtgac atccttgttg gtaaagtaac gcctaaaggt    2700
gaaactcagt taactcctga agaaaaattg cttcgtgcaa tctttggtga aaagcagct    2760 gacgttaaag attcatcttt acgtgttcca tctggtacaa aaggtacagt tatcgatgtt    2820
caagtcttca ctcgtgatgg cttagagaaa atgaccgtg cattggcgat cgaaaaagca    2880
caacttgatg cttaccgtaa agacttgaaa aagaataca agatctttga agaagcagct    2940
cgtgagcgtg taattcgttt gcttaaaggc caagagtcta atggcggtgg ttcaactaaa    3000
cgtggtgaca aactcgttga agaagtgtta tctggtttag agcttgttga tttacttgaa    3060
attcaaccgg cagatgaagc aatcgctgag cgtttaactc aaattcaagt gttcttaaaa    3120
gaaaagagcg cagaaattga tgagaaattc gctgagaaga aacgtaagct tgcaacaggt    3180
gatgaattaa caactggcgt attgaaagtt gttaaagttt acttagctgt taaacgtcgt    3240
attcagcctg gtgataagat ggctggtcgt cacggtaaca agggtgttgt atctaacatc    3300
ttacctgttg aagacatgcc acacgatgct aacggtgtac cagtagatat cgtattgaac    3360
ccgttgggcg taccatctcg tatgaacgtg ggtcagattc ttgagactca cttaggtatg    3420
gcggctaaag ggcttggtga taaaatcgag aaaatgttga agaacagcg tacagtttta    3480 gaactgcgtg aattcttaga caagatttat aacaaagtcg gtggtgagca agaagatctt    3540
gatagcttaa ctgatgctga agtcttggca ctttcaggca acttacgtgc tggtgtacct    3600
ttggctactc ctgtattcga tggtgctgaa gaaagccaaa ttaaagactt gcttgagtta    3660
gctggtatct ctcgtacagg tcaaacagta ttgtttgatg gccgtactgg tgaacagttt    3720
gatcgtcctg taactgtggg ttacatgtac atgctcaaat tgaaccactt ggttgatgac    3780
aagatgcatg cgccgttcaac tggttcttac tctcttgtta cacagcaacc gcttggtggt    3840
aaagcacaat tcggtggtca gcgtttcggt gagatggagg tctgggcact cgaagcttac    3900
ggcgcagcat atactctcca agagatgtta actgttaagt cggatgacgt tgaaggtcgt    3960
acacgcatct ataagaatat tgtagatggt aaccattata tggacccggg tatgcctgaa    4020
tcgttcaacg tattgaccaa agagatccgt tctttaggta tcaacattga actgaaaaat    4080
ggtgactaa                                                           4089
```

<210> SEQ ID NO 12
<211> LENGTH: 4089
<212> TYPE: DNA
<213> ORGANISM: Acinetobacter haemolyticus

<400> SEQUENCE: 12

```
atggcatact catataccga aaagaaacgg attcgtaaga attttggtaa attgccccac     60
gtaatggaag caccgtactt actttcgatt caagtcgatt cgtaccgtac tttcttacaa    120
ggtggcaaaa ctccaaaaaa tcgcgaagat atcggtctcc aagccgcatt tcgttcagtt    180
tttcctattg aaagttattc tggcaatgct gctttagaat tgttgagta tagtcttggt    240 aaaccagagt ttgacgtacg tgaatgtatt ttacgtggtt caacttatgc ggcaccaatg    300
cgcgtaaaaa ttcgtttgat cattaaagat cgcgaaacca atcaattaa agacgttcgt    360 gaacaagaag tttacatggg tgaaatgcca ctcatgaccg ataacggtac attcgttatt    420
```

```
aacggtactg agcgtgtaat cgtatctcaa ttacaccgtt cgccaggcgt attctttgat    480
catgacaagg gtaagaccca ctcaagcggt aaagtgttgt attcagcacg tattatccct    540
taccgtggtt catggttaga tttcgaattt gatgctaaag atttagtatt cgtacgtatt    600
gaccgtcgtc gtaaattatt ggcgactgtg attttacgtg ctttaaatta taccaatgag    660
caaatcctga atttgttcta cgaaaaagta cctgtctatt tagatatggg cagctatcaa    720
attgatctcg ttccagatcg cctacgtggt gagatggcgc aatttgatat cttagataac    780
gatggcaaag cgattgttga acaaggcaaa cgtattaatg cacgtcacgt acgtcaaatg    840
gaagcagcga acttagcgaa gcttcagta cctgatgaat acttgtatga gcgtattaca    900
gctgaagata tcacattgaa agatggtgat gtaattcctg caaatacggt gcttagccat    960
gaagtgatgg tgaaaatcgc tgaaggcggc gtgaaacagt ttaatattct gttcaccaac   1020
gatatcgatc gtggtccttt cgttgcggat actttacgtg cagatacaac aacaggtcgt   1080
gaagaagcac ttgttgaaat ctataaagtc atgcgtccag gtgagccgcc aacgaaagaa   1140
gctgctgaaa acttatttaa taacttgttc ttctcttctg agcgttatga cctgtctcca   1200
gtgggtcgta tgaagttcaa ccgtcgtttg ggtcgtcctt acgaagtggg tactgatcag   1260
aagtctcgtg aagttgaagg tattttatca cacgacgata tcattgatgt acttcgtaca   1320
ttggtggaaa tccgtaacgg taaaggtgaa gtcgatgata tcgatcactt aggtaaccgg   1380
cgtgtacgtt ctgttggcga aatgacagaa aaccaattcc gtgttggttt agtgcgtgtt   1440
gaacgtgctg ttaaagagcg tttaagccaa gcagaaactg ataacttgtc tccacaagat   1500
ttaatcaacg cgaaaccagt tgctgctgca atcaaagagt tctttggttc aagccagtta   1560
tctcagttca tggaccaaaa caacccattg tctgagatta cacacaaacg tcgtgtatct   1620
gcacttggtc ctgggggttt gacacgtgaa cgcgcgggct tcgaagtacg tgacgtacat   1680
caaactcact atggtcgtgt ttgtccgatt gaaacgcctg aaggtccaaa cattggtttg   1740
atcaactcgc tttctgttta tgcaaaagca aatgacttcg gtttcttgga aacaccatac   1800
cgtaaagttg tcgatggtcg tgtaactgat gatgttgaat atttatctgc aattgaagaa   1860
gtagggactg tcattgcaca agccgactct gcagttgata aagatggtaa tttaactgaa   1920
gaaatggttt ctgtgcgtca tcaaggtgaa ttcgtacgta tgtcgcctga acgcgtaacg   1980
catatggacg tttctgcaca gcaggtagta tcagttgcgg catcattgat tccattcctt   2040
gaacacgatg atgcgaaccg tgcattgatg ggttcgaaca tgcaacgtca ggctgttcct   2100
acattacgtg ctgacaagcc gcttgttggt acaggtatgg aagcgaacgt agcgcgcgac   2160
tcgggtgtgt gtgtgatcgc aaaccgtggt ggtgcgattg agtatgtaga tgcatctcgt   2220
atcgttattc gtgtcaacga agatgaaatg attgcgggtg aagcaggtgt agatatctat   2280
aacctgatca aatatacacg ttcaaaccag aacacatgta ttaaccagaa tgtcatcgtg   2340
aacttgggcg acaaagttgc tcgtggtgat atcttggctg acggtccttc gactgacatg   2400
ggtgaacttg cgctgggtca aaacatgcgc gtcgcgttca tgacatggaa cggttataac   2460
tatgaagact cgattttact ttctgagcgt gttcttcaag aagatcgttt aacgtcgatt   2520
cacattcaag aattgtcatg tgtagcacgt gatactaagt taggtgcaga agaaattact   2580
gccgatattc ctaacgttgg tgaagcagca ctgtctaaat tggatgagtc aggtattgtt   2640
tatatcggtg ctgaagtgac tgcgggtgat atcctagttg gtaaggtaac gcctaaaggt   2700
gaaactcagt taacacctga agaaaaatta cttcgcgcaa tctttggtga aaagcggca   2760 gacgtaaaag attcatcttt gcgtgttccg tctggtacca aaggaacagt gattgacgtt   2820
```

```
caagtcttca cacgtgatgg tttagaaaag gacgagcgtg cgcaagcaat tgagaaagct    2880
caacttgatg cataccgtaa agacttgaaa gaagaataca aaatcttcga agaagcagca    2940
cgtgaacgta ttgttcgctt gttgaaaggt caagagtcaa atggtggcgg tacaactaag    3000
cgcggcgata aactctcaga agatgtattg tctggtttag agcttgttga tttacttgaa    3060
atccaaccag ctgatgaagc gattgctgaa cgtttaacgc aaattcaagt gttcttgaaa    3120
gagaagagca tcgaaatcga tgagaaattt gcagagaaga agcgtaagct ttctacaggt    3180
gatgaattaa caacgggtgt attaaaagtt gttaaggttt accttgcggt taagcgtcgt    3240
attcagcctg gtgataagat ggcgggtcgt cacggtaaca agggtgtggt atcaaatatc    3300
ttacctgtag aagacatgcc gcatgatatt cacggtgtgc cagttgatat cgtattgaac    3360
ccattgggtg taccatcacg tatgaacgtg ggtcagattc ttgaaactca cttgggtatg    3420
gcggcaaaag gtctgggtga gcaaattgat aagatgctcc aacagcaacg tacgattgct    3480
gaattgcgtc gttcctcga caagatttac aacaaagttg gtggcgaaca agaagatctt    3540
gatagcttaa ccgacgaaga agttttaaaa cttgcaggta acctgcgtgc aggtgtgcct    3600
ttggcgacac cagtatttga tggtgctgaa gaaagtcaaa ttaaagagtt acttgagctt    3660
gctgaattgc cacgtactgg tcaaaccgta ttgtttgatg gtcgtactgg tgaacagttt    3720
gatcgtcctg taactgtcgg ttatatgtac atgctcaaat tgaaccactt ggttgatgac    3780
aagatgcatg cgcgttcaac tggttcttac tcactagtga cacaacagcc gcttggtggt    3840
aaagcacaat cggtggtca gcgtttcggt gagatggaag tatgggcact tgaagcatac    3900
ggtgcagcat atacgcttca agaaatgctt actgtgaagt cggatgacgt tgaaggtcgt    3960
acacgcatct ataagaatat tgtagatggt aaccattata tggatccggg tatgcctgaa    4020
tcgttcaacg tattgaccaa agagatccgt tctttaggta tcaacattga actgaaaaat    4080
ggtgactaa                                                           4089

<210> SEQ ID NO 13
<211> LENGTH: 4089
<212> TYPE: DNA
<213> ORGANISM: Acinetobacter junii

<400> SEQUENCE: 13
atggcatact catataccga aaagaaacgg atccgtaaga attttggtaa attgccccac      60
gtaatggaag caccgtactt actttcgatt caggtcgatt cgtatcgtac attcttacaa     120
ggtggtaaaa ctccaaaaaa tcgcgaagat atcggtctcc aagccgcatt tcgttcagtt     180
tttcctattg aaagttattc tggcaatgct gctttagaat tgttgagta tagccttggt      240 aaacccgagt tgacgtgcg tgaatgtatt ttacgtggtt cgacttatgc ggcaccaatg      300
cgtgtaaaaa ttcgtttgat cattaaagat cgcgaaacga aatcaatcaa agatgttcgt     360
gaacaagaag tgtacatggg cgaaatgccg ctcatgaccg acaacggtac tttcgttatt     420
aacggtactg aacgtgtaat cgtatctcaa ttacaccgtt caccaggcgt attctttgat     480
catgataagg gtaaaacaca ctcaagcggt aaagtgttgt attcagcacg tatcattcct     540
taccgtggtt catggttaga ttttgaattc gatgcaaaag atttagtttt cgtacgtatt     600
gaccgtcgtc gtaaattgtt ggcgactgtg atcttacgtg cttttaaatta tagcaatgaa    660 caaatcttga atttgttcta tgaaaaagta cctgtatatc ttgatatggg tagctatcaa     720 attgaccctcg ttccagatcg cttacgtggt gaaatggcgc aatttgatat cttggacaat    780
gatggtaaag caatcgttga acaaggtaag cgtattaatg cacgtcatgt acgccaaatg      840
```

```
gaagcagcta acttagctaa gctttctgta cctgatgaat atttatatga acgtattaca    900
gctgaagata tcacactgaa aagtggtgat gtgattcctg caaataccgt acttagccat    960
gaaattatgg tgaaattggc tgaaggtggt gttaaacaat ttaacatcct attcactaat   1020
gacatcgatc gtggttcgtt cattgcagat acattacgtg cagatacaac aacaggtcgt   1080
gaagaagcgc ttgttgaaat ctataaagta atgcgtccag gtgaaccacc gacaaaagaa   1140
gcagcagaga acttatttaa taacttattc ttctcttctg aacgttatga cctttctcca   1200
gtaggtcgta tgaagtttaa ccgtcgtttg ggtcgtcctt acgaagtggg tactgatcag   1260
aagtcacgtg aagttgaagg tatttatcg catgacgata tcattgatgt acttcgtaca   1320
ttggtggaga tccgcaatgg taaaggtgaa gtcgacgata tcgatcactt gggtaaccgt   1380
cgcgtacgtt ctgttggtga atgacagaa aaccaattcc gtgttggttt ggttcgtgtt   1440
gaacgtgctg tgaaagagcg tttaagccaa gctgaaactg ataacttgtc tccacaagat   1500
ttaatcaacg cgaaaccagt tgctgcggca atcaaagaat tctttggttc aagccagtta   1560
tctcagttca tggaccaaaa caacccatta tctgagatta cacataaacg tcgtgtgtct   1620
gcgcttggtc ctggtggttt gacacgtgaa cgcgcaggct tcgaagtgcg tgacgtacat   1680
caaactcact atggtcgtgt ttgtccaatt gaaacacctg aaggtccaaa cattggtttg   1740
atcaactcgc tttctgtcta tgcaaaagcg aatgacttcg gtttcttgga acaccatac   1800
cgtaaggttg tagacggtcg tgtgacagat gaagttgaat atttatctgc aattgaagaa   1860
gtaggcactg tcattgcaca agccgactca gcagtggata agatggcaa cttgactgaa   1920
gaaatggttt ctgtacgtca tcaaggtgaa ttcgtacgta tgtcgcctga gcgcgtaaca   1980
catatgacg tttctgcaca gcaggttgtt tctgttgcag cgtcattaat tccattcctt   2040
gaacacgatg acgcaaaccg tgcattgatg ggttcgaaca tgcaacgtca ggctgttcct   2100
acacttcgtg ctgacaaacc acttgtcggt acgggtatgg aagcaaacgt agcacgcgac   2160
tcaggtgtat gtgtgatcgc gggtcgtggt ggtgtaattg aatatgttga tgcatctcgt   2220
atcgttattc gtgtgaacga agatgaaatg attgcaggtg aagcaggtgt agatatttac   2280
aacctgatca aatatacacg ttcaaaccaa aatacatgta ttaaccaaaa tgtcatcgta   2340
aacttgggcg acaaagttgc tcgtggcgat atttggctg acggtccatc gactgacatg   2400
ggtgaacttg cgctaggtca aaacatgcgc gtcgcgttca tgacatggaa cggttataac   2460
tatgaagact cgatcttact ttctgagcgt gtgcttcaag aagaccgttt aacgtcgatt   2520
catattcaag aattgtcatg tgtagcgcgt gatactaagt taggtgcaga agaaattact   2580
gctgatattc ctaacgtcgg tgaagctgca ctgtctaaac ttgatgagtc aggtattgtt   2640
tatatcggtc ctgaagttac tgcaggtgat attctggttg gtaaggtaac acctaaaggt   2700
gaaactcagt taacacctga agaaaaacta cttcgtgcaa tctttggtga aaaagcggct   2760
gacgtaaaag attcatcttt acgtgttccg tcaggcacta aagtacagt gattgacgtt   2820
caagtcttca cacgtgatgg tttagaaaaa gatgaacgtg cgcaagcaat tgagaaagct   2880
cagcttgatg cataccgtaa agacttgaaa gaagaataca aaatcttcga agaagcagca   2940
cgtgagcgta ttgttcgttt gttgaaaggt caagaatcta acggtggtgg ttcgactaaa   3000
cgtggtgaga agctttcaga agatattgtt tctggtctag agttagttga tctacttgaa   3060
atccaaccaa cagatgaagc aattgctgag cgtttaactc aaattcaagt gttcttgaaa   3120
gaaaagagcc atgaaattga tgaaaaattt gctgagaaga acgtaaaact ttctacaggg   3180
gatgagttaa caactggtgt attgaaagtt gttaaggttt acctagcagt taaacgtcga   3240
```

-continued

```
atccaacctg gtgataagat ggcgggtcgt cacggtaaca agggtgttgt atcaaacatc      3300
ttaccagttg aagatatgcc acatgatgcc aatggtgtgc cagttgatat cgtattgaac      3360
ccactcggtg taccatcgcg tatgaacgtg ggtcagattc ttgaaactca cttaggtatg      3420
gcagcaaaag gtttgggtga gcagattgat aaaatgctca acaacaacg tacaattgcc       3480
gagttacgtt cattccttga caagatttat aataaagtgg gtggtgagca agaacagctt      3540
gacacactaa ctgacgaaga gatctttaag cttgcaggta atttacgtgc tggtgtgcct      3600
ttggcaactc cagtatttga tggtgctgaa gagtcacaaa tcaaagagtt acttgagctt      3660
gcagagttac cacgttctgg tcaacaaatc ttgtttgatg gacgtacagg tgaacagttt      3720
gatcgtccag taactgtcgg ttacatgtac atgcttaagt tgaaccactt ggttgacgat      3780
aagatgcatg cacgttcaac tggttcttac tcacttgtga cacaacaacc gcttggtggt      3840
aaagcacaat tcggtggtca gcgtttcggt gagatggaag tatgggcact tgaagcatat      3900
ggtgcagcat ataccctcca agaaatgctc actgtgaagt cggatgacgt cgaaggtcgt      3960
acacgcatct ataagaacat tgtagatgga aaccattata tggatccggg tatgcctgaa      4020
tcgttcaacg tattgaccaa agagatccgt tctttaggta tcaacattga actgaaaaat      4080
ggtgactaa                                                              4089

<210> SEQ ID NO 14
<211> LENGTH: 4089
<212> TYPE: DNA
<213> ORGANISM: Acinetobacter sp. CIP-A165

<400> SEQUENCE: 14
atggcatact catataccga aaagaaacgg atccgtaaga attttggtaa attgccccaa       60
gtgatggaag caccgtactt actttcgatt caagtcgatt cgtaccgtac gttttacaa      120
ggtggcaaaa ctccaaagaa ccgcgaagat atcggtctcc aagccgcatt tcgttcagtt      180
tttcctattg aaagttattc tggcaatgct gctttagaat tgttgagta tagtcttggt      240
aagcctgagt ttgacgtgcg tgaatgtatt ttacgtggtt cgacttatgc agcaccaatg      300
cgcgtaaaaa ttcgtttgat cattaaagat cgtgaaacga atcaattaa agacgttcgt      360
gagcaagaag tgtacatggg tgaaatgcca ctcatgaccg ataacggtac tttcgttatc      420
aatggtactg agcgtgtgat cgtatctcag ttacaccgtt cgccaggtgt gttctttgac      480
catgacaagg gtaaaactca ctcaagtggt aaagtgttgt attcagcacg tattatccct      540
taccgtggtt catggttaga ctttgaattt gacgcaaaag atcttgtgtt tgtacgtatt      600
gaccgtcgtc gtaaattgtt ggcgactgtg attttacgtg ctttaaatta tagcaatgcg      660
caaattttga atttgttcta cgaaaaagta cctgtatatc ttgatatggg tagctatcaa      720
attgacctca ttccagatcg cttgcgtgga gaaatggcgc agtttgatat tgctgacaat      780
gacggtaaag tgattgtaga gcaaggtaaa cgtattaatg cgcgtcacgt acgtcaaatg      840
gaagcggcta acttagccaa gctttctgta cctgatgaat acttgtatga gcgtatcacc      900
gctgaagata tcccattaaa agatggtgag gtgattgctg caaataccct tgttaagcca      960
gaagtgatgg tgaagttagc tgaaggcggt gttaagcaat ttaacatcct atttactaac      1020
gatatcgacc gtggttcttt tattgctgac accttacgtg cagatactac aacgggcgt      1080
gaagaagcac tcgttgaaat ctacaaagta atgcgtccag gtgagccacc gacgaaagaa      1140
gctgcagata attatttaa taacttattc ttctcttctg agcgttatga cttgtcgcct      1200
gttggtcgta tgaagttaa ccgtcgcttg ggtcgtccat acgaagtcgg tactgatcaa      1260
```

```
aagtctcgtg aagttgaagg tattttatcg cacgacgata tcattgatgt acttcgtaca   1320
ttggttgaaa tccgtaacgg taaaggtgaa gtcgacgata tcgaccactt gggtaaccgt   1380
cgcgtacgtt ctgttggtga aatgacagaa aaccaattcc gtgttggttt agtacgtgtt   1440
gagcgtgctg ttaaagagcg tttaagccaa gctgaagcgg ataacctgtc tccacaggat   1500
ttgattaacg caaaaccagt tgctgctgcg attaaagaat tctttggttc aagccaattg   1560
tctcagttca tggatcaaaa caacccatta tctgaaatta cacacaaacg tcgtgtatca   1620
gcgcttgggc ctggtggttt gacacgtgaa cgtgcgggct ttgaggttcg tgacgtacat   1680
caaacgcatt atggtcgtgt ttgtccaatt gaaacgcctg aaggtccaaa cattggtttg   1740
atcaactcgc tttctgttta tgcaaaaacg aacaactttg gtttcttaga aacaccttac   1800
cgtaaagttg tagatggtcg tgttactgat gcggttgagt atttatctgc gattgaagaa   1860
gtaggtactg ttattgcaca ggccgattca gcaattgata agaaggtac tttgactgaa    1920
gaaatggttt ctgtacgtca tcagggtgat ttcgttcgta tgtcacctga gcgtgtcact   1980
catatggatg tatctgcaca gcaggttgtt tctgttgcag cgtcattgat tccgttcctt   2040
gaacacgatg atgcgaaccg tgcattgatg ggttcaaaca tgcagcgtca ggcagttcca   2100
acgttacgtg ctgacaagcc gcttgttggt acgggtatgg aagcaaacgt agcgcgtgac   2160
tctggtgtgt gtgtgatcgc aaaccgtggt ggtgcgattg agtatgttga tgcctcacgt   2220
attgttattc gtgtaaacga agatgaaatg attgctggtg aagcaggtgt agatatctac   2280
aacctgatca aatatacccg ttcgaaccaa acacctgta tcaaccaaaa tgttatcgta    2340
aacatgggcg acaaagttgc gcgtggtgat atcttggctg atggtccatc gacggatatg   2400
ggtgagcttg cgcttggtca aaacatgcgc gtcgcgttca tgacatggaa cggttataac   2460
tacgaagact cgatcttact ttcagagcgt gtgcttcaag aagaccgttt aacttcgatt   2520
catatccaag agttgtcatg tgtcgcacgt gataccaagt taggtgcaga agaaatcact   2580
gccgatattc ctaacgttgg tgaagcagcg cttttctaagt tggatgagtc tggtattgtt   2640
tatatcggtg ctgaagttac agcaggtgac atccttgttg gtaaagtaac acctaaaggt   2700
gaaacacagt taacacctga agaaaaatta cttcgtgcta tctttggcga aaaagcagct   2760
gatgtaaaag attcatcttt acgcgttcca tctggtacca aaggtacagt gatcgatgtt   2820
caagtcttca cgcgtgatgg tttggaaaaa gatgatcgtg cacaagcgat tgaaaaagca   2880
cagcttgatg cttaccgtaa agatttgaaa gaagaataca aaatctttga gaagcagca    2940
cgtgaacgta ttgttcgctt gttgaaaggt aaagagtcta tggtggcgg tacaacgaag    3000
cgcggcgata aacttgcaga agatatgttg tctggtttag agctggttga tttgttagaa   3060
atccaaccaa cagatgaagc aatcgctgaa cgtttaactc aaattcaggt attcttgaaa   3120
gagaagagta tcgagattga tgagaaattt gctgagaaga acgcaaaact ctctacaggt   3180
gatgaattaa caacgggtgt attaaaagtt gttaaggttt accttgcagt gaaacgtcgt   3240
atccaaccgg gtgataagat ggcgggtcgt cacgggaaca agggtgttgt ctctaacatc   3300
ttacctgttg aagatatgcc acatgatgcc aatggtgtac ctgttgacat cgtattgaac   3360
ccattgggtg taccgtcgcg tatgaacgtg ggtcagattc ttgaaaccca tttgggcttg   3420
gcggcaaaag gtttgggtga gcagatcgat aagatgctgc aacaacaacg taccgttgct   3480
gaacttcgtt tgttccttga taagatttac aacaaagttg gtggcgagca agaagatctt   3540
gatagcttaa ctgatgaaga agtgttgaag cttgcaggta acttacgtgc aggtgttcct   3600
ttggcaacac cagtgtttga tggtgctgaa gaaagccaaa ttaagaatt acttgaactt    3660
```

```
gctgaattgc cgcgttctgg tcaacagact ttgtttgatg gccgtacagg tgaacagttt    3720
gaccgtcctg taactgttgg ttacatgtat atgctcaaat tgaaccactt ggttgatgac    3780
aaaatgcacg cgcgttcaac tggttcttac tcgcttgtga cacagcagcc gcttggtggt    3840
aaagcacaat tcggtggtca gcgttttggt gagatggaag tatgggcact tgaagcatat    3900
ggtgcagcat ataccctcca agaaatgctc actgtgaagt cggatgacgt cgaaggtcgt    3960
acacgcatct ataagaacat tgtagatgga aaccattata tggatccggg tatgcctgaa    4020
tcgttcaacg tattgaccaa agagatccgt tctttaggta tcaacattga actgaaaaat    4080
ggtgactaa                                                             4089

<210> SEQ ID NO 15
<211> LENGTH: 4089
<212> TYPE: DNA
<213> ORGANISM: Acinetobacter johnsonii

<400> SEQUENCE: 15
atggcatact catataccga aaagaaacgg atccgtaaga attttggtaa attgcctagt      60
gttatggatg ctccgtactt gctcgcgatt caagtcgact cgtacagaac atttttacaa     120
gatggcaaat caccaaaaaa ccgcgaagat atcggtctgc aagccgcgtt tcgttcagtt     180
tttcctatag aaagttattc tggcaatgct gctttagaat tgttgagtaa tagtcttggt     240
aagcctgagt ttgatgtacg cgaatgtatt cttcgtggct caacttatgc agcaccaatg     300
cgcgtaaaaa ttcgtttgat cttaaaagat cgcgaaacta atcaattaa agacgtgcgc      360 gagcaagaag tgtacatggg tgaaatgcca ctcatgaccg ataacggtac attcgttatt     420
aatggtactg agcgtgtaat cgtatctcaa ttacaccgtt caccaggcgt gttcttttgac    480 cacgataaag gcaaaaccca ctctagtggt aaagtgcttt attctgcgcg tattattcct     540
taccgtggtt catggttaga cttcgaattt gacgcaaaag accttgtatt tgtgcgtatt     600
gaccgtcgtc gtaaattact cgcgactgtg gttcttcgtg ctttgggtta taacaatgcg     660
aaaatcttag acttgttcta tgaaaaagtg cctgtatacc tagacatggg tagctaccag     720
attgaccttg ttccagaacg cttacgtggc gaaatggcac aatttgacat cgtagataat     780
gatggcaaaa ccattgttga gcaaggcaag cgtatcaacg cgcgtcatgt gcgtcaaatg     840
gaagctgctg gcctagaaaa actttctgtg ccagatgagt acttgtacga gcgcattact     900
gcagaagaca tcccacttaa agatggtgat gtgattgcag ctaatacctt gttaagccat     960
gaagtgatgg tgaaattggc tgaagggggt gttaaacaat ttaacattct attcaccaat    1020
gacatcgacc gtggttcatt cgttgcagat actttacgtg cagacaccac gacaggtcgt    1080
gaagaagcat tggtagaaat ctacaaagta atgcgtccag cgagccacc aacgaaagaa     1140 gcggctgaaa atttattcaa taacttgttc ttctcttcag aacgttatga cctctctcca    1200
gtgggtcgta tgaagttcaa ccgtcgttta ggtcgtcctt acgaagtggg tacggatcag    1260
aagtctcgtg aagttgaagg tattttgtcg aacgaagata tcactgatgt attaaaaaca    1320
ttggttgaaa tccgtaacgg taaaggtgaa gtcgacgata tcgatcactt gggtaaccgt    1380
cgcgtgcgtt cagtaggcga atgactgaa aaccaattcc gtgttggtct agttcgtgta     1440
gaacgtgctg ttaagaacg tttaagccaa gctgaaacag ataacttgtc tccgcaagat    1500
ttgatcaatg cgaaaccagt ggctgctgca atcaaagaat tctttggttc aagccagtta    1560
tctcagttca tggaccaaaa caacccattg tctgagatta cgcacaaacg tcgtgtatcg    1620
gcgcttggtc ccggtggttt tgacacgtga acgtgcgggct ttgaggtacg tgacgtacac   1680
```

```
caaactcact acggtcgtgt atgtccaatt gaaacgccgg aaggtccaaa cattggtttg    1740
atcaactcgc tttctgttta tgcgaaatgt aacaatttcg gtttcttaga aacaccatac    1800
cgtaaagtgc ttgatggtcg tgtaacggat gaagttgagt atttatctgc aattgaagaa    1860
gtaggtactg tgattgcaca ggccgattct ggcgtagata agacggtaa cttaacagaa     1920 gaatttgttt ctgtacgtca ccaaggtgat ttcgtacgta tgccgcctga aaaagtgacg    1980
catatggacg tttctgcaca gcaggttgtt tctgttgctg catcactcat tccattcctt    2040
gaacacgatg acgccaaccg tgcattgatg ggttcaaaca tgcagcgtca agctgtgcct    2100
acattgattg ctgacaaacc gcttgtaggt acaggcatgg aagcaaatgt agcgcatgac    2160
tctggtgtgt gtgtgattgc gggtcgtggt ggtcgtatcg aattcgtcga tgcttcacgt    2220
gttgtgattc gtgtcaatga agatgaaatg gttgcaggcg aggcaggtgt agatatctat    2280
aacctgatca aatatacacg ttcgaaccaa acacttgta ttaaccaaaa agttcttgtg     2340
aaacttggtg ataaagtggg tcgtggcgat gtattggctg atggtccatc aacagatggt    2400
ggtgagcttg cgctaggtca aaacatgcgc gttgcgttca tgacgtggaa tggttacaac    2460
tatgaagact cgatcttact ttcagagcgc gtacttcaag aagaccgttt aacctcgatt    2520
cacattcaag aattatcatg tgttgcacgt gatacgaaat tgggtgcgga agagatcaca    2580
gcggatatcc cgaatgtggg tgaagctgca ctgtctaagc ttgatgaatc aggtatcgta    2640
tatatcggtg ctgaagtgac tgctggtgat atccttgtag gtaaagtaac gcctaaaggt    2700
gaaacgcagt taacaccaga agaaaaattg cttcgtgcaa tcttcggtga aaaagcagct    2760
gacgtaaaag actcatcttt acgtgttcca tcaggtacca aaggtacagt gattgacgtt    2820
caagtgttta cacgtgacgg tcttgagaaa gacgaacgtg cgcaagcaat gaaaaagct    2880 cagcttgatt catatcgtaa agacttgaaa gaagaataca aaatcttcga agaagcagca    2940
cgtgaacgta ttgttcgttt gttgacaggt caagagtcta acggtggtgg tacaaccaag    3000
cgtggcgata agctttctgt agacgtattg tctggtttag agttggttga tttacttgaa    3060
atccaaccga ctgatgaagc tattgcagag cgtttaactc aaattcaagt gttcttgaaa    3120
gagaagagct ttgaaattga tgagaagttt gcagagaaaa aacgcaaact ttctacaggt    3180
gatgaattaa caacaggtgt attgaaagtt gttaaggttt acttggctgt taaacgtcgc    3240
atccaaccgg gtgataagat ggcgggtcgt cacggtaaca agggtgttgt ttctaacatc    3300
ttgcctgttg aagacatgcc gcacgatgcc aatggtgttc cagtcgacat cgtattgaac    3360
ccactgggtg taccgtcacg tatgaacgtg ggtcagattc tagagactca cttaggtatg    3420
gcagcgaaag gtcttggcga agaaatcgac aagatgttaa agcgcaacg tactgtactt    3480 gagcttcgtg gattcttaga caagatttat aacaaagttg gtggcgagca agaagatctt    3540
gatagcttaa ctgatgatga aattttggtg ctttcgggta acttgcgtgc gggtgttcct    3600
cttgcaacgc cagtattcga tggtgctgaa gaatctcaaa ttaaagactt gttagagctt    3660
gcgaacattt cacgtactgg tcaaacagta ttgtatgatg gtcgtacagg tgaacagttt    3720
gaccgtcctg taactgtagg ttacatgtac atgttgaaac tgaaccactt ggtagacgac    3780
aagatgcacg cacgttctac tggttcttac tcattagtaa ctcaacagcc gcttggtggt    3840
aaagcacaat tcggtggtca gcgtttcggt gagatggaag tctgggcgct tgaagcatat    3900
ggcgcagctt acacgcttca agaaatgctt actgttaagt cggatgacgt tgaaggtcgt    3960
acccgtatct ataagaacat tgtagatggt aaccattata tggacccagg tatgcctgaa    4020
tcgttcaacg tattgaccaa agagatccgt tctttaggta tcaacattga actgaaaaat    4080
``` ggtgactaa 4089

<210> SEQ ID NO 16
<211> LENGTH: 4089
<212> TYPE: DNA
<213> ORGANISM: Acinetobacter lwoffii

<400> SEQUENCE: 16

| | | | | | |
|---|---|---|---|---|---|
| atggcatact | catataccga | aaagaaacgg | atccgtaaga | attttggtaa | attgcctagc | 60 |
| gttatggatg | ctccgtacct | gctcgcgatt | caagtcgact | cgtacagaac | gttcttacaa | 120 |
| gatggcaaat | caccaaaaaa | ccgcgaagat | atcggtctcc | aagccgcatt | tcgttcagtt | 180 |
| tttcctatag | aaagttattc | tggcaatgct | gctttagaat | tgttgagta | tagtcttggt | 240 |
| aagcctgagt | tgatgtacg | cgaatgtatt | cttcgtggct | caacttatgc | agcaccaatg | 300 |
| cgtgtaaaaa | ttcgtttgat | cctgaaagat | cgtgaaacga | agtcaattaa | agacgtacgt | 360 |
| gaacaagaag | tctatatggg | cgaaatgcca | ttgatgacgg | ataacgggac | ctttgtaatt | 420 |
| aatggtaccg | agcgtgtaat | cgtatctcaa | ttacaccgtt | caccaggcgt | attctttgac | 480 |
| cacgataaag | gtaagactca | ctcaagtggt | aaagtccttt | attcagcgcg | tatcattcct | 540 |
| taccgtggtt | catggttaga | ttttgaattc | gatgccaaag | acctagtcta | tgtacgtatt | 600 |
| gaccgtcgtc | gtaaattact | tgcgactgtg | gtgctgcgtg | cgctgggtta | tagcaacgaa | 660 |
| aacattctca | acatgttcta | cgagaaagtc | cctgtgtatc | ttgacatggg | tagctatcaa | 720 |
| attgacttgg | tgccggaacg | tctgcgcggc | gaaatggcac | aatttgacat | cttggataaa | 780 |
| gatggcaagg | caatcgttga | acaaggtaaa | cgtattaacg | cgcgtcatgt | acgtcaaatg | 840 |
| gaagcttcag | gtcttgaaaa | acttgcagtg | cctgatgagt | attgtatga | gcgtatcacg | 900 |
| gctgaagaca | tcgcattaaa | agatggcgac | gtgattgctg | caaataccgt | attgagccat | 960 |
| gaagtcatgg | tgaaaattgc | agaaggcggc | gtgaagcagt | ttaatgttct | gttcaccaat | 1020 |
| gatatcgacc | gtggttcatt | cgttgcagat | tctctacgtg | cagatactac | gaccactcgt | 1080 |
| gaagaagcat | tagtagaaat | ctacaaagtc | atgcgtccgg | gcgagccacc | aaccaaagaa | 1140 |
| gcagctgaga | acctgttcaa | taacctgttc | ttctcttctg | agcgttatga | cttgtctcca | 1200 |
| gtcggtcgta | tgaagttcaa | ccgtcgtttg | ggtcgtcctt | atgaagtggg | tacagaccag | 1260 |
| aagtcgcgtg | aagttgaagg | tattctctcg | aacgaagata | tcactgatgt | attgaaaaca | 1320 |
| ttagttgaaa | tccgtaacgg | taaaggtgaa | gtcgacgata | tcgatcactt | gggtaaccgt | 1380 |
| cgtgttcgtt | ctgtgggcga | aatgacagaa | aaccaattcc | gtgtcggtct | ggttcgtgta | 1440 |
| gaacgtgctg | ttaaagaacg | tttatctcaa | gctgaaacag | acaacctgtc | tccgcaagat | 1500 |
| ctaatcaatg | cgaagcctgt | tgctgctgca | atcaaagaat | tctttggttc | aagccagttg | 1560 |
| tctcagttca | tggatcaaaa | caacccgttg | tctgaaatca | cgcacaagcg | tcgtgtatca | 1620 |
| gcacttggtc | ccggtggttt | gacgcgtgaa | cgtgcgggct | tgaagtacg | tgacgtacat | 1680 |
| caaacgcatt | acgtcgtgt | atgtccaatt | gaaacgccgg | aaggtccaaa | cattggtttg | 1740 |
| atcaactcgc | tttctgtata | tgctaaagcg | aacaacttcg | gttcctgga | aacgccttac | 1800 |
| cgtaaagtag | ttgatggccg | tgtaaccatg | gacattgaat | acctgtctgc | gattgaagaa | 1860 |
| gtgggtactg | tgattgcaca | ggccgattct | gcagtagatg | ctgatggtaa | tttattagaa | 1920 |
| gaagttgtat | ctgtacgtca | ccaaggtgac | ttcgtacgca | tgccgccgga | aaaagtaacg | 1980 |
| catatggatg | tatctgctca | gcaggttgta | tctgtggctg | cgtcactgat | tccgttcctt | 2040 |
| gaacacgatg | atgccaaccg | tgcattgatg | ggttcaaaca | tgcaacgtca | ggctgttcct | 2100 |

```
acgttaatcg ctgacaaacc actcgtaggt acgggtatgg aagcgaacgt agcacatgac      2160
tctggtgtat gtgtgatcgc tcagcgtggt ggtcgtatcg agtttgttga tgcatctcgt      2220
gtcgtgattc gtgtgaacga agaagagatg atcgcaggtg aggcaggtgt agatatctat      2280
aacctgatca aatacacccg ttcaaaccaa aacacctgta tcaaccagaa agttctggtg      2340
aacctgggcg ataaagtggg tcgtggtgac gtattagctg atggtccatc gactgatggc      2400
ggtgagctag cgcttggtca aaacatgcgc gtcgcattca tgacctggaa cggttacaac      2460
tacgaagact cgatcttact ttcagagcgt gtacttcaag aagaccgttt aacctcgatt      2520
catatccagg aattgtcatg tgtcgcacgt gatactaagc ttggtgctga gaaaatcacg      2580
gccgatatcc cgaatgtggg tgaagcagcg ctttctaaac ttgatgaatc aggtattgtt      2640
tacatcggtg ctgaagtaac agcaggtgat attcttgttg gtaaagtgac gcctaaaggt      2700
gaaacgcagc taacgccgga agaaaaattg cttcgtgcaa tcttcggtga aaaagcagct      2760
gacgttaaag attcatcttt acgcgttcca tctggtacca aaggtactgt gattgatgtt      2820
caagtgttta cacgtgatgg tcttgaaaaa gacgaacgtg ctcaagcaat gaaaaagct      2880 cagcttgatg cttaccgtaa agacttgaaa gaagagttca agatctttga agaagcagca      2940
cgtgaacgtg taattcgttt gttgaacggt caagagtcga atggtggcgg taccactaaa      3000
cgtggcgaca aactgtctga agacgtgttg tctggttttag agcttgttga tcttcttgaa      3060
attcaaccgg ttgatgaagc aatcgctgaa cgtctaacgc aaattcaagt gttcttgaaa      3120
gagaagagct tcgaaattga cgagaaattt gctgagaaaa aacgcaaact ttctacaggc      3180
gatgagctga ccactggcgt attgaaagta gttaaagttt atcttgcggt aaaacgtcgc      3240
atccagccgg gtgataagat ggccggtcgt cacggtaaca agggtgttgt atcaaacatc      3300
ttgccggtag aagacatgcc acacgatgcc aatggtgtac ctgttgatat cgtactgaac      3360
ccgctgggcg taccatcgcg tatgaacgtg ggtcagattc ttgaaactca cttaggtatg      3420
gctgccaaag tcttggcga tcaaatcgac aagatgatga agaacagcg tactgtactt      3480 gagcttcgtg atttcctgga caagatttat aacaaagttg gtggcgagca agaagatctt      3540
gacagcttga ctgatgaaga atcttgaaa ctttctggta acttgcgtgc tggtgtgcct      3600
ttggcaacac ctgtattcga tggtgctgaa gaaggtcaga tcaaagaatt gttacaactt      3660
gcaggtctat caagtactgg tcagacagta ttatatgatg gtcgtactgg tgagcgtttc      3720
gaccgtccag taactgtagg ttatatgtac atgctgaaac tgaaccactt agttgatgac      3780
aagatgcatg cgcgttcaac tggttcttat tctctagtca cgcaacagcc gctgggtggt      3840
aaagcacaat tcggtggtca gcgtttcggt gagatggaag tctgggcact agaagcttac      3900
ggtgcagcat atacgctaca agaaatgctg actgtgaaat cggatgacgt tgaaggccgt      3960
acccgtatct acaagaatat tgtagatggt aaccattata tggacccggg tatgcctgaa      4020
tcgttcaacg tattgaccaa agagatccgt tctttaggta tcaacattga actgaaaaat      4080
ggtgactaa                                                              4089

<210> SEQ ID NO 17
<211> LENGTH: 4089
<212> TYPE: DNA
<213> ORGANISM: Acinetobacter sp.

<400> SEQUENCE: 17
atggcatact catataccga aaagaaacgg atccgtaaga attttggtaa attgcctagc        60
gtcatggatg ctccgtactt gctcgcgatt caagtcgact cgtacagaac attcttacaa       120
```

```
gatggcaaat caccaaaaaa ccgcgaagat atcggtctcc aagccgcatt tcgttcagtt    180
tttcctattg aaagttattc tggcaatgct gctttagaat tgttgagta tagtcttggt     240 aagcctgagt ttgatgtacg cgaatgtatc cttcgtggct caacttatgc agcaccaatg   300
cgtgtaaaaa ttcgtttgat cctgaaagat cgtgaaacga agtcaattaa agacgtacgt   360
gaacaagaag tctatatggg cgaaatgcca ttgatgacgg ataacggtac ctttgtaatt   420
aacggtaccg agcgtgtgat cgtgtcacaa ttacaccgtt caccaggcgt attctttgac   480
cacgataaag gcaagactca ctcaagtggt aaagtccttt attcagcacg tatcattcct   540
taccgtggtt catggttaga ctttgaattc gatgccaaag acctcgtcta tgtacgtatt   600
gaccgtcgtc gtaaattgct tgcgactgtg gtactccgtg ccttgggtta tagcaacgaa   660
aacattctcg acatgttcta cgagaaagta cctgtgtatc ttgacatggg tagctaccag   720
attgacctgg tgcctgaacg tttgcgtggc gaaatggcac aatttgacat tctggacaag   780
gatggcaagg caattgttga gcaaggtaaa cgtatcaatg cgcgtcatgt acgtcaaatg   840
gaagcttcag gtcttgaaaa acttgcagtg ccagatgagt acctatatga gcgtatcact   900
gctgaagaca tccagttaaa agatggcgat gtgattgcag ccaatactgt attaagccat   960
gaaatcatgg tgaaaattgc agaaggcggc gtgaagcagt tcaatattct gttcaccaat  1020
gatatcgacc gcggttcatt tgttgcagat tctctacgtg cagatacaac gagcaatcgt  1080
gaagaagcat tggtagaaat ctacaaagtg atgcgtccgg gcgaaccacc aaccaaagaa  1140
gctgctgaaa acttattcaa caacttgttc ttctcttctg aacgttatga cttgtctcca  1200
gttggtcgta tgaagttcaa ccgtcgtttg ggtcgtcctt atgaagtggg tacagaccag  1260
aagtcacgtg aggttgaagg cattctctcg aacgaagata tcactgatgt attaaaaaca  1320
ttagttgaaa tccgtaacgg taaaggtgaa gtcgacgata tcgatcactt gggtaaccgt  1380
cgtgttcgtt ctgtgggtga aatgacagaa aaccaattcc gtgtaggtct ggttcgtgta  1440
gaacgtgctg ttaaagaacg tctatctcaa gctgaaactg acaacctgtc tccgcaagat  1500
ttgatcaatg cgaaacctgt tgctgctgca atcaaagaat tctttggttc aagccagttg  1560
tctcagttta tggatcaaaa caacccgtta tctgagatta cgcacaaacg tcgtgtttct  1620
gcacttggtc ctggcggttt gacgcgtgaa cgtgcaggct ttgaagtacg tgacgtacat  1680
caaactcact acggtcgtgt atgtccaatt gaaacgcctg aaggtccaaa cattggtttg  1740
atcaactcgc tttctgttta tgcgaaatgt aacaactttg gttttctgga accccatac  1800 cgtaaggttt tgatggtcg tgtaacagat gaagttgaat acctgtctgc gattgaagaa  1860
gtaggtactg tcattgcaca ggccgattct gcaatggata agacggtaa cttaacagaa  1920 gagtttgtat ctgttcgtca tcagggtgac ttcgtacgta ttcctcctga aaagtaacg   1980 catatggatg tatctgctca gcaggtcgta tctgtagcag cgtcactgat tccattccta  2040
gaacacgatg acgccaaccg tgcgttaatg ggttcgaaca tgcaacgtca ggcagttccg  2100
acgttgatcg ctgacaagcc gcttgttggt accggtatgg aagcgaacgt agcacatgac  2160
tcaggtgtat gtgtgatcgc tcagcgtggt ggtcgtatcg agtttgttga tgcgtctcgt  2220
gtggttattc gtgtgaatga agacgaaatg atcgcaggtg aagcaggtgt agatatctac  2280
aacctgatca gtacacccg ttcgaaccag aacacttgta tcaaccagaa agttcttgtg  2340
aacctgggcg ataaagtggg tcgtggtgat gtcctggctg atggtccatc gactgatggc  2400
ggtgagctgg cactgggtca aaacatgcgc gttgcgttca tgacctggaa tggttacaac  2460
tacgaagact cgatcttact ttctgagcgt gttcttcaag aagaccgttt aacgtctatt  2520
```

| | |
|---|---|
| catatccagg aattatcatg tgtcgcacgt gataccaaac tgggtgcgga agaaatcact | 2580 |
| gctgatattc cgaacgtagg tgaagctgct ctgtctaaac tggacgagtc aggtatcgtt | 2640 |
| tacatcggtg ctgaagtaac tgctggcgat atcctggttg gtaaagtaac ccctaaaggt | 2700 |
| gaaacacaac ttactccgga agaaaaattg ctacgtgcaa tcttcggtga aaaagcagct | 2760 |
| gacgtaaaag actcatcttt acgcgttcca tcaggtacta aaggtacagt cattgacgtt | 2820 |
| caagtgttta cacgtgacgg tcttgaaaaa gacgaacgtg ctcaagcaat tgaaaaagcg | 2880 |
| caattggatg cataccgtaa agacttgaaa gaagaattca aaatcttcga agaagctgca | 2940 |
| cgtgaacgtg taatccgtct actgaatggc aagagtcga atggtggcgg tacaactaaa | 3000 |
| cgtggcgaca aactgtctga agacgtgttg tctggtttag agcttgttga tcttcttgaa | 3060 |
| attcaaccag ttgatgaagc aattgctgaa cgtttaactc aaattcaagt gttcttgaaa | 3120 |
| gagaagagct tcgaaattga cgagaaattt gctgagaaaa aacgcaaact ttctacaggc | 3180 |
| gatgaactga ccactggcgt tttaaaagtt gttaaggttt atcttgctgt aaaacgtcgc | 3240 |
| atccaaccgg gtgataagat ggcgggtcgt cacggtaaca aaggtgttgt atcaaacatc | 3300 |
| ttgccggtag aagacatgcc acatgatgcc aacggtgtac ctgttgatat cgtattgaac | 3360 |
| ccgcttggcg taccatcacg tatgaacgtg ggtcagattc ttgaaactca cttgggtatg | 3420 |
| gcggcgaaag tcttggcgga tcaaatcgac aagatgatga aagagcaacg tactgtactt | 3480 |
| gagcttcgtg atttcctgga caagatttac aataaagttg gtggcgagca agaagatctt | 3540 |
| gatagcttga ctgatgaaga aatcttgaaa ctttctggca acttgcgtgc tggtgtgcct | 3600 |
| ttggctactc ctgtattcga tggtgctgaa gaaggtcaga tcaaagagtt gttacaactt | 3660 |
| gcaggcctat ctagtactgg tcagaccgta ttatatgatg gtcgtactgg tgaacgtttc | 3720 |
| gatcgtccgg taactgttgg ttatatgtac atgctgaaac tgaaccattt ggttgatgac | 3780 |
| aagatgcatg cgcgttcaac tggctctctat tctctggtaa cgcaacgcc gctgggtggt | 3840 |
| aaagcacaat tcggtggtca gcgtttcggt gagatggaag tctgggcact agaagcttac | 3900 |
| ggtgcagcat atacgctaca agaaatgctg actgtgaaat cggatgacgt tgaaggccgt | 3960 |
| acccgtatct acaagaacat tgtggatggc aaccattata tggacccggg catgcctgaa | 4020 |
| tcgttcaacg tattgaccaa agagatccgt tctttaggta tcaacattga actgaaaaat | 4080 |
| ggtgactaa | 4089 |

<210> SEQ ID NO 18
<211> LENGTH: 4089
<212> TYPE: DNA
<213> ORGANISM: Acinetobacter sp.

<400> SEQUENCE: 18

| | |
|---|---|
| atggcatact catataccga aaagaaacgg atccgtaaga attttggtaa attgccccaa | 60 |
| gtcatgcatg ctccgtactt gctcgcgatt caagtcgact cgtacagaac attcttgcaa | 120 |
| gatggcaaaa ctccaaaaaa tcgcgaagat atcggtctcc aagctgcatt tcgttcagtt | 180 |
| tttcctattg aaagttattc gggcaatgct gctttagaat tcgttgagta tagtcttggt | 240 |
| aaaccagagt ttgatgttcg cgagtgtatt cttcgcggtt caacctttgc ggcaccaatg | 300 |
| cgcgttaaaa ttcgtttgat catcaaagat cgtgaaacga atctatcaa agacgtacgt | 360 |
| gaacaagaag tgtacatggg tgaaatgcca ctcatgactg agaatggtac ttttgtaatc | 420 |
| aatggtactg agcgtgtaat cgtatctcaa ttacaccgtt ctccgggcgt cttcttgat | 480 |
| cacgataagg gtaaaactca ttcaagtggt aaagtgcttt attcagcacg tatcattcct | 540 |

```
taccgtgggt catggttgga ttttgaattt gatgctaaag acttagtatt tgttcgtatt      600
gaccgtcgtc gtaaattgtt ggcgactgtt attctacgtg cattgaacta tagcaatgaa      660
caaattctca atatgttcta tgagaaagta cctgtatatc ttgatatggg tagctatcag      720
attgaccttg ttccagaacg ccttcgcggt gaaatggcgc agttcgatat tgcagacaat      780
gacggtaaag tgattgttga acaaggtaaa cgtatcaatg cacgtcatgt gcgtcaaatg      840
gaagctgcgg gtttaactaa actttctgtt cctgatgaat acttgtatga gcgtattaca      900
gctgaagata ttactttacg tgatggtgaa gtgattgctg ctaataccat tttaagccat      960
gaagtattgg ttaaaatcgc tgaaggtggt gttaaacaat ttaacatctt gttcaccaat     1020
gatatcgatc gtggttcgtt tgttgcagat acactacgtg cagatacgac aacaggtcgt     1080
gaagaagcac ttgtagaaat ctacaaagtc atgcgtccag gtgagccacc aacaaaagaa     1140
gcggctgaaa acttattcaa taacttattc ttctctacag agcgttatga cttgtctcct     1200
gtaggtcgta tgaagtttaa tcgtcgtttg ggtcgtcctt atgaagtcgg tacagatcag     1260
aagtctcgtg aagtagaagg tattctttct aacgatgaca tcattgatgt attgaaaaca     1320
ttggtagaaa tccgtaacgg taaaggtgaa gtcgacgata tcgatcactt aggtaaccgt     1380
cgtgtacgtt ctgttggtga aatgacagaa aaccaattcc gtgttggtct agttcgtgtt     1440
gaacgtgctg taaagagcg tttaaaccaa gctgaaacag ataacttgtc tccacaagat     1500
ttgatcaatg cgaaaccagt tgcagctgca atcaaagaat ctttggttc aagccaattg     1560 tctcagttta tggatcaaaa caatccattg tctgaaatta cgcacaaacg tcgtgtttca     1620
gcgcttggtc ctggtggttt gacacgtgaa cgcgcaggct ttgaggtacg tgacgtacat     1680
caaactcact atggtcgtgt gtgtccaatt gagacacctg aaggtccaaa cattggtttg     1740
atcaactcac tttctgtata tgcaaaagcc aacaacttcg gtttcttgga aacaccatac     1800
cgtaaagtgg ttgatggtcg tgtaacggat gatgttgagt atttatctgc gattgaagaa     1860
gtaggcactg taattgcaca agccgattct ggtgtagata aagacggtca cttgactgaa     1920
gaattcgttt ctgtacgtca tcaaggtgaa ttcgttcgta tgcctcctga aaaagtgacg     1980
catatggatg tatctgctca gcaggttgtt tctgttgctg catcacttat tccattcctt     2040
gaacacgatg atgcgaaccg tgcattaatg ggttcaaaca tgcaacgtca ggctgttcct     2100
acattgcttg ctgacaagcc acttgttggt acaggtatgg aagcaaacgt agcgcatgac     2160
tctggcgtgt gtgtaatcgc aaaacgtggc ggacgtattg agttcgttga tgcttctcgt     2220
gttgttattc gtgtgaacga agatgaaatg atcgcgggtg aagcaggtgt agacatctac     2280
aacttgatca atacacacg ttcaaaccaa acacttgta tcaaccaaaa agttcttgtg     2340
agcttgggcg ataaagtagg tcgtggtgac gttcttgctg atggtccatc gactgacggt     2400
ggtgaattag cgcttggtca aaacatgcgt gtcgcgttca tgacgtggaa cggttataac     2460
tacgaagact cgatcttatt atctgagcgt gtacttcaag aagaccgttt gacttcgatt     2520
cacatccaag agttgtcatg tgtagcgcgt gataccaagt taggtgcaga agaaattact     2580
gcagatattc ctaacgtggg tgaagcagct ttatctaaac ttgatgaatc aggtattgtt     2640
tatatcggtg ctgaagtttc agcaggtgac atccttgttg gtaaggtaac gcctaaaggt     2700
gaaacacaat aaaacctga agaaaaatta cttcgtgcaa ttttcggtga aaaagctgcg     2760
gatgtaaaag actcttcttt acgtgtttct tcaagcgtaa aggtacagt gattgacgtt     2820 caagtgttta cacgtgacgg tatcgagaaa gatgagcgtg ctcaagcaat tgaaaaagcg     2880
caacttgatg cttaccgtaa agacttgaaa gaagagttca aatcttcga agaagctgct     2940
```

```
cgtgaacgta ttgtgcgttt attgaaaggt caagagtcaa atggtggtgg tacaacgaaa    3000
cgtggtgaca agctaactga agacgtattg tctaacttag agcttgttga tctgttagaa    3060
gttcaaccag cagacgaagg tattgctgag cgtttaacgc agattcaagt gttcttgaaa    3120
gagaagagcc acgagatcga tgagaagttt gctgagaaaa acgtaaaact ttcaacgggt    3180
gatgaactga caactggtgt gttgaaagtt gttaaagttt atcttgctgt taaacgtcgt    3240
atccagcctg gtgataagat ggcgggtcgt cacggtaaca agggtgttgt atcaaacatc    3300
ttaccagttg aagatatgcc gcatgacatc catggtgttc cagtggatgt ggtacttaac    3360
ccactcggtg taccatcacg tatgaacgtg ggtcagattc ttgaaactca cttgggtatg    3420
gcagcgaaag gtcttggcga taagatcgac aagatgatga agagcaacg tactgttctt    3480 gaacttcgtg aattcttaga caagatttat aacaaagttg gtggcgagca agaagatctt    3540
gatagcttga ctgatgaaga aatcttggtg ttatcaggta acttgcgtaa aggtgttcct    3600
ttagctacac cagtatttga tggtgcagaa gaaggacaaa tcaaagagtt acttgaactt    3660
ggtggtatct cacgtacagg tcaaacagta ttgtatgatg gacgtacagg tgagcgtttt    3720
gaccgcccag taacagtagg ttatatgtac atgctcaagt tgaaccactt ggttgacgac    3780
aagatgcatg cacgttctac tggttcttac tcactggtga ctcaacaacc gcttggtggt    3840
aaagcacaat tcggtggtca gcgtttcggt gagatggaag tttgggcact tgaggcttat    3900
ggtgctgctt atacacttca agaaatgtta actgtgaaat cggatgacgt tgaaggtcgt    3960
actcgcatct ataagaacat tgtagatggt aaccattata tggatccggg tatgcctgaa    4020
tcgttcaacg tattgaccaa agagatccgt tctttaggta tcaacattga actgaaaaat    4080
ggtgactaa                                                             4089

<210> SEQ ID NO 19
<211> LENGTH: 4089
<212> TYPE: DNA
<213> ORGANISM: Acinetobacter sp.

<400> SEQUENCE: 19
atggcatact catataccga aaagaaacgg atccgtaaga attttggtaa attgccccaa      60
gtcatgcatg ctccgtacct gctctcgatt caagtcgact cgtacagaac attcttgcaa     120
gacggcaaaa caccaaaaaa tcgcgaagat atcggtctcc aagctgcatt tcgttcagtt     180
tttcctattg aaagttattc gggcaatgct gctttagaat tcgttgagta tagtcttggt     240
aaaccagagt ttgatgttcg cgaatgtatt cttcgtggct caaccttgc ggcaccaatg     300 cgcgttaaaa ttcgtttgat catcaaagat cgtgaaacga atctattaa agacgtacgt     360 gaacaagaag tgtacatggg tgaaatgcca ctcatgactg agaatggtac ctttgtcatc     420
aatggtactg agcgtgtaat cgtatctcaa ttacaccgtt caccaggcgt attctttgac     480
catgataaag gtaaaacgca ttcaagcggt aaagtgcttt attcagcacg tattattcct     540
tatcgtggtt catggttaga ttttgagttt gatgctaaag atttagtctt tgtacgtatt     600
gaccgtcgtc gtaaattgct tgcgactgtt gtgttgcgtg cattgagcta tagcaatgaa     660
caaattctga atatgttcta cgaaaaagta cctgtatatc ttgatatggg tagctatcag     720
attgaccttg tgcctgaacg tcttcgtggt gaaatggctc aatttgatat cgtggacaat     780
gatggtaaag ccattgttga acaaggtaaa cgtattaatg ctcgccatgt acgtcaaatg     840
gaagctgctg gttaactaa acttccagtt ccagatgaat atttgtatga gcgtattact     900
gctgaagata tcgtacttaa agacggtgaa gtaattactg ctaacactgt attaagtcat     960
```

```
gagattttgg tcagaattgc tgaaggtggt attaaacaat ttaatatcct gttcaccaat    1020
gacatcgatc gtggttcttt tgttgctgac accttacgtg cagatacaac atctggtcgt    1080
gaagaagcac ttgtagaaat ctacaaagtg atgcgtccag gtgagccacc aacgaaagaa    1140
gcggctgaaa acttattcaa taacttattc ttctctacag agcgttatga tttatcgcct    1200
gtgggtcgta tgaagtttaa ccgtcgtttg ggtcgtcctt acgaagtagg tacagatcag    1260
aagtctcgtg aagtagaagg tattctttct aacgatgaca tcattgatgt actgaaaaca    1320
ctggtagaaa ttcgtaacgg taaaggtgaa gtcgacgata tcgatcactt gggtaaccgt    1380
cgcgtacgtt ctgttggtga aatgacagaa aaccaattcc gtgttggttt agttcgtgtt    1440
gaacgtgctg ttaaagagcg tttaaaccaa gctgaaacag ataacttgtc tccacaagat    1500
ttgatcaatg cgaaaccagt tgctgctgca atcaaagaat tctttggttc aagccaattg    1560
tcacagttta tggatcaaaa caacccattg tcagaaatta cacacaaacg tcgtgtatct    1620
gcgcttgggc ctggtggttt gacacgtgaa cgtgcgggct ttgaagtacg tgacgtacat    1680
caaactcact atggtcgtgt atgtccaatt gaaacacctg aaggaccaaa cattggtttg    1740
atcaactcgc tttctgttta tgcaaaagcg aacaacttcg gtttcttgga aacaccatac    1800
cgtcgcgttg ttgatggtcg tgtaacagat gatgttgaat atttatctgc aattgaagaa    1860
gtaggtactt ttattgcaca ggccgattct gcattggata agatggaca tttaacagaa    1920 gacttcgttt cagtacgtca ccaaggtgac ttcgttcgta tgccacctga aaaagtgacg    1980
catatggatt tatctgctca acaggttgta tctgtcgctg catcacttat tccattcctt    2040
gaacacgatg atgccaaccg tgcattgatg ggttcaaaca tgcaacgtca ggctgttcct    2100
acattgcttg ctgataaacc acttgtgggt accggcatgg aagcaaacgt agcgcacgac    2160
tctggtgtat gtgtgatcgc gaaacgtggc ggacgcattg agtttgtaga tgcatcacgt    2220
gtggttattc gtgtcaacga agatgaaatg atcgcgggtg aagcaggtgt agatatctac    2280
aacttgatca aatacacgcg ttcaaaccaa aacacatgta ttaaccaaaa agtgcttgtg    2340
agcatgggcg ataaagtcgg ccgtggtgac gttcttgctg atggtccatc aactgatggt    2400
ggtgaattag cattgggtca gaacatgcgt gtcgcgttca tgacttggaa cggttataac    2460
tacgaagact cgattttatt atctgaacgt gttcttcaag agatcgtttt aacttcaatt    2520
catattcaag aattatcatg tgttgcgcgt gatacgaagt taggtgcgga agaaatcact    2580
gccgatattc ctaacgtagg tgaagcagcg ttatctaaac ttgatgaatc aggtattgtt    2640
tatatcggtc ctgaagttgc agcgggtgat attcttgttg gtaaagtgac gcctaaaggt    2700
gaaacacaat taaccctga agaaaaatta cttcgtgcaa tctttggtga gaaagcggca    2760
gacgttaaag attcatcttt acgtgtttct tcaagcgtta aggtacagt catcgacgtt    2820 caagtgtttta cacgtgacgg tatcgagaaa gatgaacgtg ctcaagcgat tgagaaagcg    2880
cagcttgatg cttaccgtaa agacttgaaa gaagaattca aaatcttcga agaagcagct    2940
cgtgaacgta ttatccgttt gttaaaaggc caagagtcga atggcggcgg tactactaag    3000
cgcggtgata agctatctga agatgtattg tctggtttag agcttgttga tcttttagaa    3060
gttcaaccaa cagatgaagg catcgctgaa cgcttaactc aaattcaagt gttcttgaaa    3120
gagaagagct acgagattga tgagaaattt gctgagaaaa aacgcaaact ttctacaggt    3180
gatgagctta caacaggtgt cttgaaagtt gttaaagttt atttagctgt aaaacgtcgt    3240
atccagcctg gtgataagat ggcgggtcgt cacggtaaca aaggtgttgt atcaaacatc    3300
ttgcctgttg aagacatgcc gcatgacatc catggtgttc cagttgatgt cgtacttaac    3360
```

```
ccattgggtg taccatcacg tatgaacgtg ggtcagattc ttgaaactca cttaggtatg   3420
gctgcaaaag gtcttggcga taagatcgac aagatgatga aagagcaacg taccgttctt   3480
gagcttcgtg atttcttaga caagatttat aacaaagttg gtggcgagca agaagatctt   3540
gatagcttaa ctgatgaaga aatcttggtg ttatcaggta acttgcgtaa aggtgttcct   3600
ttagctacgc cagtatttga tggtgcagaa gaaagtcaga tcaaagagtt acttgagctt   3660
ggtggtatct cacgtacagg tcaaacagta ttgtatgacg gacgtacagg tgagcgtttt   3720
gaccgcccag taactgttgg ttatatgtac atgctcaagt tgaaccattt ggttgatgac   3780
aagatgcatg cacgttctac tggttcttat tcacttgtaa ctcaacaacc gcttggtggt   3840
aaagcacaat tcggtggtca gcgtttcggt gagatggaag tctgggcact agaagcttat   3900
ggtgctgctt atacacttca agaaatgctt actgtgaagt cggatgacgt tgaaggtcgt   3960
actcgcatct ataagaacat cgtagatggt aaccattata tggatccggg tatgcctgaa   4020
tcgtttaacg tattgaccaa agagatccgt tctttaggta tcaacattga actgaaaaat   4080
ggtgactaa                                                           4089

<210> SEQ ID NO 20
<211> LENGTH: 4089
<212> TYPE: DNA
<213> ORGANISM: Acinetobacter radioresistens

<400> SEQUENCE: 20
atggcatact catataccga aaagaaacgg atccgtaaga attttggtaa attgccccaa     60
gtcatggaag caccgtacct gttgtctatt caagtcgact cgtaccgtac tttcctgcaa    120
gacggcaaaa ctccaaaaaa ccgcgaagat atcggtctcc aagccgcatt tcgttcagtt    180
tttcctatag aaagttattc tggcaatgct gctttagaat tgttgagta tagccttggt    240 aaacccgagt tgatgtccg cgaatgtatt cttcgtggct caacctatgc ggcaccaatg    300
cgcgtaaaga ttcgtctgat cattaaagat cgcgaaacga atcaatcaa agatgttcgt    360 gaacaagaag tctatatggg tgaaattcca ctcatgactg aaaatggtac ctttgtcatc    420
aatggtaccg agcgtgtaat cgtatctcag ttacatcgtt caccgggtgt attctttgac    480
catgacaaag gtaaaaccca ctcaagcggt aaagtgttgt attcagcacg tattattcct    540
taccgtggtt catggcttga ttttgagttt gatgccaaag acctggtata tgtacgtatc    600
gaccgtcgtc gtaaattact tgctactgta gttatgcgtg cactgggcta taacaatgaa    660
cagattctgg atctgttcta tgagaaagtc cctgtgtatc tggatatggg cagttatcag    720
attgatctcg tgcctgaacg cctgcgtggt gaaatggcgc agttcgatat tgctgacaat    780
gatggcaaag tgattgttga gcagggtaaa cgtatcaatg cacgtcatgt acgtcaaatg    840
gaagcttctg gcctgactaa actgccagtt cctgatgagt acctgtacga acggattact    900
gctgaagata ttagcctgaa atcaggcgat gtaattgctg cgaataccct tgctgagcca    960
gaaatcatgg tgaagattgc tgaaggtggc gtgaagcagt ttaatatctt gtataccaat   1020
gatattgacc gtggttcatt cgtggcagat accttacgtg cagatacaac aagtggccgt   1080
gaagaagccc tggttgagat ctataaggta atgcgtccag gcgagccgcc aacaaaagaa   1140
gctgctgaga acctgttcaa taacctgttc ttctcttctg agcgttatga cctgtcacct   1200
gttggtcgta tgaagttcaa ccgtcgttta ggtcgcccat acgaagtagg aactgaccag   1260
aagtcacgtg aagttgaagg tattctctcg aatgaagata tcatcgatgt attacgtact   1320
ttagttgaaa ttcgtaacgg taagggtgag gtcgatgata ttgaccattt gggtaaccgt   1380
```

```
cgtgtccgtt ctgtaggtga aatgactgag aaccagttcc gtgtaggtct ggtccgtgtt    1440
gaacgtgcag ttaaagagcg tctgtcacag gcagaaactg acaacctgtc tccacaggac    1500
ctgatcaatg ctaaaccggt agctgctgca atcaaagaat tctttggttc aagccagttg    1560
tcccagttta tggatcagaa taacccgcta tctgaaatta cacataagcg tcgtgtatcg    1620
gcacttggac caggcggttt gacccgtgag cgcgcaggct ttgaggtgcg tgacgtacac    1680
cagacccact atggtcgtgt gtgtccgatt gaaaccccty aaggaccaaa catcggtctg    1740
attaactcgc tgtctgtata cgcaaaaacc aatgaatttg gtttcttgga aacgccttac    1800
cgtaaagtgg tagatggccg tgtaacagat gaagttgaat atctgtctgc aattgaagaa    1860
gtaggaactg tgattgctca ggccgactct gcactcgata agatggttta tttaaccgaa    1920
gagctggttt ctgtacgtta ccagggcgaa tttgtgcgta tggctccaga gcgtattacg    1980
catatggatg tttctgcaca gcaggtagtt tctgtagcgg catctctgat tccattcctt    2040
gagcacgatg atgccaaccg tgcattgatg ggttcaaaca tgcagcgtca ggctgtaccg    2100
acactgattg cggacaaacc gctagtaggg acaggtatgg aagcgaatgt tgcacgtgac    2160
tcaggtgtat gtgtaattgc aaaacgtggc ggtaccattg aattcgtaga tgcgtcacgt    2220
gtagttattc gtgttaacga agacgagatg attgcgggtg aagcgggtgt agatatctat    2280
aacctgatca atacacacg ttcaaaccag aatacctgta ttaaccgaaa agttctggtg    2340
aatctgggtg ataaagttgg tcgtggtgat gtactggctg atggcccgtc tacggatggt    2400
ggtgaattag cacttggtca gaacatgcgt gttgcattca tgacttggaa tggttacaac    2460
tacgaagact caatcctgct ttctgaacgt gtacttcagg aagaccgttt aacttctatt    2520
cacattcagg aattgtcatg tgtagcacgt gataccaaac tgggtgcaga agaaattact    2580
gcggatattc caaacgtagg tgaagctgcg ctttctaaac tggatgaatc cggtattgtt    2640
tatatcggtg cagaagtaac ggctggcgat attctggttg gtaaagtgac acctaaaggt    2700
gaaactcagc tcacacctga agaaaaactg cttcgcgcta tcttcggtga gaaagcagct    2760
gatgtaaaag attcatcttt acgtgttcca tcaggtacca aggtacggt aattgacgtc    2820 caggtgttta cacgtgatgg tctggaaaaa gatgaccgtg cactggcgat tgagaaagca    2880
caacttgacg cttatcgtaa agatttgaaa gaagaatata aaatctttga agaagcggct    2940
cgtgaacgta ttgtacgttt gctgaaagat caggtgtcta acggcggtgg aaatactaaa    3000
cgtggtgaga actgtctga agaattgcta tctggccttg aactgattga tctgctcgaa    3060
atccagccaa gcgatgaagc gattgctgaa cgtttaaccc agatccaggt gttcttgaaa    3120
gagaaaagca ccgagattga cgagaagttt gccgagaaga aacgcaagct ttctacgggt    3180
gatgagctga ctcatggcgt attgaaagtt gtgaaggttt atctagcagt taaacgtcgt    3240
atccagccgg gtgataaaat ggcgggtcgt cacgggaaca agggtgtggt atcacaaatc    3300
ctgcctgtag aagacatgcc acatgatgcc aatggtgttc cggttgatgt ggtattaaac    3360
ccgctaggtg taccatcacg tatgaacgtg ggacagattc tggaaacaca tttgggtctt    3420
gctgcaaaag gttaggtga gcagatcgac aagatgctta acagcagcg tgctattgtt    3480 gaactgcgtg attttcttga taagatttac aataaagtcg gtggtgagca agaacagctt    3540
gatacactga ctgatgatga atcttgaaa cttgcaggaa acctcagcaa gggtgtgcca    3600
ctggcaactc cagtatttga tggtgccgaa gaaggccaga tcaaagagtt acttgaactt    3660
gcagaactgc cacgttctgg ccagcagatc ctgtttgatg gacgtacagg cgaacagttt    3720
gaccgtccgg taactgtagg ttacatgtat atgcttaaac tcaaccactt ggtggatgac    3780
```

| | |
|---|---|
| aagatgcatg cgcgttctac cggttcttac tctcttgtaa cgcaacagcc gcttggtggt | 3840 |
| aaagcacaat tcggtggtca gcgtttcggt gagatggaag tctgggcact tgaagcttac | 3900 |
| ggtgcagcat atactcttca agagatgctg accgtgaagt cggatgacgt tgaaggccgt | 3960 |
| acccgcatct ataagaatat tgtagatgga aaccattata tggatccggg catgcctgaa | 4020 |
| tcgttcaacg tattgaccaa agagatccgt tctttaggta tcaacattga actgaaaaat | 4080 |
| ggtgactaa | 4089 |

<210> SEQ ID NO 21
<211> LENGTH: 4089
<212> TYPE: DNA
<213> ORGANISM: Acinetobacter sp.

<400> SEQUENCE: 21

| | |
|---|---|
| atggcatact catataccga aaagaaacgg atccgtaaga attttggtaa attgccccac | 60 |
| gtaatggaag caccgtactt actttcgatt caggtcgatt cgtaccgtac attcttacaa | 120 |
| ggcggtaaaa ctccaaaaaa tcgcgaagat atcggtctcc aagccgcatt tcgttcagtt | 180 |
| tttcctattg aaagttattc tggcaatgct gctttagaat tgttgagta tagtcttggt | 240 |
| aagcctgagt ttgacgtacg tgaatgtatt ttacgtggtt caacttatgc agcaccaatg | 300 |
| cgcgtaaaaa ttcgtttgat cattaaagat cgtgaaacga atcaattaa agacgttcgt | 360 |
| gaacaagaag tttacatggg tgaaatgcca ctcatgaccg ataacggtac tttcgttatc | 420 |
| aacggtacag agcgtgtaat cgtatctcaa ttacaccgtt caccaggcgt attctttgac | 480 |
| catgataagg gtaaaaccca ctcaagcggt aaagtgttgt attcagcacg tattattcct | 540 |
| taccgtggtt catggttaga ctttgaattt gatgctaaag atttagtctt tgtacgtatt | 600 |
| gaccgtcgtc gtaaattatt ggcaacggtg gtttttacgtg ccttaaatta cagcaatgaa | 660 |
| cagatcttga atttgttcta cgaaaaagtg cctgtatatc ttgatatggg tagctatcag | 720 |
| attgaccttg ttccagatcg cttacgtggt gaaatggcgc aatttgatat cttggacaat | 780 |
| gatggtaaag cgatcgttga acaaggtaag cgtattaatg cacgtcacgt acgtcaaatg | 840 |
| gaagctgcta acttagcgaa gctttctgta cctgatgaat atttatatga gcgtattaca | 900 |
| gctgaagaca ttccattgaa aaatggcgat gtgattgctg cgaatacagt gcttagccat | 960 |
| gaaatcttgg tgaaattggc tgaaggtggt gttaaacaat ttaacatcct gttcaccaat | 1020 |
| gacatcgacc gtggttcttt cgttgcagat acattacgtg cagatacgac aacaggccgt | 1080 |
| gaagaagcgc ttgttgaaat ctataaagta atgcgtccag cgagccacc aacaaaagaa | 1140 |
| gctgctgaaa acttattcaa caacttgttc ttctcttctg agcgttatga cctttctcca | 1200 |
| gtgggtcgta tgaagttcaa ccgtcgtttg ggtcgtcctt acgaagtggg tacagatcag | 1260 |
| aagtcgcgtg aagttgaagg tatttttatcg cacgaagata ttattgatgt actgcgtaca | 1320 |
| ttggttgaaa tccgtaacgg taaaggtgaa gtcgatgata tcgatcactt gggtaaccgt | 1380 |
| cgtgtacgtt ctgttggtga aatgacagaa aaccaattcc gtgttggttt agtccgtgtt | 1440 |
| gaacgtgctg ttaaagagcg tttaagccaa gcagaaacag taacttgtc tccgcaagat | 1500 |
| ttgatcaatg caaaaccagt tgctgctgca atcaaagaat tctttggttc aagccagttg | 1560 |
| tctcagttca tggatcaaaa caacccattg tctgagatta cacataaacg tcgtgtatct | 1620 |
| gcgcttggtc ctggtggttt gacacgtgaa cgtgcgggct ttgaagtacg tgacgtacat | 1680 |
| caaactcact atggtcgtgt ttgtccaatt gaaacgcctg aaggtccaaa cattggtttg | 1740 |
| atcaactcgc tttctgttta tgcaaaagca acgatttcg gttcttgga aacaccttac | 1800 |

```
cgtaaagttg ttgatggccg tgtaactgat gatgttgaat atttatctgc aattgaagaa    1860
gtagggactg tcattgcaca ggccgattct gctgttgata agatggtca cctgactgaa     1920
gaaatggttt ctgtacgtca tcaaggtgaa ttcgtacgta tgtcgcctga gcgcgtaaca    1980
catatggacg tttctgcaca gcaggttgtt tctgttgcag catcattgat tccattcctt    2040
gaacacgatg atgcgaaccg tgcattgatg ggttcgaaca tgcaacgtca ggctgttcct    2100
accttacgtg ctgacaagcc gcttgttggt acgggtatgg aagcaaacgt agcacgtgac    2160
tctggcgtgt gtgtgattgc tgaccgtggt ggtgcgattg aatatgtaga tgcatctcgt    2220
atcgtgattc gtgtaaacga agatgaaatg atcgcgggtg aagcgggtgt agatatctac    2280
aacctgatca aatacacacg ttcaaaccaa aatacatgta tcaaccaaaa cgttatcgta    2340
aacttggggtg acaaagttgc tcgtggcgat atcttggctg atggtccatc gactgatatg    2400
ggtgaacttg cgcttggtca aaacatgcgc gtcgcgttca tgacatggaa cggttataac    2460
tacgaagact cgatcttact ttctgagcgt gtacttcaag aagaccgttt aacctcgatt    2520
cacattcaag aattgtcatg tgtagcgcgt gatactaagt taggtgcaga agaaattact    2580
gccgatattc ctaacgttgg tgaggctgca ctgtctaagt tggatgagtc tggtattgtt    2640
tatatcggtg ctgaagtaac tgctggtgac atccttgttg gtaaggtaac gcctaaaggt    2700
gaaactcagt taacacctga agaaaaacta cttcgcgcaa tctttggtga aaaagctgct    2760
gatgttaaag actcttcttt acgtgttcca tctggcacta aaggtactgt gattgacgtt    2820
caagtcttca cacgtgatgg tttgaaaaaa gatgaacgtg ctcaagcaat tgagaaagct    2880
cagcttgatg cataccgtaa agacttgaaa gaagagtaca aaatcttcga agaagcagca    2940
cgtgaacgta ttgttcgttt gttgaaaggt caagagtcta acggtggcgg ttcaactaaa    3000
cgcggtgata aacttgctga agacgtattg tctggtttag agcttgttga tttacttgaa    3060
atccaaccga ctgatgaggc aattgcagag cgtctaactc aaattcaagt gttcttgaaa    3120
gagaagagct atgaaattga tgagaagttt gcagagaaga agcgtaaact ttctacaggt    3180
gatgaattaa ccactggcgt attgaaagtt gttaaggttt accttgcggt taaacgtcgt    3240
atccagcctg gtgataaaat ggcgggtcgt cacggtaaca aaggtgttgt gtcaaacatc    3300
ttgcctgttg aagacatgcc acacgatgcg aatggtgtac cagtcgatat cgtattgaac    3360
ccattgggtg taccgtcacg tatgaacgtg ggtcagattc ttgagactca cttaggtatg    3420
gcggccaaag gtcttggcga taaacttgaa aaaatgttga agaacaacg tacagtgtta    3480
gaactacgtg acttcttaga caagatttat aacaaggtcg gtggtgagca agaagagctt    3540
gatagcttaa ctgatgccga aatcttggcg cttttcaggta acttacgtgc tggtgttcca    3600
ttagcaacac ctgtatttga tggtgctgaa gaaagccaga tcaaagactt acttgaatta    3660
gcagacatct cacgtacagg tcaaacggta ttgtttgacg gacgtacagg tgagcagttt    3720
gatcgtcctg taactgtagg ttacatgtac atgctcaaat tgaaccactt ggttgatgac    3780
aagatgcatg cgcgttcaac aggttcttac tcacttgtta cacaacagcc gcttggtggt    3840
aaagcacaat tcggtggtca gcgtttcggt gagatggaag tatgggcact tgaagcatac    3900
ggtgcagcat atacactcca agaaatgctc actgtgaagt cggatgacgt cgaaggtcgt    3960
acacgcatct ataagaatat tgtagatggt aaccattata tggatccggg tatgcctgaa    4020
tcgttcaacg tattgaccaa agagatccgt tctttaggta tcaacattga actgaaaaat    4080
ggtgactaa                                                           4089
```

<210> SEQ ID NO 22

<211> LENGTH: 4089
<212> TYPE: DNA
<213> ORGANISM: Acinetobacter sp.

<400> SEQUENCE: 22

| | | | | | |
|---|---|---|---|---|---|
| atggcatact | catataccga | aaagaaacgg | atccgtaaga | attttggtaa | attgccccac | 60 |
| gtaatggaag | caccgtactt | actttcgatt | caggtcgatt | cgtaccgtac | attcttacaa | 120 |
| ggcggtaaaa | caccaaaaaa | tcgcgaagat | atcggtctcc | aagccgcatt | tcgttcagtt | 180 |
| tttcctattg | aaagttattc | tggcaatgct | gctttagaat | tgttgagta | tagccttggt | 240 |
| aagcctgagt | ttgacgtacg | tgaatgtatt | ttacgtggtt | caacttatgc | ggcaccaatg | 300 |
| cgcgtaaaaa | ttcgtttgat | catcaaagat | cgtgaaacga | atcaattaa | agacgttcgt | 360 |
| gaacaagaag | tttacatggg | tgaaatgcca | ctcatgaccg | ataacggtac | attcgttatt | 420 |
| aacggtactg | agcgtgtaat | cgtatctcaa | ttacaccgtt | caccaggcgt | attctttgac | 480 |
| catgacaagg | taaaaaccca | ctcaagcggt | aaagtgttgt | attcagcacg | tattattcct | 540 |
| taccgtggtt | catggttaga | cttttgaattt | gatgccaaag | atttagtctt | tgtacgtatt | 600 |
| gaccgtcgtc | gtaagttgct | tgcaacggtg | attttacgtg | ccttgaatta | tagcaatgaa | 660 |
| caaatcttga | atttgttcta | tgaaaaagta | cctgtatatc | ttgatatggg | tagctatcaa | 720 |
| attgacctgg | ttccagatcg | cttacgtggc | gagatggcgc | aatttgatat | cttggataac | 780 |
| gatggcaaaa | caatcgttga | acaaggtaaa | cgtattaatg | cacgtcacgt | acgtcaaatg | 840 |
| gaagcggcta | acttagccaa | gctttctgta | cctgatgagt | acttgtatga | gcgtattacg | 900 |
| gctgaagaca | ttaccttgaa | aagtggtgat | gtgattcctg | ccaataccgt | acttagccat | 960 |
| gaaattatgg | tgaagttggc | tgaagtggt | gtgaagcagt | ttaacatcct | gttcaccaat | 1020 |
| gacatcgatc | gtggttcttt | cgttgcagat | accttgcgcg | cagatacaac | gacaggccgc | 1080 |
| gaagaagcgc | ttgtcgaaat | ctataaagtg | atgcgtccag | tgagccacc | aacgaaagaa | 1140 |
| gctgctgaaa | acttattcaa | taacttgttc | ttctcttctg | agcgttatga | cctgtctcca | 1200 |
| gtcggtcgta | tgaagttcaa | ccgtcgtttg | ggtcgtcctt | acgaagtggg | tactgatcag | 1260 |
| aagtcacgtg | aagttgaagg | tatttttatcg | cacgacgata | tcatcgatgt | attgcgtaca | 1320 |
| ttggttgaga | ttcgtaacgg | taaaggtgaa | gtcgatgata | tcgatcactt | gggtaaccgt | 1380 |
| cgtgtacgtt | ctgtaggcga | aatgacagaa | aaccaattcc | gtgttggttt | agtccgtgtt | 1440 |
| gaacgtgctg | ttaaagaacg | tttaagccaa | gcagaaacag | ataacttgtc | tccacaagat | 1500 |
| ttgatcaatg | caaaaccagt | tgctgctgca | atcaaagagt | tctttggctc | gagccagttg | 1560 |
| tctcagttca | tggaccaaaa | caacccattg | tctgagatta | cacacaaacg | tcgcgtatct | 1620 |
| gcgcttggtc | ctggtggttt | aacacgtgaa | cgcgcgggct | tcgaagtacg | tgacgtacat | 1680 |
| caaactcact | atggtcgtgt | ttgtccaatt | gaaacacctg | aaggtccaaa | cattggtttg | 1740 |
| atcaattcgc | tttctgtcta | tgctaaagcg | aatgacttcg | gtttcttgga | aacaccttac | 1800 |
| cgtaaagttg | ttgatggccg | tgtgactgat | gaagttgaat | acttatctgc | aattgaagaa | 1860 |
| gtaggtactg | tcattgcaca | ggccgattct | gcagttgata | agatggtat | gttgactgaa | 1920 |
| gagatggttt | ctgtacgtca | tcaaggtgac | ttcgttcgta | tgtcgcctga | gcgcgtaacc | 1980 |
| catatggacg | tttctgcgca | acaggtcgta | tctgtcgcag | cgtcattgat | tccattcctt | 2040 |
| gaacacgatg | atgcgaaccg | tgcattgatg | ggttcaaaca | tgcaacgtca | ggctgttcct | 2100 |
| accttacgtg | ctgacaagcc | gcttgttggt | acaggtatgg | aagcaaacgt | agcacgcgac | 2160 |
| tctggtgtgt | gtgtgatcgc | aaaccgtggt | ggtgcgattg | aatatgttga | tgcatctcgt | 2220 |

| | |
|---|---|
| atcgttattc gtgtcaacga agatgaaatg attgcgggtg aagcaggtgt agatatctat | 2280 |
| aacctgatca aatatacacg ttcaaaccag aatacatgta ttaaccagaa tgtcatcgtg | 2340 |
| aacttgggcg acaaagttgc tcgtggtgat atcttggctg acggtccatc gacagatatg | 2400 |
| ggtgaacttg cgctgggtca aaacatgcgc gtcgcgttca tgacctggaa tggttataac | 2460 |
| tatgaagact cgatcttact ttctgagcgt gtacttcaag aagaccgttt aacctcgatt | 2520 |
| cacattcagg aattgtcatg tgtagcacgt gataccaagt taggcgcaga agaaattact | 2580 |
| gccgatattc ctaacgtcgg tgaagctgca ctgtctaaac tggatgagtc tggtattgtt | 2640 |
| tacatcggtg ctgaagtaac tgcgggtgac atccttgttg gtaaggtaac gcctaaaggt | 2700 |
| gaaactcagt tgacacctga agaaaaatta ctgcgcgcaa tctttggtga aaaagcggct | 2760 |
| gacgtaaaag attcatcttt acgtgttccg tctggtacta aggtacggt tatcgacgtt | 2820 |
| caagtcttca cacgtgatgg cttggagaaa gatgaacgtg cacaagcaat tgaaaaagct | 2880 |
| cagcttgatg cataccgtaa agacttgaaa gaagaataca aaatcttcga agaagcagca | 2940 |
| cgtgaacgta ttgttcgttt gttgaaaggt caagaatcta acggtggcgg ttcaaccaaa | 3000 |
| cgcggcgata aactttcaga agatgtattg tctggcttag agcttgttga tttacttgaa | 3060 |
| atccagccaa atgatgaagc aattgctgaa cgtttaactc agattcaagt gttcttgaaa | 3120 |
| gagaagagct acgagattga cgagaagttt gctgagaaga agcgtaaaact ttctacaggt | 3180 |
| gatgaattaa caacgggcgt attgaaagtt gttaaggttt accttgcggt gaaacgtcgt | 3240 |
| atccagcctg gtgataagat ggcgggtcgt cacggtaaca agggtgttgt atcaaacatc | 3300 |
| ttaccggttg aagacatgcc acatgatgcg aatggcgtac cagtcgacat cgtattgaac | 3360 |
| ccactgggtg taccgtcacg tatgaacgtg ggtcagattc ttgagactca cttgggtatg | 3420 |
| gcagcgaaag gtcttggcga taaatcgaa aaaatgttga agaacaacg tacagtgatt | 3480 |
| gaactgcgtg aattcttaga caagatttat aacaaggttg gcggtgagca ggaagagctt | 3540 |
| gatagcttga ctgatgcaga aatcttggcg cttctcaggta acttacgtgc tggtgttcca | 3600 |
| ttggcaacac ctgtatttga tggtgctgaa gaaagccaga tcaaagacct acttgaactt | 3660 |
| gctgatatct cacgtactgg tcaaacggta ttgtttgacg acgtacagg tgaacagttt | 3720 |
| gaccgtcctg taactgtagg ttacatgtac atgctcaaat tgaaccactt ggttgatgac | 3780 |
| aagatgcatg cgcgttcaac gggttcttac tcacttgtga ctcaacagcc gcttggtggt | 3840 |
| aaagcacaat tcggtggtca gcgtttcggt gagatggaag tatgggcact tgaagcatac | 3900 |
| ggtgctgcat atacgctcca agaaatgctt actgtgaagt cggatgacgt cgaaggccgt | 3960 |
| acacgcatct acaagaacat tgtagatggt aaccattata tggatccggg tatgcctgaa | 4020 |
| tcgttcaacg tattgaccaa agagatccgt tcttaggta tcaacattga actgaaaaat | 4080 |
| ggtgactaa | 4089 |

<210> SEQ ID NO 23
<211> LENGTH: 4089
<212> TYPE: DNA
<213> ORGANISM: acinetobacter schindleri

<400> SEQUENCE: 23

| | |
|---|---|
| atggcatact catataccga aaagaaacgg atccgtaaga attttggtaa attgcctagc | 60 |
| gttatggatg ctccgtactt gctttcgatt caagtcgact cgtacagaac attcttacaa | 120 |
| gatggcaaat caccaaaaaa ccgcgaagat atcggtctcc aagccgcatt tcgttcagtt | 180 |
| tttcctattg aaagttattc tggcaatgct gctttagaat ttgttgagta tagtcttggt | 240 |

```
aagcctgagt ttgatgtacg cgaatgtatt cttcgtggct caacttatgc agcaccaatg      300
cgtgtgaaga ttcgtttgat cctgaaagat cgtgaaacga aatcgatcaa agacgtacgt      360
gaacaagaag tctatatggg cgaaatgcca ttgatgacgg ataacggtac tttcgtaatt      420
aacggtaccg agcgtgtaat cgtatctcaa ttacaccgtt caccaggcgt attctttgac      480
cacgataaag gtaaaactca ctcaagtggt aaagtccttt attctgcgcg tatcattcct      540
taccgtggtt catggttaga ctttgaattc gatgccaaag acctagtcta tgtacgtatt      600
gaccgtcgtc gtaaattgct tgcgactgtg gtacttcgtg cattgggtta taacaacgaa      660
caaattctga acatgttcta tgagaaagtg cctgtatatc ttgatatggg tagctatcag      720
attgaccttg ttccagaacg cctgcgtggt gaaatggcac aatttgatat tgctgacaaa      780
gacggcaaga tcattgttga gcaaggtaaa cgtattaacg cacgtcacgt acgtcaaatg      840
gaagcttcag gtcttgaaaa acttgcagtg cctgatgaat acctgtacga acgtatcact      900
gctgaagaca tccagttaaa agatggcgat gtgatcgcgg ccaatactgt attaagccat      960
gaaatcatgg tgaagattgc agaaggcggc gtgaagcaat tcaacttact gttcacaaat     1020
gatatcgacc gtggttcatt catcgcggat acattacgtg ccgatacgac gacaggtcgt     1080
gaagaagcac tagtagaaat ctacaaagta atgcgtccag gtgagccacc aacaaaagaa     1140
gctgctgaaa acctgttcaa caacctgttc ttctcttctg agcgttatga cttgtcgcca     1200
gtcggccgta tgaagttcaa ccgtcgtttg ggtcgtcctt acgaagtggg tacagaccag     1260
aagtcacgtg aagttgaagg tatcctctcg aacgacgata tcactgatgt attgaaaaca     1320
ttagttgaaa ttcgtaacgg taagggtgaa gtcgatgata tcgaccactt gggtaaccgt     1380
cgtgttcgtt cagttggtga atgactgaa aaccaattcc gtgtcggtct ggttcgtgta      1440
gagcgtgcgg ttaaagaacg tctatcacag gctgaaacta taacctgtc tccgcaagat      1500 ttaatcaatg cgaagccagt ggctgctgca atcaaggaat tctttggttc aagccagtta     1560
tctcagttca tggaccaaaa caacccattg tctgaaatca cccacaagcg tcgtgtatca     1620
gcgcttgggc ctggtggttt gacgcgtgaa cgtgctggct tcgaagtacg tgacgtacat     1680
caaactcact acggtcgtgt ttgtccaatt gaaacgcctg aaggtccaaa cattggtttg     1740
atcaactcgc tttctgtata tgcaaaatgt aacaactttg gtttcttaga aacgccttac     1800
cgtaaagttg ttgatggtcg tgtaacggat gaagttgaat acctgtctgc aatcgaagaa     1860
gtaggtactg ttatcgcaca ggccgactct gcaatcgata agatggcaa cctgactgaa      1920 gaattcgtat ctgtacgtca ccaaggtgaa ttcgtacgta ttccaccaga aaagtgacg      1980 catatggatg tatctgctca gcaggtggta tctgtcgctg catcactgat tccgttcctt     2040
gaacacgatg atgcgaaccg tgcattgatg ggttcaaaca tgcaacgtca ggcagttcct     2100
acgttaatcg ctgacaagcc actggttggt accggtatgg aagcgaacgt agcacatgac     2160
tctggtgtat gtgtgatcgc gaaacgtggt ggccgtattg aatatgtaga cgcttctcgt     2220
gtcgtgattc gtgtcaacga agacgaaatg gtggcgggcg aagcaggtgt agatatctac     2280
aacctgatca aatacacacg ttctaaccag aacacttgta tcaaccagaa agttcttgtg     2340
aacatgggcg ataaagtggg tcgcggtgac gttcttgctg atggtccatc gactgatggc     2400
ggtgaactgg cactgggtca aaacatgcgc gtagcattca tgacctggaa cggttacaac     2460
tatgaagact cgatcttgtt atctgagcgt gtacttcagg aagaccgttt aacgtctatc     2520
cacatccagg aactttcatg tgttgcacgt gatactaaac tgggtgctga agaaattact     2580
gccgatatcc cgaacgtggg tgaagctgca ctttctaaac tggatgagtc tggtatcgtt     2640
```

-continued

| | |
|---|---|
| tatatcggtg ctgaagtgac tgctggtgac atcctggtag gtaaagtaac acctaaaggt | 2700 |
| gaaactcagt taacacctga agaaaaactg cttcgcgcaa ttttcggtga aaaagcagct | 2760 |
| gacgtaaagg actcttcttt acgtgttcca tcgggtacta aaggtaccgt gattgacgtt | 2820 |
| caagtgttta cacgtgatgg tcttgaaaaa gacgaacgtg ctcaagcaat tgaaaaagct | 2880 |
| cagcttgatg cttaccgtaa agacttgaaa gaagaataca aaatcttcga gaagcagca | 2940 |
| cgtgaacgta ttattcgtct gttgaaaggt caggaatcta acggtggtgg cacaactaaa | 3000 |
| cgcggtgaca aactgtctga agatgttctg tctggtttag agcttgttga tctgttagac | 3060 |
| atccaaccag tagatgaagc aattgctgag cgtttaactc aaattcaagt gttcttgaaa | 3120 |
| gagaagagcc ttgaaattga tgaaaagttt gctgagaaga acgcaaatt atctacaggc | 3180 |
| gatgaactta caactggcgt actgaaagtt gttaaggttt atctagcggt taaacgtcgt | 3240 |
| atccagcctg gtgataagat ggcgggtcgt cacggtaaca agggtgttgt atctaacatc | 3300 |
| ttgccggtag aagacatgcc acacgatgcc aacggtgtac ctgttgatat cgttcttaac | 3360 |
| ccgctaggtg taccgtcacg tatgaacgtg ggtcagattc ttgagactca cttgggtatg | 3420 |
| gccgccaaag gtcttggcga caaaatcgac aagatgcttc aagagcaacg tacggtgctt | 3480 |
| gagcttcgtg aattcttaga caagatttac aacaaagttg gtggtgagca agaagatctt | 3540 |
| gatagcctga ctgatgatga aatcttggca ttgtctggta acttgcgtaa aggtgttcct | 3600 |
| ttggcaactc cagtattcga cggtgctgaa gaatcgcaaa tcaaagaatt gttagagctt | 3660 |
| ggtggcattt cacgtactgg tcaaacagta ttgtatgatg gccgtactgg tgaacgtttc | 3720 |
| gaccgtccgg taactgtagg ttacatgtac atgctgaaac tgaaccactt ggttgacgac | 3780 |
| aagatgcatg cgcgttctac tggttcttac tctctagtaa cgcaacagcc gcttggtggt | 3840 |
| aaagcacaat tcggtggtca gcgtttcggt gagatggaag tatgggcact ggaagcatac | 3900 |
| ggtgcagcat atacactcca ggaaatgctt actgtgaaat cggatgacgt tgaaggtcgt | 3960 |
| acccgtatct ataagaatat tgtagatggt aaccattaca tggacccagg tatgcctgaa | 4020 |
| tcgttcaacg tattgaccaa agagatccgt tctttaggta tcaacattga actgaaaaat | 4080 |
| ggtgactaa | 4089 |

<210> SEQ ID NO 24
<211> LENGTH: 4089
<212> TYPE: DNA
<213> ORGANISM: acinetobacter ursingii

<400> SEQUENCE: 24

| | |
|---|---|
| atggcatact catataccga aaagaaacgg atccgtaaga ttttggtaa attgcctagc | 60 |
| gtcatggacg ctccgtactt gctttcgatt caggtcgatt cgtacagaac gttttttacaa | 120 |
| gatggcaaaa caccgaaaaa ccgcgaagat atcggtctcc aagccgcatt tcgttcagtt | 180 |
| tttcctatag aaagttattc tggcaatgct gctttagaat tgttgagta tagtcttggt | 240 |
| aaaccagagt ttgatgtacg cgagtgtatt cttcgcggat caacttatgc ggcaccaatg | 300 |
| cgcgtaaaaa ttcgtttgat cattaaagat cgtgaaacga atcaattaa agatgttcgc | 360 |
| gaacaagaag tgtatatggg tgaaatgcca ctcatgactg agaacggaac atttgtgatt | 420 |
| aacggtactg agcgtgtcat cgtatctcag ttacaccgtt caccaggtgt gttcttcgat | 480 |
| catgataaag gtaaaactca ttcaagcggt aaagtgctgt attcagcacg tattattcct | 540 |
| taccgtggtt catggttaga cttgaattt gatgccaaag attggttta cgtgcgtatt | 600 |
| gaccgtcgtc gtaagctatt ggctacggtt attctacgtg cactgggtta taacaatgag | 660 |

-continued

```
caaatccttg atttgttcta tgaaaaagta cctgtgtatc tggacatggg cagctaccaa    720
attgatcttg tgcctgaacg tttacgcggt gaaatggcgc agtttgatat tactgataat    780
gacggtaaag tcattgtaga acaaggcaaa cgtattaatg cgcgtcatgt tcgtcaaatg    840
gaagcgtctg gtctaagcaa gctttcagtg cctgatgagt atctgtatga gcgtatcact    900
gctgaagata ttacactaaa agatggtgat atcattcctg ccaacacttt gctcagccat    960
gaagtcatgg tcaagctagc tgaaggcggc gtaaagcagt ttaatatcct gtataccaac   1020
gatatcgatc atggtccgtt tattgcggat actttacgtg ctgataccac atcaggtcgt   1080
gaagaagcac tggttgaaat ctacaaggta atgcgtccag gtgagccacc aacgaaagaa   1140
gcggctgaaa acttgtttaa taacttgttc ttctcttctg aacgttatga tttgtcacct   1200
gttggtcgta tgaagtttaa ccgtcgtttg ggtcgtcctt acgaagttgg tacagatcaa   1260
aaatcacgtg aagttgaagg tatcctctct aatgaggata tcactgatgt attacgtaca   1320
ttggttgaga ttcgtaacgg taaggtgaa gtcgacgata tcgatcactt gggtaaccgt    1380
cgtgtccgtt cagttggtga atgacagag aaccagttcc gtgtgggtct ggtgcgtgtt    1440
gaacgtgctg ttaaagagcg tttaagccaa gctgaaaccg ataacttgtc tccacaagac   1500
ttgatcaatg cgaaacctgt tgctgccgcg atcaaagaat tctttggttc aagccaattg   1560
tctcagttca tggatcaaaa caacccattg tctgaaatta cacacaaacg tcgtgtatca   1620
gcgcttgggc caggtggttt gacacgtgaa cgtgcaggct ttgaggtacg tgacgtacat   1680
caaactcact atggtcgtgt gtgtccgatt gaaacgcctg aaggtccaaa cattggtttg   1740
atcaactcgc tatctgttta tgcaaaagcc aacgatttcg gtttcttgga aacgccttat   1800
cgtaaggtag tcgatggtcg tgtaacggac gatgttgaat atctttctgc gattgaagaa   1860
gtggggactg tgattgcaca ggccgactct ggtgttgatg cagagggtaa cctcgttgaa   1920
gaaatggttt cagtccgtca tcagggcgaa tttgtacgta tgcctcctga aaaagtgacg   1980
catatggatg tttctgcgca gcaagttgtt tctgtagcag catcattgat tccattccta   2040
gaacacgatg atgcgaaccg tgccttaatg ggttcgaaca tgcaacgtca ggcagtgcca   2100
accttacttg cggataaacc gcttgtgggt acgggtatgg aagcgaccgt tgcacgtgac   2160
tcaggcgtat gtgtaattgc aaaacgtggt ggtgtgattg agtttgttga tgcatcacgt   2220
gtggtcattc gtgttcatga aaatgaaatg atcgcgggtg aagcaggtgt tgatatttat   2280
aacctgatca aatacacccg ttctaaccaa aatacttgta ttaaccagaa agttcttgtg   2340
aatctgggcg ataaagttgg tcgtggtgat gtattgctg atggtccttc taccgatggt   2400
ggtgagttgg cattgggtca aaacatgcgc gtcgcgttca tgacgtggaa tggttataac   2460
tacgaagact caatccttgt tatctgagcga gttttgcagg aagatcgttt aacttcaatt   2520
cacattcagg aattatcatg tgttgcacgt gatactaaat tgggtgcaga agaaattact   2580
gccgatattc cgaatgtagg tgaagctgct ctatccaagc tagatgaatc tggtattgtt   2640
tatatcggtg cggaagtgac tgcgggtgat attctggtag gtaaagttac gcctaaaggt   2700
gaaactcaac ttacgccaga agaaaaattg cttcgtgcga tcttcggtga aaagcggct    2760 gatgtgaaag attcatcttt acgtgttccg tctggtacga aaggtactgt catcgatgta   2820
caagtcttca cacgtgatgg tcttgagaaa gatgatcgtg cacttgcgat tgaaaaagcg   2880
caattggatt cgtaccgtaa agatttgaaa gaagaataca aatctttga agaagcagca   2940 cgtgaacgta ttgtgcgctt attaaaaggt caggattcta acggtggtgg cacgactaaa   3000
cgtggtgaca aactgactga agatttattg tctggtcttg agctggtcga tttacttgaa   3060
```

-continued

```
attcaaccaa gtgatgaagg catcgctgag cgtttaagtc aaattcaagt attcttgaaa    3120
gagaagagtg ctgaaattga tgagaaattt gctgagaaaa aacgcaaatt agcgacgggt    3180
gatgagttaa cgacgggtgt cttgaaagtc gttaaagtct accttgcagt taaacgtcgt    3240
atccagccag gtgataaaat ggcgggtcgt cacgggaaca aaggtgttgt ttctaacatc    3300
ttgcctgtag aagacatgcc acatgatgcc aatggtgtac ctgtcgatat cgtcttgaac    3360
ccattaggtg taccatcgcg tatgaacgtg ggtcagattc tggagacaca tctaggattg    3420
gcagccaaag gtctgggtga acaaatcgat aagatgttgc aacaacagcg taccattgcc    3480
gaacttcgta tcttccttga taagatttac aacaaggtcg gtggtgagca agaagatcta    3540
aacagtctga ctgatgatga agtcttggta ttggctggca acttgcgtaa aggtgtacca    3600
ctagcaactc ctgtatttga tggtgctgaa gaaagtcaaa ttaaagagtt acttgagttg    3660
gctgaattgc cacgtactgg tcaacagatt ttgtttgatg gacgtacagg tgaacagttt    3720
gaccgtcctg taaccgtagg ttatatgtac atgttgaaac tgaaccactt ggtggatgac    3780
aagatgcatg cgcgttcaac aggttcatat tctctggtaa cgcaacaacc attgggtggt    3840
aaagctcaat tcggtggtca gcgtttcggt gagatggaag tctgggcact ggaagcttat    3900
ggcgcagcat ataccttca ggaaatgctc actgtgaagt cggatgacgt tgaaggtcgt    3960
acacgcatct ataagaacat tgtagatggt aaccattata tggatccggg tatgcctgaa    4020
tcattcaacg tattgaccaa agagatccgt tctttaggta tcaacattga actgaaaaat    4080
ggtgactaa                                                            4089
```

<210> SEQ ID NO 25
<211> LENGTH: 4089
<212> TYPE: DNA
<213> ORGANISM: acinetobacter baylyi

<400> SEQUENCE: 25

```
atggcatact catataccga aaagaaacgg atccgtaaga attttggtaa attgccccaa      60
gtcatgcatg ctccgtacct gctctcgatt caagtcgact cgtacagaac attcttgcaa     120
gacggcaaaa caccaaaaaa tcgcgaagat atcggtctcc aagctgcatt tcgttcagtt     180
tttcctattg aaagttattc gggcaatgct gctttagaat tcgttgagta tagtcttggt     240
aaaccagagt ttgatgttcg cgaatgtatt cttcgtggct caacctttgc ggcaccaatg     300
cgcgttaaaa ttcgtttgat catcaaagat cgtgaaacga atctattaa agacgtacgt      360 gaacaagaag tgtacatggg tgaaatgcca ctcatgactg agaatggtac ctttgtgatc     420
aatggtactg agcgtgtaat cgtatctcaa ttacaccgtt caccaggcgt attctttgac     480
catgataaag gtaaacgca ttcaagcggt aaagtgcttt attcagcacg tatcattcct      540
taccgtggtt catggttaga ttttgagttt gatgctaaag atttagtctt tgtacgtatt     600
gaccgtcgtc gtaaattgct tgcgactgtt gtgttacgtg cattgagcta tagcaatgaa     660
caaattctga atatgttcta cgaaaaagta cctgtatatc ttgatatggg tagctatcag     720
attgaccttg tgcctgaacg tcttcgtggt gaaatggctc aatttgatat cgtggacaat     780
gatggtaaag ccattgttga acaaggtaaa cgtattaatg ctcgccatgt acgtcaaatg     840
gaagctgctg gttaactaa acttccagtt ccagatgaat atttgtatga gcgtattact     900
gctgaagata tcgtacttaa agacggtgaa gtaattactg ctaacactgt attaagtcat     960
gagattttgg tcagaattgc tgaaggtggt attaaacaat ttaatatcct gttcaccaat    1020
gacatcgatc gtggttcttt tgttgctgac accttacgtg cagatacaac atctggtcgt    1080
```

```
gaagaagcgc ttgtagaaat ctacaaagtg atgcgtccag gtgagccacc aacgaaagaa   1140
gcggctgaaa acttattcaa taacttattc ttctctacag agcgctatga tttatcgcct   1200
gtgggtcgta tgaagtttaa ccgtcgtttg ggtcgccctt acgaagtagg tacagatcag   1260
aagtctcgtg aagtagaagg tattctttct aacgatgaca tcatcgatgt actgaaaaca   1320
ctggtagaaa ttcgtaacgg taaaggtgaa gtcgatgata tcgatcactt gggtaaccgt   1380
cgcgtacgtt ctgttggtga aatgacagaa aaccaattcc gtgttggttt agttcgtgtt   1440
gaacgtgctg ttaaagagcg tttaaaccaa gctgaaacag ataacttgtc tccacaagat   1500
ttgatcaatg cgaaaccagt tgctgctgca atcaaagaat ctttggttc aagccaattg    1560 tcacagttta tggatcaaaa caacccattg tcagaaatta cacacaaacg tcgtgtatca   1620
gcattgggac caggtggttt gacacgtgaa cgtgcaggct ttgaagtgcg tgacgtacat   1680
caaactcact atggtcgtgt atgtccaatt gaaactcctg aaggaccaaa cattggtttg   1740
atcaactcgc tttctgttta tgcaaaagcg aacaacttcg gtttcttgga acaccatac    1800 cgtcgcgttg ttgatggtcg tgtaacagat gatgttgaat atttatctgc aattgaagaa   1860
gtaggtactt ttattgcaca ggccgattct gcattggata agatggaca tttaacagaa    1920 gacttcgttt cagtacgtca ccaaggtgac ttcgttcgta tgccacctga aaaagtgacg   1980
catatggatg tatctgctca acaggttgta tctgtcgctg catcacttat tccattcctt   2040
gaacacgatg atgccaaccg tgcattgatg ggttcaaaca tgcaacgtca ggctgttcct   2100
acattgcttg ctgataaacc acttgtgggt accggcatgg aagcaaacgt agcgcacgac   2160
tctggtgtat gtgtgatcgc gaaacgtggc ggacgcattg agtttgtaga tgcatcacgt   2220
gtggttattc gtgtcaacga agatgaaatg atcgcgggtg aagcaggtgt agatatctac   2280
aacttgatca aatacacgcg ttcaaaccaa aacacatgta ttaaccaaaa agtgcttgtg   2340
agcatgggcg ataaagtcgg ccgtggtgac gttcttgctg atggtccatc aactgatggt   2400
ggtgaattag cattgggtca gaacatgcgt gtcgcgttca tgacttggaa cggttataac   2460
tacgaagact cgattttatt atctgaacgt gttcttcaag aagatcgttt aacgtcaatt   2520
catattcaag aattatcatg tgttcacgc gatacgaagt taggtgcgga agaaatcact    2580
gccgatattc ctaacgtagg tgaagcagcg ttatctaaac ttgatgaatc aggtattgtt   2640
tatatcggtg ctgaagttgc agcgggtgat attcttgttg gtaaagtgac acctaaaggt   2700
gaaacacaat taacccctga agaaaaatta cttcgtgcaa tctttggtga gaaagcagca   2760
gacgttaaag attcatcttt acgtgtttct tcaagcgtta aaggtacagt catcgacgtt   2820
caagtgttta cacgtgacgg tatcgagaaa gatgaacgtg ctcaagcgat tgagaaagcg   2880
caacttgatg cttatcgtaa agacttgaaa gaagaattca aaatcttcga agaagctgct   2940
cgtgaacgta ttatccgttt gttaaaaggc caagagtcaa atggcggcgg tacgaccaag   3000
cgcggtgata agctatctga agatgtattg tctggtttag agcttgttga tcttttagaa   3060
gttcaaccaa cagacgaagg catcgctgaa cgcttaactc aaaattcaagt gttcttgaaa   3120 gagaagagct acgagattga tgagaaattt gctgagaaaa aacgcaaact ttctacaggt   3180
gatgagctta caacaggtgt attgaaagtt gttaaagttt acttagctgt aaaacgtcgt   3240
atccagcctg gtgataaaat ggcgggtcgt cacggtaaca aaggtgttgt atcaaacatc   3300
ttgcctgttg aagacatgcc gcatgatatc catggtgttc cagttgatgt cgtacttaac   3360
ccattgggtg taccatcacg tatgaacgtg ggtcagattc ttgaaactca cttaggtatg   3420
gctgcaaaag gtcttggcga taagatcgac aagatgatga aagagcaacg taccgttcct   3480
```

-continued

| | |
|---|---|
| gagcttcgtg atttcttaga caagatttat aacaaagttg gtggcgagca agaagatctt | 3540 |
| gatagcttaa ctgatgaaga aatcttggtg ttatcaggta acttgcgtaa aggtgttcct | 3600 |
| ttagctacgc cagtatttga tggtgcagaa gaaagtcaga tcaaagagtt acttgagctt | 3660 |
| ggtggtatct cacgtacagg tcaaacagta ttgtatgacg gacgtacagg tgagcgtttt | 3720 |
| gaccgcccag taactgttgg ttatatgtac atgctcaagt tgaaccattt ggttgatgac | 3780 |
| aagatgcatg cacgttctac tggttcttat tcacttgtaa ctcaacaacc gcttggtggt | 3840 |
| aaagcacaat tcggtggtca gcgtttcggt gagatggaag tctgggcact agaagcttat | 3900 |
| ggtgctgctt atacacttca agaaatgctt actgtgaagt cggatgacgt tgaaggtcgt | 3960 |
| actcgcatct ataagaacat cgtagatggt aaccattata tggatccggg tatgcctgaa | 4020 |
| tcgtttaacg tattgaccaa agagatccgt tctttaggta tcaacattga actgaaaaat | 4080 |
| ggtgactaa | 4089 |

<210> SEQ ID NO 26
<211> LENGTH: 4089
<212> TYPE: DNA
<213> ORGANISM: acinetobacter bouvetii

<400> SEQUENCE: 26

| | |
|---|---|
| atggcatact catataccga aaagaaacgg atccgtaaga attttggtaa attgcccaag | 60 |
| gtaatggatg ttccgtactt gctcgcgatt caagtcgact cgtacagaac tttcttgcaa | 120 |
| gatggcaaaa ctccaaaaaa ccgcgaagat atcggtctcc aagccgcatt tcgttcagtt | 180 |
| tttcctatag aaagttattc tggcaatgct gctttagaat tgttgagta tagtcttggt | 240 |
| aagcctgagt tgatgtgcg tgagtgtatt ctccgcggct caacttatgc agcgccaatg | 300 |
| cgtgtaaaaa ttcgtctgat cttaaaagac cgcgaaacta aatcaatcaa agacgtgcgc | 360 |
| gagcaagaag tctacatggg cgaaatgccg ctcatgactg ataacggtac cttcgttatt | 420 |
| aacggtactg agcgtgtcat cgtatctcaa ttgcaccgtt cgccgggcgt gttctttgac | 480 |
| cacgataagg gcaaaaccca ttcaagcggt aaagtgcttt attcagcgcg gattattcct | 540 |
| taccgcggtt catggttaga ctttgaattt gatgcgaaag acctggtctt tgtacgtatt | 600 |
| gaccgccgcc gcaaattgct tgcgactgtg gtgcttcgtg ccttaggtta caacaactct | 660 |
| caaattcttg atttgttcta tgaaaaagtg cctgtctacc tagacatggg cagctatcag | 720 |
| attgatcttg tgcctgaacg cctgcgcggt gaaatggccc aatttgatat tgctgataaa | 780 |
| gacggcaaag tcattgtaga gcaaggcaaa cgtatcaacg cgcgtcacgt gcgtcagatg | 840 |
| gaagcagcag ggcttgagaa gctttctgtt ccagatgaat acttgtatga acgcattatt | 900 |
| gctgaagacg tggctttacg cggcggcgat gtgattgcgg caaataccgt gcttagccat | 960 |
| gaaattatgg tgaaattggc tgaaggcggt gtgaagcaat tcaacatcct gttcaccaac | 1020 |
| gatattgacc gcggttcatt catcgcggac tctttgcgtg cagatacaac gtccagccgt | 1080 |
| gaagaagcgc ttgtagaaat ctacaaagta atgcgtccag gcgagccgcc gacgaaagaa | 1140 |
| gcggctgaaa acttattcaa caacctgttc ttctcttctg aacgttatga cctgtctcct | 1200 |
| gtaggtcgca tgaagttcaa ccgccgtttg ggccgccctt acgaagtggg tacagatcag | 1260 |
| aagtcacgtg aagttgaagg cattctttca aacgaagaca ttacagatgt tcttcaaaca | 1320 |
| ctgattgaaa tccgcaacgg taaaggtgaa gtcgatgata tcgatcactt gggtaaccgc | 1380 |
| cgtgtgcgtt ctgtcggtga aatgacagaa aaccaattcc gtgtaggcct agttcgtgta | 1440 |
| gagcgtgctg ttaaagaacg tctatctcaa gctgaaactg acaacttgtc tccgcaagat | 1500 |

```
ttaatcaatg cgaagccagt tgctgctgca atcaaagaat tctttggttc aagccaattg    1560
tctcagttca tggaccaaaa caacccattg tctgaaatta cacacaaacg tcgtgtatca    1620
gcgcttgggc ctggtggttt gactcgtgaa cgcgcgggct tcgaagtacg tgacgtacat    1680
caaactcact acggtcgtgt gtgcccaatt gagactcctg aaggtccaaa cattggtttg    1740
atcaactcac tttcagttta cgctaaatgt aacaacttcg gtttcttgga aactccatac    1800
cgtaaagttg ttgatggccg tgtaacggat gacgttgaat acttatctgc aattgaagaa    1860
gtaggtactg ttattgcaca ggccgattct ggcgtcgata agacggtaa cttgcaagaa     1920 gagtttgttt ctgtacgtca tcaaggtgaa ttcgtacgta tgcctcctga aaaagtgacg    1980
catatggacg tgtctgcaca acaggttgta tctgtagcag catcattgat tccgttcctt    2040
gaacacgatg acgccaaccg tgcattgatg ggttcgaaca tgcagcgtca agctgtgcct    2100
acgttaattg ctgacaagcc gcttgtaggt acaggcatgg aagcaaatgt agcgcatgac    2160
tctggtgtgt gtgtaattgc gaaccgcggc ggccgcattg aatttgttga cgcatcacgt    2220
gtcgtgatcc gtgtgaatga agacgaaatg gttgctggtg aagcaggcgt agatatctac    2280
aacctgatca aatacacccg ttcgaaccaa aacacctgta tcaaccagaa agttcttgta    2340
aaactgggtg ataaagttgg ccgcggtgac gtattggctg atggtccatc gacggatggc    2400
ggtgagctgg cgctgggtca aaacatgcgc gtagcgttca tgacttggaa cggttacaac    2460
tacgaagact cgatcttatt atctgagcgc gtacttcaag aagaccgttt gacgtctatt    2520
cacatccaag aattatcatg cgtcgcgcgt gatactaaac tgggtgctga agaaatcact    2580
gcggatattc caaacgtggg tgaagctgca ctgtctaagc ttgatgaatc aggtattgtt    2640
tacatcggtg ctgaagtcac tgctggcgat atcttggttg gtaaagtgac gcctaaaggt    2700
gaaactcagc tgactcctga agaaaaactg cttcgcgcaa tcttcggtga aaaagcggct    2760
gacgtaaaag attcatcttt acgtgtatct tcatctgtga aggtacggt tattgacgtt     2820 caagtgtttta cacgtgatgg tcttgaaaaa gacgaacgtg ctcaagcaat tgaaaaagcg    2880
cagttagatg cataccgcaa agacttgaaa gaagaataca aaatcttcga agaagctgcg    2940
cgtgaacgta ttgtgcgctt gctaaaaggt caagaatcga atggcggcgg cacaactaaa    3000
cgcggtgaca aactttctga agaagtattg tctggtttag agcttgctga tctgcttgaa    3060
attcagccta cagacgaagg cattgctgag cgcttaactc aaattcaagt gttcttgaaa    3120
gagaagagca ctgaaattga tgagaaattt gctgagaaaa aacgcaaaact ttctacaggc    3180 gatgagctta caactggtgt attgaaagtt gttaaagttt acttagctgt aaaacgccgc    3240
atccagccgg gtgataagat ggcgggtcgt cacggtaaca aggtgttgt atctaacatc     3300 ttgcctgtag aagacatgcc gcacgatgcc aacggtgttc ctgtagacgt ggtgcttaac    3360
ccgctgggtg taccgtcacg tatgaacgtg ggtcagattc ttgagactca cttgggcatg    3420
gcagcgaaag gtcttggcga caaatcgac aagatgatga aagagcagcg cactgttctt      3480
gaacttcgtg aattcttaga caagatttac aacaaagttg gcggcgagca agaagatctt    3540
gacagcttaa ctgatgatga atcttggcg ctttcaggca acctgcgtgc aggtgttcct      3600
ttggcaacgc ctgtatttga cggtgctgaa gaatcacaaa ttaaagaatt gctagagctt    3660
ggcggcattt cacgtactgg tcaaacagta ttgtatgatg ccgtactggg tgagcgtttc    3720
gaccgtcctg taactgtagg ttacatgtac atgctgaaac tgaaccactt ggtagacgac    3780
aaaatgcatg cgcgttctac tggttcttat tctcttgtta cgcagcagcc attgggcggt    3840
aaagcgcagt tcggtggtca gcgtttcggt gagatggaag tctgggcact ggaagcatat    3900
```

```
ggcgcagcgt acacgctcca agaaatgctt acagttaagt cggatgacgt tgaaggccgt    3960
acccgcatct ataagaacat tgtagatggc aaccattata tggatccggg catgcctgaa    4020
tcgttcaacg tattgaccaa agagatccgt tctttaggta tcaacattga actgaaaaat    4080
ggtgactaa                                                            4089

<210> SEQ ID NO 27
<211> LENGTH: 4089
<212> TYPE: DNA
<213> ORGANISM: acinetobacter gerneri

<400> SEQUENCE: 27
atggcatact catataccga aaagaaacgg atccgtaaga attttggtaa attgcccgaa      60
gtaatggaag ctccgtactt gctcgcgatt caagtcgact cgtacagaac cttccttcaa     120
gatggcaaaa caccaaaaaa ccgcgaagat atcggtctcc aagccgcatt tcgttcagtt     180
tttccaattg aaagttattc tggcaatgct gctttagaat tcgttgagta tagccttggt     240
aaaccagagt ttgatgttcg tgagtgtatt cttcgcggct cgacttttgc ggcaccaatg     300
cgcgttaaaa ttcgtttgat catcaaagat cgtgaaacga atcgatcaa agacgttcgt      360 gaacaagaag tttacatggg tgaaatgcca ctcatgactg agaacggtac ctttgttatt     420
aacggtactg aacgtgtaat cgtttctcaa ttacaccgtt ctccaggtgt gttctttgac     480
cacgataaag gtaagactca ttcaagtggt aaagtgcttt attctgcacg tatcattcct     540
taccgtggtt catggttgga ctttgagttt gatgcgaaag atttagttta tgttcgtatc     600
gaccgtcgtc gtaaattatt agcaactgct attcttcgtg ctttagatta tacaaatgaa     660
caaatcttag aaatgttcta tgagaaagtt cctgtatatc tagatatggg tagctaccaa     720
attgaccttg tgcctgaacg tctgcgtggc gaaatggctc aattcgacat tactgatgct     780
gatggcaaag tgattgttga acaaggtaaa cgtattaatg cgcgtcatgt tcgtcaaatg     840
gaagcttctg gtttaactaa gctttctgtt cctgatgaat atttatatga gcgtattaca     900
gctgaagata tcacactgaa agatggtgaa gtgattcaag caaacactgt gcttggtcat     960
gacattatgg tgaaattggc tgaaggcggt attaaacaat taatatcct attcaccaac    1020 gatatcgacc gtggttcatt tatcgcagat acattacgta cagatactac aacaggccgt    1080
gaagaagcgc ttgttgaaat ctataaagta atgcgtccag cgagccacc aacaaaagaa     1140 gctgctgaaa acttattcaa caacttgttc ttctcttctg aacgttatga cttatctcct    1200
gtaggtcgta tgaagttcaa ccgtcgtttg ggtcgtcctt acgaagtggg tactgatcag    1260
aagtctcgtg aagttgaagg tattctttct aacgaagaca ttatcgacgt attaaaaact    1320
ctcgttgaaa tccgtaacgg taaaggcgaa gtcgacgata tcgaccattt aggtaaccgt    1380
cgtgtacgtt cagttggtga atgactgaa aaccaattcc gtgttggttt agttcgtgtt      1440
gaacgtgctg ttaagaacg tttaagccaa gctgaaacag taacttgtc tccacaagat      1500 ttaatcaatg cgaaaccagt tgctgctgca atcaaagaat tctttggttc aagccaattg    1560
tctcagttca tggaccaaaa caacccattg tctgaaatca cacacaaacg tcgtgtatca    1620
gctctcggac ctggtggttt gactcgtgaa cgtgcgggct ttgaggtacg tgacgtacat    1680
caaactcact atggtcgtgt atgtcctatt gaaacgcctg aaggtccaaa cattggtttg    1740
atcaactcgc tttctgtttta tgcaaaatgt aataacttcg gtttcttgga aactccatac   1800
cgtaaagttg ttgatggtcg tgtaactgaa gatgttgagt atttatcgc tattgaagaa    1860 gtaggtactg ttattgcaca ggccgattct agtgtagatg gcgataataa cttaactgaa    1920
```

```
gaattcgttt ctgtacgtca tcaaggtgaa ttcgttcgta tgcctcctga aaaagtgacg    1980
catatggatg tatcagctca acaggttgta tctgtagctg catcattgat tccgttcctt    2040
gaacacgatg atgccaaccg tgcattgatg ggttcaaaca tgcaacgtca ggctgttcct    2100
acattgcttg ctgacaaacc acttgttggt acaggtatgg aagcaaacgt agcgcgtgac    2160
tcaggtgtat gtgtgatcgc gaaacgtggc ggtatgatcg aatttgttga cgcttcacgt    2220
gttgtgattc gtgttaacga agatgaaatg attgctggtg aagctggtgt agatatctac    2280
aacctcatca aatatacccg ttcgaaccaa atacttgta tcaaccaaaa agttctcgtg    2340
agcttgggtg ataaagtagg tcgcggtgat gtattggctg atggtccatc tacagacggt    2400
ggtgaacttg ctcttggtca gaacatgcgc gtagcgttca tgacttggaa cggttataac    2460
tacgaagact cgattttatt atctgaacgt gttcttcaag aagatcgttt gacttctatt    2520
cacattcaag aattgtcatg tgtagctcgt gatactaagt taggtgcaga agaaatcact    2580
gcagatattc ctaacgttgg tgaagctgcg ctgtctaaac ttgatgagtc aggtatcgtt    2640
tatatcggtg ctgaagtaac tgctggtgac attcttgtag gtaaagtaac gcctaaaggt    2700
gaaactcagt tgactcctga agaaaaactt cttcgtgcga tcttcggtga aaaagctgct    2760
gacgttaaag attcatcttt acgcgttcca tctggtacta aaggtacagt gattgacgtt    2820
caagtctttta ctcgtgatgg tattgaaaaa gatgaacgtg ctcaagcaat tgagaaagct    2880
cagcttgatg cttaccgtaa agatttgaaa gaagaatata aaatctttga agaagctgct    2940
cgtgaacgta ttgttcgctt gttgaaaggt caagaatcaa atggtggtgg ttcaactaaa    3000
cgtggtgaca aactttctga agaattgtta tctggtttag agctagttga tcttcttgaa    3060
attcaaccaa gtgatgaagg tattgctgaa cgtttaactc aaattcaagt gttcttgaaa    3120
gaaagagcc atgaaattga tgagaaattt gctgagaaaa acgcaaaact ttctacaggt    3180
gatgagctta caactggtgt attgaaagtt gttaaagtgt atttggctgt taaacgtcgt    3240
atccaaccgg gtgataaaat ggcgggtcgt cacgggaaca aaggtgttgt atcaaacatc    3300
cttcctgtag aagatatgcc gcatgacatc aacggtgttc ctgttgacgt agtacttaac    3360
ccactgggtg taccgtcacg tatgaacgtg ggtcagattc ttgaaacaca tttaggtta    3420
gctgccaaag gtcttggtga gcaaatcgat aagatgctca aagagcaacg tacgattgct    3480
gaacttcgtg tgttcttgga caagatttat aacaaagttg gtggcgagca agaagatctt    3540
gatagcttaa ctgatgaaga aatccttgtt ctttcaggta atttacgtaa aggtgttcct    3600
ttagcaactc cagtatttga tggtgctgaa gaaggtcaaa ttaaagagct tcttgaactt    3660
gctgaacttc cacgttctgg tcaaacagta ttgtatgacg gacgtacagg tgagcgtttt    3720
gaccgtcctg taaccgttgg ttatatgtac atgttgaaac ttaaccactt ggttgatgac    3780
aagatgcatg cacgttctac tggttcttac tcattagtga cacaacaacc gcttggtggt    3840
aaagcacaat tcggtggtca gcgtttcggt gagatggaag tctgggcact tgaagcatac    3900
ggtgcggctt acacactaca agaaatgctt acagttaagt cggatgacgt tgaaggtcgt    3960
acacgtgtct acaaaaacat tgtagatggc aaccattata tggatccggg tatgcctgaa    4020
tcgttcaacg tattgaccaa agagatccgt tctttaggta tcaacattga actgaaaaat    4080
ggtgactaa                                                            4089
```

<210> SEQ ID NO 28
<211> LENGTH: 4089
<212> TYPE: DNA
<213> ORGANISM: acinetobacter grimontii -continued

```
<400> SEQUENCE: 28
atggcatact catataccga aaagaaacgg atccgtaaga attttggtaa attgccccac     60
gtaatggaag caccgtactt actttcgatt caggtcgatt cgtatcgtac attcttacaa    120
ggtggtaaaa ctccaaaaaa tcgcgaagat atcggtctcc aagccgcatt tcgttcagtt    180
tttcctattg aaagttattc tggcaatgct gctttagaat tgttgagta tagccttggt     240 aaacccgagt ttgacgtgcg tgaatgtatt ttacgtggtt cgacttatgc ggcaccaatg    300
cgtgtaaaaa ttcgtttgat cattaaagat cgcgaaacga atcaatcaa agatgttcgt     360 gaacaagaag tgtacatggg cgaaatgccg ctcatgaccg acaacggtac tttcgttatt    420
aacggtactg aacgtgtaat cgtatctcaa ttacaccgtt caccaggcgt attctttgat    480
catgataagg gtaaaacaca ctcaagcggt aaagtgttgt attcagcacg tatcattcct    540
taccgtggtt catggttaga ttttgaattc gatgcaaaag atttagtttt cgtacgtatt    600
gaccgtcgtc gtaaattgtt ggcgactgtg atcttacgtg ctttaaatta tagcaatgaa    660
caaatcttga atttgttcta tgaaaaagta cctgtatatc ttgatatggg tagctatcaa    720
attgacctcg ttccagatcg cttacgtggt gaaatggcgc aatttgatat cttggacaac    780
gatggtaaag caatcgttga gcaaggtaag cgtattaatg cacgtcatgt acgccaaatg    840
gaagcagcta acttagctaa gctttctgta cctgatgaat attttatatga gcgtattaca    900 gctgaagaca tcacacttaa gaatggtgat gtgattcctg caaataccgt acttagccat    960
gaaattatgg tgaaattggc tgaaggtggt gttaaacaat ttaacatcct attcactaat   1020
gacatcgatc gtggttcgtt cattgcagat acattacgtg cagatacaac aacaggtcgt   1080
gaagaagcgc ttgttgaaat ctataaagta atgcgtccag gtgaaccacc gacaaaagaa   1140
gcagcagaga acttatttaa taacttattc ttctcttctg aacgttatga cctttctcca   1200
gtaggtcgta tgaagtttaa ccgtcgtttg ggtcgtcctt acgaagtggg tactgatcag   1260
aagtcacgtg aagttgaagg tatttatcg catgacgata tcattgatgt acttcgtaca   1320
ttagttgaga tccgcaatgg taaaggtgaa gtcgacgata tcgatcactt gggtaaccgt   1380
cgcgtacgtt ctgttggtga aatgacagaa aaccaattcc gtgttggttt ggttcgtgtt   1440
gaacgtgctg tgaaagagcg tttaagccaa gctgaaactg ataacttgtc tccacaagat   1500
ttaatcaacg cgaaaccagt tgctgcggca atcaaagaat tctttggttc aagccagtta   1560
tctcagttca tggaccaaaa caacccatta tctgagatta cacataaacg tcgtgtgtct   1620
gcgcttggtc ctggtggttt gacacgtgaa cgcgcaggct tcgaagtgcg tgacgtacat   1680
caaactcact atggtcgtgt ttgtccaatt gaaacacctg aaggtccaaa cattggtttg   1740
atcaactcgc tttctgtcta tgctaaagcg aatgacttcg gtttcttgga aacaccatac   1800
cgtaaagttg tagacggtcg tgttacagat gaagttgaat atttatctgc aattgaagaa   1860
gtaggcaccg tcattgcaca agccgactca gcagtggata agatggcaa cttgactgaa   1920 gaaatggttt ctgtacgtca tcaaggtgaa ttcgtacgta tgtcgcctga gcgcgtaaca   1980
catatggacg tttctgcaca gcaggttgtt tctgttgcag cgtcattaat tccattcctt   2040
gaacacgatg acgcaaaccg tgcattgatg ggttcgaaca tgcaacgtca ggctgttcct   2100
acacttcgtg ctgacaaacc acttgtcggt acgggtatgg aagcaaacgt agcacgcgac   2160
tcaggtgtat gtgtgatcgc gggtcgtggt ggtgtaattg aatatgttga tgcatctcgt   2220
atcgttattc gtgttaacga agatgaaatg attgcaggtg aagcaggtgt agatattttac   2280 aacctgatca aatatacacg ttcaaaccaa aatacatgta ttaaccaaaa tgtcatcgta   2340
```

-continued

```
aacttgggcg acaaagttgc tcgtggcgat attttggctg acggtccatc gactgacatg    2400
ggtgaacttg cgctaggtca aaacatgcgc gtcgcgttca tgacatggaa cggttataac    2460
tatgaagact caatcttact ttctgagcgt gtgcttcaag aagaccgttt aacgtcgatt    2520
catattcaag aattgtcatg tgtagcgcgt gatactaagt taggtgcaga agaaattact    2580
gctgatattc ctaacgtcgg tgaagctgca ctgtctaaac ttgatgagtc aggtattgtt    2640
tatatcggtg ctgaagttac tgcaggtgat attcttgttg gtaaggtaac acctaaaggt    2700
gaaactcagt taacacctga agaaaaacta cttcgtgcaa tctttggtga aaaagcggct    2760
gacgtaaaag attcatcttt acgtgttccg tcaggcacta aaggtacagt gattgacgtt    2820
caagtcttca cacgtgatgg tttagaaaaa gatgaacgtg cgcaagcaat tgagaaagct    2880
cagcttgatg cataccgtaa agacttgaaa gaagaataca aaatcttcga agaagcagca    2940
cgtgagcgta ttgttcgttt gttgaaaggt caagaatcta acggtggtgg ttcgactaaa    3000
cgtggtgaga agctttcaga agatatgttg tctggtctag agttagttga tctacttgaa    3060
atccaaccaa cagatgaagc aattgctgag cgtttaactc aaattcaagt gttcttgaaa    3120
gaaaagagcc atgaaattga tgaaaagttt gctgagaaga acgtaaaact ttctacaggt    3180
gatgagttaa caactggtgt attgaaagtt gttaaggttt acctagcagt taaacgtcgt    3240
atccaacctg gtgataagat ggcgggtcgt cacggtaaca agggtgttgt atcaaacatc    3300
ttaccagttg aagacatgcc acatgatgcc aatggtgtgc cagttgatat cgtattgaac    3360
ccactcggtg taccatcgcg tatgaacgtg ggtcagattc ttgaaactca cttaggtatg    3420
gcagcaaaag gtttgggtga gcagattgat aaaatgctca acaacaacg tacaattgcc    3480 gagttacgtt cattccttga caagatttat aataaagtgg gtggtgagca agaacagctt    3540
gacacactga ctgatgaaga gatcttgaaa cttttcaggta atttacgtgc tggtgtgcct    3600
ttggcaactc cagtattcga tggtgctgaa gagtcacaaa tcaaagagtt acttgaactt    3660
gcagagttac cacgttctgg tcaacagatc ttgtttgatg gacgtacagg tgagcagttt    3720
gatcgtccag taactgtcgg ttacatgtat atgcttaagt tgaaccactt ggttgacgac    3780
aagatgcatg cacgttcaac tggttcttac tcacttgtga cacaacaacc gcttggtggt    3840
aaagcacaat tcggtggtca gcgtttcggt gagatggaag tatgggcact tgaagcatat    3900
ggtgcagcat ataccctcca agaaatgctc actgtgaagt cggatgacgt cgaaggtcgt    3960
acacgcatct ataagaacat tgtagatgga aaccattata tggatccggg tatgcctgaa    4020
tcgttcaacg tattgaccaa agagatccgt tctttaggta tcaacattga actgaaaaat    4080
ggtgactaa                                                           4089

<210> SEQ ID NO 29
<211> LENGTH: 4089
<212> TYPE: DNA
<213> ORGANISM: acinetobacter tandoii

<400> SEQUENCE: 29
atggcatact catataccga aaagaaacgg atccgtaaga attttggtaa attgcctagt      60
gttatggatg ctccgtactt gctcgcgatt caagtcgact cgtacagaac gttcttgcaa     120
gatggcaaat caccaaaaaa ccgcgaagat atcggtctcc aagccgcatt tcgttcagtt     180
tttcctatag aaagttattc tggcaatgct gctctagaat ttgttgagta tagccttggt     240
aagccggagt tgatgttcg cgaatgtatt cttcgtggct caacttatgc ggcaccaatg     300
cgtgtaaaaa ttcgtttgat cattaaagat cgtgaaacga aatcaatcaa agacgtgcgt     360
```

```
gagcaagaag tgtacatggg tgaaatgcca ctcatgacgg ataacgggac attcgttatt    420
aatggtactg agcgtgtaat cgtatctcag ttacaccgtt cgccaggcgt gttctttgat    480
catgataagg gtaaaactca ctcaagcggt aaagtgcttt attcggcacg tattattcct    540
taccgtggtt catggttaga ctttgaattt gatgcaaaag atttagtcta tgtccgtatt    600
gaccgtcgtc gtaaattgct tgcgactgtg gttttacgtg cattggatta cagcaacgaa    660
caaattctag atttattcta cgagaaagta cctgtctatt tagacatggg tagctaccaa    720
attgaccttg taccagaacg cctgcgtggc gaaatggctc aattcgacat taccgataat    780
gacggtaaag tgattgttga acaaggtaag cgtattaacg cgcgtcatgt acgtcaaatg    840
gaagcttcag gcttaacgaa gctttctgtt ccagacgaat atttatatga gcgtattact    900
gcccaagata tcactttacg tgatggcgaa gtgattcctg cgaataccct gctaagccat    960
gaagtgatgg tgaagctggc tgaaggtggc gtgaagcagt ttaatattct gtttacgaat   1020
gacatcgatc gtggttcgtt cattgcggat tctctacgtg cagatacaac aacaggtcgt   1080
gaagaagcgc ttgttgaaat ctacaaagta atgcgtccag gtgagccacc aacaaaagaa   1140
gcagctgaaa acttatttaa taacttattc ttctcttctg agcgttacga tttatcgcca   1200
gttggtcgta tgaagtttaa ccgtcgtttg ggtcgtcctt acgaagtcgg tactgatcag   1260
aagtcacgtg aagttgaagg tatcctttcg aacagcgata tcactgatgt attaaaaaca   1320
ttggttgaaa ttcgtaacgg taaaggcgaa gtggatgata ttgaccactt gggtaaccgt   1380
cgtgttcgtt ctgttggtga atgacagaa aaccaattcc gtgttggttt ggttcgtgtt   1440
gagcgtgctg taaaagagcg tttaagccaa gcagaagcag ataacttgtc tccgcaagat   1500
ttaatcaatg cgaaaccagt tgcagcggca atcaaagaat tctttggttc aagccagtta   1560
tctcagttca tggatcaaaa caacccattg tctgagatta cacacaaacg tcgtgtatct   1620
gcacttggtc ctggtggttt aacacgtgaa cgtgcgggct ttgaagtacg tgacgtacat   1680
caaactcact atggtcgtgt atgtccgatt gaaacgcctg aaggtccaaa cattggtttg   1740
atcaactcgc tatctgttta tgcaaaatgt aataacttcg gtttcttgga aactccatac   1800
cgtaaagttg ttgatggacg tgtaacggat gaagttgaat acttatctgc gattgaagaa   1860
gtaggcactg tcattgcaca agccgactct gcagtcgatg cagacaatca cttgacggaa   1920
gagtttgttt ctgtacgtca ccaaggtgat ttcgtgcgta tgccacctga aaaagtgacg   1980
catatggatg tatctgctca acaggttgta tctgttgcag catcattgat tccgttcctt   2040
gaacacgatg atgcgaaccg tgcattaatg ggttcgaaca tgcaacgtca ggctgttccg   2100
acattattgg cggataaacc gcttgttggt acagggatgg aagcaaatgt agcacgtgat   2160
tctggtgtgt gtgtcattgc aaaccgtggt ggtgcgattg aatacgtaga cgcttctcgt   2220
atcgtgattc gtgtaaacga agaagagatg gtagcgggtg aagcgggtgt agatatctac   2280
aacctgatca aatatacacg ttctaaccaa aatacatgta tcaaccaaaa cgtcgtagtt   2340
cgcatgggtg acaaagttgc tcgtggtgat gtattggctg atggtccatc gactgatggt   2400
ggtgaacttg cgcttggtca aaacatgcgc gtcgcgttca tgacttggaa cggttataac   2460
tatgaagact cgatcttact ttctgagcgt gttcttcaag aagaccgttt aacttcgatc   2520
catatccaag agttatcgtg tgttgcacgt gatactaaat tgggtgctga agaaattact   2580
gcggatatcc cgaacgtggg tgaagctgca ctttctaagc ttgatgaatc aggtattgtt   2640
tatatcggtc tgaagttgc agcgggcgac atccttgttg gtaaagtaac gcctaaaggt   2700
gaaacgcaat taacaccaga agaaaaactg cttcgtgcaa ttttttggtga aaaagcagct   2760
```

-continued

```
gacgttaaag attcttcttt acgtgttcca tctggtacga aaggtacagt aattgacgtt      2820
caagtgttta cacgtgatgg tcttgaaaaa gacgaacgtg cgcaagcaat tgaaaaagcg      2880
caattagatg cttaccgtaa agacttgaaa gaagaatata aaatcttcga agaagcagca      2940
cgtgaacgta ttgttcgctt gttgagcggt caagaatcga atggcggtgg cggcacgaag      3000
cgtggtgaca aactttcaga agatatgttg tctggcttag agttggttga tttacttgaa      3060
atccagccaa gtgatgaagc gattgctgaa cgtttaaccc aaattcaagt gttcttgaaa      3120
gagaagagct ttgaaattga cgagaaattt gctgagaaaa aacgcaaact ttctacaggt      3180
gatgaactaa caactggcgt attgaaagtt gtgaaggttt accttgcagt taaacgtcgt      3240
atccagcctg gtgataagat ggcgggtcgt cacggtaaca aaggtgttgt gtctaacatc      3300
ctaccagtcg aagacatgcc gcatgatgcc aatggtgttc cagtcgatat cgtattgaac      3360
ccgttgggtg taccgtcacg tatgaacgtg gggcagattc ttgaaactca cttgggtatg      3420
gctgcgaaag gtttgggtga gcaaattgat aagatgctca acaacagcg tgaaattgct      3480 gaactacgtg ttttcctaga caaaatctac aacaaagtgg gcggtcagca agaagattta      3540
gacagcttaa cagatgatga atcttggtg ttggcaggta acttacgtgc aggtgtacct      3600
ttagcaactc ctgtatttga tggtgctgaa gaaagccaaa tcaaagagtt actagagctg      3660
gctgaaattc cacgttcggg tcaaaccgta ttgtatgatg gacgtacagg tgaacgtttc      3720
gaccgtcctg taactgtagg ctatatgtac atgcttaagt tgaaccactt ggttgacgac      3780
aagatgcatg cccgttctac aggttcttac tcattagtaa cgcaacaacc attgggtggt      3840
aaagctcagt tcggtggtca gcgtttcggt gagatggagg tctgggcact tgaggcttat      3900
ggcgcagctt atacacttca agaaatgctc actgtgaagt cggatgacgt tgaaggtcgt      3960
actcgtatct ataagaatat tgtagatggt aaccattata tggacccagg tatgcctgaa      4020
tcgttcaacg tattgaccaa agagatccgt tctttaggta tcaacattga actgaaaaat      4080
ggtgactaa                                                              4089

<210> SEQ ID NO 30
<211> LENGTH: 4089
<212> TYPE: DNA
<213> ORGANISM: acinetobacter tjernbergiae

<400> SEQUENCE: 30
atggcatact catataccga aaagaaacgg atccgtaaga attttggtaa attgccccat       60
gtaatggaag caccgtactt actttcgatt caggtcgatt cgtatcgtac attcttacaa      120
ggcggtaaaa ctccaaaaaa tcgcgaagat atcggtctcc aagccgcatt tcgttcagtt      180
tttcctattg aaagttattc tggcaatgct gctttagaat tgttgagtta tagtcttggt      240
aagcccgagt tgacgtacg tgaatgtatt ttacgtggtt caacttatgc agcaccaatg      300
cgcgtaaaaa ttcgtttgat tattaaagat cgtgaaacga atcaattaa agatgttcgt      360 gaacaagaag tctacatggg tgaaatgcca ctcatgaccg ataacggtac ttttgttatc      420
aatggtactg agcgtgtgat tgtgtctcag ttacaccgtt cgccaggtgt attctttgat      480
catgataaag gtaagaccca ttcaagtggt aaagtgttgt attcggcacg tattattcct      540
taccgtggtt catggttaga ttttgaattt gatgctaaag atcttgttta tgtgcgtatt      600
gaccgtcgtc gtaaactatt agcaactgta attctgcgcg ctttaggcta tgcaaatgca      660
caaatcttga attattcta tgaaaaagtg cctgtatatc ttgatatggg tagttatcag      720
attgatcttg tgccagatcg attacgcggt gaaatggcgc agtttgatat tgccgataat      780
```

```
gacggtaaag tcattgttga acaaggtaaa cgtattaatg tacgtcatgt acgtcaaatg    840
gaagcggcta atttagccaa actttctgta cctgatgagt atttatatga acgtattacc    900
gctgaagata ttaccttaaa agatggtgat gtgattcctg caaatacgct gcttagtcat    960
gaagtcatgg tgaagttagc tgaaggtggc gttaaacagt tcaatatctt gtttactaat   1020
gatattgatc gtggctcttt tattgctgat agtttacgtg cagacacaac ttcagggcgt   1080
gaagaagcat tagtagaaat ttacaaagta atgcgtccag gtgaaccacc aacaaaagaa   1140
gctgctgaaa acttatttaa taatttattc ttctcttctg aacgttatga cctttctcca   1200
gtaggtcgca tgaagtttaa ccgtcgtttg ggtcgtcctt acgaagtggg tacagatcag   1260
aaatcgcgtg aagttgaagg tattttatcg cacgacgata tcatcgatgt actgcgtaca   1320
ttggttgaaa ttcgtaacgg taaaggtgaa gtcgatgata tcgaccactt aggtaaccgt   1380
cgtgtacgtt ctgttggtga aatgacagaa aaccaattcc gtgttggttt agttcgtgtt   1440
gaacgtgctg ttaaagagcg tttaagccaa gcagagacag ataatttgtc tccacaagat   1500
ttaatcaatg cgaaaccagt tgctgctgca atcaaagaat ctttggttc aagccaattg    1560
tctcagttca tggatcaaaa caatccattg tctgaaatta cacataaacg tcgtgtatct   1620
gcgcttggcc ctggtggttt gacacgtgag cgtgcgggct tcgaagtccg tgacgtacat   1680
caaactcact atggtcgtgt tgtccaatt gaaacgcctg aaggtccaaa cattggtttg     1740
atcaactcgc tttctgtcta tgcaaaagcg aatgactttg gtttcttgga acaccatac    1800
cgtaaagtcg ttgatggtcg tgtgactgat gaggttgaat atttatctgc aattgaagaa   1860
gttgggactg tgattgcaca ggccgattct ggtgtagata agatggtaa cttaacagaa    1920
gaaatggctt ctgtacgtca tcagggcgaa tttgtacgta tgccacctga aaaagtgacg   1980
catatggacg tatctgctca gcaggttgtt tctgttgctg catcgcttat tccgtttctt   2040
gaacacgatg atgcgaaccg tgcattgatg ggttcaaaca tgcaacgtca ggctgttccg   2100
acattgcgtg ctgacaagcc gcttgttggt acgggtatgg aagcaaacgt agcacgtgat   2160
tctggtgtgt gtgtgatcgc agaccgtggt ggtgcgattg aatatgttga tgcatctcgt   2220
atcgtgattc gtgtaaacga agatgaaatg attgcgggtg aagcgggtgt agatatctat   2280
aacctgatca aatatacacg ttcaaaccaa aatacctgta tcaaccaaaa cgttatcgta   2340
aacttgggtg acaaagttgc tcgtggcgat atccttggctg atggtccatc gactgatatg   2400
ggtgaacttg cgcttggtca aaacatgcgc gtcgcgttca tgacatggaa cggttataac   2460
tacgaagact cgatcttact ttctgagcgt gtacttcaag aagaccgttt aacgtcgatt   2520
catatccaag aattgtcatg tgtagcgcgt gatactaagt taggtgcaga agaaattact   2580
gccgatattc ctaacgtggg tgaagctgca ctgtctaagt tggatgagtc tggtattgtt   2640
tatatcggtg ctgaagtgac tgcgggtgac atccttgttg gtaaggtaac gcctaaaggt   2700
gaaactcagt taacacctga agaaaaacta cttcgcgcga tctttggtga aaaagctgct   2760
gacgttaaag actcttcttt acgcgttcca tctggtacca aaggtactgt gattgacgtt   2820
caagtcttta cgcgtgatgg tttggaaaaa gatgaacgtg ctcaagccat tgagaaagct   2880
cagcttgatg cataccgtaa agatttgaaa gaagaataca aaatcttcga agaagcagca   2940
cgtgaacgta ttgttcgttt gttgacaggt caagagtcta cggtggtgg ctcaactaag    3000
cgtggtgata aacttctctgc agatgtcttg tctggtttag agctggttga tttacttgaa   3060
attcaaccga ctgatgaagc aattgcagag cgtttaactc agattcaagt gttcttgaaa   3120
gagaagagct acgaaattga cgagaagttt gcagagaaga aacgtaaact ttctacaggt   3180
```

```
gatgaattaa caacgggtgt attgaaagtt gttaaggttt acctcgctgt taaacgtcgt    3240
atccagcctg gtgataagat ggcgggtcgt catggtaaca aaggtgttgt atctaacatc    3300
ttacctgttg aagacatgcc tcatgatgcg aatggtgtgc cagtcgatat cgtattgaac    3360
ccattgggtg taccgtcacg tatgaacgtg ggtcagattc ttgagactca cttaggtatg    3420
gcggcgaaag gtcttggcga taaaatcgaa aaaatgttga agaacagcg tacagtgatt    3480 gaactgcgtg aattcttaga caagatttat aacaaggtcg gtggtgagca agaagagctt    3540
gacagcttaa ctgatgcgga agtcttggca cttttcaggca acttacgtgc tggtgttcca    3600
ttggcaacgc ctgtatttga cggtgctgaa gaaagtcaga ttaaagactt acttgaattg    3660
gcagacatct cacgtacggg tcaaacggta ttgtttgacg gacgtacagg tgaacagttt    3720
gatcgtcctg taactgtagg ttacatgtac atgctcaaat tgaaccactt ggttgatgac    3780
aagatgcatg cgcgttcaac gggttcttac tcacttgtga ctcaacagcc gcttggtggt    3840
aaagcacaat tcggtggtca gcgtttcggt gagatggaag tatgggcact tgaagcatac    3900
ggtgctgcat acacgctcca agaaatgctt acagtgaagt cggatgacgt cgaaggtcgt    3960
acacgcatct ataagaacat tgtagatggt aaccattata tggatccggg tatgcctgaa    4020
tcgttcaacg tattgaccaa agagatccgt tctttaggta tcaacattga actgaaaaat    4080
ggtgactaa                                                            4089

<210> SEQ ID NO 31
<211> LENGTH: 4089
<212> TYPE: DNA
<213> ORGANISM: acinetobacter towneri

<400> SEQUENCE: 31
atggcatact catataccga aaagaaacgg atccgtaaga attttggtaa attgccccaa      60
gtaatggatg caccgtactt gctttcgatt caagtcgact cgtaccgtac tttccttcaa     120
gatggcaaaa ctccaaaaag ccgcgaagat atcggtctcc aagccgcatt tcgttcagtt     180
tttcctatag aaagttattc tggcaatgct gctttagaat tgttgagta tagtcttggt     240 aagcctgagt ttgatgtacg tgagtgtatt cttcgcggct caacttatgc ggcaccaatg     300
cgcgtaaaaa ttcgtttgat cattaaagat cgtgaaacga atcaatcaa agatgtgcgt     360 gagcaagaag tctacatggg cgaaatgcca ttgatgacgg ataacggtac ctttgtgatt     420
aacggtactg agcgtgtaat tgtttctcaa ttacaccgtt caccaggcgt gttctttgac     480
cacgataaag gtaagaccca ctcgagcggt aaagtgttgt attcagcacg cattattcct     540
taccgtggct catggttaga ctttgaattc gatgccaaag acctcgttta tgtgcgtatt     600
gaccgtcgtc gtaaattgct tgcgactgta gtgttgcgtg cattgggcta tagcaatgaa     660
caaatcctag acttgttctt tgagaaagta cctgtctatt tagacatggg tagctaccaa     720
attgaccttg tcccagaacg cttacgtggc gaaatggcac aatttgacat cactgatact     780
gacggcaaag tgattgttga gcaaggtaaa cgcattaatg cgcgtcacgt acgtcaaatg     840
gaagcagctg gtcttgagaa gctttcagtt cctgatgagt acttgtacga acgtattact     900
gcagaagaca tccagctaaa agatggcgat gtgattgctg caaacacctt gttaagccat     960
gaaatcatgg tgaaacttgc agaaggtggt gttaaacaat ttaacatcct attcaccaat    1020
gacatcgacc gtggttcgtt cattgcggac accttacgtg cagatacaac tgttggtcgt    1080
gaagatgctt tggtagaaat ctacaaagtg atgcgtccag gtgagccacc gacgaaagaa    1140
gccgctgaaa atctgttcaa taacttgttc ttctcttctg agcgttatga tttatcgcca    1200
```

```
gtaggtcgta tgaagttcaa ccgtcgtttg ggtcgtcctt acgaagtggg tacagatcag    1260
aaatcacgtg aagttgaagg tattttgtct aacgaagaca ttaccgatgt acttaaaaca    1320
ttgatcgaaa tccgtaacgg taaaggtgaa gtcgacgata tcgaccactt gggtaaccgt    1380
cgcgtacgtt cagtgggcga gatgactgaa aaccaattcc gtgttggttt ggtacgtgtt    1440
gagcgtgctg taaaagagcg tttgtcacaa gctgaaacag acaacctgtc tccgcaagat    1500
ttaatcaatg cgaagccagt ggctgctgca atcaaagaat tctttggttc aagccaattg    1560
tctcagttca tggaccaaaa caacccgttg tctgaaatta cccacaagcg tcgcgtatct    1620
gcgcttggtc caggtggttt gacacgtgaa cgtgcaggct ttgaggtacg tgacgtacac    1680
caaactcact atggtcgtgt gtgtccaatt gaaacgcctg aaggtccaaa cattggtttg    1740
atcaactcgc tttctgttta tgcaaaatgt aataattttg gcttcttgga aacgccatac    1800
cgtaaagtgg ttgatggtcg tgtaaccgat gaggttgagt atttatctgc aattgaagaa    1860
gtgggcacga tcattgcgca agcggactca agcgtagacc aagatggcaa tttaacagaa    1920
gaattcgtat ctgtacgtca ccaaggtgac ttcgtgcgta tgccgccaga gcgcgtgacg    1980 cacatgacg tttctgcaca gcaggttgta tctgtagcag catcactgat tccattcctt    2040
gagcacgatg acgccaaccg tgccttgatg ggatcgaaca tgcaacgtca ggctgttccg    2100
acgcttatcg ctgataaacc acttgtgggt acagggatgg aagcgaacgt agcacatgac    2160
tcaggtgtat gtgtgattgc aaaccgtggt ggtcgtattg aatatgtcga tgcttcacgt    2220
gtagtcattc gtgtgaacga agaagaaatg atcgcgggtg aagcaggtgt agatatctac    2280
aacctgatca aatacacacg ttcaaaccaa aacacttgta ttaaccaaaa agttttggtg    2340
aagatgggtg ataaggtagg tcgtggtgat gtattggctg acggtccatc tacagatggc    2400
ggtgagcttg cactcggtca gaacatgcgt gtcgcgttca tgacttggaa tggctataac    2460
tacgaagact cgatcttgct ttctgagcgt gtacttcaag aagaccgttt aacttcgatt    2520
cacattcaag aattgtcatg tgttcacgt gataccaaat tgggtgcgga agaaatcaca    2580
gctgatattc caaacgtggg cgaagctgca ctgtctaaac tagacgagtc tggtatcgtt    2640
tacattggtg ctgaagttac tgcaggcgac atcctggtag gtaaagtaac gccgaagggt    2700
gaaactcagt taaccctga agaaaaattg cttcgtgcaa tcttcggtga aaaagcagca    2760
gatgtgaaag attcatcatt gcgcgttcca tcaggtacta aagtacagt gattgacgtt    2820 caagtgttta cccgcgatgg tctagaaaaa gacgaacgtg cgcaagcaat tgaaaaagca    2880
cagttagatg catatcgcaa agacttgaaa gaagaatact aaatctttga agaagctgca    2940
cgtgaacgta ttatccgctt attgaaaggc caagagtcta acggtggcgg tacaaccaaa    3000
cgtggcgaca gctttctga agatatgttg tcaggcttgg ctttagtgga tttacttgaa    3060
attcaaccaa gtgatgaagc gattgctgaa cgcttaacgc aaattcaaac cttcttgaaa    3120
gagaagagct ttgaaattga tgagaaattt gctgagaaga aacgtaaaact ttctacaggc    3180 gatgagctca ctacaggcgt gttgaaagtt gttaaggtgt acttggctgt taaacgtcgc    3240
atccaaccgg gtgataagat ggcgggtcgt cacggtaaca aggtgttgt atctaacatc    3300 ttgccagtag aagacatgcc gcacgatgct aacggtgtac ctgttgacat cgtattgaac    3360
ccactaggtg taccatctcg tatgaacgtg ggtcagattc ttgaaacaca cttgggtatg    3420
gcagccaaag gtttgggtga gcaaattgac aagatgctca acaacaacg tgagattgct    3480 gaactacgtg cgttcctaga caagatttat aacaaagtgg gtggcgagca agaagatctt    3540
gacagcttaa ctgatgatga aatcttggta ttggcgggta acttgcgtgc aggtgttcca    3600
```

-continued

| | |
|---|---:|
| ttggctactc ctgtatttga tggtgctgaa gaaggtcaaa tcaaagaatt gcttgaactg | 3660 |
| gctgaattac cacgttcagg tcagaccgta ttgtatgatg gacgtacagg cgagaaattc | 3720 |
| gaccgtcctg tgactgtagg ttatatgtac atgctcaaac ttaaccactt ggtggatgac | 3780 |
| aagatgcacg cacgttctac aggttcttac tcacttgtaa cgcaacagcc gttaggtggt | 3840 |
| aaggcacaat tcggtggtca gcgtttcggt gagatggaag tctgggcact gaagcatac | 3900 |
| ggtgctgctt atacgctgca agaaatgctc actgtgaagt cggatgacgt tgaaggtcgt | 3960 |
| acccgcatct ataagaacat tgtagatggc aaccattata tggatccggg catgcctgaa | 4020 |
| tcatttaacg tattgaccaa agagatccgt tctttaggta tcaacattga actgaaaaat | 4080 |
| ggtgactaa | 4089 |

<210> SEQ ID NO 32
<211> LENGTH: 4089
<212> TYPE: DNA
<213> ORGANISM: acinetobacter parvus

<400> SEQUENCE: 32

| | |
|---|---:|
| atggcatact catataccga aaagaaacgg atccgtaaga attttggtaa attgccccac | 60 |
| gtaatggaag caccgtactt actgtcgatt caggtcgatt cgtaccgtac attcttacaa | 120 |
| ggcggtaaaa ctccaaaaaa tcgcgaagat atcggtctcc aagccgcatt tcgttcagtt | 180 |
| tttcctattg aaagttattc tggcaatgct gctttagaat tgttgagta tagtcttggt | 240 |
| aagcctgagt tgacgtacg tgaatgtatt ttacgtggtt caacttatgc agcaccaatg | 300 |
| cgcgtaaaaa ttcgtttgat cattaaagat cgtgaaacga atcaattaa agacgtgcgt | 360 |
| gaacaagaag tttacatggg tgaaatgcca ctcatgaccg ataacggtac tttcgttatc | 420 |
| aacggtactg agcgtgtcat cgtatctcaa ttacaccgtt caccaggtgt attctttgac | 480 |
| catgacaagg gtaaaaccca ctcaagtggt aaagtgttgt attcagcacg tattattcct | 540 |
| taccgtggtt catggttaga ttttgaattt gatgctaaag atttagtatt cgtacgtatt | 600 |
| gaccgtcgtc gtaagttact ggcaacggtg attctacgtg ccttgaatta cagcaatgaa | 660 |
| caaatcttga atttgttcta tgaaaaagta cctgtatatc ttgatatggg tagctatcaa | 720 |
| attgatcttg ttccagatcg cttacgtggt gaaatggcac aatttgatat cttagacaat | 780 |
| gatggtaaag cgatcgttga acaaggtaaa cgtattaacg cacgtcacgt acgtcaaatg | 840 |
| gaagctgcga acttagccaa gcttctctgta cctgatgaat attatatga gcgtattaca | 900 |
| gctgaagata tcacactgaa aagtggtgat gtgattcctg cgaataccgt tcttagccat | 960 |
| gacatcatgg tgaagatcgc tgaaaatggt gtgaagcagt ttaacatcct attcacgaat | 1020 |
| gatattgatc gtggttcgtt tgttgcggat acattacgtg cagatacaac aacaggtcgt | 1080 |
| gaagaagcac ttgttgaaat ctataaagtc atgcgtccag gcgagccgcc gacgaaagaa | 1140 |
| gctgctgaaa acctattcaa taatttgttc ttctcttctg agcgttatga cctttctcca | 1200 |
| gtgggtcgta tgaagttcaa ccgtcgtttg gggcgtccat acgaagtcgg tactgaccag | 1260 |
| aagtcacgtg aagttgaagg tattctgtca cacgacgata ttattgatgt attacgtaca | 1320 |
| ttagtagaaa tccgtaacgg taaaggtgaa gtcgacgata tcgatcactt aggtaaccgt | 1380 |
| cgtgtacgtt ctgtgggtga atgacagaa aaccaattcc gtgttggtct agtccgtgtt | 1440 |
| gaacgtgctg tgaaagagcg tttaagccaa gcagaaactg ataacttgtc tccgcaagat | 1500 |
| ttaattaacg ccaaaccagt tgctgcggca atcaaagaat tctttggttc aagccaattg | 1560 |
| tctcagttca tggaccaaaa taacccattg tctgagatta cgcacaaacg tcgtgtatct | 1620 |

```
gcgcttggtc ctggtggttt gacgcgtgaa cgtgcaggct ttgaagtacg tgacgtacat    1680
caaactcact atggtcgtgt ttgtccaatt gaaacacctg aaggtccaaa cattggtttg    1740
atcaactcgc tttctgtcta tgctaaagcg aatgacttcg gtttcttgga aacaccatac    1800
cgtaaagttg ttgatggtcg tgtgactgat gaagttgaat acttatctgc aattgaagaa    1860
gtaggcactg tcattgcaca agccgactca gcagtggata agatggcaa cttgactgaa     1920 gaaatggttt ctgtccgtca tcaaggtgaa tttgtgcgta tgtcgcctga gcgcgtcaca    1980
catatggatg tttctgcaca gcaggttgtt tctgttgcag catcattgat tccattcctt    2040
gaacacgatg atgcgaaccg tgccttgatg ggttcgaaca tgcaacgtca ggctgttcct    2100
acattgcgtg ctgacaagcc gcttgttggt acaggtatgg aagcaaacgt agcacgtgac    2160
tcaggtgtgt gtgtaatcgc caaccgcggt ggtgcgattg aatatgttga tgcatctcgt    2220
atcgtgattc gtgtcaacga agatgaaatg attgcgggtg aagcaggtgt agatatctat    2280
aacctgatca atatacacg atcaaaccaa aatacctgta ttaaccagaa tgtcatcgtg      2340
aacctgggcg acaaagttgc tcgtggtgat attttggctg acggtccatc gactgacatg    2400
ggtgaacttg cgctgggtca aaacatgcgc gtcgcgttca tgacatggaa cggttataac    2460
tatgaagact cgatcttact ttctgagcgt gtgcttcaag aagatcgttt aacgtcgatt    2520
cacattcagg aattgtcatg tgtcgcacgt gatactaagt tgggctcgga agaaattacc    2580
gctgatattc caaacgttgg cgaagcagct ttatctaagt tggatgagtc aggtattgtg    2640
tatatcggtg cggaagtgac tgcgggtgac atccttgttg gtaaagtcac gcctaaaggt    2700
gaaactcagt taacacctga agaaaaatta cttcgtgcaa tctttggtga aaaagcggct    2760
gacgtaaaag actcgtcttt acgtgttcca tcgggtacta aggtacagt gattgacgtt     2820 caagtcttca cacgtgatgg tttggaaaaa gatgaacgtg cgcaggcaat tgagaaagct    2880
cagcttgatg cataccgtaa agacttgaaa gaagaataca aaatcttcga agaagcagca    2940
cgtgaacgta ttgttcgttt gttgaaaggt caagaatcta atggtggtgg ttcaaccaaa    3000
cgcggtgata aacttctgc agaggtattg tctggtttag agttggttga tttacttgaa      3060
atccagccaa atgatgaagc aattgctgag cgtttaactc aaattcaagt gttcttgaaa    3120
gagaagagtt acgagattga cgagaagttt gctgagaaga agcgtaaaact ttctacaggt    3180 gatgaattaa caactggcgt attgaaagtt gttaaggttt acctggcagt taaacgtcgt    3240
atccagcctg gtgataagat ggcgggtcgt cacggtaaca aggtgttgt atcaaacatc      3300 ttgccagttg aagacatgcc acatgatgcg aatggtgtgc cagtcgacat cgtattgaac    3360
ccacttggtg taccgtcacg tatgaacgtg ggtcagattc ttgagactca cttgggtatg    3420
gcggcgaaag gtcttggcga taagatcgaa aaaatgttga agaacaacg tacagtgatt     3480 gaactgcgtg aattcttaga caagatttat aacaaggttg gtggtgagca ggaagagctt    3540
gatagcttga ctgacgcaga aatcttggcg ctttcaggta acttacgtgc tggtgttcca    3600
ttagcgactc ctgtatttga tggtgctgaa gaaagccaga tcaaagactt acttgaattg    3660
gcagacattt ctcgtacagg tcaaacagta ttgtttgatg gtcgtacagg tgaacagttt    3720
gaccgtcctg taactgtagg ttacatgtac atgctgaaac tgaaccactt ggttgatgac    3780
aagatgcatg cgcgttcaac aggttcttac tcacttgtaa ctcaacaacc gcttggtggt    3840
aaagcacaat tcggtggtca gcgtttcggt gagatggaag tctgggcact tgaagcatac    3900
ggtgctgcat atacgctcca agaaatgctt acagtgaagt cggatgacgt cgaaggtcgt    3960
acacgcatct ataagaacat tgtagatggg aaccattaca tggatccggg tatgcctgaa    4020
```

```
tcgttcaacg tattgaccaa agagatccgt tctttaggta tcaacattga actgaaaaat    4080
ggtgactaa                                                            4089
```

<210> SEQ ID NO 33
<211> LENGTH: 350
<212> TYPE: DNA
<213> ORGANISM: Acinetobacter calcoaceticus

<400> SEQUENCE: 33

```
agacttgaaa gaagaataca agatctttga agaagcagct cgtgagcgtg taattcgttt     60
gcttaacggc caagagtcta acggtggtgg ttcgactaaa cgtggcgaca agctcgttga    120
cggtatgttg tctggtttag agcttgttga cttacttgaa atccaaccta cagatgaagc    180
aattgctgaa cgtttatctc aaattcaagt gttcttgaaa gagaagagcg cagaaattga    240
tgagaagttt gcagagaaga aacgtaagct ttcgactggt gatgagttaa caacaggtgt    300
tctgaaagtt gttaaagttt acctagcagt taaacgtcgt attcagcctg               350
```

<210> SEQ ID NO 34
<211> LENGTH: 350
<212> TYPE: DNA
<213> ORGANISM: Acinetobacter baumannii

<400> SEQUENCE: 34

```
agacttgaaa gaagaataca agatcttcga agaagcggct cgtgagcgtg taattcgttt     60
gcttaaaggc caagagtcta atggcggtgg ttcaactaaa cgtggtgata aactttctga    120
agatttatta tctggtttag agcttgttga tttacttgaa attcaaccag cagatgaagc    180
aatcgctgag cgtttaactc aaattcaagt gttcttgaaa gagaagagcg cagaaatcga    240
tgagaaattc gctgagaaga aacgtaagct tgccacaggt gatgaattaa cgactggcgt    300
attaaaagtt gttaaggttt acttagctgt taaacgtcgt attcagcctg               350
```

<210> SEQ ID NO 35
<211> LENGTH: 350
<212> TYPE: DNA
<213> ORGANISM: Acinetobacter sp.

<400> SEQUENCE: 35

```
agacttgaaa gaagaataca agatctttga agaagcagct cgtgagcgtg taattcgttt     60
gcttaaaggc caagagtcta atggcggtgg ttcaactaaa cgtggtgaca aactcgttga    120
agaagtgtta tctggtttag agcttgttga tttacttgaa attcaaccgg cagatgaagc    180
aatcgctgag cgtttaactc aaattcaagt gttcttaaaa gaaaagagcg cagaaattga    240
tgagaaattc gctgagaaga aacgtaagct tgcaacaggt gatgaattaa caactggcgt    300
attgaaagtt gttaaagttt acttagctgt taaacgtcgt attcagcctg               350
```

<210> SEQ ID NO 36
<211> LENGTH: 350
<212> TYPE: DNA
<213> ORGANISM: Acinetobacter haemolyticus

<400> SEQUENCE: 36

```
agacttgaaa gaagaataca aaatcttcga agaagcagca cgtgaacgta ttgttcgctt     60
gttgaaaggt caagagtcaa atggtggcgg tacaactaag cgcggcgata aactctcaga    120
agatgtattg tctggtttag agcttgttga tttacttgaa atccaaccag ctgatgaagc    180
gattgctgaa cgtttaacgc aaattcaagt gttcttgaaa gagaagagca tcgaaatcga    240
```

```
tgagaaattt gcagagaaga agcgtaagct ttctacaggt gatgaattaa caacgggtgt    300
attaaaagtt gttaaggttt accttgcggt taagcgtcgt attcagcctg              350
```

<210> SEQ ID NO 37
<211> LENGTH: 350
<212> TYPE: DNA
<213> ORGANISM: Acinetobacter junii

<400> SEQUENCE: 37

```
agacttgaaa gaagaataca aaatcttcga agaagcagca cgtgagcgta ttgttcgttt    60
gttgaaaggt caagaatcta acggtggtgg ttcgactaaa cgtggtgaga agctttcaga   120
agatatgttg tctggtctag agttagttga tctacttgaa atccaaccaa cagatgaagc   180
aattgctgag cgtttaactc aaattcaagt gttcttgaaa gaaaagagcc atgaaattga   240
tgaaaaattt gctgagaaga aacgtaaact ttctacaggg gatgagttaa caactggtgt   300
attgaaagtt gttaaggttt acctagcagt taaacgtcga atccaacctg              350
```

<210> SEQ ID NO 38
<211> LENGTH: 350
<212> TYPE: DNA
<213> ORGANISM: Acinetobacter sp.

<400> SEQUENCE: 38

```
agatttgaaa gaagaataca aaatctttga agaagcagca cgtgaacgta ttgttcgctt    60
gttgaaaggt aaagagtcta atggtggcgg tacaacgaag cgcggcgata aacttgcaga   120
agatatgttg tctggtttag agctggttga tttgttagaa atccaaccaa cagatgaagc   180
aatcgctgaa cgtttaactc aaattcaggt attcttgaaa gagaagagta tcgagattga   240
tgagaaattt gctgagaaga aacgcaaact ctctacaggt gatgaattaa caacgggtgt   300
attaaaagtt gttaaggttt accttgcagt gaaacgtcgt atccaaccgg              350
```

<210> SEQ ID NO 39
<211> LENGTH: 350
<212> TYPE: DNA
<213> ORGANISM: Acinetobacter johnsonii

<400> SEQUENCE: 39

```
agacttgaaa gaagaataca aaatcttcga agaagcagca cgtgaacgta ttgttcgttt    60
gttgacaggt caagagtcta acggtggtgg tacaaccaag cgtggcgata agctttctgt   120
agacgtattg tctggtttag agttggtgga tttacttgaa atccaaccga ctgatgaagc   180
tattgcagag cgtttaactc aaattcaagt gttcttgaaa gagaagagct tgaaattga    240 tgagaagttt gcagagaaaa aacgcaaact ttctacaggt gatgaattaa caacaggtgt   300
attgaaagtt gttaaggttt acttggctgt taaacgtcgc atccaaccgg              350
```

<210> SEQ ID NO 40
<211> LENGTH: 350
<212> TYPE: DNA
<213> ORGANISM: Acinetobacter lwoffii

<400> SEQUENCE: 40

```
agacttgaaa gaagagttca agatcttga agaagcagca cgtgaacgtg taattcgttt     60
gttgaacggt caagagtcga atggtggcgg taccactaaa cgtggcgaca aactgtctga   120
agacgtgttg tctggtttag agcttgttga tcttcttgaa attcaaccgg ttgatgaagc   180
aatcgctgaa cgtctaacgc aaattcaagt gttcttgaaa gagaagagct tcgaaattga   240
```

```
cgagaaattt gctgagaaaa aacgcaaact ttctacaggc gatgagctga ccactggcgt    300
attgaaagta gttaaagttt atcttgcggt aaaacgtcgc atccagccgg              350
```

```
<210> SEQ ID NO 41
<211> LENGTH: 350
<212> TYPE: DNA
<213> ORGANISM: Acinetobacter sp.

<400> SEQUENCE: 41
```

```
agacttgaaa gaagaattca aaatcttcga agaagctgca cgtgaacgtg taatccgtct    60
actgaatggc caagagtcga atggtggcgg tacaactaaa cgtggcgaca aactgtctga   120
agacgtgttg tctggtttag agcttgttga tcttcttgaa attcaaccag ttgatgaagc   180
aattgctgaa cgtttaactc aaattcaagt gttcttgaaa gagaagagct tcgaaattga   240
cgagaaattt gctgagaaaa aacgcaaact ttctacaggc gatgaactga ccactggcgt   300
tttaaaagtt gttaaggttt atcttgctgt aaaacgtcgc atccaaccgg              350
```

```
<210> SEQ ID NO 42
<211> LENGTH: 350
<212> TYPE: DNA
<213> ORGANISM: Acinetobacter sp.

<400> SEQUENCE: 42
```

```
agacttgaaa gaagagttca aaatcttcga agaagctgct cgtgaacgta ttgtgcgttt    60
attgaaaggt caagagtcaa atggtggtgg tacaacgaaa cgtggtgaca agctaactga   120
agacgtattg tctaacttag agcttgttga tctgttagaa gttcaaccag cagacgaagg   180
tattgctgag cgtttaacgc agattcaagt gttcttgaaa gagaagagcc acgagatcga   240
tgagaagttt gctgagaaaa aacgtaaact ttcaacgggt gatgaactga caactggtgt   300
gttgaaagtt gttaaagttt atcttgctgt taaacgtcgt atccagcctg              350
```

```
<210> SEQ ID NO 43
<211> LENGTH: 350
<212> TYPE: DNA
<213> ORGANISM: Acinetobacter sp.

<400> SEQUENCE: 43
```

```
agacttgaaa gaagaattca aaatcttcga agaagcagct cgtgaacgta ttatccgttt    60
gttaaaaggc caagagtcga atggcggcgg tactactaag cgcggtgata agctatctga   120
agatgtattg tctggtttag agcttgttga tcttttagaa gttcaaccaa cagatgaagg   180
catcgctgaa cgcttaactc aaattcaagt gttcttgaaa gagaagagct acgagattga   240
tgagaaattt gctgagaaaa aacgcaaact ttctacaggt gatgagctta caacaggtgt   300
cttgaaagtt gttaaagttt atttagctgt aaaacgtcgt atccagcctg              350
```

```
<210> SEQ ID NO 44
<211> LENGTH: 350
<212> TYPE: DNA
<213> ORGANISM: Acinetobacter radioresistens

<400> SEQUENCE: 44
```

```
agatttgaaa gaagaatata aaatctttga agaagcggct cgtgaacgta ttgtacgttt    60
gctgaaagat caggtgtcta acggcggtgg aaatactaaa cgtggtgaga aactgtctga   120
agaattgcta tctggccttg aactgattga tctgctcgaa atccagccaa gcgatgaagc   180
gattgctgaa cgtttaaccc agatccaggt gttcttgaaa gagaaaagca ccgagattga   240
```

```
cgagaagttt gccgagaaga aacgcaagct ttctacgggt gatgagctga ctcatggcgt    300
attgaaagtt gtgaaggttt atctagcagt taaacgtcgt atccagccgg              350
```

<210> SEQ ID NO 45
<211> LENGTH: 350
<212> TYPE: DNA
<213> ORGANISM: Acinetobacter sp.

<400> SEQUENCE: 45

```
agacttgaaa gaagagtaca aaatcttcga agaagcagca cgtgaacgta ttgttcgttt    60
gttgaaaggt caagagtcta acggtggcgg ttcaactaaa cgcggtgata aacttgctga   120
agacgtattg tctggtttag agcttgttga tttacttgaa atccaaccga ctgatgaggc   180
aattgcagag cgtctaactc aaattcaagt gttcttgaaa gagaagagct atgaaattga   240
tgagaagttt gcagagaaga agcgtaaact ttctacaggt gatgaattaa ccactggcgt   300
attgaaagtt gttaaggttt accttgcggt taaacgtcgt atccagcctg              350
```

<210> SEQ ID NO 46
<211> LENGTH: 350
<212> TYPE: DNA
<213> ORGANISM: Acinetobacter sp.

<400> SEQUENCE: 46

```
agacttgaaa gaagaataca aaatcttcga agaagcagca cgtgaacgta ttgttcgttt    60
gttgaaaggt caagaatcta acggtggcgg ttcaaccaaa cgcggcgata aactttcaga   120
agatgtattg tctggcttag agcttgttga tttacttgaa atccagccaa atgatgaagc   180
aattgctgaa cgtttaactc agattcaagt gttcttgaaa gagaagagct acgagattga   240
cgagaagttt gctgagaaga agcgtaaact ttctacaggt gatgaattaa caacgggcgt   300
attgaaagtt gttaaggttt accttgcggt gaaacgtcgt atccagcctg              350
```

<210> SEQ ID NO 47
<211> LENGTH: 350
<212> TYPE: DNA
<213> ORGANISM: acinetobacter schindleri

<400> SEQUENCE: 47

```
agacttgaaa gaagaataca aaatcttcga agaagcagca cgtgaacgta ttattcgtct    60
gttgaaaggt caggaatcta acggtggtgg cacaactaaa cgcggtgaca aactgtctga   120
agatgttctg tctggtttag agcttgttga tctgttagac atccaaccag tagatgaagc   180
aattgctgag cgtttaactc aaattcaagt gttcttgaaa gagaagagcc ttgaaattga   240
tgaaaagttt gctgagaaga aacgcaaatt atctacaggc gatgaactta caactggcgt   300
actgaaagtt gttaaggttt atctagcggt taaacgtcgt atccagcctg              350
```

<210> SEQ ID NO 48
<211> LENGTH: 350
<212> TYPE: DNA
<213> ORGANISM: acinetobacter ursingii

<400> SEQUENCE: 48

```
agatttgaaa gaagaataca aaatctttga agaagcagca cgtgaacgta ttgtgcgctt    60
attaaaaggt caggattcta acggtggtgg cacgactaaa cgtggtgaca aactgactga   120
agatttattg tctggtcttg agctggtcga tttacttgaa attcaaccaa gtgatgaagg   180
catcgctgag cgtttaagtc aaattcaagt attcttgaaa gagaagagtg ctgaaattga   240
```

```
tgagaaattt gctgagaaaa aacgcaaatt agcgacgggt gatgagttaa cgacgggtgt    300
cttgaaagtc gttaaagtct accttgcagt taaacgtcgt atccagccag              350
```

<210> SEQ ID NO 49
<211> LENGTH: 350
<212> TYPE: DNA
<213> ORGANISM: acinetobacter baylyi

<400> SEQUENCE: 49

```
agacttgaaa gaagaattca aaatcttcga agaagctgct cgtgaacgta ttatccgttt    60
gttaaaaggc caagagtcaa atggcggcgg tacgaccaag cgcggtgata agctatctga   120
agatgtattg tctggtttag agcttgttga tcttttagaa gttcaaccaa cagacgaagg   180
catcgctgaa cgcttaactc aaattcaagt gttcttgaaa gagaagagct acgagattga   240
tgagaaattt gctgagaaaa aacgcaaact ttctacaggt gatgagctta caacaggtgt   300
attgaaagtt gttaaagttt acttagctgt aaaacgtcgt atccagcctg              350
```

<210> SEQ ID NO 50
<211> LENGTH: 350
<212> TYPE: DNA
<213> ORGANISM: acinetobacter bouvetii

<400> SEQUENCE: 50

```
agacttgaaa gaagaataca aaatcttcga agaagctgcg cgtgaacgta ttgtgcgctt    60
gctaaaaggt caagaatcga atggcggcgg cacaactaaa cgcggtgaca aactttctga   120
agaagtattg tctggtttag agcttgctga tctgcttgaa attcagccta cagacgaagg   180
cattgctgag cgcttaactc aaattcaagt gttcttgaaa gagaagagca ctgaaattga   240
tgagaaattt gctgagaaaa aacgcaaact ttctacaggc gatgagctta caactggtgt   300
attgaaagtt gttaaagttt acttagctgt aaaacgccgc atccagccgg              350
```

<210> SEQ ID NO 51
<211> LENGTH: 350
<212> TYPE: DNA
<213> ORGANISM: acinetobacter gerneri

<400> SEQUENCE: 51

```
agatttgaaa gaagaatata aaatctttga agaagctgct cgtgaacgta ttgttcgctt    60
gttgaaaggt caagaatcaa atggtggtgg ttcaactaaa cgtggtgaca aactttctga   120
agaattgtta tctggtttag agctagttga tcttcttgaa attcaaccaa gtgatgaagg   180
tattgctgaa cgtttaactc aaattcaagt gttcttgaaa gaaaagagcc atgaaattga   240
tgagaaattt gctgagaaaa aacgcaaact ttctacaggt gatgagctta caactggtgt   300
attgaaagtt gttaaagtgt atttggctgt taaacgtcgt atccaaccgg              350
```

<210> SEQ ID NO 52
<211> LENGTH: 350
<212> TYPE: DNA
<213> ORGANISM: acinetobacter grimontii

<400> SEQUENCE: 52

```
agacttgaaa gaagaataca aaatcttcga agaagcagca cgtgagcgta ttgttcgttt    60
gttgaaaggt caagaatcta acggtggtgg ttcgactaaa cgtggtgaga agcttttcaga  120 agatatgttg tctggtctag agttagttga tctacttgaa atccaaccaa cagatgaagc   180
aattgctgag cgtttaactc aaattcaagt gttcttgaaa gaaaagagcc atgaaattga   240
```

```
tgaaaagttt gctgagaaga aacgtaaact ttctacaggt gatgagttaa caactggtgt      300
attgaaagtt gttaaggttt acctagcagt taaacgtcgt atccaacctg                 350

<210> SEQ ID NO 53
<211> LENGTH: 350
<212> TYPE: DNA
<213> ORGANISM: acinetobacter tandoii

<400> SEQUENCE: 53
agacttgaaa gaagaatata aaatcttcga agaagcagca cgtgaacgta ttgttcgctt      60
gttgagcggt caagaatcga atggcggtgg cggcacgaag cgtggtgaca aactttcaga     120
agatatgttg tctggcttag agttggttga tttacttgaa atccagccaa gtgatgaagc     180
gattgctgaa cgtttaaccc aaattcaagt gttcttgaaa gagaagagct ttgaaattga     240
cgagaaattt gctgagaaaa acgcaaaact ttctacaggt gatgaactaa caactggcgt     300
attgaaagtt gtgaaggttt accttgcagt taaacgtcgt atccagcctg                350

<210> SEQ ID NO 54
<211> LENGTH: 350
<212> TYPE: DNA
<213> ORGANISM: acinetobacter tjernbergiae

<400> SEQUENCE: 54
agatttgaaa gaagaataca aaatcttcga agaagcagca cgtgaacgta ttgttcgttt      60
gttgacaggt caagagtcta acggtggtgg ctcaactaag cgtggtgata aactttctgc     120
agatgtcttg tctggtttag agctggttga tttacttgaa attcaaccga ctgatgaagc     180
aattgcagag cgtttaactc agattcaagt gttcttgaaa gagaagagct acgaaattga     240
cgagaagttt gcagagaaga acgtaaaact ttctacaggt gatgaattaa caacgggtgt     300
attgaaagtt gttaaggttt acctcgctgt taaacgtcgt atccagcctg                350

<210> SEQ ID NO 55
<211> LENGTH: 350
<212> TYPE: DNA
<213> ORGANISM: acinetobacter towneri

<400> SEQUENCE: 55
agacttgaaa gaagaataca aaatctttga agaagctgca cgtgaacgta ttatccgctt      60
attgaaaggc caagagtcta acggtggcgg tacaaccaaa cgtggcgaca agctttctga     120
agatatgttg tcaggcttgg ctttagtgga tttacttgaa attcaaccaa gtgatgaagc     180
gattgctgaa cgcttaacgc aaattcaaac cttcttgaaa gagaagagct ttgaaattga     240
tgagaaattt gctgagaaga acgtaaaact ttctacaggc gatgagctca ctacaggcgt     300
gttgaaagtt gttaaggtgt acttggctgt taaacgtcgc atccaaccgg                350

<210> SEQ ID NO 56
<211> LENGTH: 350
<212> TYPE: DNA
<213> ORGANISM: acinetobacter parvus

<400> SEQUENCE: 56
agacttgaaa gaagaataca aaatcttcga agaagcagca cgtgaacgta ttgttcgttt      60
gttgaaaggt caagaatcta atggtggtgg ttcaaccaaa cgcggtgata aactttctgc     120
agaggtattg tctggtttag agttggttga tttacttgaa atccagccaa atgatgaagc     180
aattgctgag cgtttaactc aaattcaagt gttcttgaaa gagaagagtt acgagattga     240
```

```
cgagaagttt gctgagaaga agcgtaaact ttctacaggt gatgaattaa caactggcgt    300
attgaaagtt gttaaggttt acctggcagt taaacgtcgt atccagcctg               350
```

<210> SEQ ID NO 57
<211> LENGTH: 350
<212> TYPE: DNA
<213> ORGANISM: Acinetobacter baumannii

<400> SEQUENCE: 57

```
agatttgaaa gaagaataca agatcttcga agaagcggct cgtgagcgtg taattcgttt    60
gcttaaaggc caagagtcta atggcggtgg ttcaactaaa cgtggtgata aactttctga    120
agatttatta tctggtttag agcttgttga cttacttgaa attcaaccag cagatgaagc    180
aatcgctgag cgtttaactc aaattcaagt gttcttgaaa gagaagagcg cagaaatcga    240
tgagaaattc gctgagaaga aacgtaagct tgcaacaggt gatgaattaa caactggtgt    300
attaaaagtt gttaaagttt acttagctgt taaacgtcgt attcagcctg               350
```

<210> SEQ ID NO 58
<211> LENGTH: 350
<212> TYPE: DNA
<213> ORGANISM: Acinetobacter baumannii

<400> SEQUENCE: 58

```
agacttgaaa gaagaataca agatcttcga agaagcggct cgtgagcgtg taattcgttt    60
gcttaaaggc caagagtcta atggcggtgg ttcaactaaa cgtggtgata aactttctga    120
agatttatta tctggtttag agcttgttga cttacttgaa attcaaccag cagatgaagc    180
aatcgctgag cgtttaactc aaattcaagt gttcttgaaa gagaagagcg cagaaatcga    240
tgagaaattc gctgagaaga aacgtaagct tgcaacaggt gatgaattaa caactggcgt    300
attaaaagtt gttaaggttt acttagctgt taaacgtcgt attcagcctg               350
```

<210> SEQ ID NO 59
<211> LENGTH: 350
<212> TYPE: DNA
<213> ORGANISM: Acinetobacter baumannii

<400> SEQUENCE: 59

```
agacttgaaa gaagaataca agatcttcga agaagcggct cgtgagcgtg taatccgttt    60
acttaaaggc caagagtcta atggcggtgg ttcaactaaa cgtggtgata aactttctga    120
agatttatta tctggtttag agcttgttga cttacttgaa attcaaccag cagatgaagc    180
aatcgctgag cgtttaactc aaattcaagt gttcttgaaa gagaagagcg cagaaatcga    240
tgagaaattc gctgagaaga aacgtaagct tgcaacaggt gatgaattaa caactggcgt    300
attaaaagtt gttaaagttt acttagctgt taaacgtcgt attcagcctg               350
```

<210> SEQ ID NO 60
<211> LENGTH: 350
<212> TYPE: DNA
<213> ORGANISM: Acinetobacter baumannii

<400> SEQUENCE: 60

```
agacttgaaa gaagaataca agatcttcga agaagcggct cgtgagcgtg taattcgttt    60
gcttaaaggc caagagtcta atggcggtgg ttcaactaaa cgtggtgata aactttctga    120
agatttatta tctggtttag agcttgttga cttacttgaa attcaaccag cagatgaagc    180
aatcgctgag cgtttaactc aaattcaagt gttcttgaaa gagaagagcg cagaaatcga    240
```

```
tgagaaattc gctgagaaga aacgtaagct tgcaacaggt gatgaattaa caactggcgt    300
attaaaagtt gttaaagttt acttagctgt taaacgtcgt attcagcctg              350

<210> SEQ ID NO 61
<211> LENGTH: 350
<212> TYPE: DNA
<213> ORGANISM: Acinetobacter baumannii

<400> SEQUENCE: 61
agacttgaaa gaagaataca agatcttcga agaagcggct cgtgagcgtg taattcgttt    60
gcttaaaggc caagagtcta atggcggtgg ttcaactaaa cgtggtgata aactttctga   120
agatttatta tctggtttag agcttgttga cttacttgaa attcaaccag cagatgaagc   180
aatcgctgag cgtttaactc aaattcaagt gttcttgaaa gagaagagcg cagaaatcga   240
tgagaaattc gctgagaaga aacgtaagct tgcaacaggt gatgaattaa caactggcgt   300
attaaaagtt gttaaggttt acttagctgt taaacgtcgt attcagcctg              350

<210> SEQ ID NO 62
<211> LENGTH: 350
<212> TYPE: DNA
<213> ORGANISM: Acinetobacter baumannii

<400> SEQUENCE: 62
agacttgaaa gaagaataca agatcttcga agaagcggct cgtgagcgtg taatccgttt    60
acttaaaggc caagagtcta atggcggtgg ttcaactaaa cgtggtgata aactttctga   120
agatttatta tctggtttag agcttgttga cttacttgaa attcaaccag cagatgaagc   180
aatcgctgag cgtttaactc aaattcaagt gttcttgaaa gagaagagcg cagaaatcga   240
tgagaaattc gctgagaaga aacgtaagct tgcaacaggt gatgaattaa caactggcgt   300
attaaaagtt gttaaagttt acttagctgt taaacgtcgt attcagcctg              350

<210> SEQ ID NO 63
<211> LENGTH: 350
<212> TYPE: DNA
<213> ORGANISM: Acinetobacter baumannii

<400> SEQUENCE: 63
agacttgaaa gaagaataca agatcttcga agaagcggct cgtgagcgtg taattcgttt    60
gcttaaaggc caagagtcta atggcggtgg ttcaactaaa cgtggtgata aactttctga   120
agatttatta tctggtttag agcttgttga tttacttgaa attcaaccag cagatgaagc   180
aatcgctgag cgtttaactc aaattcaagt gttcttgaaa gagaagagcg cagacatcga   240
tgagaaattc gctgagaaga aacgtaagct tgcaacaggt gatgaattaa cgactggcgt   300
attaaaagtt gttaaggttt acttagctgt taaacgtcgt attcagcctg              350

<210> SEQ ID NO 64
<211> LENGTH: 350
<212> TYPE: DNA
<213> ORGANISM: Acinetobacter baumannii

<400> SEQUENCE: 64
agacttgaaa gaagaataca agatcttcga agaagcggct cgtgagcgtg taattcgttt    60
gcttaaaggc caagagtcta atggcggtgg ttcaactaaa cgtggtgata aactttctga   120
agatttatta tctggtttag agcttgttga cttacttgaa attcaaccag cagatgaagc   180
aatcgctgag cgtttaactc aaattcaagt gttcttgaaa gagaagagcg cagaaatcga   240
```
tgagaaattc gctgagaaga aacgtaagct tgcaacaggt gatgaattaa caactggcgt        300
attaaaagtt gttaaagttt acttagctgt taaacgtcgt attcagcctg                   350

<210> SEQ ID NO 65
<211> LENGTH: 350
<212> TYPE: DNA
<213> ORGANISM: Acinetobacter baumannii

<400> SEQUENCE: 65
agacttgaaa gaagaataca agatcttcga agaagcggct cgtgagcgtg taatccgttt        60
acttaaaggc caagagtcta atggcggtgg ttcaactaaa cgtggtgata aactttctga       120
agatttatta tctggtttag agcttgttga cttacttgaa attcaaccag cagatgaagc       180
aatcgctgag cgtttaactc aaattcaagt gttcttgaaa gagaagagcg cagaaatcga       240
tgagaaattc gctgagaaga aacgtaagct tgcaacaggt gatgaattaa caactggcgt        300
attaaaagtt gttaaagttt acttagctgt taaacgtcgt attcagcctg                   350

<210> SEQ ID NO 66
<211> LENGTH: 350
<212> TYPE: DNA
<213> ORGANISM: Acinetobacter baumannii

<400> SEQUENCE: 66
agacttgaaa gaagaataca agatcttcga agaagcggct cgtgagcgtg taattcgttt        60
gcttaaaggc caagagtcta atggcggtgg ttcaactaaa cgtggtgata aactttctga       120
agatttatta tctggtttag agcttgttga cttacttgaa attcaaccag cagatgaagc       180
aatcgctgag cgtttaactc aaattcaagt gttcttgaaa gagaagagcg cagaaatcga       240
tgagaaattc gctgagaaga aacgtaagct tgcaacaggt gatgaattaa caactggtgt        300
attaaaagtt gttaaagttt acttagctgt taaacgtcgt attcagcctg                   350

<210> SEQ ID NO 67
<211> LENGTH: 350
<212> TYPE: DNA
<213> ORGANISM: Acinetobacter baumannii

<400> SEQUENCE: 67
agacttgaaa gaagaataca agatcttcga agaagcggct cgtgagcgtg taattcgttt        60
gcttaaaggc caagagtcta atggcggtgg ttcaactaaa cgtggtgata aactttctga       120
agatttatta tctggtttag agcttgttga cttacttgaa attcaaccag cagatgaagc       180
aatcgctgag cgtttaactc aaattcaagt gttcttgaaa gagaagagcg cagaaatcga       240
tgagaaattc gctgagaaga aacgtaagct tgcaacaggt gatgaattaa caactggtgt        300
attaaaagtt gttaaagttt acttagctgt taaacgtcgt attcagcctg                   350

<210> SEQ ID NO 68
<211> LENGTH: 350
<212> TYPE: DNA
<213> ORGANISM: Acinetobacter baumannii

<400> SEQUENCE: 68
agacttgaaa gaagaataca agatcttcga agaagcggct cgtgagcgtg taattcgttt        60
gcttaaaggc caagagtcta atggcggtgg ttcaactaaa cgtggtgata aactttctga       120
agatttatta tctggtttag agcttgttga cttacttgaa attcaaccag cagatgaagc       180
aatcgctgag cgtttaactc aaattcaagt gttcttgaaa gagaagagcg cagaaatcga       240

```
tgagaaattc gctgagaaga aacgtaagct tgcaacaggt gatgaattaa caactggcgt    300
attgaaagtt gttaaagttt acttagctgt taaacgtcgt attcagcctg              350
```

<210> SEQ ID NO 69
<211> LENGTH: 350
<212> TYPE: DNA
<213> ORGANISM: Acinetobacter baumannii

<400> SEQUENCE: 69

```
agacttgaaa gaagaataca agatcttcga agaagcggct cgtgagcgtg taattcgttt    60
gcttaaaggc caagagtcta atggcggtgg ttcaactaaa cgtggtgata aactttctga   120
agatttatta tctggtttag agcttgttga tttacttgaa attcaaccag cagatgaagc   180
aatcgctgag cgtttaactc aaattcaagt gttcttgaaa gagaagagcg cagaaatcga   240
tgagaaattc gctgagaaga aacgtaagct tgcaacaggt gatgaattaa cgactggcgt   300
attaaaagtt gttaaggttt acttagctgt taaacgtcgt attcagcctg              350
```

<210> SEQ ID NO 70
<211> LENGTH: 350
<212> TYPE: DNA
<213> ORGANISM: Acinetobacter baumannii

<400> SEQUENCE: 70

```
agacttgaaa gaagaataca agatcttcga agaagcggct cgtgagcgtg taattcgttt    60
gcttaaaggc caagagtcta atggcggtgg ttcaactaaa cgtggtgata aactttctga   120
agatttatta tctggtttag agcttgttga cttacttgaa attcaaccag cagatgaagc   180
aatcgctgag cgtttaactc aaattcaagt gttcttgaaa gagaagagcg cagaaatcga   240
tgagaaattc gctgagaaga aacgtaagct tgcaacaggt gatgaattaa caactggtgt   300
attgaaagtt gttaaagttt acttagctgt taaacgtcgt attcagcctg              350
```

<210> SEQ ID NO 71
<211> LENGTH: 350
<212> TYPE: DNA
<213> ORGANISM: Acinetobacter baumannii

<400> SEQUENCE: 71

```
agacttgaaa gaagaataca agatcttcga agaagcggct cgtgagcgtg taattcgttt    60
gcttaaaggc caagagtcta atggcggtgg ttcaactaaa cgtggtgata aactttctga   120
agatttatta tctggtttag agcttgttga tttacttgaa attcaaccag cagatgaagc   180
aatcgctgag cgtttaactc aaattcaagt gttcttgaaa gagaagagcg cagaaatcga   240
tgagaaattc gctgagaaga aacgtaagct tgccacaggt gatgaattaa cgactggcgt   300
attaaaagtt gttaaggttt acttagctgt taaacgtcgt attcagcctg              350
```

<210> SEQ ID NO 72
<211> LENGTH: 350
<212> TYPE: DNA
<213> ORGANISM: Acinetobacter baumannii

<400> SEQUENCE: 72

```
agacttgaaa gaagaataca agatcttcga agaagcggct cgtgagcgtg taatccgttt    60
acttaaaggc caagagtcta atggcggtgg ttcaactaaa cgtggtgata aactttctga   120
agatttatta tctggtttag agcttgttga cttacttgaa attcaaccag cagatgaagc   180
aatcgctgag cgtttaactc aaattcaagt gttcttgaaa gagaagagcg cagaaatcga   240
```

```
tgagaaattc gctgagaaga aacgtaagct tgcaacaggt gatgaattaa caactggcgt    300
attaaaagtt gttaaagttt acttagctgt taaacgtcgt attcagcctg              350
```

<210> SEQ ID NO 73
<211> LENGTH: 350
<212> TYPE: DNA
<213> ORGANISM: Acinetobacter baumannii

<400> SEQUENCE: 73

```
agacttgaaa gaagaataca agatcttcga agaagcggct cgtgagcgtg taattcgttt    60
gcttaaaggc caagagtcta atggcggtgg ttcaactaaa cgtggtgata aactttctga   120
agatttatta tctggtttag agcttgttga cttacttgaa attcaaccag cagatgaagc   180
aatcgctgag cgtttaactc aaattcaagt gttcttgaaa gagaagagcg cagaaatcga   240
tgagaaattc gctgagaaga aacgtaagct tgcaacaggt gatgaattaa caactggtgt   300
attgaaagtt gttaaagttt acttagctgt taaacgtcgt attcagcctg              350
```

<210> SEQ ID NO 74
<211> LENGTH: 350
<212> TYPE: DNA
<213> ORGANISM: Acinetobacter baumannii

<400> SEQUENCE: 74

```
agacttgaaa gaagaataca agatcttcga agaagcggct cgtgagcgtg taattcgttt    60
gcttaaaggc caagagtcta atggcggtgg ttcaactaaa cgtggtgata aactttctga   120
agatttatta tctggtttag agcttgttga cttacttgaa attcaaccag cagatgaagc   180
aatcgctgag cgtttaactc aaattcaagt gttcttaaaa gagaagagcg cagaaatcga   240
tgagaaattc gctgagaaga aacgtaagct tgcaacaggt gatgaattaa caactggcgt   300
attgaaagtt gttaaagttt acttagctgt taaacgtcgt attcagcctg              350
```

<210> SEQ ID NO 75
<211> LENGTH: 350
<212> TYPE: DNA
<213> ORGANISM: Acinetobacter baumannii

<400> SEQUENCE: 75

```
agacttgaaa gaagagtata aaatcttcga agaagcggct cgtgaacgtg taattcgttt    60
acttaaaggt caagagtcta atggcggtgg ttcaactaaa cgtggcgata aactttctga   120
agatttattg tctggcttag agcttgttga tttacttgaa attcaaccga cagatgaagc   180
aatcgctgag cgtttaactc agattcaagt gttcttgaaa gagaagagcg cagaaattga   240
tgagaaattc gctgagaaga aacgtaagct tgcaacaggt gatgagttaa caactggcgt   300
attgaaagtt gttaaagttt acttagctgt taaacgtcgt attcagcctg              350
```

<210> SEQ ID NO 76
<211> LENGTH: 350
<212> TYPE: DNA
<213> ORGANISM: Acinetobacter baumannii

<400> SEQUENCE: 76

```
agacttgaaa gaagaataca agatcttcga agaagcggct cgtgagcgtg taatccgttt    60
acttaaaggc caagagtcta atggcggtgg ttcaactaaa cgtggtgata aactttctga   120
agatttatta tctggtttag agcttgttga cttacttgaa attcaaccag cagatgaagc   180
aatcgctgag cgtttaactc aaattcaagt gttcttgaaa gagaagagcg cagaaatcga   240
```

```
tgagaaattc gctgagaaga aacgtaagct tgcaacaggt gatgaattaa caactggcgt    300
attaaaagtt gttaaagttt acttagctgt taaacgtcgt attcagcctg              350

<210> SEQ ID NO 77
<211> LENGTH: 450
<212> TYPE: DNA
<213> ORGANISM: Acinetobacter calcoaceticus

<400> SEQUENCE: 77
gtgataaaat ggctggtcgt cacggtaaca aggtgttgt atctaacatt ttacctgttg     60
aagacatgcc acacgatgct aacgtgtgc cggtagatat cgtattgaac ccattgggtg    120
taccatctcg tatgaacgtg ggtcagattc ttgagactca cttgggtatg gcagctaaag   180
ggcttggtga taaaatcgaa aaaatgttga agaacagcg cacagtttta gaacttcgcg    240
aattcttaga caagatttat aacaaagtcg gcggcgagca agaagatctt gatagcttaa   300
ctgatgctga agtcttagca ctttcaggca acttacgtgc tggtgtgcct ttagctactc   360
ctgtatttga tggtgctgaa gaaagtcaaa ttaaagactt acttgaatta gctgatattt   420
cgcgtactgg tcaaacagta ttgtttgatg                                    450

<210> SEQ ID NO 78
<211> LENGTH: 450
<212> TYPE: DNA
<213> ORGANISM: Acinetobacter baumannii

<400> SEQUENCE: 78
gtgataagat ggctggtcgt cacggtaaca agggtgttgt atctaacatc ttacctgttg    60
aagacatgcc acatgatgct aacgtgtgc cggtagatat cgtattgaac ccgctgggtg   120
taccatctcg tatgaacgtg ggtcagattc tagagactca cttgggtatg gcggctaaag   180
ggcttggtga caaaatcgaa aaaatgttga agaacaacg tacagtttta gaactgcgcg    240
aattcttaga caagatttat aacaaagtcg gcggtgagca agaagatctt gatagcttga   300
ctgatgaaga aattctagcg cttgcaggta acttgcgtgc gggtgtgcct ttagctactc   360
ctgtatttga tggtgctgaa gaaagtcaaa ttaaagactt acttgaattg gctgacattt   420
cacgtacggg tcaaacagta ttgtttgacg                                    450

<210> SEQ ID NO 79
<211> LENGTH: 450
<212> TYPE: DNA
<213> ORGANISM: Acinetobacter sp.

<400> SEQUENCE: 79
gtgataagat ggctggtcgt cacggtaaca agggtgttgt atctaacatc ttacctgttg    60
aagacatgcc acacgatgct aacggtgtac cagtagatat cgtattgaac ccgttgggcg   120
taccatctcg tatgaacgtg ggtcagattc ttgagactca cttaggtatg gcggctaaag   180
ggcttggtga taaaatcgag aaaatgttga agaacagcg tacagtttta gaactgcgtg    240
aattcttaga caagatttat aacaaagtcg gtggtgagca agaagatctt gatagcttaa   300
ctgatgctga agtcttggca ctttcaggca acttacgtgc tggtgtacct ttggctactc   360
ctgtattcga tggtgctgaa gaaagccaaa ttaaagactt gcttgagtta gctggtatct   420
ctcgtacagg tcaaacagta ttgtttgatg                                    450

<210> SEQ ID NO 80
<211> LENGTH: 450
<212> TYPE: DNA
```

<213> ORGANISM: Acinetobacter haemolyticus

<400> SEQUENCE: 80

| | | | | | |
|---|---|---|---|---|---|
| gtgataagat | ggcgggtcgt | cacggtaaca | agggtgtggt | atcaaatatc | ttacctgtag | 60 |
| aagacatgcc | gcatgatatt | cacggtgtgc | cagttgatat | cgtattgaac | ccattgggtg | 120 |
| taccatcacg | tatgaacgtg | ggtcagattc | ttgaaactca | cttgggtatg | gcggcaaaag | 180 |
| gtctgggtga | gcaaattgat | aagatgctcc | aacagcaacg | tacgattgct | gaattgcgtg | 240 |
| cgttcctcga | caagatttac | aacaaagttg | gtggcgaaca | agaagatctt | gatagcttaa | 300 |
| ccgacgaaga | agtttaaaa | cttgcaggta | acctgcgtgc | aggtgtgcct | ttggcgacac | 360 |
| cagtatttga | tggtgctgaa | gaaagtcaaa | ttaaagagtt | acttgagctt | gctgaattgc | 420 |
| cacgtactgg | tcaaaccgta | ttgtttgatg | | | | 450 |

<210> SEQ ID NO 81
<211> LENGTH: 450
<212> TYPE: DNA
<213> ORGANISM: Acinetobacter junii

<400> SEQUENCE: 81

| | | | | | |
|---|---|---|---|---|---|
| gtgataagat | ggcgggtcgt | cacggtaaca | agggtgttgt | atcaaacatc | ttaccagttg | 60 |
| aagatatgcc | acatgatgcc | aatggtgtgc | cagttgatat | cgtattgaac | ccactcggtg | 120 |
| taccatcgcg | tatgaacgtg | ggtcagattc | ttgaaactca | cttaggtatg | gcagcaaaag | 180 |
| gtttgggtga | gcagattgat | aaaatgctca | aacaacaacg | tacaattgcc | gagttacgtt | 240 |
| cattccttga | caagatttat | aataaagtgg | gtggtgagca | agaacagctt | gacacactaa | 300 |
| ctgacgaaga | gatctttaag | cttgcaggta | atttacgtgc | tggtgtgcct | ttggcaactc | 360 |
| cagtatttga | tggtgctgaa | gagtcacaaa | tcaaagagtt | acttgagctt | gcagagttac | 420 |
| cacgttctgg | tcaacaaatc | ttgtttgatg | | | | 450 |

<210> SEQ ID NO 82
<211> LENGTH: 450
<212> TYPE: DNA
<213> ORGANISM: Acinetobacter sp.

<400> SEQUENCE: 82

| | | | | | |
|---|---|---|---|---|---|
| gtgataagat | ggcgggtcgt | cacgggaaca | agggtgttgt | ctctaacatc | ttacctgttg | 60 |
| aagatatgcc | acatgatgcc | aatggtgtac | ctgttgacat | cgtattgaac | ccattgggtg | 120 |
| taccgtcgcg | tatgaacgtg | ggtcagattc | ttgaaaccca | tttgggcttg | gcggcaaaag | 180 |
| gtttgggtga | gcagatcgat | aagatgctgc | aacaacaacg | taccgttgct | gaacttcgtt | 240 |
| tgttccttga | taagatttac | aacaaagttg | gtggcgagca | agaagatctt | gatagcttaa | 300 |
| ctgatgaaga | agtgttgaag | cttgcaggta | acttacgtgc | aggtgttcct | ttggcaacac | 360 |
| cagtgtttga | tggtgctgaa | gaaagccaaa | ttaaagaatt | acttgaactt | gctgaattgc | 420 |
| cgcgttctgg | tcaacagact | ttgtttgatg | | | | 450 |

<210> SEQ ID NO 83
<211> LENGTH: 450
<212> TYPE: DNA
<213> ORGANISM: Acinetobacter johnsonii

<400> SEQUENCE: 83

| | | | | | |
|---|---|---|---|---|---|
| gtgataagat | ggcgggtcgt | cacggtaaca | agggtgttgt | ttctaacatc | ttgcctgttg | 60 |
| aagacatgcc | gcacgatgcc | aatggtgttc | cagtcgacat | cgtattgaac | ccactgggtg | 120 |

```
taccgtcacg tatgaacgtg ggtcagattc tagagactca cttaggtatg gcagcgaaag      180
gtcttggcga agaaatcgac aagatgttaa aagcgcaacg tactgtactt gagcttcgtg      240
gattcttaga caagatttat aacaaagttg gtggcgagca agaagatctt gatagcttaa      300
ctgatgatga aattttggtg ctttcgggta acttgcgtgc gggtgttcct cttgcaacgc      360
cagtattcga tggtgctgaa gaatctcaaa ttaaagactt gttagagctt gcgaacattt      420
cacgtactgg tcaaacagta ttgtatgatg                                       450
```

<210> SEQ ID NO 84
<211> LENGTH: 450
<212> TYPE: DNA
<213> ORGANISM: Acinetobacter lwoffii

<400> SEQUENCE: 84

```
gtgataagat ggccggtcgt cacggtaaca agggtgttgt atcaaacatc ttgccggtag      60
aagacatgcc acacgatgcc aatggtgtac ctgttgatat cgtactgaac ccgctgggcg     120
taccatcgcg tatgaacgtg ggtcagattc ttgaaactca cttaggtatg gctgccaaag     180
gtcttggcga tcaaatcgac aagatgatga agaacagcg tactgtactt gagcttcgtg     240
atttcctgga caagatttat aacaaagttg gtggcgagca agaagatctt gacagcttga     300
ctgatgaaga aatcttgaaa ctttctggta acttgcgtgc tggtgtgcct ttggcaacac     360
ctgtattcga tggtgctgaa gaaggtcaga tcaaagaatt gttacaactt gcaggtctat     420
caagtactgg tcagacagta ttatatgatg                                       450
```

<210> SEQ ID NO 85
<211> LENGTH: 450
<212> TYPE: DNA
<213> ORGANISM: Acinetobacter sp.

<400> SEQUENCE: 85

```
gtgataagat ggcgggtcgt cacggtaaca aaggtgttgt atcaaacatc ttgccggtag      60
aagacatgcc acatgatgcc aacggtgtac ctgttgatat cgtattgaac ccgcttggcg     120
taccatcacg tatgaacgtg ggtcagattc ttgaaactca cttgggtatg gcggcgaaag     180
gtcttggcga tcaaatcgac aagatgatga agagcaacg tactgtactt gagcttcgtg     240
atttcctgga caagatttac aataaagttg gtggcgagca agaagatctt gatagcttga     300
ctgatgaaga aatcttgaaa ctttctggca acttgcgtgc tggtgtgcct ttggctactc     360
ctgtattcga tggtgctgaa gaaggtcaga tcaaagagtt gttacaactt gcaggcctat     420
ctagtactgg tcagaccgta ttatatgatg                                       450
```

<210> SEQ ID NO 86
<211> LENGTH: 450
<212> TYPE: DNA
<213> ORGANISM: Acinetobacter sp.

<400> SEQUENCE: 86

```
gtgataagat ggcgggtcgt cacggtaaca agggtgttgt atcaaacatc ttaccagttg      60
aagatatgcc gcatgacatc catggtgttc cagtggatgt ggtacttaac ccactcggtg     120
taccatcacg tatgaacgtg ggtcagattc ttgaaactca cttgggtatg gcagcgaaag     180
gtcttggcga taagatcgac aagatgatga agagcaacg tactgttctt gaacttcgtg     240
aattcttaga caagatttat aacaaagttg gtggcgagca agaagatctt gatagcttga     300
ctgatgaaga aatcttggtg ttatcaggta acttgcgtaa aggtgttcct ttagctacac     360
```

```
cagtatttga tggtgcagaa gaaggacaaa tcaaagagtt acttgaactt ggtggtatct    420
cacgtacagg tcaaacagta ttgtatgatg                                     450
```

<210> SEQ ID NO 87
<211> LENGTH: 450
<212> TYPE: DNA
<213> ORGANISM: Acinetobacter sp.

<400> SEQUENCE: 87

```
gtgataagat ggcgggtcgt cacggtaaca aaggtgttgt atcaaacatc ttgcctgttg     60
aagacatgcc gcatgacatc catggtgttc cagttgatgt cgtacttaac ccattgggtg    120
taccatcacg tatgaacgtg ggtcagattc ttgaaactca cttaggtatg gctgcaaaag    180
gtcttggcga taagatcgac aagatgatga aagagcaacg taccgttctt gagcttcgtg    240
atttcttaga caagatttat aacaaagttg gtggcgagca agaagatctt gatagcttaa    300
ctgatgaaga aatcttggtg ttatcaggta acttgcgtaa aggtgttcct ttagctacgc    360
cagtatttga tggtgcagaa gaaagtcaga tcaaagagtt acttgagctt ggtggtatct    420
cacgtacagg tcaaacagta ttgtatgacg                                     450
```

<210> SEQ ID NO 88
<211> LENGTH: 450
<212> TYPE: DNA
<213> ORGANISM: Acinetobacter radioresistens

<400> SEQUENCE: 88

```
gtgataaaat ggcgggtcgt cacgggaaca agggtgtggt atcacaaatc ctgcctgtag     60
aagacatgcc acatgatgcc aatggtgttc cggttgatgt ggtattaaac ccgctaggtg    120
taccatcacg tatgaacgtg ggacagattc tggaaacaca tttgggtctt gctgcaaaag    180
gtttaggtga gcagatcgac aagatgctta acagcagcg tgctattgtt gaactgcgtg     240 atttttcttga taagatttac aataaagtcg gtggtgagca agaacagctt gatacactga    300
ctgatgatga aatcttgaaa cttgcaggaa acctcagcaa gggtgtgcca ctggcaactc    360
cagtatttga tggtgccgaa gaaggccaga tcaaagagtt acttgaactt gcagaactgc    420
cacgttctgg ccagcagatc ctgtttgatg                                     450
```

<210> SEQ ID NO 89
<211> LENGTH: 450
<212> TYPE: DNA
<213> ORGANISM: Acinetobacter sp.

<400> SEQUENCE: 89

```
gtgataaaat ggcgggtcgt cacgtaaca aaggtgttgt gtcaaacatc ttgcctgttg     60
aagacatgcc acacgatgcg aatggtgtac cagtcgatat cgtattgaac ccattgggtg    120
taccgtcacg tatgaacgtg ggtcagattc ttgagactca cttaggtatg gcggccaaag    180
gtcttggcga taaacttgaa aaaatgttga agaacaacg tacagtgtta gaactacgtg     240
acttcttaga caagatttat aacaaggtcg gtggtgagca agaagagctt gatagcttaa    300
ctgatgccga aatcttggcg ctttcaggta acttacgtgc tggtgttcca ttagcaacac    360
ctgtatttga tggtgctgaa gaaagccaga tcaaagactt acttgaatta gcagacatct    420
cacgtacagg tcaaacggta ttgtttgacg                                     450
```

<210> SEQ ID NO 90
<211> LENGTH: 450
<212> TYPE: DNA

<213> ORGANISM: Acinetobacter sp.

<400> SEQUENCE: 90

```
gtgataagat ggcgggtcgt cacggtaaca agggtgttgt atcaaacatc ttaccggttg    60
aagacatgcc acatgatgcg aatggcgtac cagtcgacat cgtattgaac ccactgggtg   120
taccgtcacg tatgaacgtg ggtcagattc ttgagactca cttgggtatg gcagcgaaag   180
gtcttggcga taaaatcgaa aaaatgttga agaacaacg tacagtgatt gaactgcgtg    240
aattcttaga caagatttat aacaaggttg gcggtgagca ggaagagctt gatagcttga   300
ctgatgcaga aatcttggcg ctttcaggta acttacgtgc tggtgttcca ttggcaacac   360
ctgtatttga tggtgctgaa gaaagccaga tcaaagacct acttgaactt gctgatatct   420
cacgtactgg tcaaacggta ttgtttgacg                                    450
```

<210> SEQ ID NO 91
<211> LENGTH: 450
<212> TYPE: DNA
<213> ORGANISM: acinetobacter schindleri

<400> SEQUENCE: 91

```
gtgataagat ggcgggtcgt cacggtaaca agggtgttgt atctaacatc ttgccggtag    60
aagacatgcc acacgatgcc aacggtgtac ctgttgatat cgttcttaac ccgctaggtg   120
taccgtcacg tatgaacgtg ggtcagattc ttgagactca cttgggtatg gccgccaaag   180
gtcttggcga caaaatcgac aagatgcttc aagagcaacg tacggtgctt gagcttcgtg   240
aattcttaga caagatttac aacaaagttg gtggtgagca agaagatctt gatagcctga   300
ctgatgatga aatcttggca ttgtctggta acttgcgtaa aggtgttcct ttggcaactc   360
cagtattcga cggtgctgaa gaatcgcaaa tcaaagaatt gttagagctt ggtggcattt   420
cacgtactgg tcaaacagta ttgtatgatg                                    450
```

<210> SEQ ID NO 92
<211> LENGTH: 450
<212> TYPE: DNA
<213> ORGANISM: acinetobacter ursingii

<400> SEQUENCE: 92

```
gtgataaaat ggcgggtcgt cacgggaaca aaggtgttgt ttctaacatc ttgcctgtag    60
aagacatgcc acatgatgcc aatggtgtac ctgtcgatat cgtccttgaac ccattaggtg  120
taccatcgcg tatgaacgtg ggtcagattc tggagacaca tctaggattg gcagccaaag   180
gtctgggtga acaaatcgat aagatgttgc aacaacagcg taccattgcc gaacttcgta   240
tcttccttga taagatttac aacaaggtcg gtggtgagca agaagatcta aacagtctga   300
ctgatgatga agtcttggta ttggctggca acttgcgtaa aggtgtacca ctagcaactc   360
ctgtatttga tggtgctgaa gaaagtcaaa ttaaagagtt acttgagttg gctgaattgc   420
cacgtactgg tcaacagatt ttgtttgatg                                    450
```

<210> SEQ ID NO 93
<211> LENGTH: 450
<212> TYPE: DNA
<213> ORGANISM: acinetobacter baylyi

<400> SEQUENCE: 93

```
gtgataaaat ggcgggtcgt cacggtaaca aaggtgttgt atcaaacatc ttgcctgttg    60
aagacatgcc gcatgatatc catggtgttc cagttgatgt cgtacttaac ccattgggtg   120
```

```
taccatcacg tatgaacgtg ggtcagattc ttgaaactca cttaggtatg gctgcaaaag    180
gtcttggcga taagatcgac aagatgatga aagagcaacg taccgttctt gagcttcgtg    240
atttcttaga caagatttat aacaaagttg gtggcgagca agaagatctt gatagcttaa    300
ctgatgaaga aatcttggtg ttatcaggta acttgcgtaa aggtgttcct ttagctacgc    360
cagtatttga tggtgcagaa gaaagtcaga tcaaagagtt acttgagctt ggtggtatct    420
cacgtacagg tcaaacagta ttgtatgacg                                     450

<210> SEQ ID NO 94
<211> LENGTH: 450
<212> TYPE: DNA
<213> ORGANISM: acinetobacter bouvetii

<400> SEQUENCE: 94
gtgataagat ggcgggtcgt cacggtaaca aggtgttgt atctaacatc ttgcctgtag      60
aagacatgcc gcacgatgcc aacggtgttc ctgtagacgt ggtgcttaac ccgctgggtg    120
taccgtcacg tatgaacgtg ggtcagattc ttgagactca cttgggcatg gcagcgaaag    180
gtcttggcga caaatcgac aagatgatga aagagcagcg cactgttctt gaacttcgtg     240
aattcttaga caagatttac aacaaagttg gcggcgagca agaagatctt gacagcttaa    300
ctgatgatga aatcttggcg cttttcaggca acctgcgtgc aggtgttcct ttggcaacgc   360
ctgtatttga cggtgctgaa gaatcacaaa ttaaagaatt gctagagctt ggcggcattt    420
cacgtactgg tcaaacagta ttgtatgatg                                     450

<210> SEQ ID NO 95
<211> LENGTH: 450
<212> TYPE: DNA
<213> ORGANISM: acinetobacter gerneri

<400> SEQUENCE: 95
gtgataaaat ggcgggtcgt cacgggaaca aggtgttgt atcaaacatc cttcctgtag      60
aagatatgcc gcatgacatc aacggtgttc ctgttgacgt agtacttaac ccactgggtg    120
taccgtcacg tatgaacgtg ggtcagattc ttgaaacaca tttaggttta gctgccaaag    180
gtcttggtga gcaaatcgat aagatgctca aagagcaacg tacgattgct gaacttcgtg    240
tgttcttgga caagatttat aacaaagttg gtggcgagca agaagatctt gatagcttaa    300
ctgatgaaga aatccttgtt ctttcaggta atttacgtaa aggtgttcct ttagcaactc    360
cagtatttga tggtgctgaa gaaggtcaaa ttaaagagct tcttgaactt gctgaacttc    420
cacgttctgg tcaaacagta ttgtatgacg                                     450

<210> SEQ ID NO 96
<211> LENGTH: 450
<212> TYPE: DNA
<213> ORGANISM: acinetobacter grimontii

<400> SEQUENCE: 96
gtgataagat ggcgggtcgt cacggtaaca agggtgttgt atcaaacatc ttaccagttg     60
aagacatgcc acatgatgcc aatggtgtgc cagttgatat cgtattgaac ccactcggtg    120
taccatcgcg tatgaacgtg ggtcagattc ttgaaactca cttaggtatg gcagcaaaag    180
gtttgggtga gcagattgat aaaatgctca acaacaacg tacaattgcc gagttacgtt     240
cattccttga caagatttat aataaagtgg tggtgagca agaacagctt gacacactga     300
ctgatgaaga gatcttgaaa ctttcaggta atttacgtgc tggtgtgcct ttggcaactc    360
```

```
cagtattcga tggtgctgaa gagtcacaaa tcaaagagtt acttgaactt gcagagttac    420
cacgttctgg tcaacagatc ttgtttgatg                                     450
```

<210> SEQ ID NO 97
<211> LENGTH: 450
<212> TYPE: DNA
<213> ORGANISM: acinetobacter tandoii

<400> SEQUENCE: 97

```
gtgataagat ggcgggtcgt cacggtaaca aggtgttgt gtctaacatc ctaccagtcg     60
aagacatgcc gcatgatgcc aatggtgttc cagtcgatat cgtattgaac ccgttgggtg   120
taccgtcacg tatgaacgtg gggcagattc ttgaaactca cttgggtatg gctgcgaaag   180
gtttgggtga gcaaattgat aagatgctca acaacagcg tgaaattgct gaactacgtg    240
ttttcctaga caaaatctac aacaaagtgg gcggtcagca agaagattta gacagcttaa   300
cagatgatga aatcttggtg ttggcaggta acttacgtgc aggtgtacct ttagcaactc   360
ctgtatttga tggtgctgaa gaaagccaaa tcaaagagtt actagagctg gctgaaattc   420
cacgttcggg tcaaaccgta ttgtatgatg                                    450
```

<210> SEQ ID NO 98
<211> LENGTH: 450
<212> TYPE: DNA
<213> ORGANISM: acinetobacter tjernbergiae

<400> SEQUENCE: 98

```
gtgataagat ggcgggtcgt catggtaaca aggtgttgt atctaacatc ttacctgttg     60
aagacatgcc tcatgatgcg aatggtgtgc cagtcgatat cgtattgaac ccattgggtg   120
taccgtcacg tatgaacgtg ggtcagattc ttgagactca cttaggtatg gcggcgaaag   180
gtcttggcga taaatcgaa aaaatgttga agaacagcg tacagtgatt gaactgcgtg     240
aattcttaga caagatttat aacaaggtcg gtggtgagca agaagagctt gacagcttaa   300
ctgatgcgga agtcttggca ctttcaggca acttacgtgc tggtgttcca ttggcaacgc   360
ctgtatttga cggtgctgaa gaaagtcaga ttaaagactt acttgaattg gcagacatct   420
cacgtacggg tcaaacggta ttgtttgacg                                    450
```

<210> SEQ ID NO 99
<211> LENGTH: 450
<212> TYPE: DNA
<213> ORGANISM: acinetobacter towneri

<400> SEQUENCE: 99

```
gtgataagat ggcgggtcgt cacggtaaca aggtgttgt atctaacatc ttgccagtag     60
aagacatgcc gcacgatgct aacggtgtac ctgttgacat cgtattgaac ccactaggtg   120
taccatctcg tatgaacgtg ggtcagattc ttgaaacaca cttgggtatg gcagccaaag   180
gtttgggtga gcaaattgac aagatgctca acaacaacg tgagattgct gaactacgtg    240
cgttcctaga caagatttat aacaaagtgg gtggcgagca agaagatctt gacagcttaa   300
ctgatgatga aatcttggta ttgcgggta acttgcgtgc aggtgttcca ttggctactc    360
ctgtatttga tggtgctgaa gaaggtcaaa tcaaagaatt gcttgaactg gctgaattac   420
cacgttcagg tcagaccgta ttgtatgatg                                    450
```

<210> SEQ ID NO 100
<211> LENGTH: 450
<212> TYPE: DNA

<213> ORGANISM: acinetobacter parvus

<400> SEQUENCE: 100

| gtgataagat ggcgggtcgt cacggtaaca aggtgttgt atcaaacatc ttgccagttg | 60 |
| aagacatgcc acatgatgcg aatggtgtgc cagtcgacat cgtattgaac ccacttggtg | 120 |
| taccgtcacg tatgaacgtg ggtcagattc ttgagactca cttgggtatg gcggcgaaag | 180 |
| gtcttggcga taagatcgaa aaaatgttga agaacaacg tacagtgatt gaactgcgtg | 240 |
| aattcttaga caagatttat aacaaggttg gtggtgagca ggaagagctt gatagcttga | 300 |
| ctgacgcaga aatcttggcg ctttcaggta acttacgtgc tggtgttcca ttagcgactc | 360 |
| ctgtatttga tggtgctgaa gaaagccaga tcaaagactt acttgaattg gcagacattt | 420 |
| ctcgtacagg tcaaacagta ttgtttgatg | 450 |

<210> SEQ ID NO 101
<211> LENGTH: 450
<212> TYPE: DNA
<213> ORGANISM: Acinetobacter baumannii

<400> SEQUENCE: 101

| gtgataagat ggctggtcgt cacggtaaca aggtgttgt atctaacatc ttacctgttg | 60 |
| aagacatgcc acatgatgct aacggtgtgc cggtagatat cgtattgaac ccgctgggtg | 120 |
| taccatctcg tatgaacgtg ggtcagattc tagagactca cttgggtatg gcggctaaag | 180 |
| ggcttggtga caaaatcgaa aaaatgttga agaacaacg tacagttta gaactgcgcg | 240 |
| aattcttaga caagatttat aacaaagtcg gcggtgagca agaagatctt gatagcttga | 300 |
| ctgatgaaga aattctagcg cttgcaggta acttgcgtgc gggtgtgcct ttagctactc | 360 |
| ctgtatttga tggtgctgaa gaaagtcaaa ttaaagactt acttgaattg gctgacattt | 420 |
| cacgtacggg tcaaacagta ttgtttgatg | 450 |

<210> SEQ ID NO 102
<211> LENGTH: 450
<212> TYPE: DNA
<213> ORGANISM: Acinetobacter baumannii

<400> SEQUENCE: 102

| gtgataagat ggctggtcgt cacggtaaca aggtgttgt atctaacatc ttacctgttg | 60 |
| aagacatgcc acatgatgct aacggtgtgc cagtagatat cgtattgaac ccgctgggtg | 120 |
| taccatctcg tatgaacgtg ggtcagattc tagagactca cttgggtatg gcggctaaag | 180 |
| ggcttggtga caaaatcgaa aaaatgttga agaacaacg tacagttta gaactgcgcg | 240 |
| aattcttaga caagatttat aacaaagtcg gtggtgagca agaagatctt gatagcttga | 300 |
| ctgatgaaga aattctagcg cttgcaggta acttgcgtgc gggtgtgcct ttagctactc | 360 |
| ctgtatttga tggtgctgaa gaaagtcaaa ttaaagactt acttgaattg gctgacattt | 420 |
| cacgtacggg tcaaacagta ttgtttgacg | 450 |

<210> SEQ ID NO 103
<211> LENGTH: 450
<212> TYPE: DNA
<213> ORGANISM: Acinetobacter baumannii

<400> SEQUENCE: 103

| gtgataagat ggctggtcgt cacggtaaca agggtgttgt atctaacatc ttacctgttg | 60 |
| aagacatgcc acatgatgct aacggtgtgc cggtagatat cgtattgaac ccgctgggtg | 120 |

```
taccatctcg tatgaacgtg ggtcagattc tagagactca cttgggtatg gcggctaaag      180
ggcttggtga caaaatcgaa aaaatgttga agaacaacg tacagtttta gaactgcgcg       240
aattcttaga caagatttat aacaaagtcg gcggtgagca agaagatctt gatagcttga      300
ctgatgaaga aattctagcg cttgcaggta acttgcgtgc gggtgtgcct ttagctactc      360
ctgtatttga tggtgctgaa gaaagtcaaa ttaaagactt acttgaattg gctgacattt      420
cacgtactgg tcaaacagta ttgtttgacg                                       450
```

<210> SEQ ID NO 104
<211> LENGTH: 450
<212> TYPE: DNA
<213> ORGANISM: Acinetobacter baumannii

<400> SEQUENCE: 104

```
gtgataagat ggctggtcgt cacggtaaca agggtgttgt atctaacatc ttacctgttg       60
aagacatgcc acatgatgct aacggtgtgc cggtagatat cgtattgaac ccgctaggtg      120
taccatctcg tatgaacgtg ggtcagattc tagagactca cttgggtatg gcggctaaag      180
ggcttggtga caaaatcgaa aaaatgttga agaacaacg tacagtttta gaactgcgcg       240
aattcttaga caagatttat aacaaagtcg gcggtgagca agaagatctt gatagcttga      300
ctgatgaaga aattctagcg cttgcaggta acttgcgtgc gggtgtgcct ttagctactc      360
ctgtatttga tggtgctgaa gaaagtcaaa ttaaagactt acttgaattg gctgacattt      420
cacgtacggg tcaaacagta ttgtttgacg                                       450
```

<210> SEQ ID NO 105
<211> LENGTH: 450
<212> TYPE: DNA
<213> ORGANISM: Acinetobacter baumannii

<400> SEQUENCE: 105

```
gtgataagat ggctggtcgt cacggtaaca agggtgttgt atctaacatc ttacctgttg       60
aagacatgcc acatgatgct aacggtgtgc cggtagatat cgtattgaac ccgctgggtg      120
taccatctcg tatgaacgtg ggtcagattc tagagactca cttgggtatg gcggctaaag      180
ggcttggtga caaaatcgaa aaaatgttga agaacaacg tacagtttta gaactgcgcg       240
aattcttaga caagatttat aacaaagtcg gcggtgagca agaagatctt gatagcttga      300
ctgatgaaga aattctagcg cttgcaggta acttgcgtgc gggtgtgcct ttagctactc      360
ctgtatttga tggtgctgaa gaaagtcaaa ttaaagactt acttgaattg gctgacattt      420
cacgtacggg tcaaacagta ttgtttgacg                                       450
```

<210> SEQ ID NO 106
<211> LENGTH: 450
<212> TYPE: DNA
<213> ORGANISM: Acinetobacter baumannii

<400> SEQUENCE: 106

```
gtgataagat ggctggtcgt cacggtaaca agggtgttgt atctaacatc ttacctgttg       60
aagacatgcc acatgatgct aacggtgtgc cggtagatat cgtattgaac ccgctgggtg      120
taccatctcg tatgaacgtg ggtcagattc tagagactca cttgggtatg gcggctaaag      180
ggcttggtga caaaatcgaa aaaatgttga agaacaacg tacagtttta gaactgcgcg       240
aattcttaga caagatttat aacaaagtcg gcggtgagca agaagatctt gatagcttga      300
ctgatgaaga aattctagcg cttgcaggta acttgcgtgc gggtgtgcct ttagctactc      360
```

```
ctgtatttga tggtgctgaa gaaagtcaaa ttaaagactt acttgaattg gctgacattt    420
cacgtactgg tcaaacagta ttgtttgacg                                     450
```

<210> SEQ ID NO 107
<211> LENGTH: 450
<212> TYPE: DNA
<213> ORGANISM: Acinetobacter baumannii

<400> SEQUENCE: 107

```
gtgataagat ggctggtcgt cacggtaaca agggtgttgt atctaacatc ttacctgttg    60
aagacatgcc acatgatgct aacggtgtgc cggtagatat cgtattgaac ccgctgggtg    120
taccatctcg tatgaacgtg ggtcagattc tagagactca cttgggtatg gcggctaaag    180
ggcttggtga caaaatcgaa aaaatgttga agaacaacg tacagtttta gaactgcgcg     240
aattcttaga caagatttat aacaaagtcg gcggtgagca agaagatctt gatagcttga    300
ctgatgaaga aattctagcg cttgcaggta acttgcgtgc gggtgtgcct ttagctactc    360
ctgtatttga tggtgctgaa gaaagtcaaa ttaaagactt acttgaattg gctgacattt    420
cacgtacggg tcaaacagta ttgtttgacg                                     450
```

<210> SEQ ID NO 108
<211> LENGTH: 450
<212> TYPE: DNA
<213> ORGANISM: Acinetobacter baumannii

<400> SEQUENCE: 108

```
gtgataagat ggctggtcgt cacggtaaca agggtgttgt atctaacatc ttacctgttg    60
aagacatgcc acatgatgct aacggtgtgc cggtagatat cgtattgaac ccgctaggtg    120
taccatctcg tatgaacgtg ggtcagattc tagagactca cttgggtatg gcggctaaag    180
ggcttggtga caaaatcgaa aaaatgttga agaacaacg tacagtctta gaactgcgcg     240
aattcttaga caagatttat aacaaagtcg gcggtgagca agaagatctt gatagcttga    300
ctgatgaaga aattctagcg cttgcaggta acttgcgtgc gggtgtgcct ttagctactc    360
ctgtatttga tggtgctgaa gaaagtcaaa ttaaagactt acttgaattg gctgacattt    420
cacgtacggg tcaaacagta ttgtttgatg                                     450
```

<210> SEQ ID NO 109
<211> LENGTH: 450
<212> TYPE: DNA
<213> ORGANISM: Acinetobacter baumannii

<400> SEQUENCE: 109

```
gtgataagat ggctggtcgt cacggtaaca agggtgttgt atctaacatc ttacctgttg    60
aagacatgcc acatgatgct aacggtgtgc cggtagatat cgtattgaac ccgctgggtg    120
taccatctcg tatgaacgtg ggtcagattc tagagactca cttgggtatg gcggctaaag    180
ggcttggtga caaaatcgaa aaaatgttga agaacaacg tacagtttta gaactgcgcg     240
aattcttaga caagatttat aacaaagtcg gcggtgagca agaagatctt gatagcttga    300
ctgatgaaga aattctagcg cttgcgggta acttgcgtgc gggtgtgcct ttagctactc    360
ctgtatttga tggtgctgaa gaaagtcaaa ttaaagactt acttgaattg gctgacattt    420
cacgtactgg tcaaacagta ttgtttgacg                                     450
```

<210> SEQ ID NO 110
<211> LENGTH: 450
<212> TYPE: DNA

<213> ORGANISM: Acinetobacter baumannii

<400> SEQUENCE: 110

| | |
|---|---|
| gtgataagat ggctggtcgt cacggtaaca aggtgttgt atctaacatc ttacctgttg | 60 |
| aagacatgcc acatgatgct aacggtgtgc cggtagatat cgtattgaac ccgctgggtg | 120 |
| taccatctcg tatgaacgtg ggtcagattc tagagactca cttgggtatg gcggctaaag | 180 |
| ggcttggtga caaaatcgaa aaaatgttga agaacaacg tacagttta gaactgcgcg | 240 |
| aattcttaga caagatttat aacaaagtag gcggtgagca agaagatctt gatagcttga | 300 |
| ctgatgaaga aattctagcg cttgcaggta acttgcgtgc gggtgtgcct ttagctactc | 360 |
| ctgtatttga tggtgctgaa gaaagtcaaa ttaaagactt acttgaattg gctgacattt | 420 |
| cacgtacggg tcaaacagta ttgtttgatg | 450 |

<210> SEQ ID NO 111
<211> LENGTH: 450
<212> TYPE: DNA
<213> ORGANISM: Acinetobacter baumannii

<400> SEQUENCE: 111

| | |
|---|---|
| gtgataagat ggctggtcgt cacggtaaca aggtgttgt atctaacatc ttacctgttg | 60 |
| aagacatgcc acatgatgct aacggtgtgc cggtagatat cgtattgaac ccgctgggtg | 120 |
| taccatctcg tatgaacgtg ggtcagattc tagagactca cttgggtatg gcggctaaag | 180 |
| ggcttggtga caaaatcgaa aaaatgttga agaacaacg tacagttta gaactgcgcg | 240 |
| aattcttaga caagatttat aacaaagtag gcggtgagca agaagatctt gatagcttga | 300 |
| ctgatgaaga aattctagcg cttgcaggta acttgcgtgc gggtgtgcct ttagctactc | 360 |
| ctgtatttga tggtgctgaa gaaagtcaaa ttaaagactt acttgaattg gctgacattt | 420 |
| cacgtacggg tcaaacagta ttgtttgatg | 450 |

<210> SEQ ID NO 112
<211> LENGTH: 450
<212> TYPE: DNA
<213> ORGANISM: Acinetobacter baumannii

<400> SEQUENCE: 112

| | |
|---|---|
| gtgataagat ggctggtcgt cacggtaaca aggtgttgt atctaacatc ttacctgttg | 60 |
| aagacatgcc acatgatgct aacggtgtgc cggtagatat cgtattgaac ccgctgggtg | 120 |
| taccatctcg tatgaacgtg ggtcagattc tagagactca cttgggtatg gcggctaaag | 180 |
| ggcttggtga caaaatcgaa aaaatgttga agaacaacg tacagttta gaactgcgcg | 240 |
| aattcttaga caagatttat aacaaagtcg gtggtgagca agaagatctt gatagcttga | 300 |
| ctgatgaaga aattctagcg cttgcaggta acttgcgtgc gggtgtgcct ttagctactc | 360 |
| ctgtatttga tggtgctgaa gaaagtcaaa ttaaagactt acttgaattg gctgacattt | 420 |
| cacgtactgg tcaaacagta ttgtttgacg | 450 |

<210> SEQ ID NO 113
<211> LENGTH: 450
<212> TYPE: DNA
<213> ORGANISM: Acinetobacter baumannii

<400> SEQUENCE: 113

| | |
|---|---|
| gtgataagat ggctggtcgt cacggtaaca agggtgttgt atctaacatc ttacctgttg | 60 |
| aagacatgcc acatgatgct aacggtgtgc cggtagatat cgtattgaac ccgctgggtg | 120 |

```
taccatctcg tatgaacgtg ggtcagattc tagagactca cttgggtatg gcggctaaag    180
ggcttggtga caaaatcgaa aaaatgttga agaacaacg tacagtttta gaactgcgcg     240
aattcttaga caagatttat aacaaagtcg gcggtgagca agaagatctt gatagcttga    300
ctgatgaaga aattctagcg cttgcaggta acttgcgtgc gggtgtgcct ttagctactc    360
ctgtatttga tggtgctgaa gaaagtcaaa ttaaagactt acttgaattg gctgacattt    420
cacgtacggg tcaaacagta ttgtttgatg                                     450
```

<210> SEQ ID NO 114
<211> LENGTH: 450
<212> TYPE: DNA
<213> ORGANISM: Acinetobacter baumannii

<400> SEQUENCE: 114

```
gtgataagat ggctggtcgt cacggtaaca aggtgttgt atctaacatc ttacctgttg      60
aagacatgcc acatgatgct aacgtgtgc cggtagatat cgtattgaac ccgctgggtg    120
taccatctcg tatgaacgtg ggtcagattc tagagactca cttgggtatg gcggctaaag    180
ggcttggtga caaaatcgaa aaaatgttga agaacaacg tacagtttta gaactgcgcg     240
aattcttaga caagatttat aacaaagtcg gcggtgagca agaagatctt gatagcttga    300
ctgatgaaga aattctagcg cttgcaggta acttgcgtgc gggtgtgcct ttagctactc    360
ctgtatttga tggtgctgaa gaaagtcaaa ttaaagattt acttgaattg gctgacattt    420
cacgtacggg tcaaacagta ttgtttgatg                                     450
```

<210> SEQ ID NO 115
<211> LENGTH: 450
<212> TYPE: DNA
<213> ORGANISM: Acinetobacter baumannii

<400> SEQUENCE: 115

```
gtgataagat ggctggtcgt cacggtaaca agggtgttgt atctaacatc ttacctgttg     60
aagacatgcc acatgatgct aacgtgtgc cggtagatat cgtattgaac ccgctgggtg    120
taccatctcg tatgaacgtg ggtcagattc tagagactca cttgggtatg gcggctaaag    180
ggcttggtga caaaatcgaa aaaatgttga agaacaacg tacagtttta gaactgcgcg     240
aattcttaga caagatttat aacaaagtcg gcggtgagca agaagatctt gatagcttga    300
ctgatgaaga aattctagcg cttgcaggta acttgcgtgc gggtgtgcct ttagctactc    360
ctgtatttga tggtgctgaa gaaagtcaaa ttaaagactt acttgaattg gctgacattt    420
cacgtacggg tcaaacagta ttgtttgacg                                     450
```

<210> SEQ ID NO 116
<211> LENGTH: 450
<212> TYPE: DNA
<213> ORGANISM: Acinetobacter baumannii

<400> SEQUENCE: 116

```
gtgataagat ggctggtcgt cacggtaaca agggtgttgt atctaacatc ttacctgttg     60
aagacatgcc acatgatgct aacggtgtgc cggtagatat cgtattgaac ccgctgggtg    120
taccatctcg tatgaacgtg ggtcagattc tagagactca cttgggtatg gcggctaaag    180
ggcttggtga caaaatcgaa aaaatgttga agaacaacg tacagtttta gaactgcgcg     240
aattcttaga caagatttat aacaaagtcg gcggtgagca agaagatctt gatagcttga    300
ctgatgaaga aattctagcg cttgcaggta acttgcgtgc gggtgtgcct ttagctactc    360
```

```
ctgtatttga tggtgctgaa gaaagtcaaa ttaaagactt acttgaattg gctgacattt    420
cacgtactgg tcaaacagta ttgtttgacg                                      450

<210> SEQ ID NO 117
<211> LENGTH: 450
<212> TYPE: DNA
<213> ORGANISM: Acinetobacter baumannii

<400> SEQUENCE: 117
gtgataagat ggctggtcgt cacggtaaca aggtgttgt atctaacatc ttacctgttg       60
aagacatgcc acatgatgct aacggtgtgc cggtagatat cgtattgaac ccgctgggtg    120
taccatctcg tatgaacgtg ggtcagattc tagagactca cttgggtatg gcggctaaag    180
ggcttggtga caaaatcgaa aaaatgttga agaacaacg tacagtttta gaactgcgcg     240
aattcttaga caagatttat aacaaagtcg gcggtgagca agaagatctt gatagcttga    300
ctgatgaaga aattctagcg cttgcaggta acttgcgtgc gggtgtgcct ttagctactc    360
ctgtatttga tggtgctgaa gaaagtcaaa ttaaagactt acttgaattg gctgacattt    420
cacgtacggg tcaaacagta ttgtttgacg                                      450

<210> SEQ ID NO 118
<211> LENGTH: 450
<212> TYPE: DNA
<213> ORGANISM: Acinetobacter baumannii

<400> SEQUENCE: 118
gtgataagat ggctggtcgt cacggtaaca aggtgttgt atctaacatc ttacctgttg       60
aagacatgcc acatgatgct aacggtgtgc cggtagatat cgtattgaac ccgctgggtg    120
taccatctcg tatgaacgtg ggtcagattc tagagactca cttgggtatg gcggctaaag    180
ggcttggtga caaaatcgaa aaaatgttga agaacaacg tacagtttta gaactgcgcg     240
aattcttaga caagatttat aacaaagtcg gcggtgagca agaagatctt gatagcttga    300
ctgatgaaga aattctagcg cttgcaggta acttgcgtgc gggtgtgcct ttagctactc    360
ctgtatttga tggtgctgaa gaaagtcaaa ttaaagactt acttgaattg gctgacattt    420
cacgtacggg tcaaacagta ttgtttgatg                                      450

<210> SEQ ID NO 119
<211> LENGTH: 450
<212> TYPE: DNA
<213> ORGANISM: Acinetobacter baumannii

<400> SEQUENCE: 119
gtgataagat ggctggtcgt catggtaaca aggtgttgt ttctaacatc ttacctgttg       60
aagacatgcc acacgatgcg aacggtgtac ctgtagatat cgtattgaac ccgttgggcg    120
taccatctcg tatgaacgtg ggtcagattc tcgaaactca cttgggtatg gcggctaaag    180
ggcttggtga caaaatcgaa aaaatgttga agaacagcg tacagtttta gaactacgtg     240
aattcttaga caagatttat aacaaagtcg gtggcgagca agaagatctt gatagcttga    300
ctgatgatga atcctagca cttttcaggca acttgcgtgc tggtgttcct ttggctactc     360
ctgtatttga tggtgctgaa gaaagtcaaa ttaaagattt acttgagttg gctgacattt    420
cacgtacagg tcaaacagta ttgtttgatg                                      450

<210> SEQ ID NO 120
<211> LENGTH: 450
<212> TYPE: DNA
```

<213> ORGANISM: Acinetobacter baumannii

<400> SEQUENCE: 120

```
gtgataagat ggctggtcgt cacggtaaca agggtgttgt atctaacatc ttacctgttg     60
aagacatgcc acatgatgct aacggtgtgc cggtagatat cgtattgaac ccgctgggtg    120
taccatctcg tatgaacgtg ggtcagattc tagagactca cttgggtatg gcggctaaag    180
ggcttggtga caaatcgaa aaaatgttga agaacaacg tacagtttta gaactgcgcg      240
aattcttaga caagatttat aacaaagtcg gcggtgagca agaagatctt gatagcttga    300
ctgatgaaga aattctagcg cttgcaggta acttgcgtgc gggtgtgcct ttagctactc    360
ctgtatttga tggtgctgaa gaaagtcaaa ttaaagactt acttgaattg gctgacattt    420
cacgtactgg tcaaacagta ttgtttgacg                                      450
```

<210> SEQ ID NO 121
<211> LENGTH: 305
<212> TYPE: DNA
<213> ORGANISM: Acinetobacter calcoaceticus

<400> SEQUENCE: 121

```
ttgtaaaagg agtcggtttt taaatcggct ccataaaatg gctgatggct cttgggtcat     60
cagccttttt gcgttacaat aatcggctcg attttttgttt gttctgtaca ataattgtcg   120
tgttttagaa taatcagagt aatttcaaat gtttaccaat attttctttt taaaaaata    180
ttgttaagcg ttttaatacc actaaaaatt gcagcatttg taaacagtgg tggccatatc    240
ggcctgtgta attccttctg agcccgttct gcaggcgggc ttggtttact ttccgaggac    300
tccag                                                                305
```

<210> SEQ ID NO 122
<211> LENGTH: 305
<212> TYPE: DNA
<213> ORGANISM: Acinetobacter baumannii

<400> SEQUENCE: 122

```
ttgtaaaagg agtcggtttt taaatcggct ccataaaatg gctgatggct cttgggtcat     60
cagccttttt gcgttacaat aatcggctcg attttttgtta gttttgtttg gttttttagag  120
aaagcctaaa taaataaat aaattcaaat gcttaccaat attttctttt tttaaaaata    180
ttgttaagcg tttttatacc actaaaaatt gcagcatttg taaacagtgg tggccatatc    240
ggcctgcgta attccttctg agcccgttct gcaggcgggc ttggtttact ttccgaggac    300
tccag                                                                305
```

<210> SEQ ID NO 123
<211> LENGTH: 304
<212> TYPE: DNA
<213> ORGANISM: Acinetobacter sp.

<400> SEQUENCE: 123

```
ttgtaaaagg agtcggtttt taaatcggct ccataaaatg gctgatggct cttgggtcat     60
cagccttttt gcgttacaat aatcggctcg attttttgtta gttttgtttg tgttttagga   120
aaattcaaat aaaacaagta atttcaaatg tttaccaata ttttctttt ttaaaaatat    180
tgttaagcgt ttttataccca ctaaaaattg cagcatttgt aaacagtggt ggccatatcg   240
gcctgcgtaa ttccttctga gcccgttctg caggcgggct tggtttactt tccgaggact    300
ccag                                                                 304
```

<210> SEQ ID NO 124
<211> LENGTH: 308
<212> TYPE: DNA
<213> ORGANISM: Acinetobacter haemolyticus

<400> SEQUENCE: 124

```
tgctgtaggg agtcgatttt ttgaaaatcg gctccaaaaa atggctgatg gctcttgggt      60
catcagcctt tttgcgttac aataatcggc tcgttttttg ttagttttgc gttttttgacg     120
catataatta gaacaaacgg ctaaatatca aacgcttacc aatattttttt gcttataaa      180
aatattgtta agcgttttaa taccactaaa aattgcagca tttgtaaaca gtggtggcca     240
tatcggcttg cgtaattcct tctaagcccg ttctgcaggc ggcttagttt actttccgag     300
gactccag                                                              308
```

<210> SEQ ID NO 125
<211> LENGTH: 308
<212> TYPE: DNA
<213> ORGANISM: Acinetobacter junii

<400> SEQUENCE: 125

```
ttctgtaggg agtcgatttt tttataatcg gctccaaaaa atggctgatg gctcttgggt      60
catcagcctt tttgcgttac aataatcggc tcgttttttg ttagttttgc atattttgtg     120
cagattttta tagaaaacaa ataaaatcaa atgcttacca atatttttttt gcttataaaa    180
atattgttaa gcgttttgat accactaaaa attgcagcat ttgtaaacag tggtggccat     240
atcggcctgc gtaattcctt ctaggcccgt tctgcaggcg gcttagttt actttccgag      300
gactccag                                                              308
```

<210> SEQ ID NO 126
<211> LENGTH: 308
<212> TYPE: DNA
<213> ORGANISM: Acinetobacter sp.

<400> SEQUENCE: 126

```
tactgtaggg agtcggtttt tttgataatc ggctccaaaa aatggctgat ggctcttggg      60
tcatcagcct ttttgcgtta caataatcgg ctcgtttttt gttagtttcg catataatat     120
gcgggttttt gcaataaaaa gactaaatatc aaacgcttaa caatgttttt tgcttataaa    180
aatattgtta agcgttttaa taccactaaa aattgcagca tttgtaaaca gtggtggcca     240
tatcggcctg cgtaatcctt ctaggcccgt tctgcaggcg gcttagttt acttcccgag      300
gactccag                                                              308
```

<210> SEQ ID NO 127
<211> LENGTH: 301
<212> TYPE: DNA
<213> ORGANISM: Acinetobacter johnsonii

<400> SEQUENCE: 127

```
tgttaccagg gggggaatat taatttcacc ccaaaaattg gctgatggct cttgggtcat      60
cagccttttt gcgttacaat aatcggctcg attttttgttt gcttggtgga aaatccatca    120
aattaaaata agaaaagaa tcaaacgttt accaatattt ttcaaattta aaaatattgg     180
taagcgtttc aataccactg aaaattgcag catttgtaaa agtggtggc catatcggcc     240
tgcgtaattc cttctgagcc cgttctgcag gcgggctcgg tttactttcc gaggactcca    300
g                                                                    301
```

```
<210> SEQ ID NO 128
<211> LENGTH: 308
<212> TYPE: DNA
<213> ORGANISM: Acinetobacter lwoffii

<400> SEQUENCE: 128
tagcttaagg gagccggttt ttttataatc agctccaaaa attggctgat ggctcttggg      60
tcatcagcct ttttgcgtta caataatcgg ctcgattttt gtttgcatga tataaaaatc     120
atacaaatta aaataaaaca taatgaacaa acgtttacca atattttca gtaaaaaaat      180 attgataagc gttttaatac cactaaaaat tgcagcattt gtaaagagtg gtggccatat     240
cggccagcgt aattccttct gagcccgttc tgcaggcggg cttggtttac actttccgag     300
gactccag                                                              308

<210> SEQ ID NO 129
<211> LENGTH: 306
<212> TYPE: DNA
<213> ORGANISM: Acinetobacter sp.

<400> SEQUENCE: 129
tttcttaagg gagccggttt tttataatcg ctccaaaaa ttggctgatg gctcttgggt      60
catcagcctt tttgcgttac aataatcggc tcgattttg tttgcatgat ataaaaatca     120
tacaaattga aaataaacat aatgaacaaa cgtttaccaa tatttttcat taaaaaatat    180
tgataagcgt tttaatacca ctaaaaattg cagcatttgt aaagagtggt ggccatatcg     240
gccagcgtaa ttccttctga gcccgttctg caggcgggct tggtttacac tttccgagga     300
ctccag                                                                306

<210> SEQ ID NO 130
<211> LENGTH: 307
<212> TYPE: DNA
<213> ORGANISM: Acinetobacter sp.

<400> SEQUENCE: 130
tcttaagggg agtcgatttt tttataatcg ctccacaaa ttggctgatg gctcttgggt      60
catcagcctt tttgcgttac aataatcggc tcgattttag attgattgat ataaaaatca     120
tcaattttta aaataaataa acataatcaa acgcttacca atatttttca gttttaaaaa     180
tattgttaag cgttttgtac cactgaaatt tgcagcattt gtataaaagt ggtggtcata     240
tcgacctgcg taattccttc taagttcgtt ctgcaggcgg gcttagttta ctttccgagg     300
actccag                                                               307

<210> SEQ ID NO 131
<211> LENGTH: 304
<212> TYPE: DNA
<213> ORGANISM: Acinetobacter sp.

<400> SEQUENCE: 131
tttcgctagg ggtcgaattt taatttgacc ccaaaaattg gctgatggct cttgggtcat     60
cagccttttt gcgttacaat aatcggctcg attttagatt gattggtaga aaaaccatca     120 atttttaaaaa taaataaaca caatcaaacg cttaccaata ttttccatt ttaaaaatat     180 tgctaagcgt tttgtaccac tgaaatttgc agcatttgta taaaagtggt ggtcatatcg     240
acctgcgtaa ttccttctaa gttcgttctg caggcggact tagtttactt tccgaggact     300
ccag                                                                  304
```

-continued

<210> SEQ ID NO 132
<211> LENGTH: 304
<212> TYPE: DNA
<213> ORGANISM: Acinetobacter radioresistens

<400> SEQUENCE: 132

```
ttctttaagg agtcgatttt ttaatcggct ccataaaatg gctgatggct cttgggtcat      60
cagccttttt gcgttacaat aatcggctcg attttgtta gtttgctgaa tatatcggtt     120
aatttaataa taaatcaaat aaattcaaac gcttaccaat attttttgat ttgaaaatat    180
tgataagcgt tttcatacca ctcaagattg cagcttttgt aaaaagtggt ggccatatcg    240
gcctgcgtaa ttccttctga gcccgttctg caggcgggct tggtttactt tccgaggact    300
ccag                                                                  304
```

<210> SEQ ID NO 133
<211> LENGTH: 309
<212> TYPE: DNA
<213> ORGANISM: Acinetobacter sp.

<400> SEQUENCE: 133

```
tgctgtaggg agtcgatttt ttgaaaatcg gctccaaaaa atggctgatg gctcttgggt      60
catcagccct tttgcgttac aataatcggc tcgcttttg ttagttttac gtttagcgtg     120
cgtattattt gaacaaaata catgaaatca acgcttacc aatattttt tgcttataaa     180 aatattgtta agcgttttaa taccactaaa aattgcagca tttgtaaaca gtggtggcca    240
tatcggcctg cgtaattcct tctagacccg ttctgcaggc gggtttagtt tacttttcga    300
ggactccag                                                             309
```

<210> SEQ ID NO 134
<211> LENGTH: 309
<212> TYPE: DNA
<213> ORGANISM: Acinetobacter sp.

<400> SEQUENCE: 134

```
ttctgtaggg agtcgatttt ttcaaaatcg gctccaaaaa atggctgatg gctcttgggt      60
catcagccct tttgcgttac aataatcggc tcgttttttg ttagttttgc atataatacg     120
cgtgttattt gagcaaattt agcaaaatca acgcttacc aatattttt tgcttataaa     180 aatattgtta agcgttttaa taccactaaa aattgcagca tttgtaaaca gtggtggcca    240
tatcggcctg cgtaattcct tctaagcccg ttctgcaggc gggcttagtt tacttttcga    300
ggactccag                                                             309
```

<210> SEQ ID NO 135
<211> LENGTH: 310
<212> TYPE: DNA
<213> ORGANISM: acinetobacter schindleri

<400> SEQUENCE: 135

```
tttcttaaag gagtcggttt ttttataatc ggctccaaaa attggctgat ggctcttggg      60
tcatcagcct ttttgcgtta caataatcgg ctcgattttt gtttgcatga tagaaattca    120
tacaaattta aaaacaaac ataattgatc aaatgcttac caatattttt gcagtaaaaa     180
atattgttaa gcgtttttaat accactaaaa attgcagcat ttgtaaagag tggtggccat    240
atcggccagc gtaattcctt ctgagcccgt tctgcaggcg ggcttagttt acactttccg    300
aggactccag                                                            310
```

<210> SEQ ID NO 136
<211> LENGTH: 308
<212> TYPE: DNA
<213> ORGANISM: acinetobacter ursingii

<400> SEQUENCE: 136

```
tgcatcaagg ggtcgatttt ttgataatcg gccccataaa atggctgatg gctcttgggt      60
catcagcctt tttgcgttac aataatcggc tcgattttg tttgtttgat ataaaaacgc     120
tcgatttaaa gaacaaatga aataaattca aacgcttacc aatattttc tggtttaaaa     180
atattgttaa gcgttttaat accacttaaa aattgcagca tttgtaaaag tggtggccat     240
atcggcctgc gtcattccat ccaagctcgt tctgcaggcg agcctggttt actttccgag     300
gactccag                                                              308
```

<210> SEQ ID NO 137
<211> LENGTH: 304
<212> TYPE: DNA
<213> ORGANISM: acinetobacter baylyi

<400> SEQUENCE: 137

```
tttcgctagg ggtcgaattt taatttgacc ccaaaaattg gctgatggct cttgggtcat      60
cagcctttt  gcgttacaat aatcggctcg attttagatt gattggtaga aaaccatca     120
atttttaaaaa taaataaaca caatcaaacg cttagcaata tttttccatt ttaaaaatat    180
tgctaagcgt tttgtaccac tgaaatttgc agcatttgta taaagtggt ggtcatatcg     240
acctgcgtaa ttccttctaa gttcgttctg caggcggact tagtttactt tccgaggact    300
ccag                                                                  304
```

<210> SEQ ID NO 138
<211> LENGTH: 305
<212> TYPE: DNA
<213> ORGANISM: acinetobacter bouvetii

<400> SEQUENCE: 138

```
tcttaagagg agccgatttt tttataatcg gctccagaaa atggctgatg gctcttgggt      60
catcagcctt tttgcgttac aataatcggc tcgattttg tttgcatgat ataaaaatca     120
tacaaattag aaatacagat aaatgtcaaa cgcttaccaa tatttttccg tttaaaaaat    180
attgttaagc gttttaatac cactataaat tgcagcattt gtcaaagtgg tggccatatc    240
ggcctgcgta attccttcta aacccgttct gcaggcgggt tagtttact ttccgaggac     300
tccag                                                                 305
```

<210> SEQ ID NO 139
<211> LENGTH: 309
<212> TYPE: DNA
<213> ORGANISM: acinetobacter gerneri

<400> SEQUENCE: 139

```
tcgctttatg gagtcgattt tttgtaatcg gctccaaaaa acggctgatg gctcttgggt      60
catcagcctt tttgcgttac aataatcggc tcgatttta gattgatcga tagaataatc    120
atcaatttta aaaataaata tacaaattca aacgcttacc aatattttc cattttaaaa    180
atattgttaa gcgttttata ccactgaaaa ttgcagcatt tgtataaagg tggtggtcat    240
atcgacctgc gtaattcctt ctaagttcgt tctgcaggcg gcttggtat  tactttccga    300
ggactccag                                                             309
```

```
<210> SEQ ID NO 140
<211> LENGTH: 308
<212> TYPE: DNA
<213> ORGANISM: acinetobacter grimontii

<400> SEQUENCE: 140
ttctgtaggg agtcgatttt tttataatcg gctccaaaaa atggctgatg gctcttgggt      60
catcagcctt tttgcgttac aataatcggc tcgttttttg ttagttttgc atattttgtg     120 cagatttttta tagaaaacaa ataaaatcaa atgcttacca atattttttt gcttataaaa    180
atattgttaa gcgttttgat accactaaaa attgcagcat ttgtaaacag tggtggccat     240
atcggcctgc gtaattcctt ctaggcccgt tctgcaggcg ggcttagttt actttccgag     300
gactccag                                                              308

<210> SEQ ID NO 141
<211> LENGTH: 306
<212> TYPE: DNA
<213> ORGANISM: acinetobacter tandoii

<400> SEQUENCE: 141
tcttaagagg agtcgatttt ttataatcgg ctccacaaaa tggctgatgg ctcttgggtc      60
atcagccttt ttgcgttaca ataatcggct cgactccaat ttgactgatt taaaaatcat     120
caaatttaaa caataaagac aaactttaaa cgcttaccaa tattttttcta ttcaaaaaat   180 attgttaagc gttttaatac cactaaaaat tgcagcattt gtaaacagtg gtggccatat    240
cggcctgcgt aattccttct aaacccgttc tgcaggcggg tttagtttac tttccgagga    300
ctccag                                                                306

<210> SEQ ID NO 142
<211> LENGTH: 307
<212> TYPE: DNA
<213> ORGANISM: acinetobacter tjernbergiae

<400> SEQUENCE: 142
tgtgtaggga gtcgattttt ttataatcgg ctccaaaaaa tggctgatgg ctcttgggtc      60
atcagccttt ttgcgttaca ataatcggct cgttttttgt tagttttacg tttgagtgcg    120
tgtttttcaa acaaataaca gaaaatcaaa cgcttaccaa tattttttg cctataaaaa     180 tattgttaag cgttttaata ccactaaaaa ttgcagcatt tgtaaacagt ggtggccata    240
tcggcctgcg taattccttc taagcccgtt ctgcaggcgg gtttagttta ctttccgagg    300
actccag                                                               307

<210> SEQ ID NO 143
<211> LENGTH: 307
<212> TYPE: DNA
<213> ORGANISM: acinetobacter towneri

<400> SEQUENCE: 143
tcttaagggg agtcgatttt tttataatcg actccaaaaa atggctgatg gctcttgggt      60
catcagcctt tttgcgttac aattatcggc tcgattttg tttgaatgat gggaaaacca     120
tcgaaaacaa tataaatcaa taaaatcaaa cgcttaccaa tattttcca catttaaaaa    180 tattgttaag cgttttaata ccactaaaaa ttgcagcatt tgtaaagagt ggtggccata    240
tcggcctgcg taattccttc taaacccgtt ctgcaggcgg gtttagttta ctttccgagg    300
actccag                                                               307
```

<210> SEQ ID NO 144
<211> LENGTH: 308
<212> TYPE: DNA
<213> ORGANISM: acinetobacter parvus

<400> SEQUENCE: 144

```
tgctgtaggg agtcgatttt ttcaaaatcg gctccaaaaa atggctgatg gctcttgggt      60
catcagcctt tttgcgttac aataatcggc tcgttttttg atagtttac gttcattgtg      120
cgtattattt aaacaaaatt tatgaaatca acgcttacc aatattttttt tgcttataaa     180
aatattgtta agcgttttaa taccactaaa attgcagcat ttgtaaacag tggtggccat     240
atcggcctgc gtaattcttt ctagacccgt tctgcaggcg ggtttagttt actttccgag     300
gactccag                                                              308
```

<210> SEQ ID NO 145
<211> LENGTH: 305
<212> TYPE: DNA
<213> ORGANISM: Acinetobacter baumannii

<400> SEQUENCE: 145

```
ttgtaaaagg agtcggtttt taaatcggct ccataaaatg gctgatggct cttgggtcat     60
cagccatttt gcgttacaat aatcggctcg attttttgtta gttttgtttg gttttttagat   120
aaagcctaaa taaataaat aaattcaaat gcttaccaat attttttcatt tttaaaaata    180
ttgttaagcg tttttatacc actaaaaatt gcagcatttg taaacagtgg tggccatatc    240
ggcctgcgta attccttctg agcccgttct gcaggcgggc ttggtttact ttccgaggac    300
tccag                                                                305
```

<210> SEQ ID NO 146
<211> LENGTH: 305
<212> TYPE: DNA
<213> ORGANISM: Acinetobacter baumannii

<400> SEQUENCE: 146

```
ttgtaaaagg agtcggtttt taaatcggct ccataaaatg gctgatggct cttgggtcat     60
cagccttttt gcgttacaat aatcggctcg attttttgtta gttttgtttg gttttttagag   120
aaagcctaaa taaataaat aaattcaaat gcttaccaat attttttcatt tttaaaaata    180
ttgttaagcg tttttatacc actaaaaatt gcagcatttg taaacagtgg tggccatatc    240
ggcctgcgta attccttctg agcccgttct gcaggcgggc ttggtttact ttccgaggac    300
tccag                                                                305
```

<210> SEQ ID NO 147
<211> LENGTH: 305
<212> TYPE: DNA
<213> ORGANISM: Acinetobacter baumannii

<400> SEQUENCE: 147

```
ttgtaaaagg agtcggtttt taaatcggct ccataaaatg gctgatggct cttgggtcat     60
cagccttttt gcgttacaat aatcggctcg attttttgtta gttttgtttg gttttttagag   120
aaagcctaaa taaataaat aaattcaaat gcttaccaat attttttcatt tttaaaaata    180
ttgttaagcg tttttatacc actaaaaatt gcagcatttg taaacagtgg tggccatatc    240
ggcctgcgta attccttctg agcccgttct gcaggcgggc ttggtttact ttccgaggac    300
tccag                                                                305
```

<210> SEQ ID NO 148
<211> LENGTH: 305
<212> TYPE: DNA
<213> ORGANISM: Acinetobacter baumannii

<400> SEQUENCE: 148

```
ttgtaaaagg agtcggtttt taaatcggct ccataaaatg gctgatggct cttgggtcat        60
cagccttttt gcgttacaat aatcggctcg attttttgtta gttttgtttg gttttttagag      120
aaagcctaaa taaataaat aaattcaaat gcttaccaat attttttcatt tttaaaaata        180
ttgttaagcg tttttatacc actaaaaatt gcagcatttg taaacagtgg tggccatatc        240
ggcctgcgta attccttctg agcccgttct gcaggcgggc ttggtttact ttccgaggac        300
tccag                                                                    305
```

<210> SEQ ID NO 149
<211> LENGTH: 305
<212> TYPE: DNA
<213> ORGANISM: Acinetobacter baumannii

<400> SEQUENCE: 149

```
ttgtaaaagg agtcggtttt taaatcggct ccataaaatg gctgatggct cttgggtcat        60
cagccttttt gcgttacaat aatcggctcg attttttgtta gttttgtttg gttttttagag      120
aaagcctaaa taaataaat aaattcaaat gcttaccaat attttttcatt tttaaaaata        180
ttgttaagcg tttttatacc actaaaaatt gcagcatttg taaacagtgg tggccatatc        240
ggcctgcgta attccttctg agcccgttct gcaggcgggc ttggtttact ttccgaggac        300
tccag                                                                    305
```

<210> SEQ ID NO 150
<211> LENGTH: 305
<212> TYPE: DNA
<213> ORGANISM: Acinetobacter baumannii

<400> SEQUENCE: 150

```
ttgtaaaagg agtcggtttt taaatcggct ccataaaatg gctgatggct cttgggtcat        60
cagccttttt gcgttacaat aatcggctcg attttttgtta gttttgtttg gttttttagag      120
aaagcctaaa taaataaat aaattcaaat gcttaccaat attttttcatt tttaaaaata        180
ttgttaagcg tttttatacc actaaaaatt gcagcatttg taaacagtgg tggccatatc        240
ggcctgcgta attccttctg agcccgttct gcaggcgggc ttggtttact ttccgaggac        300
tccag                                                                    305
```

<210> SEQ ID NO 151
<211> LENGTH: 305
<212> TYPE: DNA
<213> ORGANISM: Acinetobacter baumannii

<400> SEQUENCE: 151

```
ttgtaaaagg agtcggtttt taaatcggct ccataaaatg gctgatggct cttgggtcat        60
cagccttttt gcgttacaat aatcggctcg attttttgtta gttttgtttg gttttttagag      120
aaagcctaaa taaataaat aaattcaaat gcttaccaat attttttcatt tttaaaaata        180
ttgttaagcg tttttatacc actaaaaatt gcagcatttg taaacagtgg tggccatatc        240
ggcctgcgta attccttctg agcccgttct gcaggcgggc ttggtttact ttccgaggac        300
tccag                                                                    305
```

<210> SEQ ID NO 152
<211> LENGTH: 305
<212> TYPE: DNA
<213> ORGANISM: Acinetobacter baumannii

<400> SEQUENCE: 152

| | | | | | |
|---|---|---|---|---|---|
| ttgtaaaagg | agtcggtttt | taaatcggct | ccataaaatg | gctgatggct | cttgggtcat | 60 |
| cagccttttt | gcgttacaat | aatcggctcg | attttttgtta | gttttgtttg | gtttttagag | 120 |
| aaagcctaaa | taaataaat | aaattcaaat | gcttaccaat | attttttcatt | tttaaaaata | 180 |
| ttgttaagcg | tttttatacc | actaaaaatt | gcagcatttg | taaacagtgg | tggccatatc | 240 |
| ggcctgcgta | attccttctg | agcccgttct | gcaggcgggc | ttggtttact | ttccgaggac | 300 |
| tccag | | | | | 305 |

<210> SEQ ID NO 153
<211> LENGTH: 305
<212> TYPE: DNA
<213> ORGANISM: Acinetobacter baumannii

<400> SEQUENCE: 153

| | | | | | |
|---|---|---|---|---|---|
| ttgtaaaagg | agtcggtttt | taaatcggct | ccataaaatg | gctgatggct | cttgggtcat | 60 |
| cagccttttt | gcgttacaat | aatcggctcg | attttttgtta | gttttgtttg | gtttttagag | 120 |
| aaagcctaaa | taaataaat | aaattcaaat | gcttaccaat | attttttcatt | tttaaaaata | 180 |
| ttgttaagcg | tttttatacc | actaaaaatt | gcagcatttg | taaacagtgg | tggccatatc | 240 |
| ggcctgcgta | attccttctg | agcccgttct | gcaggcgggc | ttggtttact | ttccgaggac | 300 |
| tccag | | | | | 305 |

<210> SEQ ID NO 154
<211> LENGTH: 305
<212> TYPE: DNA
<213> ORGANISM: Acinetobacter baumannii

<400> SEQUENCE: 154

| | | | | | |
|---|---|---|---|---|---|
| ttgtaaaagg | agtcggtttt | taaatcggct | ccataaaatg | gctgatggct | cttgggtcat | 60 |
| cagccttttt | gcgttacaat | aatcggctcg | attttttgtta | gttttgtttg | gtttttagag | 120 |
| aaagcctaaa | taaataaat | aaattcaaat | gcttaccaat | attttttcatt | tttaaaaata | 180 |
| ttgttaagcg | tttttatacc | actaaaaatt | gcagcatttg | taaacagtgg | tggccatatc | 240 |
| ggcctgcgta | attccttctg | agcccgttct | gcaggcgggc | ttggtttact | ttccgaggac | 300 |
| tccag | | | | | 305 |

<210> SEQ ID NO 155
<211> LENGTH: 305
<212> TYPE: DNA
<213> ORGANISM: Acinetobacter baumannii

<400> SEQUENCE: 155

| | | | | | |
|---|---|---|---|---|---|
| ttgtaaaagg | agtcggtttt | taaatcggct | ccataaaatg | gctgatggct | cttgggtcat | 60 |
| cagccttttt | gcgttacaat | aatcggctcg | attttttgtta | gttttgtttg | gtttttagag | 120 |
| aaagcctaaa | taaataaat | aaattcaaat | gcttaccaat | attttttcatt | tttaaaaata | 180 |
| ttgttaagcg | tttttatacc | actaaaaatt | gcagcatttg | taaacagtgg | tggccatatc | 240 |
| ggcctgcgta | attccttctg | agcccgttct | gcaggcgggc | ttggtttact | ttccgaggac | 300 |
| tccag | | | | | 305 |

<210> SEQ ID NO 156
<211> LENGTH: 305
<212> TYPE: DNA
<213> ORGANISM: Acinetobacter baumannii

<400> SEQUENCE: 156

```
ttgtaaaagg agtcggtttt taaatcggct ccataaaatg gctgatggct cttgggtcat     60
cagccttttt gcgttacaat aatcggctcg attttgtta gttttgtttg gtttttagag    120
aaagcctaaa taaataaat aaattcaaat gcttaccaat attttcatt tttaaaaata    180
ttgttaagcg ttttatacc actaaaaatt gcagcatttg taaacagtgg tggccatatc    240
ggcctgcgta attccttctg agcccgttct gcaggcgggc ttggtttact ttccgaggac    300
tccag                                                                305
```

<210> SEQ ID NO 157
<211> LENGTH: 305
<212> TYPE: DNA
<213> ORGANISM: Acinetobacter baumannii

<400> SEQUENCE: 157

```
ttgtaaaagg agtcggtttt taaatcggct ccataaaatg gctgatggct cttgggtcat     60
cagccttttt gcgttacaat aatcggctcg attttgtta gttttgtttg gtttttagag    120
aaagcctaaa taaataaat aaattcaaat gcttaccaat attttcatt tttaaaaata    180
ttgttaagcg ttttatacc actaaaaatt gcagcatttg taaacagtgg tggccatatc    240
ggcctgcgta attccttctg agcccgttct gcaggcgggc ttggtttact ttccgaggac    300
tccag                                                                305
```

<210> SEQ ID NO 158
<211> LENGTH: 305
<212> TYPE: DNA
<213> ORGANISM: Acinetobacter baumannii

<400> SEQUENCE: 158

```
ttgtaaaagg agtcggtttt taaatcggct ccataaaatg gctgatggct cttgggtcat     60
cagccttttt gcgttacaat aatcggctcg attttgtta gttttgtttg gtttttagag    120
aaagcctaaa taaataaat aaattcaaat gcttaccaat attttcatt tttaaaaata    180
ttgttaagcg ttttatacc actaaaaatt gcagcatttg taaacagtgg tggccatatc    240
ggcctgcgta attccttctg agcccgttct gcaggcgggc ttggtttact ttccgaggac    300
tccag                                                                305
```

<210> SEQ ID NO 159
<211> LENGTH: 305
<212> TYPE: DNA
<213> ORGANISM: Acinetobacter baumannii

<400> SEQUENCE: 159

```
ttgtaaaagg agtcggtttt taaatcggct ccataaaatg gctgatggct cttgggtcat     60
cagccttttt gcgttacaat aatcggctcg attttgtta gttttgtttg gtttttagag    120
aaagcctaaa taaataaat aaattcaaat gcttaccaat attttcatt tttaaaaata    180
ttgttaagcg ttttatacc actaaaaatt gcagcatttg taaacagtgg tggccatatc    240
ggcctgcgta attccttctg agcccgttct gcaggcgggc ttggtttact ttccgaggac    300
tccag                                                                305
```

<210> SEQ ID NO 160
<211> LENGTH: 305
<212> TYPE: DNA
<213> ORGANISM: Acinetobacter baumannii

<400> SEQUENCE: 160

```
ttgtaaaagg agtcggtttt taaatcggct ccataaaatg gctgatggct cttgggtcat      60
cagccttttt gcgttacaat aatcggctcg attttgtta gttttgtttg gttttagag      120
aaagcctaaa taaataaat aaattcaaat gcttaccaat attttcatt tttaaaaata      180
ttgttaagcg tttttatacc actaaaaatt gcagcatttg taaacagtgg tggccatatc      240
ggcctgcgta attccttctg agctcgttct gcaggcgggc ttggtttact ttccgaggac      300
tccag                                                                  305
```

<210> SEQ ID NO 161
<211> LENGTH: 305
<212> TYPE: DNA
<213> ORGANISM: Acinetobacter baumannii

<400> SEQUENCE: 161

```
ttgtaaaagg agtcggtttt taaatcggct ccataaaatg gctgatggct cttgggtcat      60
cagccttttt gcgttacaat aatcggctcg attttgtta gttttgtttg gttttagag      120
aaagcctaaa taaataaat aaattcaaat gcttaccaat attttcatt tttaaaaata      180
ttgttaagcg tttttatacc actaaaaatt gcagcatttg taaacagtgg tggccatatc      240
ggcctgcgta attccttctg agcccgttct gcaggcgggc ttggtttact ttccgaggac      300
tccag                                                                  305
```

<210> SEQ ID NO 162
<211> LENGTH: 305
<212> TYPE: DNA
<213> ORGANISM: Acinetobacter baumannii

<400> SEQUENCE: 162

```
ttgtaaaagg agtcggtttt taaatcggct ccataaaatg gctgatggct cttgggtcat      60
cagccttttt gcgttacaat aatcggctcg attttgtta gttttgtttg gttttagag      120
aaagcctaaa taaataaat aaattcaaat gcttaccaat attttcatt tttaaaaata      180
ttgttaagcg tttttatacc actaaaaatt gcagcatttg taaacagtgg tggccatatc      240
ggcctgcgta attccttctg agcccgttct gcaggcgggc ttggtttact ttccgaggac      300
tccag                                                                  305
```

<210> SEQ ID NO 163
<211> LENGTH: 304
<212> TYPE: DNA
<213> ORGANISM: Acinetobacter baumannii

<400> SEQUENCE: 163

```
ttgtaaaagg agtcggtttt taaatcggct ccataaaatg gctgatggct cttgggtcat      60
cagccttttt gcgttacaat aatcggctcg attttgtta gttttgtttg attttagaa      120
aaatctaaat aaaacaagaa atttcaaatg tttaccaata ttttctttt ttaaaaatat      180
tgttaagcgt ttttatacca ctaaaaattg cagcatttgt aaacagtggt ggccatatcg      240
gcctgcgtaa ttccttctga gcccgttctg caggcgggct tagtttactt tccgaggact      300
ccag                                                                   304
```

<210> SEQ ID NO 164
<211> LENGTH: 305
<212> TYPE: DNA
<213> ORGANISM: Acinetobacter baumannii

<400> SEQUENCE: 164
ttgtaaaagg agtcggtttt taaatcggct ccataaaatg gctgatggct cttgggtcat    60 cagcctttt gcgttacaat aatcggctcg attttgtta gttttgtttg gttttagag     120 aaagcctaaa taaataaat aaattcaaat gcttaccaat attttcatt tttaaaata    180 ttgttaagcg tttttatacc actaaaaatt gcagcatttg taaacagtgg tggccatatc    240
ggcctgcgta attccttctg agcccgttct gcaggcgggc ttggtttact ttccgaggac    300
tccag                                                                305

<210> SEQ ID NO 165
<211> LENGTH: 86
<212> TYPE: DNA
<213> ORGANISM: Acinetobacter calcoaceticus

<400> SEQUENCE: 165
gtcgtaagac tcacgatttt ttaggaaaaa acaatatttg tgacccagtc gggtaagcgt    60
tgcttcccga cacacggaga aaaaaa                                          86

<210> SEQ ID NO 166
<211> LENGTH: 86
<212> TYPE: DNA
<213> ORGANISM: Acinetobacter baumannii

<400> SEQUENCE: 166
gtcgtaagac tcacgatttt ttaggtaaaa acaatatttg tgacccagtc gggtaagcga    60
ggcttcccga cacacggaga aaaaaa                                          86

<210> SEQ ID NO 167
<211> LENGTH: 86
<212> TYPE: DNA
<213> ORGANISM: Acinetobacter sp.

<400> SEQUENCE: 167
gtcgtaagac tcacgatttt ttaggtaaaa acaatatttg tgacccagtc gggtaagcat    60
tgcttcccga cacacggaga aaaaaa                                          86

<210> SEQ ID NO 168
<211> LENGTH: 172
<212> TYPE: DNA
<213> ORGANISM: Acinetobacter haemolyticus

<400> SEQUENCE: 168
ttagccatta atccccctc agcccccttt atgaaagggg gagttcccac tcgaaagagt    60
aggggcttcc ctcctcagaa aaggaggga ctgagggagg attattcagt taaaaaacaa    120
tatttgtgac ccagttgagt gagtgtagct cctcgacaca cggagaaaaa aa           172

<210> SEQ ID NO 169
<211> LENGTH: 149
<212> TYPE: DNA
<213> ORGANISM: Acinetobacter junii

<400> SEQUENCE: 169
ttagccatta attctcctag tttccactcg aaaagggtgg gggcttccct cctgagaaaa    60

```
ggagaggttg agggagggtt gttcagttaa aaaacaatat ttgtgaccca gtcaggtaag      120
cctagcttcc tgacacacgg agaaaaaaa                                        149
```

<210> SEQ ID NO 170
<211> LENGTH: 170
<212> TYPE: DNA
<213> ORGANISM: Acinetobacter sp.

<400> SEQUENCE: 170

```
ttagccatta atccccgag ccccttgac gaaaggggga gttcccactt gaaagggtag       60
gagcttccct ccttagaaaa aagagggact gaggaggat tattcagtta aaaaacaata      120
tttgtgaccc agtcgggcga gcttagctcc ctgacacacg gagaaaaaaa                170
```

<210> SEQ ID NO 171
<211> LENGTH: 141
<212> TYPE: DNA
<213> ORGANISM: Acinetobacter johnsonii

<400> SEQUENCE: 171

```
gtttctccat tgaatctccc caacctctct tgttcaaaga gaggcttcct cgaaaggtaa      60
gcggggagat ttctcagtta aaaacaata tttgtgaccc agttgtgtag tgaaagtctc      120
cacaacacac ggagaaaaaa a                                               141
```

<210> SEQ ID NO 172
<211> LENGTH: 177
<212> TYPE: DNA
<213> ORGANISM: Acinetobacter lwoffii

<400> SEQUENCE: 172

```
ttagttccat tgaatctccc ttgcgaagca gtgcttctca cctctttaag aaagagggga      60
aagtccctct ttataaggg ggatttaggg ggattcttgg gattcccaat tcagttaaaa     120
acaatatttg tgacccagtc gagaagtgaa atctcctcg acacacggag aaaaaaa        177
```

<210> SEQ ID NO 173
<211> LENGTH: 150
<212> TYPE: DNA
<213> ORGANISM: Acinetobacter sp.

<400> SEQUENCE: 173

```
ttagttccat ttaatccctc caaccctct ttgataaaga gggcttcccc cttaacaaag      60
ggggactgag ggggattaaa attcagttaa aaaacaatat ttgtgaccca gttgttgagt     120
gaaaatctcc acaacacacg gagaaaaaaa                                      150
```

<210> SEQ ID NO 174
<211> LENGTH: 144
<212> TYPE: DNA
<213> ORGANISM: Acinetobacter sp.

<400> SEQUENCE: 174

```
atccccttg atcccctttt gttaaagggg ggatttccct tctttcttaa agaggggca       60 ggggagattc caaatctcag tgaaaaaaca atatttgtga cccagccgta gagaaaatgc     120
ctcttcggca cacggagaaa aaaa                                            144
```

<210> SEQ ID NO 175
<211> LENGTH: 154
<212> TYPE: DNA
<213> ORGANISM: Acinetobacter sp.

-continued

<400> SEQUENCE: 175
acttcaccat tgaatctccc taaatccctc tttatgaaag agggactttc cccttagaa    60 aaaggggat caagggggat taaaattcag tgaaaaaaca atatttgtga cccagtcgta   120
gcctgaaaag cgcttcgaca cacggagaaa aaaa                              154

<210> SEQ ID NO 176
<211> LENGTH: 89
<212> TYPE: DNA
<213> ORGANISM: Acinetobacter radioresistens

<400> SEQUENCE: 176
ggtctaggac ccttcacctt ttcaggtaaa acaatatttt gtgacccagc cgggcgggca    60
atgtgccccc cggtacacgg agaaaaaaa                                     89

<210> SEQ ID NO 177
<211> LENGTH: 154
<212> TYPE: DNA
<213> ORGANISM: Acinetobacter sp.

<400> SEQUENCE: 177
aaaatctccc ccaacccctc tttaagaaag aggggagaaa gtcctccttt gtaaaggggg    60
atttaggggg gattatagat tcccaaattt cagtaaaaac aatatttgtg acccagtcgg   120
gtgagcttag cttcccgaca cacggagaaa aaaa                              154

<210> SEQ ID NO 178
<211> LENGTH: 153
<212> TYPE: DNA
<213> ORGANISM: Acinetobacter sp.

<400> SEQUENCE: 178
aaaatctccc ccaacccctc tttgagaaag aggggagaaa gtcccccttt ataagggggg    60
atttaggggg attagatatt cccaaatttc agtaaaaaca atatttgtga cccagtcggg   120
tgagcttagc tcctcgacac acggagaaaa aaa                                153

<210> SEQ ID NO 179
<211> LENGTH: 159
<212> TYPE: DNA
<213> ORGANISM: acinetobacter schindleri

<400> SEQUENCE: 179
gaaatctccc ctgacccctc tttgagaaag aggggagaag tcccccccctt ttttaaaggg    60 ggatttaggg ggattcttaa aattcccaaa tttcagtaaa aacaatatat tgtgacccag   120
ttgttgagtg aaaatctcca caacacacgg agaaaaaaa                          159

<210> SEQ ID NO 180
<211> LENGTH: 136
<212> TYPE: DNA
<213> ORGANISM: acinetobacter ursingii

<400> SEQUENCE: 180 atcccccctcg attccccttt gttaaagggg gcccctcttt tcaaagaggg gttagaggag    60
attttcaaat ttcagtaaaa acaatatttg tgacccagtc ggatgagcct agctctctga   120
cacacggaga aaaaaa                                                   136

<210> SEQ ID NO 181
<211> LENGTH: 88
<212> TYPE: DNA

```
<213> ORGANISM: acinetobacter baylyi

<400> SEQUENCE: 181
gcgttaagct gactcagatt tttcaggaaa aacagtattt gtgacccagc cgagtgagcg      60
aatgctcctc ggtatacgga gaaataaa                                        88

<210> SEQ ID NO 182
<211> LENGTH: 156
<212> TYPE: DNA
<213> ORGANISM: acinetobacter bouvetii

<400> SEQUENCE: 182
gaaatctccc ccgacccctc tttgaaaaag aggggagaaa atccccctTT ataaggggg      60 atttaggggg atttttcaaga ttccagaaat tcagtaaaaa caatatttgt gacccagttg   120
tgaagtgaaa atctccacaa cacacggaga aaaaaa                              156

<210> SEQ ID NO 183
<211> LENGTH: 170
<212> TYPE: DNA
<213> ORGANISM: acinetobacter gerneri

<400> SEQUENCE: 183
ttaaccatta atcccccaa ccccctttga aaaggggag gtccagcact taaatagttg       60 caacctcccct cctttattaa aggagggatt gagggaggat tctcagttaa aaaacaatat   120
ttgtgaccca gtcgagaagt gaaaatctcc tcgacgcacg gagaaaaaaa              170

<210> SEQ ID NO 184
<211> LENGTH: 150
<212> TYPE: DNA
<213> ORGANISM: acinetobacter grimontii

<400> SEQUENCE: 184
ttagccatta attctcctag tttccactcg aaaagggtgg gggcttccct cctgagaaaa      60
ggaggggttg agggagggtt gttcagttaa aaaaacaata tttgtgaccc agtcaggtaa   120
gcctagcttc ctgacacacg gagaaaaaaa                                     150

<210> SEQ ID NO 185
<211> LENGTH: 156
<212> TYPE: DNA
<213> ORGANISM: acinetobacter tandoii

<400> SEQUENCE: 185
gaaatctccc ccgatccctc tttaagaaag aggggagaag tcccccttag taaggggga      60 tttaggggga ttttttgaga ttccctattc agtgaaaaaa caatatttgt gacccagtcg   120
agaagtgaaa atctcctcga cacacggaga aaaaaa                              156

<210> SEQ ID NO 186
<211> LENGTH: 143
<212> TYPE: DNA
<213> ORGANISM: acinetobacter tjernbergiae

<400> SEQUENCE: 186 atcccccctcg atccccctttt gttaaagggg gaagttcccc tcttttttcaa agaggggtta    60 ggggagattt cataatttca gtaaaaaaca atatttgtga cccagtcggg tgagcgtagc   120
tccccgacac acggagaaaa aaa                                            143

<210> SEQ ID NO 187
```

<211> LENGTH: 157
<212> TYPE: DNA
<213> ORGANISM: acinetobacter towneri

<400> SEQUENCE: 187

```
tcatctccat taaatctccc tagatccctc tttataaaag agggactttt cccctttga      60
aaaggggga ttaaggggga ttaaaactca gttaaaaaac aatatttgtg acccagttgg     120
gatgtgaaaa cagcctccca gcacacggag aaaaaaa                             157
```

<210> SEQ ID NO 188
<211> LENGTH: 143
<212> TYPE: DNA
<213> ORGANISM: acinetobacter parvus

<400> SEQUENCE: 188

```
atccccctcg ttcccccttt aaaaagggg ggaagttccc ctctttgaaa agaggggcta      60
ggcggagatt ccataatttc agtaaaaaca atatttgtga cccagtcgga agagcgtagc   120
tccccgacac acggagaaaa aaa                                           143
```

<210> SEQ ID NO 189
<211> LENGTH: 86
<212> TYPE: DNA
<213> ORGANISM: Acinetobacter baumannii

<400> SEQUENCE: 189

```
gtcgtaagac tcacgatttt ttaggtaaaa acaatatttg tgacccagtc gggtaagcga      60
ggcttcccga cacacggaga aaaaa                                          86
```

<210> SEQ ID NO 190
<211> LENGTH: 86
<212> TYPE: DNA
<213> ORGANISM: Acinetobacter baumannii

<400> SEQUENCE: 190

```
gtcgtaagac tcacgatttt ttaggtaaaa acaatatttg tgacccagtc gggtaagcga      60
gccttcccga cacacggaga aaaaa                                          86
```

<210> SEQ ID NO 191
<211> LENGTH: 86
<212> TYPE: DNA
<213> ORGANISM: Acinetobacter baumannii

<400> SEQUENCE: 191

```
gtcgtaagac tcacgatttt ttaggtaaaa acaatatttg tgacccagtc gggtaagcga      60
ggcttcccga cacacggaga aaaaa                                          86
```

<210> SEQ ID NO 192
<211> LENGTH: 86
<212> TYPE: DNA
<213> ORGANISM: Acinetobacter baumannii

<400> SEQUENCE: 192

```
gtcgtaagac tcacgatttt ttaggtaaaa acaatatttg tgacccagtc gggtaagcga      60
ggcttcccga cacacggaga aaaaa                                          86
```

<210> SEQ ID NO 193
<211> LENGTH: 86
<212> TYPE: DNA
<213> ORGANISM: Acinetobacter baumannii

<400> SEQUENCE: 193
gtcgtaagac tcacgatttt ttaggtaaaa acaatatttg tgacccagtc gggtaagcga    60
ggcttcccga cacacggaga aaaaaa    86

<210> SEQ ID NO 194
<211> LENGTH: 86
<212> TYPE: DNA
<213> ORGANISM: Acinetobacter baumannii

<400> SEQUENCE: 194
gtcgtaagac tcacgatttt ttaggtaaaa acaatatttg tgacccagtc gggtaagcga    60
ggcttcccga cacacggaga aaaaaa    86

<210> SEQ ID NO 195
<211> LENGTH: 86
<212> TYPE: DNA
<213> ORGANISM: Acinetobacter baumannii

<400> SEQUENCE: 195
gtcgtaagac tcacgatttt ttaggtaaaa acaatatttg tgacccagtc gggtaagcga    60
ggcttcccga cacacggaga aaaaaa    86

<210> SEQ ID NO 196
<211> LENGTH: 86
<212> TYPE: DNA
<213> ORGANISM: Acinetobacter baumannii

<400> SEQUENCE: 196
gtcgtaagac tcacgatttt ttaggtaaaa acaatatttg tgacccagtc gggtaagcga    60
ggcttcccga cacacggaga aaaaaa    86

<210> SEQ ID NO 197
<211> LENGTH: 86
<212> TYPE: DNA
<213> ORGANISM: Acinetobacter baumannii

<400> SEQUENCE: 197
gtcgtaagac tcacgatttt ttaggtaaaa acaatatttg tgacccagtc gggtaagcga    60
ggcttcccga cacacggaga aaaaaa    86

<210> SEQ ID NO 198
<211> LENGTH: 86
<212> TYPE: DNA
<213> ORGANISM: Acinetobacter baumannii

<400> SEQUENCE: 198
gtcgtaagac tcacgatttt ttaggtaaaa acaatatttg tgacccagtc gggtaagcga    60
ggcttcccga cacacggaga aaaaaa    86

<210> SEQ ID NO 199
<211> LENGTH: 86
<212> TYPE: DNA
<213> ORGANISM: Acinetobacter baumannii

<400> SEQUENCE: 199
gtcgtaagac tcacgatttt ttaggtaaaa acaatatttg tgacccagtc gggtaagcga    60
ggcttcccga cacacggaga aaaaaa    86

<210> SEQ ID NO 200

```
<211> LENGTH: 86
<212> TYPE: DNA
<213> ORGANISM: Acinetobacter baumannii

<400> SEQUENCE: 200
gtcgtaagac tcacgatttt ttaggtaaaa acaatatttg tgacccagtc gggtaagcga      60
ggcttcccga cacacggaga aaaaaa                                           86

<210> SEQ ID NO 201
<211> LENGTH: 86
<212> TYPE: DNA
<213> ORGANISM: Acinetobacter baumannii

<400> SEQUENCE: 201
gtcgtaagac tcacgatttt ttaggtaaaa acaatatttg tgacccagtc gggtaagcga      60
ggcttcccga cacacggaga aaaaaa                                           86

<210> SEQ ID NO 202
<211> LENGTH: 86
<212> TYPE: DNA
<213> ORGANISM: Acinetobacter baumannii

<400> SEQUENCE: 202
gtcgtaagac tcacgatttt ttaggtaaaa acaatatttg tgacccagtc gggtaagcga      60
ggcttcccga cacacggaga aaaaaa                                           86

<210> SEQ ID NO 203
<211> LENGTH: 86
<212> TYPE: DNA
<213> ORGANISM: Acinetobacter baumannii

<400> SEQUENCE: 203
gtcgtaagac tcacgatttt ttaggtaaaa acaatatttg tgacccagtc gggtaagcga      60
ggcttcccga cacacggaga aaaaaa                                           86

<210> SEQ ID NO 204
<211> LENGTH: 86
<212> TYPE: DNA
<213> ORGANISM: Acinetobacter baumannii

<400> SEQUENCE: 204
gtcgtaagac tcacgatttt ttaggtaaaa acaatatttg tgacccagtc gggtaagcga      60
ggcttcccga cacacggaga aaaaaa                                           86

<210> SEQ ID NO 205
<211> LENGTH: 86
<212> TYPE: DNA
<213> ORGANISM: Acinetobacter baumannii

<400> SEQUENCE: 205
gtcgtaagac tcacgatttt ttaggtaaaa acaatatttg tgacccagtc gggtaagcga      60
ggcttcccga cacacggaga aaaaaa                                           86

<210> SEQ ID NO 206
<211> LENGTH: 86
<212> TYPE: DNA
<213> ORGANISM: Acinetobacter baumannii

<400> SEQUENCE: 206
gtcgtaagac tcacgatttt ttaggtaaaa acaatatttg tgacccagtc gggtaagcga      60
```

```
ggcttcccga cacacggaga aaaaaa                                                    86

<210> SEQ ID NO 207
<211> LENGTH: 86
<212> TYPE: DNA
<213> ORGANISM: Acinetobacter baumannii

<400> SEQUENCE: 207
gtcgtaagac tcacgatttt ttaggaaaaa acaatatttg tgacccagtc gggtaagcga              60
ggcttcccga cacacggaga aaaaa                                                    86

<210> SEQ ID NO 208
<211> LENGTH: 86
<212> TYPE: DNA
<213> ORGANISM: Acinetobacter baumannii

<400> SEQUENCE: 208
gtcgtaagac tcacgatttt ttaggtaaaa acaatatttg tgacccagtc gggtaagcga              60
ggcttcccga cacacggaga aaaaa                                                    86

<210> SEQ ID NO 209
<211> LENGTH: 21
<212> TYPE: DNA
<213> ORGANISM: Artificial Sequence
<220> FEATURE:
<223> OTHER INFORMATION: Primer

<400> SEQUENCE: 209
ggtaaagtda crcctaaagg t                                                        21

<210> SEQ ID NO 210
<211> LENGTH: 20
<212> TYPE: DNA
<213> ORGANISM: Artificial Sequence
<220> FEATURE:
<223> OTHER INFORMATION: Primer

<400> SEQUENCE: 210
gtatgaacgt gggdcagatt                                                          20

<210> SEQ ID NO 211
<211> LENGTH: 18
<212> TYPE: DNA
<213> ORGANISM: Artificial Sequence
<220> FEATURE:
<223> OTHER INFORMATION: Primer

<400> SEQUENCE: 211
gtdggtacvg gyatggaa                                                            18

<210> SEQ ID NO 212
<211> LENGTH: 21
<212> TYPE: DNA
<213> ORGANISM: Artificial Sequence
<220> FEATURE:
<223> OTHER INFORMATION: Primer

<400> SEQUENCE: 212
gaacgygcrt gcatyttgtc a                                                        21

<210> SEQ ID NO 213
<211> LENGTH: 20
<212> TYPE: DNA
<213> ORGANISM: Artificial Sequence
<220> FEATURE:
```

-continued

<223> OTHER INFORMATION: Primer

<400> SEQUENCE: 213
cgyaaagayt tgaaagaaga                                          20

<210> SEQ ID NO 214
<211> LENGTH: 21
<212> TYPE: DNA
<213> ORGANISM: Artificial Sequence
<220> FEATURE:
<223> OTHER INFORMATION: Primer

<400> SEQUENCE: 214
cttctttcaa rtctttrcgr t                                        21

<210> SEQ ID NO 215
<211> LENGTH: 21
<212> TYPE: DNA
<213> ORGANISM: Artificial Sequence
<220> FEATURE:
<223> OTHER INFORMATION: Primer

<400> SEQUENCE: 215
gaygtdaaag aytcatcttt a                                        21

<210> SEQ ID NO 216
<211> LENGTH: 19
<212> TYPE: DNA
<213> ORGANISM: Artificial Sequence
<220> FEATURE:
<223> OTHER INFORMATION: Primer

<400> SEQUENCE: 216
gaacgygcrt gcatyttgt                                           19

<210> SEQ ID NO 217
<211> LENGTH: 20
<212> TYPE: DNA
<213> ORGANISM: Artificial Sequence
<220> FEATURE:
<223> OTHER INFORMATION: Primer

<400> SEQUENCE: 217
cgtaaagatg artctttthac                                         20

<210> SEQ ID NO 218
<211> LENGTH: 19
<212> TYPE: DNA
<213> ORGANISM: Artificial Sequence
<220> FEATURE:
<223> OTHER INFORMATION: Primer

<400> SEQUENCE: 218
gacaaratgc aygcrcgtt                                           19

<210> SEQ ID NO 219
<211> LENGTH: 18
<212> TYPE: DNA
<213> ORGANISM: Artificial Sequence
<220> FEATURE:
<223> OTHER INFORMATION: Primer

<400> SEQUENCE: 219
aagaagcwgg ygctamag                                            18

<210> SEQ ID NO 220

```
<211> LENGTH: 20
<212> TYPE: DNA
<213> ORGANISM: Artificial Sequence
<220> FEATURE:
<223> OTHER INFORMATION: Primer

<400> SEQUENCE: 220
ctkggyctka aagaagcyaa                                                  20

<210> SEQ ID NO 221
<211> LENGTH: 19
<212> TYPE: DNA
<213> ORGANISM: Artificial Sequence
<220> FEATURE:
<223> OTHER INFORMATION: Primer

<400> SEQUENCE: 221
ctgctgcygy tgttgaaga                                                   19

<210> SEQ ID NO 222
<211> LENGTH: 19
<212> TYPE: DNA
<213> ORGANISM: Artificial Sequence
<220> FEATURE:
<223> OTHER INFORMATION: Primer

<400> SEQUENCE: 222
ggtagttrat ggtttcmgg                                                   19

<210> SEQ ID NO 223
<211> LENGTH: 21
<212> TYPE: DNA
<213> ORGANISM: Artificial Sequence
<220> FEATURE:
<223> OTHER INFORMATION: Primer

<400> SEQUENCE: 223
gttratggtt tcmggcttyt t                                                21

<210> SEQ ID NO 224
<211> LENGTH: 20
<212> TYPE: DNA
<213> ORGANISM: Artificial Sequence
<220> FEATURE:
<223> OTHER INFORMATION: Primer

<400> SEQUENCE: 224
ggtttcmggc ttyttaactt                                                  20

<210> SEQ ID NO 225
<211> LENGTH: 20
<212> TYPE: DNA
<213> ORGANISM: Artificial Sequence
<220> FEATURE:
<223> OTHER INFORMATION: Primer

<400> SEQUENCE: 225
atggcwtact cayatacyga                                                  20

<210> SEQ ID NO 226
<211> LENGTH: 20
<212> TYPE: DNA
<213> ORGANISM: Artificial Sequence
<220> FEATURE:
<223> OTHER INFORMATION: Primer

<400> SEQUENCE: 226
```

```
gcwtactcat ayacygaraa                                                  20

<210> SEQ ID NO 227
<211> LENGTH: 21
<212> TYPE: DNA
<213> ORGANISM: Artificial Sequence
<220> FEATURE:
<223> OTHER INFORMATION: Primer

<400> SEQUENCE: 227
actcatayac ygaraaraaa c                                                21

<210> SEQ ID NO 228
<211> LENGTH: 20
<212> TYPE: DNA
<213> ORGANISM: Artificial Sequence
<220> FEATURE:
<223> OTHER INFORMATION: Primer

<400> SEQUENCE: 228
garcaagaag tmtacatggg                                                  20

<210> SEQ ID NO 229
<211> LENGTH: 19
<212> TYPE: DNA
<213> ORGANISM: Artificial Sequence
<220> FEATURE:
<223> OTHER INFORMATION: Primer

<400> SEQUENCE: 229
gttcaaccgy cgtwtsggt                                                   19

<210> SEQ ID NO 230
<211> LENGTH: 18
<212> TYPE: DNA
<213> ORGANISM: Artificial Sequence
<220> FEATURE:
<223> OTHER INFORMATION: Primer

<400> SEQUENCE: 230
gatcaacgcc aagccdgt                                                    18

<210> SEQ ID NO 231
<211> LENGTH: 18
<212> TYPE: DNA
<213> ORGANISM: Artificial Sequence
<220> FEATURE:
<223> OTHER INFORMATION: Primer

<400> SEQUENCE: 231
ggytcraaca tgcagcgt                                                    18

<210> SEQ ID NO 232
<211> LENGTH: 19
<212> TYPE: DNA
<213> ORGANISM: Artificial Sequence
<220> FEATURE:
<223> OTHER INFORMATION: Primer

<400> SEQUENCE: 232
gygtvgayat ctacaacct                                                   19

<210> SEQ ID NO 233
<211> LENGTH: 17
<212> TYPE: DNA
<213> ORGANISM: Artificial Sequence
<220> FEATURE:
```

<223> OTHER INFORMATION: Primer

<400> SEQUENCE: 233
tgaygghcgt acdggyg                                                   17

<210> SEQ ID NO 234
<211> LENGTH: 21
<212> TYPE: DNA
<213> ORGANISM: Artificial Sequence
<220> FEATURE:
<223> OTHER INFORMATION: Primer

<400> SEQUENCE: 234
ccayttrgtd gaygacaaaa t                                              21

<210> SEQ ID NO 235
<211> LENGTH: 18
<212> TYPE: DNA
<213> ORGANISM: Artificial Sequence
<220> FEATURE:
<223> OTHER INFORMATION: Primer

<400> SEQUENCE: 235
ttcggtggtc agcgyttc                                                  18

<210> SEQ ID NO 236
<211> LENGTH: 21
<212> TYPE: DNA
<213> ORGANISM: Artificial Sequence
<220> FEATURE:
<223> OTHER INFORMATION: Primer

<400> SEQUENCE: 236
gtttyttytc rgtrtatgag t                                              21

<210> SEQ ID NO 237
<211> LENGTH: 19
<212> TYPE: DNA
<213> ORGANISM: Artificial Sequence
<220> FEATURE:
<223> OTHER INFORMATION: Primer

<400> SEQUENCE: 237
gcaayttrcy aaartyctt                                                 19

<210> SEQ ID NO 238
<211> LENGTH: 19
<212> TYPE: DNA
<213> ORGANISM: Artificial Sequence
<220> FEATURE:
<223> OTHER INFORMATION: Primer

<400> SEQUENCE: 238
cagcattgcc rgartarct                                                 19

<210> SEQ ID NO 239
<211> LENGTH: 20
<212> TYPE: DNA
<213> ORGANISM: Artificial Sequence
<220> FEATURE:
<223> OTHER INFORMATION: Primer

<400> SEQUENCE: 239
cccatgtaka cttcttgytc                                                20

<210> SEQ ID NO 240

```
<211> LENGTH: 20
<212> TYPE: DNA
<213> ORGANISM: Artificial Sequence
<220> FEATURE:
<223> OTHER INFORMATION: Primer

<400> SEQUENCE: 240
gttgaacttc atvcgdccwa                                               20

<210> SEQ ID NO 241
<211> LENGTH: 17
<212> TYPE: DNA
<213> ORGANISM: Artificial Sequence
<220> FEATURE:
<223> OTHER INFORMATION: Primer

<400> SEQUENCE: 241
gchachggct tggcgtt                                                  17

<210> SEQ ID NO 242
<211> LENGTH: 17
<212> TYPE: DNA
<213> ORGANISM: Artificial Sequence
<220> FEATURE:
<223> OTHER INFORMATION: Primer

<400> SEQUENCE: 242
gcctgacgct gcatgtt                                                  17

<210> SEQ ID NO 243
<211> LENGTH: 19
<212> TYPE: DNA
<213> ORGANISM: Artificial Sequence
<220> FEATURE:
<223> OTHER INFORMATION: Primer

<400> SEQUENCE: 243
tgttctggtt bgaacgvgt                                                19

<210> SEQ ID NO 244
<211> LENGTH: 18
<212> TYPE: DNA
<213> ORGANISM: Artificial Sequence
<220> FEATURE:
<223> OTHER INFORMATION: Primer

<400> SEQUENCE: 244
ghgchgcttc ttcraaga                                                 18

<210> SEQ ID NO 245
<211> LENGTH: 18
<212> TYPE: DNA
<213> ORGANISM: Artificial Sequence
<220> FEATURE:
<223> OTHER INFORMATION: Primer

<400> SEQUENCE: 245
cgytcacghg chgcttct                                                 18

<210> SEQ ID NO 246
<211> LENGTH: 19
<212> TYPE: DNA
<213> ORGANISM: Artificial Sequence
<220> FEATURE:
<223> OTHER INFORMATION: Primer

<400> SEQUENCE: 246
```

| | |
|---|---|
| gcttccatyt ggcghacrt | 19 |

```
<210> SEQ ID NO 247
<211> LENGTH: 19
<212> TYPE: DNA
<213> ORGANISM: Artificial Sequence
<220> FEATURE:
<223> OTHER INFORMATION: Primer

<400> SEQUENCE: 247
```

| | |
|---|---|
| gtacgtcacg bacytcraa | 19 |

```
<210> SEQ ID NO 248
<211> LENGTH: 20
<212> TYPE: DNA
<213> ORGANISM: Artificial Sequence
<220> FEATURE:
<223> OTHER INFORMATION: Primer

<400> SEQUENCE: 248
```

| | |
|---|---|
| tccatraact gdgayaaytg | 20 |

```
<210> SEQ ID NO 249
<211> LENGTH: 20
<212> TYPE: DNA
<213> ORGANISM: Artificial Sequence
<220> FEATURE:
<223> OTHER INFORMATION: Primer

<400> SEQUENCE: 249
```

| | |
|---|---|
| gtatcacgyg cdacacahga | 20 |

```
<210> SEQ ID NO 250
<211> LENGTH: 19
<212> TYPE: DNA
<213> ORGANISM: Artificial Sequence
<220> FEATURE:
<223> OTHER INFORMATION: Primer

<400> SEQUENCE: 250
```

| | |
|---|---|
| gtcatgaayg cdacrcgca | 19 |

```
<210> SEQ ID NO 251
<211> LENGTH: 20
<212> TYPE: DNA
<213> ORGANISM: Artificial Sequence
<220> FEATURE:
<223> OTHER INFORMATION: Primer

<400> SEQUENCE: 251
```

| | |
|---|---|
| cggttaccya artgrtcrat | 20 |

```
<210> SEQ ID NO 252
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n is a, c, g, or t

<400> SEQUENCE: 252
```

| | |
|---|---|
| gaacgnacrc gvcggtta | 18 |

```
<210> SEQ ID NO 253
```

```
<211> LENGTH: 21
<212> TYPE: DNA
<213> ORGANISM: Artificial Sequence
<220> FEATURE:
<223> OTHER INFORMATION: Primer

<400> SEQUENCE: 253
gttratacad gtrttytggt t                                              21

<210> SEQ ID NO 254
<211> LENGTH: 18
<212> TYPE: DNA
<213> ORGANISM: Artificial Sequence
<220> FEATURE:
<223> OTHER INFORMATION: Primer

<400> SEQUENCE: 254
gaacgcracr cgcatgtt                                                  18

<210> SEQ ID NO 255
<211> LENGTH: 18
<212> TYPE: DNA
<213> ORGANISM: Artificial Sequence
<220> FEATURE:
<223> OTHER INFORMATION: Primer

<400> SEQUENCE: 255
catgaacgcr acrcgcat                                                  18
```

NUCLEIC ACID FRAGMENTS AND SPECIFIC DETECTION METHOD BY MOLECULAR IDENTIFICATION OF DIFFERENT BACTERIA SPECIES OF THE GENUS *ACINETOBACTER*

The present invention relates to the area of diagnosis. More precisely, the invention concerns a method for the molecular identification of bacteria of the genus *Acinetobacter* using nucleic acid amplifying and sequencing techniques with oligonucleotide primers.

Bacteria of the genus *Acinetobacter* are bacteria appearing in the form of Gram-negative cocco-bacilli, having aerobic growth. Currently almost 60 species are known and 2 subspecies.

These bacteria are essentially, but not solely, agents of nosocomial infection. Their spectrum ranges from mere colonization to life-threatening infections, in particular pneumonia, urinary infection, bacteraemia and meningitis (van Dessel et al., 2004). Their excellent survival capacity in the external hospital environment and their ability to develop rapid resistance to most antibiotics are major factors in their emergence as agents of nosocomial infections, in particular in intensive care units (Bergogne-Berezin and Towner, 1996; Towner, 1997).

Although most species are responsible for infections in man, some species have only been isolated in the environment (Nemec et al., 2001, 2003; Carr et al., 2003).

Whereas in the genus *Acinetobacter*, 32 species have been proposed (van Dessel et al, 2004), 24<<genomic species>> according to nomenclature currently in force and abbreviated below to <<genospecies>> or <<g.sp.>>) are recognized and only 17 species have a validated name (Nemec et al., 2003; Carr et al., 2003). Unfortunately, the members of this genus have very broad intra-specific phenotype variability, and therefore cannot be differentiated at phenotype level. The increase in the number of infections related to these agents has prompted research into analysis methods for the identification and taxonomy of these bacteria. It has therefore been shown that identification methods based on phenotypical characteristics and sequencing of the 16S ribosomal RNA gene by comparison with DNA-DNA hybridisation are not valid. Therefore the search for rapid identification methods of these bacteria is still an issue (Gerner-Smidt et al., 1991; Ibrahim et al., 1997; Rainey et al., 1994). In particular, molecular techniques based on sequencing of the 16S ribosomal RNA gene do not allow a distinction to be made between the closest species, in particular due the lack of polymorphism of this gene within this genus. (Yamamoto and Harayama, 1998; Ochman and Wilson, 1987; Stackebrandt and Goebel, 1994). Additionally, owing to this lack of polymorphism, there is a need to determine the complete sequence of the 16S rRNA gene if it is wished to be able to identify a species. This requires sequencing the entirety of the gene which has around 1600 base pairs. The practical consequence is that sequencing must be based on a minimum of 6 sequencing reactions in addition to the amplification reaction to obtain an assessable result. Phylogenetic attempts have been made using the comparison of gyrB genes (Yamamoto and Harayama, 1996; Yamamoto et al., 1999) and recA genes (Krawczyk et al., 2002) as an alternative to the 16S ribosomal RNA gene (Ibrahim et al., 1997). Unfortunately, the sequences of these genes have not been determined on the 10 most recent species (Nemec et al., 2001, 2003; Carr et al., 2003).

There is therefore still a demand for a molecular identification tool to identify the bacteria species of genus *Acinetobacter*, which can be routinely used in bacteriology laboratories, in particular having a sufficiently polymorphic gene so that the determination of a short sequence (less than 500 base pairs) with only 1 amplification reaction and two sequence reactions is identifying i.e. can be amplified and sequenced using a single set of primers.

The inventors have discovered and shown according to the present invention that:
  the rpoB gene and its non-coding boundary sequences, namely
  the non-coding sequences at 5' between the sequences of the rp/L and rpoB genes (called "rplL-rpoB spacers" or <<rp/L-rpoB intergenic fragments>> below), and
  the non-coding sequences at 3' between the sequences of the rpoC and rpoB genes (called "rpoB-rpoC spacers" or <<rpoB-rpoC intergenic fragments>> below),
  form a genetic marker allowing the detection and specific identification of the bacterium of each species of genus *Acinetobacter*, and in particular of the following 24 species: *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A. schindleri, A. ursingii, A. baylyi, A. bouvetii, A. gerneri, A. grimontii, A. tandoii, A. tjernbergiae, A. towneri, A. parvus*.

The genomic species 1 to 16 ("genomic species>>) correspond to strains referenced in GENBANK, for some of which (no 3, 6, 9, 10, 13 and 16) no name has yet been given.

The inventors have discovered some hypervariable regions between the different species and hence specific to each species, flanked by conserved sequences between the different species, which can be used to implement a molecular identification method of the different species of *Acinetobacter* bacteria by amplification, using primers chosen from the conserved sequences and hybridisation and/or sequencing of the specific sequences so amplified.

More particularly, the present invention concerns sequences of nucleic acids specific to each species of genus *Acinetobacter* cited above whose nucleotide sequence is drawn from the rpoB gene of said bacteria.

According to Lazcano et al. [J. Mol. Evol. (1988) 27:365-376], the RNA polymerases are divided into two groups according to their origin, one consisting of RNA- or DNA-dependent viral RNA polymerises, and the other of DNA-dependent RNA polymerases of eukaryote or prokaryote origin (archaebacteria and eubacteria). The eubacterial, DNA-dependent RNA polymerases are characterized by a simple, conserved, multimeric constitution called a "core enzyme", represented by $\alpha\beta\beta'$, or "holoenzyme" represented by $\alpha\beta\beta'\sigma$ [Yura and Ishihama, Ann. Rev. Genet. (1979) 13:59-97]. Numerous studies have evidenced the functional role, within the multimeric enzymatic complex, of the $\beta$ subunit of the eubacterial RNA polymerase. On the other hand, the archaebacterial, eukaryote RNA polymerases have a more complex structure which may reach around ten, even thirty subunits [Pühlet et al. Proc. Natl. Acad. Sci. USA (1989) 86:4569-4573].

The genes encoding the different $\alpha\beta\beta'\sigma$ subunits of DNA-dependent RNA polymerase in eubacteria, respectively the rpoA, rpoB, rpoC and rpoD genes, are classified in different groups comprising the genes coding for constituent proteins of the ribosomal subunits or for enzymes involved in the replication and repair of the genome [Yura and Yshihma, Ann. Rev. Genet. (1979) 13:59-97]. Some authors have shown that the sequences of the rpoB and rpoC genes could be used to construct phylogenetic trees [Rowland et al. Biochem. Soc. Trans. (1992) 21:40 S] allowing separation of the different branches and sub-branches of the living kingdoms.

Before setting forth the invention in detail, different terms used in the description and claims are defined as follows:

by "nucleic acid extracted from bacteria" is meant either the total nucleic acid, or the genomic DNA, or the messenger RNAs, or the DNA obtained from reverse transcription of the messenger RNAs;

"nucleotide fragment" or "oligonucleotide" are two synonymous terms designating a chain of nucleotide patterns characterized by an information sequence of the natural (or possibly modified) nucleic acids and able to hybridise, like the natural nucleic acids, with a complementary or substantially complementary nucleotide fragment, under predetermined high-stringency conditions. The chain may contain nucleotide patterns having a different structure to that of the natural nucleic acids. A nucleotide fragment (or oligonucleotide) may for example contain up to 100 nucleotide patterns. It generally contains at least 10, preferably from 18 to 35 nucleotide patterns and can be obtained from a natural nucleic acid molecule and/or by genetic recombination and/or by chemical synthesis, a nucleotide pattern is derived from a monomer which may be a natural nucleotide of nucleic acid whose constituent elements are a sugar, a phosphate group and a nitrogen-containing base chosen from among adenine (A), guanine (G), uracil (U), cytosine (C), thymine (T); or else the monomer is nucleotide of which at least one of the three previous constituent elements is modified; for example the modification may concern a base, with modified bases such as inosine which can hybridise with any base A, T, U, C or G, methyl-5-deoxycytidine, deoxyuridine, dimethylamino-5-deoxyuridine or any other modified base capable of hybridisation either at the sugar e.g. the replacement of at least one deoxyribose by a polyamide [Nielsen P E et al., Science (1991) 254: 1497-1500], or at the phosphate group e.g. through replacement by esters chosen in particular from among the diphosphates, alkylphosphonates and phosphorothioates, by "hybridisation", is meant the process during which, under suitable conditions, two nucleotide fragments having sufficiently complementary sequences are able to combine under stable specific hydrogen bonds to form a double strand. The hybridisation conditions are determined by "stringency", i.e. the strictness of operating conditions. Hybridisation is all the more specific the higher the stringency under which it is conducted. Stringency is related in particular to the base composition of a probe/target duplex, and to the extent of mismatch between two nucleic acids. Stringency may also be related to parameters of the hybridisation reaction, such as concentration and the type of ion species present in the hybridisation solution, the type and concentration of denaturing agents and/or hybridisation temperature. The stringency of the conditions under which a hybridisation reaction must be performed depends in particular on the probes used. All these data items are well known and suitable conditions can possibly be determined in each case by routine experiments. In general, depending on the length of the probes used, the temperature for the hybridisation reaction lies between approximately 20 and 65° C., in particular between 35 and 65° C. in a saline solution at a concentration of approximately 0.8 to 1 M.

a "probe" is a nucleotide fragment having hybridisation specificity under determined conditions to form a hybridisation complex with a nucleic acid having, in the present case, a nucleotide sequence included either in a messenger RNA, or in a DNA obtained by reverse transcription of said messenger RNA, a transcription product; a probe may be used for diagnostic purposes (capture or detection probes in particular) or for therapeutic purposes, a probe may be immobilized or able to immobilized on a solid support by any suitable means, e.g. by covalency, by adsorption, or by direct synthesis on a solid. Examples of supports comprise microtitration plates and DNA chips, a "probe" is generally labelled with a marking agent chosen for example from among radioactive isotopes, enzymes, in particular enzymes able to act on a chromogenic, fluorigenic or luminescent substrate (in particular a peroxydase or an alkaline phosphatase), or from among chromophorous chemical compounds, chromogenic, fluorigenic or luminescent chemical compounds, analogs of nucleotide bases. This marking may be direct between the DNA and said marker, or indirect i.e. via ligands such as biotin or other molecule able to bind to markers, a "species probe" is a probe allowing specific identification of the species of a bacterium of a given genus, *Acinetobacter* in this case, a "genus probe" is a probe allowing specific identification of the genus of the bacterium, irrespective of the species of the bacterium of said genus, under certain hybridisation conditions, a "primer" is a probe comprising for example 10 to 100 nucleotide patterns and having hybridisation specificity under determined conditions for enzymatic amplification reactions, by "genus primer", is meant a set of primers allowing specific amplification of any bacterium of one same given genus, with no distinction as to species, under certain hybridisation and amplification conditions (the "genus primers" are also called "consensus primers" or "universal primers" in the present application), by "amplification reaction" is meant an enzymatic polymerisation reaction, e.g. in an amplification technique such as PCR, initiated by primer oligonucleotides and using a DNA polymerase, by "sequencing reaction", is meant a reaction leading to determination of the sequence of a nucleic acid fragment, or of a complete gene by an abortive polymerisation process starting with oligonucleotide primers and using said dideoxynucleotides (Sanger F, Coulson A R (1975), J. Mol. Biol. 94: 441) or by multiple hybridisations with multiple probes fixed onto a solid support such as used in DNA chips for example, or other techniques known to those skilled in art.

The inventors have determined the complete sequences of the rpoB genes and their non-coding boundary sequences separating them from the rp/L and rpoC genes ("rplL-rpoB spacer" and "rpoB-rpoC spacer") of 24 species of the genus *Acinetobacter*. *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A. schindleri, A. ursingii, A. baylyi, A. bouvetii, A. gerneri, A. grimontii, A. tandoii, A. tjernbergiae, A. towneri, A. parvus.*

To arrive at determining said complete sequences of rpoB and its flanking sequences in all the species of *Acinetobacter* bacteria, the inventors after a large number of unsuccessful tests and from the sole rpoB sequence and its non-coding boundary regions in bacteria of genus *Acinetobacter*—were firstly compelled to determine 51 primers (Table 2) of corresponding sequences of bacteria which they identified as being close and available from GENBANK, namely *Acinetobacter* sp. ADP1 (GenBank accession number NC_005966), *Pseudomonas syringae* pv. tomato str.DC3000 (GenBank accession number NC_004578) and *P. putida* KT2440 (GenBank accession number NC_006347).

*Acinetobacter* strain sp. ADP1 is a strain which had not been characterized before the invention, and which does not correspond to any of the pathogenic strains described in the present patent application and listed below.

The subject-matter of the present invention is therefore a complete rpoB gene of a bacterium of the genus *Acinetobacter* chosen from among the following 23 species: *A. calcoaceticus* (genomic species 1), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A. schindleri, A. ursingii, A. baylyi, A. bouvetii, A. gerneri, A. grimontii, A. tandoii, A. tjernbergiae, A. towneri, A. parvus,* characterized in that its sequence comprises and more particularly consists of a sequence chosen from among the sequences such as described in sequences SEQ. ID. no 9 and 11 to 32 respectively, and the sequences having at least 98% similarity, and their complementary sequences.

A further subject of the present invention concerns nucleic acid fragments comprising and more particularly consisting of a non-coding fragment flanking the rpoB gene of a bacterium of the genus *Acinetobacter* chosen from among the following 24 species: *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A. schindleri, A. ursingii, A. baylyi, A. bouvetii, A. gerneri, A. grimontii, A. tandoii, A. tjernbergiae, A. towneri, A. parvus,* characterized in that its sequence comprises and more particularly consists of a sequence chosen from among the sequences such as described in sequences SEQ. ID. no 121 to 144 respectively, and sequences SEQ. ID. no 165 to 188 respectively, and the sequences having at least 98% similarity and their complementary sequences.

The said sequences having similarity rates of at least 98% with said sequences SEQ. ID. 9 to 32, 121 to 144 and 165 to 188 correspond to the possible variations between the different strains of one same species possibly corresponding to sub-species. Therefore sequences SEQ. ID. no 145 to 164 and 189 to 208 correspond to various strains of *A. baumannii* having at least 98% homology with sequences SEQ. ID. no 122 and 166 respectively.

By "similarity rate" or "homology percentage", is meant a percentage of sequence identity i.e. a percentage of nucleotides of the sequences which are identical at the same position with respect to another sequence.

Sequences SEQ. ID. no 121 to 144 correspond to the 5' flanking sequences representing the complete rpoB spacer bordering the rpoB gene between genes rp/L and rpoB, having a length of between 301 and 310 bp, for each species of the bacterium of the genus *Acinetobacter*, in the 24 above-mentioned species.

Sequences SEQ. ID. no 165 to 188 correspond to 3' flanking sequences representing the complete rpoB-rpoc spacer bordering the rpoB gene between the rpoB and rpoC genes, having a length of between 86 and 177 bp, for each species of the bacterium of genus *Acinetobacter*, in the 24 above-mentioned species.

The spacers rpoB-rpoC and rp/L-rpoB which border the rpoB gene, and the complete sequence of the rpoB gene can be used to identify the bacterium not only as probe and/or by investigating its primary sequence, but also by investigating the secondary and tertiary structures of the messenger RNA derived from transcription of the complete DNA sequence.

In these rpoB genes and their non-coding boundary sequences (rplL-rpoB spacer and rpoB-rpoC spacer) of *Acinetobacter*, the inventors have evidenced consensus sequences SEQ. ID. no 1, 2, 3, 4, 5, 6, 7 and 8 (Table 3) which are conserved sequences between all bacteria of the genus *Acinetobacter*, i.e. able to be used as primers to amplify the same portion of the rpoB gene and its non-coding boundary regions (rp/L-rpoB spacer and rpoB-rpoC spacer) of all said *Acinetobacter* bacteria, namely:

SEQ. ID. no 1, and 2 for a first region of the rpoB gene,
SEQ. ID. no 3, and 4 for a second region of the rpoB gene,
SEQ. ID. no 5, and 6 for the rp/L-rpoB spacer and
SEQ. ID. no 7, and 8 for the rpoB-rpoC spacer,
SEQ. ID. no 1 to 4 and 6-7 lie inside the rpoB gene, with:
SEQ. ID. no 8 and 6 are close to the 5' ends of the rpoB and rpoC genes respectively,
SEQ. ID. no 7 and 5 are close to the 3' ends of the rp/L and rpoB genes respectively.

The present invention therefore provides oligonucleotides which have conserved sequences of an *Acinetobacter* bacterium chosen from among the said 24 species comprising a sequence of at least 12, preferably at least 18 consecutive nucleotide patterns included in one of the sequences chosen from the sequences such as described in following sequences SEQ. ID. no 1 to 8, and their complementary sequences, and preferably consisting of said sequences:

```
SEQ ID NO: 1:
5'-TAYCGYAAAGAYTTGAAAGAAG-3',

SEQ ID NO: 2:
5'-CMACACCYTTGTTMCCRTGA-3',

SEQ ID NO: 3:
5'-GTGATAARATGGCBGGTCGT-3',

SEQ ID NO: 4:
5'-CGBGCRTGCATYTTGTCRT-3',

SEQ ID NO: 5:
5'-GAAGARCTTAAGAMDAARCTTG-3'

SEQ ID NO: 6:
5'-CGTTTCTTTTCGGTATATGAGT-3',

SEQ ID NO: 7:
5'-GTTCTTTAGGTATCAACATTGAA-3',

SEQ ID NO: 8:
5'-GACGCAAGACCAATACGRAT-3',
``` in which:
D represents A, G or T,
Y represents C or T,
B represents C, G or T,
R represents A or G, and
M represents A or C.

At the position corresponding to a nucleotide D, Y, B, M or R in sequences SEQ. ID. no 1 2, 3, 4, 5 and 8, variable nucleotides are found in the complementary target sequences in relation to the species of bacterium under consideration, but all the other nucleotides are conserved in all the species of bacteria of the genus *Acinetobacter*.

Sequences SEQ. ID. no 1, 3, 5 and 7 are used as primers on the direct strand, and sequences SEQ. ID. no 2, 4, 6 and 8 are used as primer on the indirect strand. Sequences SEQ. ID. no 2, 4, 6 and 8 therefore correspond to sequences complementary to those of the direct strand.

To be used as consensus primers, these oligonucleotides of sequences SEQ. ID. no 1, 2, 3, 4, 5 and 8 are therefore used in the form of equimolar mixtures of oligonucleotides of different sequences, said oligonucleotides of different sequences for each sequence SEQ. ID. no 1 to 8 meeting the various possible definitions of respective sequences no 1, 2, 3, 4, 5 and 8.

These equimolar mixtures of oligonucleotides are obtained through the use, during oligonucleotide synthesis, of equimolar mixtures of the different nucleotides concerned, respectively:
A, G and T for D,
C and T for Y,
C, G and T for B,
A and G for R,
A and C for M.

The mixtures of oligonucleotides, meeting the definition nucleotides of sequences SEQ. ID. no 1 2, 3, 4, 5 and 8, are therefore able to hybridise with the different target complementary sequences included in the rpoB genes and at the ends of the rp/L and rpoC genes flanking their boundary non-coding regions (rplL-rpoB spacer and rpoB-rpoC spacer) of all the species of bacteria of the genus *Acinetobacter* and, more particularly, the 24 above-mentioned species.

The capacity of these primers to amplify rpoB gene fragments and their non-coding boundary regions (rplL-rpoB spacer and rpoB-rpoC spacer), of all species of *Acinetobacter*, allows the consideration to be made that these primers will be efficient in identifying additional species of *Acinetobacter* which may be described in the future.

A further subject of the invention is therefore a mixture of oligonucleotides characterized in that it comprises an equimolar mixture of oligonucleotides of different sequences comprising at least 12, preferably at least 18 consecutive nucleotide patterns included in one of sequences SEQ. ID. no 1 to 5 and 8, or the oligonucleotides of complementary sequences.

More particularly, the subject of the present invention is the following mixtures of oligonucleotides:
an equimolar mixture of 8 oligonucleotides of different sequences, consisting of sequence SEQ. ID. no 1 or oligonucleotides of complementary sequences.
an equimolar mixture of 16 oligonucleotides of different sequences, consisting of sequence SEQ. ID. no 2 or oligonucleotides of complementary sequences.
an equimolar mixture of 6 oligonucleotides of different sequences, consisting of sequence SEQ. ID. no 3 or oligonucleotides of complementary sequences.
an equimolar mixture of 24 oligonucleotides of different sequences, consisting of sequence SEQ. ID. no 4 or oligonucleotides of complementary sequences.
an equimolar mixture of 24 oligonucleotides of different sequences, consisting of sequence SEQ. ID. no 5 or oligonucleotides of complementary sequences.
sequence oligonucleotide consisting of sequence SEQ. ID. no 6 or a complementary sequence.
sequence oligonucleotide consisting of sequence SEQ. ID. no 7 or a complementary sequence.
an equimolar mixture of 2 oligonucleotides of different sequences consisting of sequence SEQ. ID. no 8 or oligonucleotides of complementary sequences.

The oligonucleotides or mixtures of oligonucleotides comprising a sequence included in one of sequences SEQ. ID. no 1 to 8 according to the invention, can be used as genus primers for bacteria of the genus *Acinetobacter*.

As mentioned previously, the consensus sequences SEQ. ID. no 1, 2, 3, 4, 5 and 8, so defined, also flank hypervariable sequences whose sequence is specific to each species of the genus *Acinetobacter*.

The inventors were therefore able to evidence sequences specific to species for each of the 24 above-cited bacteria species, corresponding to sequences:
SEQ. ID. no 33 to 56, flanked by consensus sequences SEQ. ID. no 1 and 2 (hereafter "region 1 of rpoB");
SEQ. ID. no 77 to 100, flanked by consensus sequences SEQ. ID. no 3 and 4 (hereunder "region 2 of rpoB");
SEQ. ID. no 121 to 144, flanked by consensus sequences SEQ. ID. no 5 and 6 (hereunder "rpo/L-rpoB spacer"); and
SEQ. ID. no 165 to 188, flanked by consensus sequences SEQ. ID. no 7 and 8 (hereunder "rpoB-rpoC spacer");

The oligonucleotides of sequences flanked by SEQ. ID. no 1 2, 3, 4, 5, 6, 7 and 8, can therefore be used as species primer for bacteria of the genus *Acinetobacter*.

Said specific hypervariable sequences SEQ. ID. no 33 to 56 flanked by sequences SEQ. ID. no 1 and 2, represent a fragment of the rpoB gene of length 350 bp, with less than 96% similarity between the different species (Table 7) with the exception of the pairs *A. baylii*/genospecies 11 and *A. grimontii*/*A. junii*, which means that they form a short specific target sequence for the specific identification of each species of the bacterium of the genus *Acinetobacter*, more precisely for the 24 above-mentioned species, with the exception of the pairs *A. baylii*/genospecies 11 and *A. grimontii*/*A. junii*.

Said specific hypervariable sequences SEQ. ID. no 77 to 100 flanked by sequences SEQ. ID. no 3 and 4, represent a fragment of the rpoB gene of length 450 bp with less than 96% similarity between the different species (Table 8) with the exception of the pairs *A. baylii*/genospecies 11 and *A. grimontii*/*A. junii*, which means that they form a second short specific target sequence to specifically identify each bacterium species of the genus *Acinetobacter*, more precisely for the 24 above-mentioned species, with the exception of the pairs *A. baylii*/genospecies 11 and *A. grimontii*/*A. juni*.

Said specific hypervariable sequences SEQ. ID. no 121 to 164 flanked by sequences SEQ. ID. no 5 and 6, represent the rplL-rpoB spacer bordering the rpoB gene by a length of between 301 and 310 bp with less than 97% similarity between the different species (see Table 5 below) with the exception of the pairs *A. baylii*/genospecies 11, *A. grimontii*/ *A. junii*, and *A. lwoffi*/genospecies 9, which means that they form a third short specific target sequence to specifically identify each bacterium species of the genus *Acinetobacter*, more precisely for the 24 above-mentioned species, with the exception of the pairs *A. baylii*/genospecies 11, *A. grimontii*/*A. junii*, and *A. lwoffii*/genospecies 9.

Finally, said specific hypervariable sequences SEQ. ID. no 165 to 188 flanked by sequences SEQ. ID. no 7 and 8, represent the rpoB-rpoC spacer bordering the rpoB gene by a length of between 86 and 177 bp with less than 97% similarity between the different species (see Table 6 below) with the exception of the pairs *A. grimontii*/*A. junii* and species of the Acb group (*A. baumannii, A. calcoaceticus* and genospecies 3), so that they form a fourth short specific target sequence for the specific identification of each bacterium species of the genus *Acinetobacter*, more precisely for the 24 above-mentioned species, with the exception of the pairs *A. grimontii*/*A. junii* and species of the Acb group (*A. baumannii, A. calcoaceticus* and genospecies 3).

A further subject of the present invention is therefore an rpoB gene fragment of a bacterium of genus *Acinetobacter* chosen from among the 24 species: *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A. schindleri, A. ursingii, A. baylyi, A. bouvetii, A. gerneri, A. grimontii, A. tandoii, A. tjernbergiae, A. towneri, A. parvus*, characterized in that its sequence consists of a sequence chosen from among the sequences such as described in sequences SEQ. ID. no 33 to 56 respectively, and sequences SEQ. ID. no 77 to 100 respectively, and the sequences having at least 98% similarity and their complementary sequences.

A further subject of the present invention is an rpoB gene fragment of a bacterium of the genus *Acinetobacter* chosen from among the 23 species: *A. calcoaceticus* (genomic species 1), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A. schindleri, A. ursingii, A. baylyi, A. bouvetii, A. gerneri, A. grimontii, A. tandoii, A. tjernbergiae, A. towneri, A. parvus*, characterized in that its sequence comprises a sequence chosen from among the sequences such as described in sequences SEQ. ID. no 33 and 35 to 56 respectively, and sequences SEQ. ID. no 77 and 79 to 100 respectively, and the sequences having at least 98% similarity and their complementary sequences.

The said sequences having similarity rates of at least 98% with said sequences SEQ. ID. no 33 to 56 and 77 to 100 correspond to possible variations between the different strains of one same species, possibly and more particularly corresponding to sub-species. Therefore the sequences SEQ. ID. no 57 to 76 and 101 to 120 correspond to various strains of *A. baumannii* having at least 98% homology with SEQ. ID. no 34 and 78 respectively.

The subject of the present invention is therefore also the use, as species probe, of a rpoB, rp/L or rpoC gene fragment according to the invention or of an oligonucleotide of sequences specific to a said species of *Acinetobacter* bacterium according to the invention.

More precisely, the present invention provides a method of detection by molecular identification to identify a bacterium of one of the species of the genus *Acinetobacter*, characterized in that the following are used:

the complete rpoB gene of said bacterium according to the invention, comprising a said sequence SEQ. ID. no 9 to 32, or preferably consisting of a said sequence SEQ. ID. no 9 to 32, or the complementary sequences, or sequences having at least 98% similarity, an rpoB gene fragment of a said bacterium according to the invention, comprising a said sequence SEQ. ID. no 33 to 56 or 77 to 100, or consisting of a said sequence SEQ. ID. no 33 to 56 or 77 to 100, or the complementary sequences, or sequences having at least 98% similarity, an rpoB gene fragment of a said bacterium according to the invention, comprising a said sequence SEQ. ID. no 77 to 100, or preferably, consisting of a said sequence SEQ. ID. no 77 to 100, or complementary sequences, or sequences having at least 98% similarity, a gene fragment comprising a complete rpIL-rpoB or rpoB-rpoC intergenic fragment of said bacterium according to the invention, comprising a said sequence SEQ. ID. no 121 to 144 or 165 to 188, or preferably consisting of a said sequence SEQ. ID. no 121 to 144 or 165 to 188, the complementary sequences or sequences having at least 98% similarity, an oligonucleotide having a sequence specific to an *Acinetobacter* bacterium chosen from among the 24 above-cited species, preferably with at least 18, further preferably 18 to 35 consecutive nucleotide patterns included in one of the sequences chosen from among the sequences such as described in sequences:

SEQ. ID. no 33 to 56 respectively,
SEQ. ID. no 77 to 100 respectively,
SEQ. ID. no 121 to 144 respectively,
SEQ. ID. no 165 to 188 respectively, and
the sequences having at least 98% similarity and their complementary sequences, or an oligonucleotide or equimolar mixture of oligonucleotides according to the invention, comprising a sequence of at least 12, preferably 18 consecutive nucleotides included in one of sequences SEQ. ID. no 1 2, 3, 4, 5, 6, 7 and 8 or their complementary sequences, or preferably consisting of one of said sequences SEQ. ID. no 1 2, 3, 4, 5, 6, 7 and 8.

In a first embodiment of a bacterium detecting method of the invention, it is sought specifically to detect a given species of an *Acinetobacter* bacterium chosen from among the following 24 species: *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A. schindleri, A. ursingii, A. baylyi, A. bouvetii, A. gerneri, A. grimontii, A. tandoii, A. tjernbergiae, A. towneri, A. parvus*, a method in which:

1—a sample containing or likely to contain nucleic acids of at least one said bacterium is contacted with at least one species probe consisting of an oligonucleotide or gene fragment according to the invention, preferably a gene fragment respectively consisting of one of said sequences chosen from among:

SEQ. ID. no 33 to 56 respectively,
SEQ. ID. no 77 to 100 respectively,
SEQ. ID. no 121 to 144 respectively,
SEQ. ID. no 165 to 188 respectively, and
the sequences having at least 98% similarity and their complementary sequences.

2—the formation or non-formation of a hybridisation complex is determined between said probe and the nucleic acids of the sample, and it is thereby determined whether said species of *Acinetobacter* is present in the sample if a hybridisation complex is formed.

In a second embodiment of a method to detect a specific species of a bacterium of the genus *Acinetobacter*, the steps are performed in which:

1—amplification primers comprising said mixtures of oligonucleotides of the invention are contacted with a sample containing or likely to contain nucleic acids of at least one said bacterium of the genus *Acinetobacter*, and nucleic acid amplification is performed by enzymatic polymerisation reaction comprising:

as 5' primer, at least one oligonucleotide or mixture oligonucleotides according to the invention comprising a sequence included in one of sequences SEQ. ID. no 1, 3, 5 and 7, preferably consisting of said complete sequence SEQ. ID. no 1, 3, 5 and 7 or the complementary sequences, and as 3' primer, at least one oligonucleotide or mixture of oligonucleotides according to the invention comprising sequences included in one of sequences SEQ. ID. no 2, 4 6, and 8 respectively, preferably consisting of said complete sequence SEQ. ID. no 2, 4, 6, and 8, or respectively a complementary sequence.

2—and the formation or non-formation of an amplification product is determined, and the presence of absence of said bacterium in the sample is thereby respectively determined if an amplification product is or is not formed.

More particularly, it is sought to determine a given species of an *Acinetobacter* bacterium chosen from among the following 24 species: *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, 11, *A. radioresistens* (genomic species 12), genomic species 13, genomic species 16, *A. schindleri, A. ursingii, A. baylyi, A. bouvetii, A. gerneri, A. grimontii, A. tandoii, A. tjernbergiae, A. towneri, A. parvus*, and, at step 2 above, the presence or absence of the given species of a said bacterium is determined by conducting the steps in which:

a) a sequencing reaction is conducted of a gene fragment is amplified with said primers, and b) the sequence of said amplified fragment obtained is compared with the sequence of a gene fragment of said bacterium respectively comprising:

said sequences SEQ. ID. no 33 to 56, when said 5' and 3' primers are oligonucleotides of sequences included in sequences SEQ. ID. no 1 and 2 respectively, said sequences SEQ. ID. no 77 to 100, when said 5' and 3' primers are oligonucleotides of sequences included in sequences SEQ. ID. no 3 and 4 respectively, and said sequences SEQ. ID. no 121 to 144, when said 5' and 3' primers are oligonucleotides of sequences included in sequences SEQ. ID. no 5 and 6 respectively, and said sequences SEQ. ID. no 165 to 188, when said 5' and 3' primers are oligonucleotides of sequences included in sequences SEQ. ID. no 7 and 8 respectively.

In another variant of said second embodiment of a method to detect a specific species of a bacterium of the genus *Acinetobacter*, it is sought to detect a specific species of an *Acinetobacter* bacterium chosen from among the 24 following species: *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A. schindleri, A. ursingii, A. baylyi, A. bouvetii, A. gerneri, A. grimontii, A. tandoii, A. tjernbergiae, A. towneri, A. parvus*, and at step 2 above the presence or absence of the given species of said bacterium is determined by conducting the steps in which:

a—a sample containing or likely to contain amplified nucleic acids of at least one said bacterium is contacted with at least one species probe consisting of an rpoB gene fragment or a specific oligonucleotide of the invention, preferably a fragment consisting respectively of one of said sequences chosen from among:

SEQ. ID. no 33 to 56 respectively, when said 5' and 3' primers are oligonucleotides of sequences included in sequences SEQ. ID. no 1 and 2 respectively, SEQ. ID. no 77 to 100 respectively, when said 5' and 3' primers are oligonucleotides of sequences included in sequences SEQ. ID. no 3 and 4 respectively, and SEQ. ID. no 121 to 144 respectively, when said 5' and 3' primers are oligonucleotides of sequences included in sequences SEQ. ID. no 5 and 6 respectively, and SEQ. ID. no 165 to 188 respectively, when said 5' and 3' primers are oligonucleotides of sequences included in sequences SEQ. ID. no 7 and 8 respectively, and b—the formation or non-formation of a hybridisation complex is determined between said probe and the amplified nucleic acids of the sample, and the presence or absence in the sample of said species of *Acinetobacter* is thereby determined according to whether or not a hybridisation complex is formed.

In one preferred embodiment of a method according to the invention, the steps are performed comprising:

1—a first amplification of the nucleic acid of said sample with a pair of 5' and 3' primers chosen from among said mixtures of oligonucleotides of the invention, comprising sequences respectively included in sequences SEQ. ID. no 1 and SEQ. ID. no 2, preferably consisting of said sequences SEQ. ID. no 1 and 2, or the complementary sequences, and 2—a first determination of the onset or absence of an amplification product containing the nucleic acids of at least one said bacterium, by hybridisation or optionally sequencing, and comparison of the amplicons obtained at step 1 with the fragments respectively consisting of one of said sequences chosen from among SEQ. ID. no 33 to 56 and 34 to 76 respectively, and if, at this step 2, the presence of species *A. grimontii* or *A. junii* is determined, the following is also performed:

3a—a second amplification reaction with avec 5' and 3' primers chosen from among said oligonucleotide mixtures according to the invention, comprising sequences respectively included in sequences SEQ. ID. no 3 and SEQ. ID. no 4, preferably consisting of said sequences SEQ. ID. no 3 and 4, or the complementary sequences, and 4a—determining the formation or non-formation of an amplification product containing nucleic acids of at least one said bacterium, by hybridisation or optionally sequencing, and comparing the amplicons obtained at step 3a with the fragments respectively consisting of one of said sequences chosen from among SEQ. ID. no 77 to 100 respectively, or if, at first step 2, the presence of species *A. baylii* or genomic species 11 is determined, the following is also performed:

3b—a second amplification reaction with 5' and 3' primers chosen from among said mixtures of oligonucleotides according to the invention containing sequences respectively included in sequences SEQ. ID. no 7 and SEQ. ID. no 8, preferably consisting of said sequences SEQ. ID. no 7 and 8, or the complementary sequences, and 4b—determining the formation or non-formation of an amplification product containing nucleic acids of at least one said bacterium, by hybridisation or optionally sequencing, and comparison of the amplicons obtained at step 3b with the fragments respectively consisting of one of said sequences chosen from among SEQ. ID. no 165 to 188 respectively.

Sequences SEQ. ID. no 1 to 208 can be prepared by genetic engineering and/or by automatic synthesis or chemical synthesis using techniques well known to those skilled in the art.

The probes of the invention can be used for diagnostic purposes, as mentioned above, by determining the formation or non-formation of a hybridisation complex between the probe and a target nucleic acid in a sample, using any known hybridisation technique and in particular so-called "DOT-BLOT" techniques [Maniatis et al. (1982) Molecular Cloning, Cold Spring Harbor], DNA transfer techniques called "SOUTHERN BLOT" [Southern E. M., J. Mol. Biol. (1975) 98:503], RNA transfer techniques called "NORTHERN BLOT", or so-called "sandwich" techniques, in particular with a capture probe and/or detection probe, said probes being able to hybridise with two different regions of the target nucleic acid, and at least one of said probes (generally the detection probe) being able to hybridise with a target region specific to the species, on the understanding that the capture probe and the detection probe must have nucleotide sequences that are at least partly different.

The nucleic acid to be detected (target) may be DNA or RNA (the first obtained after PCR amplification). When detecting a target of double strand nucleic acid type, this acid must be denatured before initiating the detection method. The target nucleic acid may be obtained by extraction using known methods for nucleic acids of a sample to be tested. The denaturing of a double strand nucleic acid can be performed using known chemical, physical or enzymatic denaturing methods, in particular by heating to a suitable temperature of more than 80° C.

To implement the above-cited hybridisation techniques, in particular the "sandwich" techniques, a probe of the invention, called a capture probe, is immobilized on a solid support, and another probe of the invention, called a detection probe, is labelled with a marking agent. The examples of support and marking agent are as previously defined.

Advantageously, one species probe is immobilized on a solid support, and another species probe is labelled with a marking agent.

Another application of a said mixture of oligonucleotides of the invention is its use as nucleotide primer comprising a monocatenary oligonucleotide chosen from among oligonucleotides having a sequence of at least 12 nucleotide patterns included in one of sequences SEQ. ID. no 1 to 8, which can be used for the synthesis of a nucleic acid in the presence of a polymerase using a method known as such, in particular in amplification methods using said synthesis in the presence of a polymerase (PCR, RT-PCR, etc.). In particular, a primer of the invention can be used for the specific reverse transcription of a messenger RNA sequence of a bacterium species of the genus *Acinetobacter*, to obtain a corresponding complementary DNA sequence. Said reverse transcription may form the first stage of the RT-PCR technique, the following stage being PCR amplification of the complementary DNA obtained.

In one particular case, said primer comprising an oligonucleotide of the invention also comprises the sense or anti-sense sequence of a promoter recognized by an RNA polymerase (promoters T7, T3, SP6 for example [Studier F W, B A Moffatt (1986) J. Mol. Biol. 189:113]: said primers can be used in nucleic acid amplification methods involving a transcription step such as, for example, NASBA or 3SR techniques [Van Gemen B. et al. Abstract MA 1091, 7$^{th}$ International Conference on AIDS (1991) Florence, Italy].

A further subject of the invention is a nucleotide primer comprising a mixture of monocatenary oligonucleotides chosen from among the oligonucleotides having sequences comprising one of sequences SEQ. ID. no 1 to 8 or preferably consisting of one of sequences SEQ. ID. no 1 to 8, which can be used for total or partial sequencing of the rpoB gene or of the rplL-rpoB spacer or rpoB-rpoC spacer of any species of the genus *Acinetobacter*.

The sequencing of the complete or partial rpoB gene or of the rplL-rpoB spacer or rpoB-rpoC spacer in any bacterium of the genus *Acinetobacter* allows the identification of any *Acinetobacter* bacterium by bio-computerized analysis of this sequence and allows the recognition of new species of unknown *Acinetobacter* bacteria.

Preferably, for use as primer or to sequence the rpoB genes or the rplL-rpoB spacer or rpoB-rpoC spacer, said mixtures of oligonucleotides of sequence SEQ. ID. no 1 and 2 are used.

A further subject of the present invention is a diagnosis kit which can be used in a method of the invention, containing at least one said rpoB gene fragment or rplL-rpoB spacer or rpoB-rpoC spacer according to the invention, comprising or consisting of one of sequences SEQ. ID. no 9 to 188 or an oligonucleotide or said equimolar mixture of oligonucleotides according to the invention, comprising sequences included in sequences SEQ. ID. no 1 to 8 and the oligonucleotides and rpoB gene fragments or rplL-rpoB spacer or rpoB-rpoC spacer of complementary sequences such as defined above, and, preferably, reagents which can be used for hybridisation reactions or amplification reactions or for sequencing accordingly.

As mentioned in the definitions, an oligonucleotide or nucleic acid fragment according to the invention, may be in the form of a deoxyribonucleic acid (DNA) or a ribonucleic acid (RNA) for which T is replaced by U in this case.

Finally, a last subject of the invention is a gene therapy probe to treat infections caused by a strain belonging to a species of the genus *Acinetobacter*, said probe comprising an oligonucleotide such as defined previously. This gene therapy probe, able to hybridise on the messenger RNA and/or on the genomic DNA of said bacteria, is able to block phenomena of translation and/or transcription and/or replication.

The principle of gene therapy methods is known and is based in particular on the use of a probe corresponding to an anti-sense strand: the formation of a hybrid between the probe and the sense strand is capable of disturbing at least one of the decoding steps of genetic data. Gene therapy probes can therefore be used as antibacterial medicinal products, to combat infections caused by bacteria species of the genus *Acinetobacter*.

Other characteristics and advantages of the present invention will become apparent and the invention will be better understood with the help of the description given below of the experiments conducted to implement the invention, together with their results, which are given solely by way of illustration.

Table 1, below, reproduces the list of species of *Acinetobacter* for which rpoB sequences and the rplL-rpoB spacer and rpoB-rpoC spacer were determined, the mentioned strains were obtained from the collection Collection de l'Institut Pasteur (CIP), sequences SEQ. ID. no 1 to 208 are described in the sequence listing appended to the description.

Table 2 lists the different primers used for amplification and sequencing of the rpoB genes.

When Table 2 gives sequences comprising nucleotides W, H, Y, V, R, B, M, K, S or D, these have the meanings known to persons skilled in the art, and in equally conventional fashion these primers are used in the form of an equimolar mixture of oligonucleotides of different sequences in the place of said nucleotides as explained above.

Table 3 gives comparisons of similarities of the sequences of the 16S rRNA and rpoB genes between the two sub-species *C. affermentans* and between the 11 pairs of species considered as close for which similarities between sequences of 16S rRNA genes are 98.5% or over, with a statistical comparison of the mean similarities obtained.

FIG. 1 is a graphical representation of the variability rate (range site variability: RSV (Y axis)) of the sequences of the rpoB genes and flanking sequences of the different species of genus *Acinetobacter* investigated per window of 50 nucleotides (X axis). The hypervariable regions, bounded by the conservative regions and used for species identification using consensus primers, are boxed.

Figure 2:
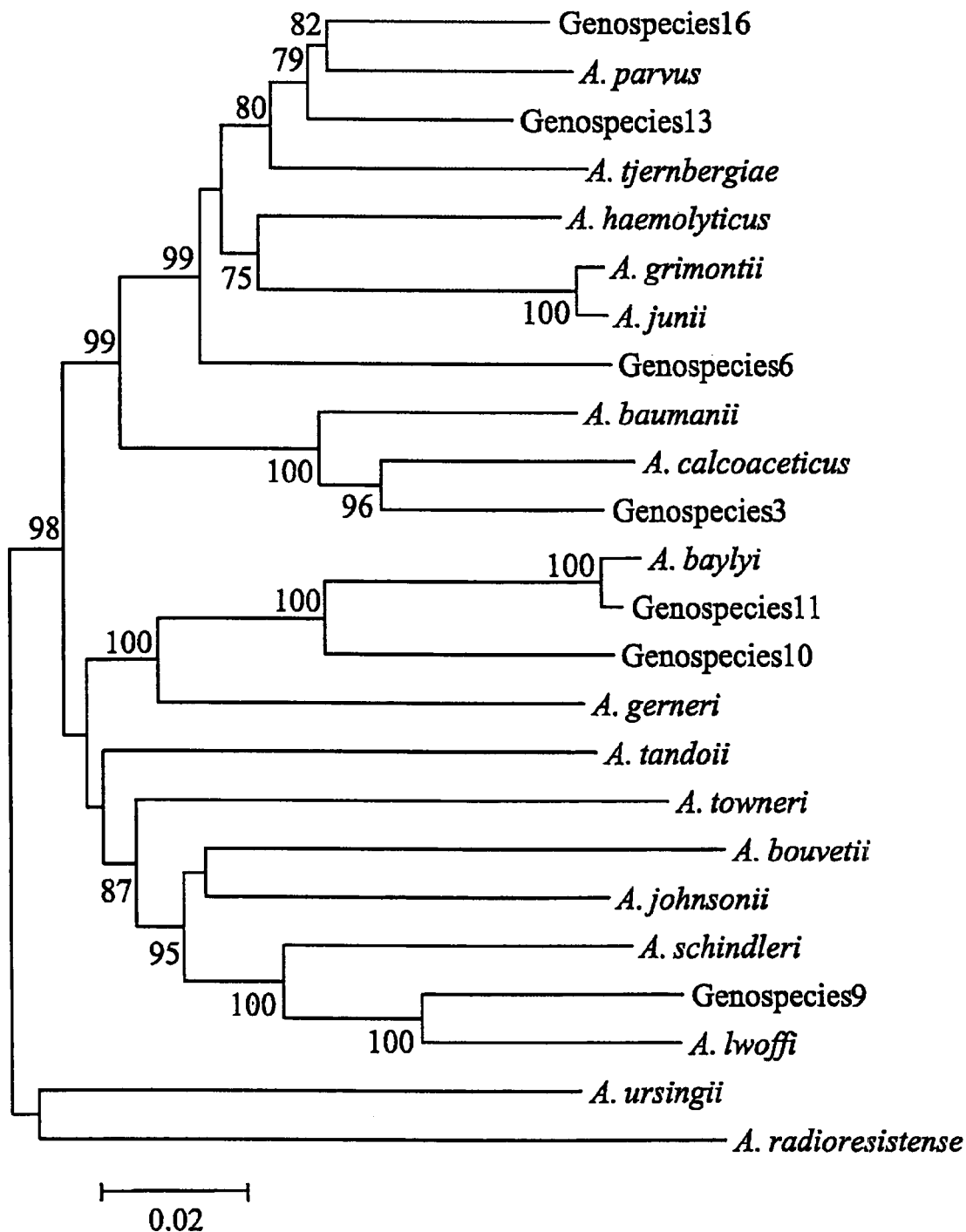

FIG. 2 is a dendogram showing the phylogenetic relationships between the different species of *Acinetobacter* using the "neighbour-joining" method. The tree was constructed by aligning sequences of the rpoB gene. "Bootstrap" sampling values (percentage probability of node accuracy) calculated on the basis of a sample of 1000 trees, are given at each node, only values of 75% or higher being indicated.

Figure 3:
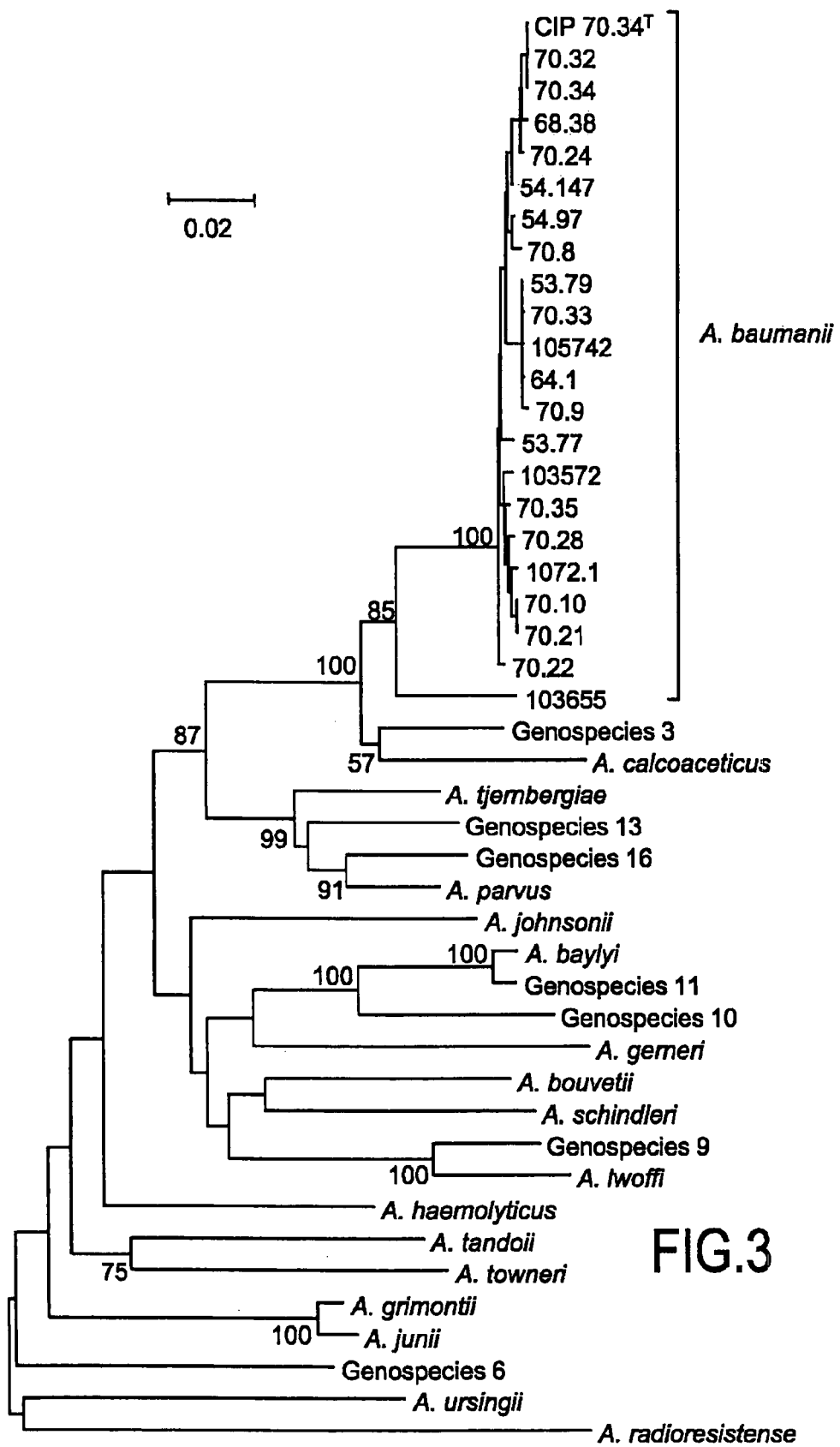

FIG. 3 is a dendogram showing the phylogenetic relationships between different species of *Acinetobacter* using the "neighbour-joining" method. The tree was constructed by aligning hypervariable sequences (region 1 and region 2) of the rpoB gene. The "bootstrap" values (percentage probability of node accuracy) calculated on the basis of a sample of 1000 trees, are indicated at each node.

Figure 4:
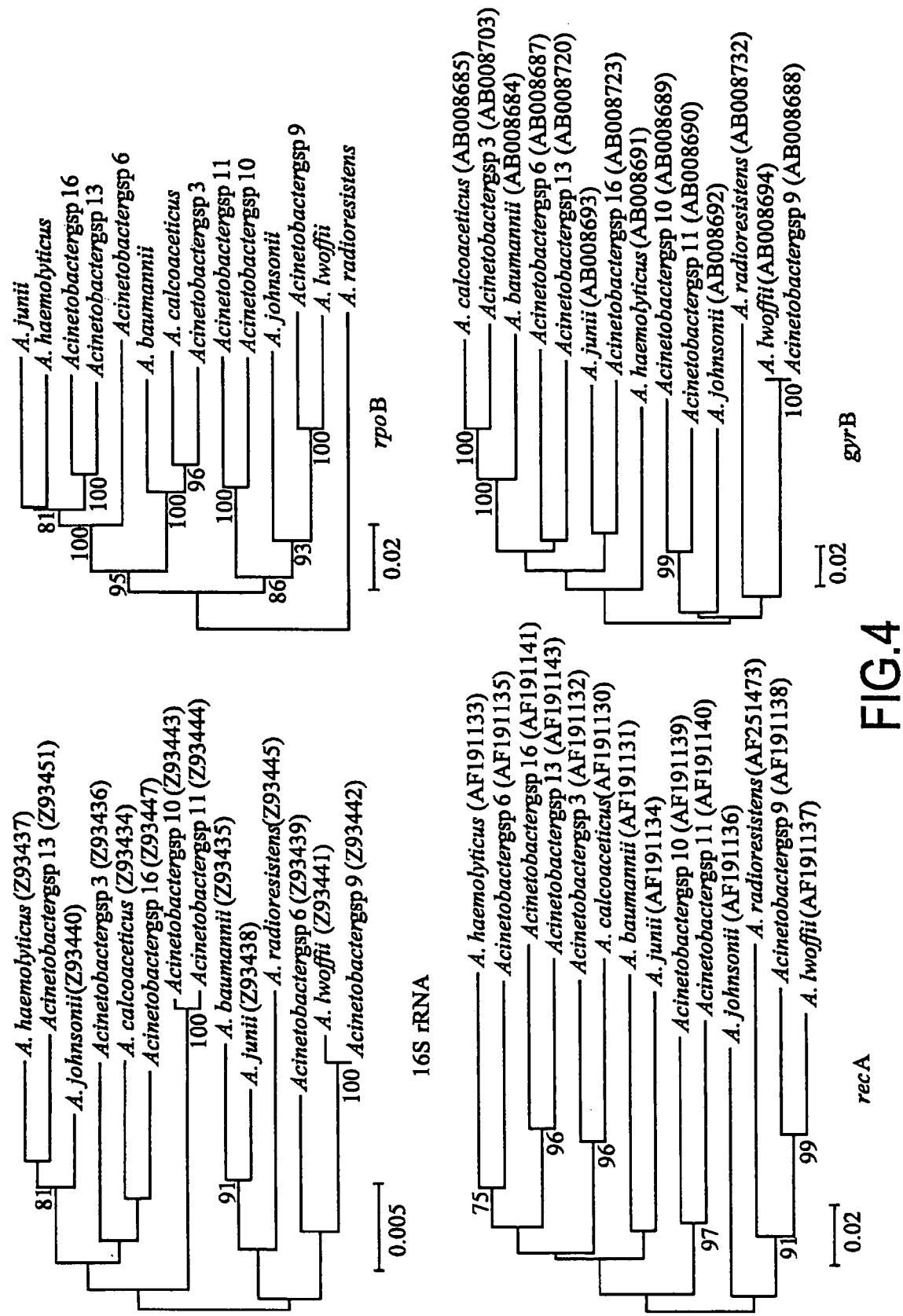

FIG. 4 is a dendogram showing the phylogenetic relationships between the different species of *Acinetobacter* using the "neighbour-joining" method. The 4 trees were constructed by aligning sequences of the rpoB, 16SRNA, rpoB, gyrB, recA genes. The "bootstrap" sampling values (percentage probability of node accuracy) calculated on the basis of a sample of 1000 trees, are given at each node, solely values of 75% or higher being indicated.

1—MATERIAL AND METHODS 1.1—Bacterial Strains

The bacterial strains used are listed in Table 1. All the strains were cultured on Columbia agar, 5% sheep blood, and were incubated 48 h at 37° C. under aerobic conditions.

1.2—Amplification and Sequencing of the rpoB Gene and of Spacers rplL-rpoB and rpoB-rpoC The sequence of the rpoB gene and of its boundary intergenic spacers in the closest species were aligned to produce a consensus sequence. The sequences chosen were those of *Acinetobacter* sp. ADP1 (GenBank accession number NC_005966), *Pseudomonas syringae* pv. tomato str.DC3000 (GenBank accession number NC_004578) and *P. putida* KT2440 (GenBank accession number NC_006347). The consensus sequence allowed determination of the primers subsequently used for PCR techniques, "genome walking" and sequencing. Some primers were determined after analysis of the results obtained. The primers are given in Table 2 below.

The bacterial DNA was extracted from strain suspensions using the QIAamp blood kit (Qiagen, Hilden, Germany) following the manufacturer's recommendations. All the PCR reaction mixtures contained $2.5 \times 10^{-2}$ U Taq polymerase per µl, 1× Taq buffer, 1.8 mM $MgCl_2$ (Gibco BRL, Life Technologies, Cergy Pontoise, France), 200 µM dATP, dCTP, dTTP and dGTP (Boehringer Manheim GmbH, Hilden, Germany), and 0.2 µM of each primer (Eurogentec, Seraing, Belgium). The PCR reaction mixtures were subjected to 35 denaturing cycles at 94° C. for 30 s, hybridisation of the primers for 30 s, and elongation at 72° C. for 2 min. Each amplification programme started with a denaturing step at 95° C. for 2 min. and ended with an elongation step at 72° C. for 10 min. Determination of the sequence of the gene ends was performed using the Universal GenomeWalker Kit (Clontech Laboratories, Palo Alto, Calif.). In short, genomic DNA was digested by Eco RV, Dra I, Pvu II, Stu I and Sca I. The DNA fragments were bound with the GenomeWalker adaptor, PCR was conducted by incorporating the "adaptor primer" provided by the manufacturer and the specific primers. For amplification, 1.5 U of ELONGASE enzyme (Boehringer Manheim) were used with 10 pmol of each primer, 20 mM of each dNTP, 10 mM Tris-HCl, 50 mM KCl, 1.6 mM $MgCl_2$ and 5 µl digested DNA for a final volume of 50 µl. The amplicons were purified with the "QIAquick spin PCR purification kit" (Qiagen). The sequence reactions were performed using reagents of the ABI Prism 3100 ADN sequencer (dRhod.Terminator RR Mix, Perkin Elmer Applied Biosystems).

These conditions for DNA extraction, PCR amplification and sequencing were described in Khamis et al 2003.

1.3—Determination of the Partial Discriminating Sequences in the rpoB Gene

To detect the sequence portions with high variability flanked by conserved regions, we used the SVARAP programme (Sequence VARiability Analysis Program). Once this analysis was made, the most polymorphic regions of the rpoB gene were determined and universal primers, chosen in the conserved boundary regions, were designated after different unsuccessful attempts. The PCR conditions incorporating the universal primers were the same as previously mentioned. These primers were used for amplification and sequencing of the 4 hypervariable regions for all the strains tested.

These primers are given in Table 3 below and FIG. 1.

1.4—Analysis of rpoB Sequences and their Boundary Intergenic Spacers

The fragments of rpoB gene sequences and of boundary intergenic spacers obtained in this study were analysed using "Sequence Analysis Software" (Applied Biosystems), and the partial sequences were combined into a single consensus sequence using "Sequence Assembler Software" (Applied Biosystems). All the deposit references of the strains with Collection de l'Institut Pasteur (<<CIP>>) (France, Paris) are listed in Table 1. The multiple alignments and similarity percentages between the genes of the different species were performed using CLUSTAL W on the EMBL-EBI server (Thompson et al. 1994). Phylogenetic trees were made from the sequences using the "neighbour—joining" method (Felsenstein et al. 1989). "Bootstrap" values were calculated to assess the solidity of the nodes, using SEQBOOT in PHYLIP software.

2—RESULTS a. Complete Sequences of the rpoB Genes of the Different *Acinetobacter* Species The designated primers allowed amplification of the test regions in all working strains; the size of the complete gene is 4089 bp for all species. The similarity percentages between strains vary from 83 to 94%, with the exception of 2 pairs of species (Table 4). Two pairs of species *A. junii/A. grimontii* and *A. baylyi*/genomic species 11 have similarities of 99%. The other species have less than 95% similarity with each other.

b. Identification of the Different Species of *Acinetobacter* Based on the Partial Sequences of the rpoB Gene The SVARAP programme enabled identification of 2 variable regions bounded by conserved regions, allowing the generation of universal primers:
region 1: between positions 2900 and 3250, and
region 2: between positions 3250 and 3700 bp (FIG. 1).

These regions were amplified using primers from all species of *Acinetobacter* and all strains of *A. baumannii*. The size of region 1 is 350 bp and region 2 has 450 bp. The similarity percentage between the different species of region 1 varies from 78.6 to 95.4% for all species except 2 pairs. As for the complete sequence, *A. baylyi*/genomic species 11 and *A. junii/A. grimontii* have the highest similarity values, respectively 98 and 99.1%, whereas the other species have less than 96%. The similarity percentage for region 2 is between 75.8 and 95.3% for all species, again with the exception of species *A. junii/A. grimontii* and *A. baylyi*/genospecies 11 which have the highest similarities i.e. 98.8 et 99.6% respectively, whereas the other species have less than 96% similarity between each other.

The intra-specific similarity of the different strains of *A. baumannii* for region 1 varies from 98.3 to 100% with the exception of strain CIP 103655. This latter strain only has between 94.9 and 95.7% similarity with the other strains. In the same manner, region 2 varies from 98.7 to 100% for all strains of *A. Baumanii* with the exception of strain CIP 103655. This strain has similarities of between 93.6 and 94.4% with the other strains of the species. The closest species to *A. baumannii* are genomic species 3 for region 1 and *A. calcoaceticus* for region 2, with similarities of 95.1% and 93.6% respectively. These are much lower values than for intraspecific variability with the exception of strain CIP 103655 for which the most distant strain of *A. baumannii* has 94.9% and 93.6% similarity in regions 1 and 2 respectively.

Overall, sequence variability ranges from 0.4 to 24.2% for the partial sequences, compared with 0.8 to 16.9% for complete rpoB sequences. The 2 partial sequences therefore allow non-ambiguous identification of the 24 species.

c. Analysis of the Regions Flanking the rpoB Gene (Intergenic Spacer rplL-rpoB and Intergenic Spacer rpoB-rpoC)

The size of the 2 intergenic spacers varies according to species. The size of the spacer between rplL and rpoB varies from 301 to 310 bp (Table 1). Between species, the similarity rate of this rp/L-rpoB spacer varies from 80.8 to 96.9%, except that the intergenic spacer is identical between *A. junnii* and *A. grimontii*, and the pairs of species such as *A. baylyi*-genomic species 11 and *A. lwoffii*-genomic species 9 have similarity rates of between 98.4 and 99.7%.

The size of the intergenic spacer between rpoB and rpoC varies from 86 to 177 bp (Table 1) with similarity rates between species of between 70.2 and 96.5%, except for *A. junnii/A. grimontii* which have a high similarity of 99.5%, and within the Acb complex (*A. calcoaceticus, A. baumannii* and genomic species 3) whose similarity rates lie between 98.5 and 99.0% for the intergenic spacer rpoB-rpoC. On the other hand, compared with the spacer rplL-rpoB, *A. baylyi*-genomic species 11 and *A. lwoffii*-genomic species 9 only have 83.8 and 87.9% similarity respectively for the rpoB-rpoC intergenic spacer.

Within the *A. baumannii* species, the size of the rplL-rpoB intergenic spacer is 305 bp for all strains, with the exception of strain CIP 103655 for which the size is 304 bp. The rpoB-rpoC intergenic spacer has a size of 86 bp for all strains. Again in this species, the similarity rate in the rpolL-rpoB spacer varies from 99 to 100% for all strains with the exception of strain CIP 103655. This latter strain has between 96.1 and 96.4% similarity with the other strains. The other intergenic spacer rpoB-rpoC has 100% similarity for all strains with the exception of strain CIP 103655 for which it has 97.7 to 98.8% similarity with the other strains. The closest species to *A. baumannii* is genomic species 3 for the rplL-rpoB spacer and *A. calcoaceticus* for the rpoB-rpoC spacer, with respective similarities of 95.9% and 98.5%. These are much higher values than intra-specific similarity, with the exception of strain CIP 103655 for which species of *A. baumannii* have similarities of 96.1% and 97.7% respectively for intergenic spacers rplL-rpoB and rpoB-rpoC.

As arises from the positions of the primers of sequences SEQ. ID. no 5, 6, 7 and 8, the fragments corresponding to the amplicons obtained using these primers have sequences which overspan those of the actual intergenic spacers at the 5' and 3' ends, but sequences SEQ. ID. no 121 to 144 and 165 to 188 given in the sequence listing appended to this description correspond to the complete intergenic spacers and do not overspan genes rp/L, rpoB and rpoC respectively.

d. Phylogenetic Analysis of *Acinetobacter* Species

The phylogenetic tree constructed with the complete sequences of the rpoB gene and constructed using the neighbour-joining technique, is supported by very high bootstrap values (FIG. 2). The number of bootstrap values $\geq 75\%$ is 17/22 when using the complete rpoB gene, whereas it is only 7/22 when using the 16S rRNA gene (p<0.01). All the species are well separated into different groups. The tree based on the partial rpoB gene (concatenated region 1 and region 2) shows a homogeneous group of *A. baumannii* strains. Strain CIP 103655 appears in the same group but is clearly separate from the other isolates of *A. baumannii*. This grouping is supported by a bootstrap value of 85%.

2.4—Discussion

With the exception of the 16S rRNA gene, there currently does not exist any sequencing of house-keeping genes on all species of *Acinetobacter*. The sequences of genes gyrB and recA are not available for the 10 species most recently described. Yamamoto et al (1996, 1999) and Krawczyk et al (2002) have sequenced the gyrB and recA genes of 14 species and compared this technique with DNA-DNA hybridisation (Bouvet and Jeanjean, 1989; Bouvet and Grimont, 1986; Tjernberg and Ursing, 1989). By constructing a tree based on the rpoB gene which incorporates 14 species, no congruency is observed between the different species. However, the tree based on the rpoB gene has significantly more bootstrap values of $\geq 75\%$ (11/12) than the tree based on the 16S rRNA gene (4/12), gyrB (5/12) and recA (6/12) (p<0.01, p=0.01 and p=0.02 respectively) (FIG. 4). This demonstrates the robustness of the tree based on the rpoB gene. *A. lwoffi* and *Acinetobacter* genomic species 9 are 100% identical on the gyrB gene, but are separated on the sequence of gyrD and recA (Yamamoto et al., 1999; Krawczyk et al (2002). The species that are ill-delimited by the rpoB gene are the pairs *A. grimontii/A. junii* and *A. baylii*/genospecies 9. Unfortunately, it is impossible to compare them at gyrB and recA, the sequences of *A. grimontii* and *A. baylii* not being available.

For the routine molecular identification of *Acinetobacter* bacteria, each of the partial sequences of the rpoB gene and of its 2 boundary intergenic spacers can be used on account of its discriminatory power and length. The disadvantage of using only one of these sequences is the lack of good discrimination between the pairs *A. grimontii/A. junii* and *A. baylii*/genomic species 9 (Tables 4 to 11). However, this disadvantage can be reduced by combining the sequence of at least 2 of these hypervariable sequences. Owing to its size we believe it is preferable to start with the sequence of region 1 since it can be used for perfect identification of 20 species out of 24. If the sequences obtained are those of *A. grimontii/A. junii*, it is better to subsequently to carry out the sequence of region 2 which better differentiates between these 2 species. If the sequence obtained is closer to *A. baylii*/genospecies 9, it is preferable to determine the sequence of the rpoB-rpoC spacer which discriminates better between these 2 species.

The intra-specific variability of the short fragments observed in the *A. baumannii* species shows that, with the exception of strain CIP 103655, all the isolates have distinctly lower similarities than those observed between *A. baumannii* and the species closest to it. However the low similarities observed between the *A. baumannii* strain CIP 103655 and the other isolates of the species show that the identification of some isolates of this species may remain ambiguous. The *A. baumannii* species is the most frequent species affecting man. The results show that the CIP 103655 strain is different to the 24 categorized species and is probably not a strain of the *A. baumannii* species.

To conclude, the results obtained through the use of partial sequences of the rpoB gene and the intergenic spacers rplL-rpoB and rpoB-rpoC show that these tools are efficient for the routine molecular identification of *Acinetobacter* strains. However, owing to the strong similarity between some species, additional work to examine intra-specific similarities in several species will be necessary. Also, the status of some strains such as strain *A. baumannii* CIP 103655 and of some species such as *A. grimontii* and *A. baylii*, must be investigated by DNA-DNA hybridisation and sequences of other house-keeping genes (recA and gyrB).

TABLE 1

*Acinetobacter* strains investigated.

| Species | Strain | SEQ. ID. rpoB-complete | SEQ. ID rpoB-region 1 | SEQ. ID. rpoB-region 2 | complete intergenic spacers rp/L-rpoB SEQ. ID. n° | Size | rpoB-rpoC SEQ. ID. | Size |
|---|---|---|---|---|---|---|---|---|
| genomic species 1, *A. calcoaceticus* | CIP 81.8[T] | 9 | 33 | 77 | 121 | 305 | 165 | 86 |
| genomic species 2, baumannii | CIP 70.34[T] | 10 | 34 | 78 | 122 | 305 | 166 | 86 |
| | 1072.1 (ref) | | 57 | 101 | 144 | 305 | 189 | 86 |
| | CIP 53.77 | | 58 | 102 | 145 | 305 | 190 | 86 |
| | CIP 53.79 | | 59 | 103 | 146 | 305 | 191 | 86 |
| | CIP 54.97 | | 60 | 104 | 147 | 305 | 192 | 86 |
| | CIP 54.147 | | 61 | 105 | 148 | 305 | 193 | 86 |
| | CIP 64.1 | | 62 | 106 | 149 | 305 | 194 | 86 |
| | CIP 68.38 | | 63 | 107 | 150 | 305 | 195 | 86 |
| | CIP 70.8 | | 64 | 108 | 151 | 305 | 196 | 86 |
| | CIP 70.9 | | 65 | 109 | 152 | 305 | 197 | 86 |
| | CIP 70.10 | | 66 | 110 | 153 | 305 | 198 | 86 |
| | CIP 70.21 | | 67 | 111 | 154 | 305 | 199 | 86 |
| | CIP 70.22 | | 68 | 112 | 155 | 305 | 200 | 86 |
| | CIP 70.24 | | 69 | 113 | 156 | 305 | 201 | 86 |
| | CIP 70.28 | | 70 | 114 | 157 | 305 | 202 | 86 |
| | CIP 70.32 | | 71 | 115 | 158 | 305 | 203 | 86 |
| | CIP 70.33 | | 72 | 116 | 159 | 305 | 204 | 86 |
| | CIP 70.35 | | 73 | 117 | 160 | 305 | 205 | 86 |
| | CIP 103572 | | 74 | 118 | 161 | 305 | 206 | 86 |
| | CIP 103655 | | 75 | 119 | 162 | 304 | 207 | 86 |
| | CIP 105742 | | 76 | 120 | 163 | 304 | 208 | 86 |
| genomic species 3 | CIP 70.15 | 11 | 35 | 79 | 123 | 305 | 167 | 86 |
| genomic species 4, *A. haemolyticus* | CIP 64.3[T] | 12 | 36 | 80 | 124 | 308 | 168 | 172 |
| genomic species 5, *A. junii* | CIP 64.5[T] | 13 | 37 | 81 | 125 | 308 | 169 | 149 |
| genomic species 6 | CIP A165 | 14 | 38 | 82 | 126 | 308 | 170 | 170 |
| genomic species 7, *A. johnsonii* | CIP 64.6[T] | 15 | 39 | 83 | 127 | 301 | 171 | 141 |
| genomic species 8, *A. lwoffii* | CIP 64.10[T] | 16 | 40 | 84 | 128 | 308 | 172 | 177 |
| genomic species 9 | CIP 64.7 | 17 | 41 | 85 | 129 | 306 | 173 | 150 |
| genomic species 10 | CIP 70.12 | 18 | 42 | 86 | 130 | 307 | 174 | 144 |
| genomic species 11 | CIP 63.46 | 19 | 43 | 87 | 131 | 304 | 175 | 154 |
| genomic species 12, *A. radioresistens* | CIP 103788[T] | 20 | 44 | 88 | 132 | 304 | 176 | 89 |
| genomic species 13 | CIP 70.18 | 21 | 45 | 89 | 133 | 309 | 177 | 154 |
| genomic species 16 | CIP 64.2 | 22 | 46 | 90 | 134 | 309 | 178 | 153 |
| *A. schindleri* | CIP 107287[T] | 23 | 47 | 91 | 135 | 310 | 179 | 159 |
| *A. ursingii* | CIP 107286[T] | 24 | 48 | 92 | 136 | 308 | 180 | 136 |

TABLE 1-continued

Acinetobacter strains investigated.

| Species | Strain | SEQ. ID. rpoB-complete | SEQ. ID rpoB-region 1 | SEQ. ID. rpoB-region 2 | complete intergenic spacers rpIL-rpoB SEQ. ID. n° | Size | rpoB-rpoC SEQ. ID. | Size |
|---|---|---|---|---|---|---|---|---|
| A. baylyi | CIP 107474[T] | 25 | 49 | 93 | 137 | 304 | 181 | 88 |
| A. bouvetii | CIP 107468[T] | 26 | 50 | 94 | 138 | 305 | 182 | 156 |
| A. gerneri | CIP 107464[T] | 27 | 51 | 95 | 139 | 309 | 183 | 170 |
| A. grimontii | CIP 107470[T] | 28 | 52 | 96 | 140 | 308 | 184 | 150 |
| A. tandoii | CIP 107469[T] | 29 | 53 | 97 | 141 | 306 | 185 | 156 |
| A. tjernbergiae | CIP 107465[T] | 30 | 54 | 98 | 142 | 307 | 186 | 143 |
| A. towneri | CIP 107472[T] | 31 | 55 | 99 | 143 | 307 | 187 | 157 |
| A. parvus | CIP 108168[T] | 32 | 56 | 100 | 144 | 308 | 188 | 143 |

TABLE 2

Primers used to amplify, the rpoB gene and its flanking regions

| No. Primer | Sequence (5'-3') | Position | Tm (° C.) | SEQ ID NO: |
|---|---|---|---|---|
| 1. AcintF[a] | GGTAAAGTDACRCCTAAAGGT | | 60° C. | 209 |
| 2. AcintR[a] | GTATGAACGTGGGDCAGATT | | 58° C. | 210 |
| 3. Ac28F[a] | GTDGGTACVGGYATGGAA | | 52° C. | 211 |
| 4. Ac1754R[a] | GAACGYGCRTGCATYTTGTCA | | 60° C. | 212 |
| 5. Ac822F | CGYAAAGAYTTGAAAGAAGA | | 54° C. | 213 |
| 6. Ac840R | CTTCTTTCAARTCTTTRCGRT | | 60° C. | 214 |
| 7. Ac660F | GAYGTDAAAGAYTCATCTTTA | | 54° C. | 215 |
| 8. Ac1720R | GAACGYGCRTGCATYTTGT | | 60° C. | 216 |
| 9. Ac660R | CGTAAAGATGARTCTTTHAC | | 54° C. | 217 |
| 10. Ac1700F | GACAARATGCAYGCRCGTT | | 60° C. | 218 |
| 11. Ac696F* | TAYCGYAAAGAYTTGAAA-GAAG | | 60° C. | 1 |
| 12. Ac1093R* | CMACACCYTTGTTMCCRTGA | | 60° C. | 2 |
| 13. Ac1055F* | GTGATAARATGGCBGGTCGT | | 60° C. | 3 |
| 14. Ac1598R* | CGBGCRTGCATYTTGTCRT | | 58° C. | 4 |
| 15. Acint1F[b] | AAGAAGCWGGYGCTAMAG | − | 55° C. | 219 |
| 16. Acint2F[b] | CTKGGYCTKAAAGAAGCYAA | − | 58° C. | 220 |
| 17. Acint3F[b] | CTGCTGCYGYTGTTGAAGA | − | 58° C. | 221 |
| 18. Acint1R[b] | GGTAGTTRATGGTTTCMGG | + | 56° C. | 222 |
| 19. Acint2R[b] | GTTRATGGTTTCMGGCTTYTT | + | 59° C. | 223 |
| 20. Acint3R[b] | GGTTTCMGGCTTYTTAACTT | + | 56° C. | 224 |
| 21. Ac1F[a] | ATGGCWTACTCAYATACYGA | 1 | 57° C. | 225 |
| 22. Ac4F[a] | GCWTACTCATAYACYGARAA | 4 | 56° C. | 226 |
| 23. Ac8F[a] | ACTCATAYACYGARAARAAAC | 8 | 56° C. | 227 |
| 24. Ac361F | GARCAAGAAGTMTACATGGG | 361 | 58° C. | 228 |
| 25. Ac1215F | GTTCAACCGYCGTWTSGGT | 1215 | 59° C. | 229 |
| 26. Ac1503F | GATCAACGCCAAGCCDGT | 1503 | 57° C. | 230 |
| 27. Ac2071F | GGYTCRAACATGCAGCGT | 2071 | 56° C. | 231 |
| 28. Ac2267F | GYGTVGAYATCTACAACCT | 2267 | 55° C. | 232 |
| 29. Ac3684F | TGAYGGHCGTACDGGYG | 3684 | 56° C. | 233 |
| 30. Ac3753F | CCAYTTRGTDGAYGACAAAAT | 3753 | 56° C. | 234 |
| 31. Ac3850F | TTCGGTGGTCAGCGYTTC | 3850 | 57° C. | 235 |
| 32. Ac28R | GTTTYTTYTCRGTRTATGAGT | 28 | 56° C. | 236 |
| 33. Ac55R | GCAAYTTRCYAAARTYCTT | 55 | 59° C. | 237 |
| 34. Ac211R | CAGCATTGCCRGARTARCT | 211 | 57° C. | 238 |
| 35. Ac380R | CCCATGTAKACTTCTTGYTC | 380 | 58° C. | 239 |
| 36. Ac1221R | GTTGAACTTCATVCGDCCWA | 1221 | 55° C. | 240 |
| 37. Ac1523R | GCHACHGGCTTGGCGTT | 1523 | 56° C. | 241 |
| 38. Ac2093R | GCCTGACGCTGCATGTT | 2093 | 55° C. | 242 |
| 39. Ac2314R[a] | TGTTCTGGTTBGAACGVGT | 2314 | 56° C. | 243 |
| 40. Ac2928R[a] | GHGCHGCTTCTTCRAAGA | 2928 | 55° C. | 244 |
| 41. Ac2936R[a] | CGYTCACGHGCHGCTTCT | 2936 | 55° C. | 245 |
| 42. Ac1170F | GCTTCCATYTGGCGHACRT | 1170 | 58° C. | 246 |
| 43. Ac1705F | GTACGTCACGBACYTCRAA | 1705 | 58° C. | 247 |
| 44. Ac1804F | TCCATRAACTGDGAYAAYTG | 1804 | 56° C. | 248 |
| 45. Ac2231F | GTATCACGYGCDACACAHGA | 2231 | 60° C. | 249 |
| 46. Ac2348F | GTCATGAAYGCDACRCGCA | 2348 | 58° C. | 250 |
| 47. Ac1379R | CGGTTACCYAARTGRTCRAT | 1379 | 58° C. | 251 |
| 48. Ac1391R | GAACGNACRCGVCGGTTA | 1391 | 58° C. | 252 |
| 49. Ac2325R | GTTRATACADGTRTTYTGGTT | 2325 | 56° C. | 253 |
| 50. Ac2439R | GAACGCRACRCGCATGTT | 2439 | 56° C. | 254 |
| 51. Ac2442R | CATGAACGCRACRCGCAT | 2442 | 56° C. | 255 |

TABLE 3

Primers used to amplify and sequence region 1 and region 2 of the rpoB gene and its boundary spacers in the *Acinetobacter* species subject of the present study.

| Primers | SEQ. ID. n° | Sequence (5'-3') | Position* | Tm (° C.) | Target |
|---|---|---|---|---|---|
| Ac696F | 1 | TAYCGYAAAGAYTTGAAAGAAG | +2916 | 60° C. | rpoB region 1 |
| Ac1093R | 2 | CMACACCYTTGTTMCCRTGA | +3267 | 60° C. | rpoB region 1 |
| Ac1055F | 3 | GTGATAARATGGCBGGTCGT | +3263 | 60° C. | rpoB region 2 |
| Ac1598R | 4 | CGBGCRTGCATYTTGTCRT | +3773 | 58° C. | rpoB region 2 |
| AcintLBF | 5 | GAAGARCTTAAGAMDAARCTTG | −361 | 60° C. | Spacer rp/L-rpoB |
| AcintLBR | 6 | CGTTTCTTTTCGGTATATGAGT | +29 | 60° C. | Spacer rp/L-rpoB |
| AcintBCF | 7 | GTTCTTTAGGTATCAACATTGAA | +4048 | 60° C. | Spacer rpoB-rpoC |
| AcintBCR | 8 | GACGCAAGACCAATACGRAT | +4207 | 59° C. | Spacer rpoB-rpoC |

*i.e. the position of the first nucleotide of the primer sequence relative to the rpoB gene.

TABLE 4

Comparison of similarity rates (%) of the rpoB gene (4089 bp) between the different *Acinetobacter* species

| | | 1 | 2 | 3 | 4 | 5 | 6 | 7 | 8 | 9 | 10 | 11 | 12 |
|---|---|---|---|---|---|---|---|---|---|---|---|---|---|
| [1] | *A. calcoaceticus* | | | | | | | | | | | | |
| [2] | *A.* genospecies 3 | 93.9 | | | | | | | | | | | |
| [3] | *A. baumannii* | 92.0 | 93.8 | | | | | | | | | | |
| [4] | *A.* genospecies 16 | 88.6 | 88.7 | 89.4 | | | | | | | | | |
| [5] | *A. parvus* | 87.9 | 88.3 | 89.0 | 93.9 | | | | | | | | |
| [6] | *A.* genospecies 13 | 89.4 | 89.5 | 90.0 | 94.4 | 93.7 | | | | | | | |
| [7] | *A. tjernbergiae* | 89.4 | 89.0 | 89.4 | 91.9 | 91.6 | 93.3 | | | | | | |
| [8] | *A. grimonti* | 87.7 | 87.9 | 88.6 | 91.8 | 91.7 | 92.1 | 90.1 | | | | | |
| [9] | *A. junii* | 87.5 | 87.8 | 88.6 | 91.6 | 91.8 | 92.0 | 90.0 | 99.2 | | | | |
| [10] | *A. haemolyticus* | 88.0 | 88.3 | 89.1 | 92.5 | 91.8 | 92.1 | 90.4 | 91.7 | 91.9 | | | |
| [11] | *A.* genospecies 6 | 87.8 | 87.8 | 87.5 | 90.1 | 89.5 | 90.4 | 89.8 | 90.1 | 90.1 | 90.6 | | |
| [12] | *A. bouvetii* | 84.8 | 85.2 | 85.6 | 85.8 | 85.4 | 86.1 | 85.4 | 84.3 | 84.4 | 85.3 | 84.8 | |
| [13] | *A. johnsonii* | 86.6 | 86.8 | 87.2 | 87.8 | 87.7 | 88.4 | 87.6 | 86.8 | 86.7 | 87.3 | 86.6 | 88.6 |
| [14] | *A.* genospecies 9 | 85.5 | 86.3 | 86.2 | 86.5 | 86.1 | 86.2 | 85.2 | 85.1 | 85.0 | 85.9 | 85.1 | 87.6 |
| [15] | *A. lwoffi* | 85.7 | 86.4 | 85.9 | 86.8 | 85.9 | 86.9 | 85.7 | 85.2 | 85.0 | 86.1 | 85.4 | 86.9 |
| [16] | *A. schindleri* | 86.0 | 86.7 | 86.9 | 87.2 | 86.8 | 87.4 | 86.4 | 85.9 | 85.7 | 86.3 | 85.7 | 88.4 |
| [17] | *A. towneri* | 85.1 | 85.2 | 85.7 | 86.2 | 86.0 | 86.5 | 85.5 | 86.4 | 86.5 | 86.5 | 86.0 | 86.0 |
| [18] | *A. tandoii* | 86.4 | 87.0 | 86.7 | 87.5 | 87.4 | 88.0 | 87.2 | 87.3 | 87.4 | 87.9 | 87.1 | 86.4 |
| [19] | *A. baylyi* | 86.5 | 86.6 | 87.2 | 87.4 | 86.7 | 87.6 | 86.6 | 86.6 | 86.7 | 87.2 | 86.3 | 86.2 |
| [20] | *A.* genospecies 11 | 86.6 | 86.9 | 87.3 | 87.6 | 87.0 | 87.9 | 86.9 | 86.8 | 86.9 | 87.4 | 86.5 | 86.3 |
| [21] | *A.* genospecies 10 | 86.6 | 86.9 | 87.3 | 87.4 | 87.4 | 88.2 | 87.6 | 87.2 | 87.2 | 87.5 | 86.9 | 86.4 |
| [22] | *A. gerneri* | 86.5 | 86.7 | 87.6 | 86.9 | 86.9 | 87.7 | 87.4 | 87.3 | 87.3 | 87.5 | 86.9 | 86.8 |
| [23] | *A. ursingii* | 85.7 | 86.0 | 85.6 | 85.4 | 85.7 | 85.9 | 86.3 | 85.3 | 85.3 | 86.2 | 86.5 | 84.3 |
| [24] | *A. radioresistense* | 84.2 | 84.5 | 84.9 | 84.6 | 84.4 | 84.4 | 84.1 | 84.4 | 84.2 | 84.4 | 84.2 | 83.1 |

| | | 13 | 14 | 15 | 16 | 17 | 18 | 19 | 20 | 21 | 22 | 23 |
|---|---|---|---|---|---|---|---|---|---|---|---|---|
| [1] | *A. calcoaceticus* | | | | | | | | | | | |
| [2] | *A.* genospecies 3 | | | | | | | | | | | |
| [3] | *A. baumannii* | | | | | | | | | | | |
| [4] | *A.* genospecies 16 | | | | | | | | | | | |
| [5] | *A. parvus* | | | | | | | | | | | |
| [6] | *A.* genospecies 13 | | | | | | | | | | | |
| [7] | *A. tjernbergiae* | | | | | | | | | | | |
| [8] | *A. grimonti* | | | | | | | | | | | |
| [9] | *A. junii* | | | | | | | | | | | |
| [10] | *A. haemolyticus* | | | | | | | | | | | |
| [11] | *A.* genospecies 6 | | | | | | | | | | | |
| [12] | *A. bouvetii* | | | | | | | | | | | |
| [13] | *A. johnsonii* | | | | | | | | | | | |
| [14] | *A.* genospecies 9 | 88.4 | | | | | | | | | | |
| [15] | *A. lwoffi* | 88.4 | 93.3 | | | | | | | | | |
| [16] | *A. schindleri* | 88.7 | 90.7 | 90.5 | | | | | | | | |
| [17] | *A. towneri* | 88.0 | 87.3 | 86.7 | 87.0 | | | | | | | |
| [18] | *A. tandoii* | 87.9 | 86.4 | 86.8 | 87.4 | 87.1 | | | | | | |
| [19] | *A. baylyi* | 87.0 | 86.9 | 86.9 | 86.7 | 86.0 | 86.7 | | | | | |

TABLE 4-continued

Comparison of similarity rates (%) of the rpoB gene (4089 bp) between the different *Acinetobacter* species

| | | | | | | | | | | | |
|---|---|---|---|---|---|---|---|---|---|---|---|
| [20] *A.* genospecies 11 | 87.3 | 87.1 | 87.2 | 86.9 | 86.1 | 86.8 | 99.2 | | | | |
| [21] *A.* genospecies 10 | 87.4 | 86.6 | 86.7 | 87.4 | 85.5 | 87.4 | 92.3 | 92.5 | | | |
| [22] *A. gerneri* | 87.7 | 86.3 | 86.4 | 86.7 | 87.0 | 87.6 | 88.7 | 88.9 | 89.0 | | |
| [23] *A. ursingii* | 85.5 | 85.1 | 84.9 | 85.2 | 85.3 | 86.5 | 85.3 | 85.5 | 85.3 | 86.1 | |
| [24] *A. radioresistense* | 83.2 | 84.6 | 84.3 | 84.9 | 84.6 | 83.9 | 84.1 | 84.0 | 83.7 | 84.3 | 85.2 |

TABLE 5

Comparison of similarity rates (%) of sequences (301-310 bp) of the rp/L-rpoB spacer in the different *Acinetobacter* species.

| | 1 | 2 | 3 | 4 | 5 | 6 | 7 | 8 | 9 | 10 | 11 | 12 |
|---|---|---|---|---|---|---|---|---|---|---|---|---|
| [1] *A. calcoaceticus* | | | | | | | | | | | | |
| [2] genospecies 3 | 92.8 | | | | | | | | | | | |
| [3] *A. baumannii* | 90.6 | 95.9 | | | | | | | | | | |
| [4] genospecies 13 | 84.0 | 86.8 | 86.5 | | | | | | | | | |
| [5] genospecies 16 | 86.5 | 87.4 | 86.8 | 93.4 | | | | | | | | |
| [6] *A. parvus* | 83.0 | 86.2 | 86.5 | 96.9 | 93.4 | | | | | | | |
| [7] *A. tjernbergiae* | 85.5 | 87.1 | 86.5 | 95.0 | 93.7 | 94.0 | | | | | | |
| [8] *A. junii* | 87.7 | 88.4 | 88.4 | 91.5 | 93.4 | 91.2 | 93.1 | | | | | |
| [9] *A. grimontii* | 87.7 | 88.4 | 88.4 | 91.5 | 93.4 | 91.2 | 93.1 | 100.0 | | | | |
| [10] *A. haemolyticus* | 85.8 | 87.1 | 86.5 | 93.4 | 93.7 | 92.1 | 93.1 | 93.4 | 93.4 | | | |
| [11] genospecies 6 | 87.1 | 87.4 | 86.2 | 91.2 | 93.1 | 90.6 | 92.1 | 93.1 | 93.1 | 91.2 | | |
| [12] genospecies 9 | 87.7 | 86.8 | 86.8 | 84.0 | 85.8 | 83.0 | 85.2 | 86.5 | 86.5 | 85.5 | 85.8 | |
| [13] *A. lwoffii* | 86.8 | 86.5 | 86.5 | 83.0 | 84.6 | 82.7 | 85.2 | 85.5 | 85.5 | 84.6 | 85.5 | 98.4 |
| [14] *A. schindleri* | 87.4 | 87.7 | 88.1 | 83.6 | 85.5 | 83.6 | 85.8 | 87.4 | 87.4 | 85.5 | 85.8 | 96.2 |
| [15] *A. bouvetii* | 87.7 | 86.5 | 86.5 | 84.6 | 85.2 | 84.3 | 86.2 | 86.5 | 86.5 | 86.2 | 85.5 | 91.8 |
| [16] *A. johnsonii* | 84.3 | 84.6 | 84.9 | 81.1 | 82.4 | 80.8 | 82.7 | 82.1 | 82.1 | 82.4 | 82.1 | 88.1 |
| [17] *A. towneri* | 84.9 | 85.8 | 87.1 | 87.1 | 85.5 | 86.5 | 87.4 | 84.6 | 84.6 | 85.8 | 84.9 | 89.0 |
| [18] *A. tandoii* | 86.2 | 85.8 | 85.8 | 84.0 | 84.3 | 83.6 | 85.2 | 84.9 | 84.9 | 84.3 | 84.3 | 89.0 |
| [19] *A. baylyi* | 82.7 | 82.4 | 83.0 | 81.4 | 83.6 | 82.4 | 82.7 | 83.6 | 83.6 | 81.8 | 82.7 | 86.2 |
| [20] genospecies 11 | 83.0 | 82.7 | 83.3 | 81.8 | 84.0 | 82.7 | 83.0 | 84.0 | 84.0 | 84.0 | 82.1 | 82.7 | 86.5 |
| [21] genospecies 10 | 84.9 | 84.6 | 84.9 | 84.3 | 85.5 | 84.9 | 85.5 | 86.2 | 86.2 | 83.6 | 84.9 | 88.1 |
| [22] *A. gerneri* | 86.8 | 85.5 | 85.8 | 83.0 | 84.6 | 83.6 | 84.9 | 85.2 | 85.2 | 83.6 | 84.0 | 88.4 |
| [23] *A. radioresistense* | 86.2 | 87.1 | 88.4 | 86.8 | 87.4 | 86.2 | 86.8 | 87.7 | 87.7 | 86.8 | 85.2 | 86.8 |
| [24] *A. ursingii* | 85.8 | 84.9 | 85.5 | 85.2 | 86.5 | 84.9 | 86.8 | 85.5 | 85.5 | 84.9 | 85.2 | 85.5 |

| | 13 | 14 | 15 | 16 | 17 | 18 | 19 | 20 | 21 | 22 | 23 |
|---|---|---|---|---|---|---|---|---|---|---|---|
| [1] *A. calcoaceticus* | | | | | | | | | | | |
| [2] genospecies 3 | | | | | | | | | | | |
| [3] *A. baumannii* | | | | | | | | | | | |
| [4] genospecies 13 | | | | | | | | | | | |
| [5] genospecies 16 | | | | | | | | | | | |
| [6] *A. parvus* | | | | | | | | | | | |
| [7] *A. tjernbergiae* | | | | | | | | | | | |
| [8] *A. junii* | | | | | | | | | | | |
| [9] *A. grimontii* | | | | | | | | | | | |
| [10] *A. haemolyticus* | | | | | | | | | | | |
| [11] genospecies 6 | | | | | | | | | | | |
| [12] genospecies 9 | | | | | | | | | | | |
| [13] *A. lwoffii* | | | | | | | | | | | |
| [14] *A. schindleri* | 95.9 | | | | | | | | | | |
| [15] *A. bouvetii* | 91.2 | 91.5 | | | | | | | | | |
| [16] *A. johnsonii* | 87.7 | 87.4 | 86.5 | | | | | | | | |
| [17] *A. towneri* | 88.4 | 89.3 | 91.2 | 87.4 | | | | | | | |
| [18] *A. tandoii* | 88.4 | 89.3 | 93.1 | 84.9 | 90.3 | | | | | | |
| [19] *A. baylyi* | 85.2 | 85.8 | 85.5 | 89.3 | 87.1 | 84.9 | | | | | |
| [20] genospecies 11 | 85.5 | 86.2 | 85.8 | 89.6 | 87.4 | 85.2 | 99.7 | | | | |
| [21] genospecies 10 | 87.1 | 87.7 | 90.3 | 86.8 | 89.3 | 89.6 | 92.5 | 92.8 | | | |
| [22] *A. gerneri* | 88.4 | 87.7 | 88.7 | 85.5 | 88.4 | 88.1 | 91.5 | 91.8 | 92.8 | | |
| [23] *A. radioresistense* | 86.2 | 85.8 | 86.2 | 84.9 | 86.5 | 84.9 | 83.0 | 83.3 | 86.5 | 86.5 | |
| [24] *A. ursingii* | 85.5 | 84.9 | 87.7 | 85.5 | 85.8 | 86.2 | 85.2 | 85.5 | 86.8 | 87.7 | 90.3 |

TABLE 6

Similarity rates (%) of sequences (301-310 bp) of the rpoB-rpoC spacer (86-177 bp) in the different *Acinetobacter* species.

|  |  | 1 | 2 | 3 | 4 | 5 | 6 | 7 | 8 | 9 | 10 | 11 | 12 |
|---|---|---|---|---|---|---|---|---|---|---|---|---|---|
| [1] | genospecies 6 | | | | | | | | | | | | |
| [2] | *A. haemolyticus* | 92.4 | | | | | | | | | | | |
| [3] | *A. junii* | 90.4 | 89.4 | | | | | | | | | | |
| [4] | *A. grimontii* | 90.9 | 89.9 | 99.5 | | | | | | | | | |
| [5] | *A. calcoaceticus* | 90.4 | 89.9 | 91.4 | 91.4 | | | | | | | | |
| [6] | genospecies 3 | 90.9 | 89.9 | 91.9 | 91.9 | 99.0 | | | | | | | |
| [7] | *A. baumannii* | 90.4 | 89.9 | 91.4 | 91.4 | 98.5 | 98.5 | | | | | | |
| [8] | genospecies 13 | 76.3 | 75.3 | 78.8 | 79.3 | 92.9 | 93.4 | 92.9 | | | | | |
| [9] | genospecies 16 | 75.3 | 75.3 | 77.8 | 78.3 | 91.9 | 92.4 | 91.9 | 96.5 | | | | |
| [10] | *A. parvus* | 79.3 | 79.3 | 79.8 | 80.3 | 91.4 | 91.4 | 91.4 | 86.4 | 85.9 | | | |
| [11] | *A. tjernbergiae* | 80.3 | 80.8 | 81.3 | 81.8 | 93.4 | 93.4 | 93.4 | 86.4 | 86.9 | 91.4 | | |
| [12] | *A. tandoii* | 74.2 | 77.8 | 75.8 | 76.3 | 90.4 | 91.4 | 90.4 | 79.8 | 80.3 | 77.3 | 79.8 | |
| [13] | *A. towneri* | 74.2 | 77.3 | 78.8 | 79.3 | 88.4 | 89.4 | 88.9 | 76.8 | 76.8 | 76.3 | 78.8 | 85.4 |
| [14] | *A. baylyi* | 82.8 | 81.8 | 80.3 | 80.8 | 88.4 | 87.9 | 87.9 | 84.8 | 86.4 | 87.4 | 87.4 | 85.9 |
| [15] | genospecies 11 | 78.3 | 79.8 | 77.3 | 77.8 | 88.9 | 89.9 | 89.4 | 77.3 | 77.8 | 79.3 | 81.3 | 84.3 |
| [16] | genospecies 10 | 75.3 | 77.3 | 77.3 | 76.8 | 88.4 | 88.4 | 88.9 | 79.3 | 79.8 | 81.8 | 84.8 | 72.7 |
| [17] | *A. gerneri* | 78.3 | 78.8 | 80.3 | 80.8 | 89.4 | 90.4 | 89.4 | 74.7 | 75.3 | 74.2 | 75.3 | 76.8 |
| [18] | *A. bouvetii* | 70.7 | 73.7 | 74.7 | 75.3 | 89.9 | 90.9 | 89.9 | 89.4 | 91.4 | 84.3 | 85.4 | 81.8 |
| [19] | *A. schindleri* | 70.2 | 73.7 | 72.7 | 73.2 | 90.9 | 91.9 | 90.9 | 88.9 | 90.4 | 84.3 | 85.9 | 80.8 |
| [20] | *A. johnsonii* | 75.3 | 77.8 | 74.2 | 73.7 | 89.4 | 89.4 | 89.4 | 73.2 | 73.7 | 75.3 | 76.8 | 76.3 |
| [21] | genospecies 9 | 76.8 | 79.8 | 80.8 | 81.3 | 90.4 | 91.4 | 90.4 | 80.3 | 82.3 | 79.3 | 81.3 | 81.8 |
| [22] | *A. lwoffii* | 74.7 | 77.3 | 78.8 | 79.3 | 90.4 | 91.4 | 90.4 | 82.3 | 83.8 | 81.3 | 82.8 | 83.8 |
| [23] | *A. radioresistense* | 86.4 | 86.4 | 85.4 | 85.4 | 94.9 | 94.9 | 94.9 | 88.4 | 87.9 | 91.9 | 93.4 | 87.9 |
| [24] | *A. ursingii* | 77.3 | 75.3 | 79.8 | 79.3 | 90.9 | 91.4 | 91.9 | 81.3 | 82.8 | 85.4 | 88.4 | 77.8 |

|  |  | 13 | 14 | 15 | 16 | 17 | 18 | 19 | 20 | 21 | 22 | 23 |
|---|---|---|---|---|---|---|---|---|---|---|---|---|
| [1] | genospecies 6 | | | | | | | | | | | |
| [2] | *A. haemolyticus* | | | | | | | | | | | |
| [3] | *A. junii* | | | | | | | | | | | |
| [4] | *A. grimontii* | | | | | | | | | | | |
| [5] | *A. calcoaceticus* | | | | | | | | | | | |
| [6] | genospecies 3 | | | | | | | | | | | |
| [7] | *A. baumannii* | | | | | | | | | | | |
| [8] | genospecies 13 | | | | | | | | | | | |
| [9] | genospecies 16 | | | | | | | | | | | |
| [10] | *A. parvus* | | | | | | | | | | | |
| [11] | *A. tjernbergiae* | | | | | | | | | | | |
| [12] | *A. tandoii* | | | | | | | | | | | |
| [13] | *A. towneri* | | | | | | | | | | | |
| [14] | *A. baylyi* | 82.8 | | | | | | | | | | |
| [15] | genospecies 11 | 84.3 | 83.8 | | | | | | | | | |
| [16] | genospecies 10 | 75.3 | 82.8 | 80.8 | | | | | | | | |
| [17] | *A. gerneri* | 71.7 | 82.3 | 70.7 | 74.7 | | | | | | | |
| [18] | *A. bouvetii* | 79.8 | 83.3 | 75.3 | 76.3 | 74.2 | | | | | | |
| [19] | *A. schindleri* | 78.3 | 84.3 | 75.3 | 77.8 | 71.7 | 92.9 | | | | | |
| [20] | *A. johnsonii* | 74.2 | 81.8 | 72.2 | 75.8 | 77.3 | 76.3 | 77.8 | | | | |
| [21] | genospecies 9 | 82.8 | 82.3 | 78.8 | 77.3 | 76.3 | 84.8 | 84.8 | 80.8 | | | |
| [22] | *A. lwoffii* | 82.3 | 85.9 | 78.3 | 76.8 | 74.2 | 83.8 | 81.8 | 73.2 | 87.9 | | |
| [23] | *A. radioresistense* | 86.4 | 90.9 | 85.9 | 89.9 | 84.3 | 86.9 | 85.4 | 86.4 | 86.9 | 87.4 | |
| [24] | *A. ursingii* | 77.8 | 85.4 | 79.3 | 81.3 | 72.2 | 77.8 | 77.8 | 76.8 | 77.8 | 78.3 | 88.4 |

TABLE 7

Comparison of similarity rates (%) of sequences (350 bp) of the partial sequences of rpoB region 2 in the different *Acinetobacter* species.

|  |  | 1 | 2 | 3 | 4 | 5 | 6 | 7 | 8 | 9 | 10 | 11 | 12 |
|---|---|---|---|---|---|---|---|---|---|---|---|---|---|
| [1] | *A. baumannii* | | | | | | | | | | | | |
| [2] | genospecies 3 | 95.1 | | | | | | | | | | | |
| [3] | *A. calcoaceticus* | 88.3 | 90.6 | | | | | | | | | | |
| [4] | *A. grimonti* | 87.1 | 86.6 | 88.0 | | | | | | | | | |
| [5] | *A. junii* | 86.9 | 86.3 | 87.1 | 99.1 | | | | | | | | |
| [6] | genospecies 16 | 86.0 | 84.3 | 84.6 | 90.3 | 89.4 | | | | | | | |
| [7] | *A. parvus* | 87.1 | 85.7 | 84.0 | 91.4 | 90.6 | 95.4 | | | | | | |
| [8] | genospecies 13 | 87.4 | 86.9 | 85.7 | 90.6 | 89.7 | 93.4 | 93.1 | | | | | |
| [9] | *A. johnsonii* | 85.1 | 84.3 | 84.6 | 90.0 | 89.4 | 89.4 | 91.1 | 91.7 | | | | |
| [10] | *A. tjernbergiae* | 87.1 | 86.3 | 85.4 | 90.6 | 89.7 | 92.3 | 92.9 | 93.1 | 93.1 | | | |
| [11] | genospecies 6 | 83.7 | 82.9 | 82.9 | 87.4 | 87.1 | 89.4 | 88.3 | 87.1 | 87.7 | 87.7 | | |
| [12] | *A. haemolyticus* | 87.7 | 85.4 | 85.1 | 87.7 | 87.4 | 92.0 | 89.7 | 91.1 | 89.1 | 90.0 | 90.3 | |
| [13] | *A. schindleri* | 84.6 | 84.0 | 82.9 | 89.1 | 88.6 | 87.7 | 88.0 | 88.3 | 86.0 | 87.1 | 85.4 | 86.3 |

TABLE 7-continued

Comparison of similarity rates (%) of sequences (350 bp) of the partial sequences of rpoB region 2 in the different *Acinetobacter* species.

| | | 1 | 2 | 3 | 4 | 5 | 6 | 7 | 8 | 9 | 10 | 11 | 12 |
|---|---|---|---|---|---|---|---|---|---|---|---|---|---|
| [14] | A. baylyi | 85.1 | 84.0 | 82.6 | 85.1 | 84.9 | 86.0 | 85.4 | 84.6 | 86.0 | 85.1 | 85.7 | 85.7 |
| [15] | genospecies 11 | 85.1 | 84.3 | 82.9 | 85.1 | 84.9 | 85.7 | 85.1 | 84.9 | 85.7 | 85.4 | 85.7 | 85.7 |
| [16] | A. bouvetii | 84.6 | 84.6 | 81.1 | 85.4 | 85.7 | 84.9 | 85.4 | 85.4 | 86.0 | 84.9 | 83.7 | 84.9 |
| [17] | genospecies 10 | 82.9 | 82.6 | 80.6 | 84.6 | 83.7 | 84.9 | 84.9 | 85.1 | 84.3 | 84.9 | 82.6 | 84.9 |
| [18] | A. gerneri | 84.9 | 85.7 | 82.3 | 89.1 | 88.9 | 85.4 | 86.9 | 85.7 | 87.4 | 86.9 | 85.4 | 85.1 |
| [19] | genospecies 9 | 85.4 | 84.3 | 82.3 | 83.7 | 84.0 | 86.0 | 85.1 | 85.7 | 86.0 | 84.9 | 84.6 | 86.0 |
| [20] | A. lwoffii | 83.7 | 85.1 | 83.1 | 83.4 | 83.7 | 85.7 | 84.6 | 87.1 | 85.1 | 84.6 | 84.0 | 85.7 |
| [21] | A. towneri | 81.7 | 80.9 | 81.4 | 85.1 | 85.4 | 84.9 | 84.0 | 83.7 | 87.1 | 83.4 | 83.4 | 84.0 |
| [22] | A. ursingii | 82.6 | 82.0 | 82.0 | 84.9 | 84.6 | 82.9 | 84.0 | 83.7 | 83.7 | 85.1 | 84.6 | 82.9 |
| [23] | A. tandoii | 83.4 | 82.6 | 82.0 | 88.6 | 88.3 | 89.4 | 90.0 | 86.9 | 88.0 | 88.3 | 86.9 | 88.0 |
| [24] | A. radioresistense | 79.7 | 78.9 | 78.6 | 82.0 | 81.1 | 82.0 | 82.0 | 80.0 | 79.4 | 81.7 | 80.6 | 79.4 |

| | | 13 | 14 | 15 | 16 | 17 | 18 | 19 | 20 | 21 | 22 | 23 |
|---|---|---|---|---|---|---|---|---|---|---|---|---|
| [1] | A. baumannii | | | | | | | | | | | |
| [2] | genospecies 3 | | | | | | | | | | | |
| [3] | A. calcoaceticus | | | | | | | | | | | |
| [4] | A. grimonti | | | | | | | | | | | |
| [5] | A. junii | | | | | | | | | | | |
| [6] | genospecies 16 | | | | | | | | | | | |
| [7] | A. parvus | | | | | | | | | | | |
| [8] | genospecies 13 | | | | | | | | | | | |
| [9] | A. johnsonii | | | | | | | | | | | |
| [10] | A. tjernbergiae | | | | | | | | | | | |
| [11] | genospecies 6 | | | | | | | | | | | |
| [12] | A. haemolyticus | | | | | | | | | | | |
| [13] | A. schindleri | | | | | | | | | | | |
| [14] | A. baylyi | 84.9 | | | | | | | | | | |
| [15] | genospecies 11 | 85.7 | 98.0 | | | | | | | | | |
| [16] | A. bouvetii | 86.3 | 90.0 | 89.4 | | | | | | | | |
| [17] | genospecies 10 | 85.1 | 88.6 | 88.0 | 85.1 | | | | | | | |
| [18] | A. gerneri | 85.7 | 87.1 | 87.1 | 89.1 | 86.0 | | | | | | |
| [19] | genospecies 9 | 86.9 | 86.0 | 86.9 | 86.3 | 85.1 | 86.6 | | | | | |
| [20] | A. lwoffii | 86.0 | 85.4 | 86.6 | 85.4 | 84.3 | 86.3 | 93.7 | | | | |
| [21] | A. towneri | 82.0 | 83.7 | 83.1 | 83.4 | 80.9 | 86.3 | 86.3 | 84.0 | | | |
| [22] | A. ursingii | 83.4 | 82.0 | 82.6 | 84.0 | 81.7 | 85.4 | 80.6 | 81.7 | 82.0 | | |
| [23] | A. tandoii | 85.7 | 83.4 | 83.7 | 85.4 | 82.3 | 87.4 | 85.1 | 85.7 | 84.9 | 83.7 | |
| [24] | A. radioresistense | 82.0 | 78.6 | 79.4 | 80.3 | 79.7 | 83.1 | 80.0 | 80.0 | 78.6 | 80.0 | 83.4 |

TABLE 8

Comparison of similarity rates (%) of sequences (450 bp) of the partial sequences of rpoB region 2 in the different *Acinetobacter* species.

| | | 1 | 2 | 3 | 4 | 5 | 6 | 7 | 8 | 9 | 10 | 11 | 12 |
|---|---|---|---|---|---|---|---|---|---|---|---|---|---|
| [1] | A. calcoaceticus | | | | | | | | | | | | |
| [2] | genospecies 3 | 94.2 | | | | | | | | | | | |
| [3] | A. baumannii | 93.6 | 91.8 | | | | | | | | | | |
| [4] | genospecies 13 | 89.3 | 90.0 | 88.4 | | | | | | | | | |
| [5] | A. tjernbergiae | 90.0 | 90.7 | 89.1 | 93.8 | | | | | | | | |
| [6] | genospecies 16 | 88.2 | 88.7 | 89.1 | 93.3 | 93.1 | | | | | | | |
| [7] | A. parvus | 88.4 | 88.7 | 89.6 | 93.6 | 93.1 | 94.9 | | | | | | |
| [8] | A. baylyi | 84.7 | 84.9 | 84.4 | 86.9 | 85.6 | 86.2 | 86.2 | | | | | |
| [9] | genospecies 11 | 84.2 | 84.9 | 84.4 | 86.4 | 85.6 | 86.2 | 86.2 | 99.6 | | | | |
| [10] | genospecies 10 | 84.0 | 84.2 | 84.9 | 84.4 | 83.8 | 87.3 | 86.9 | 94.9 | 95.3 | | | |
| [11] | A. bouvetii | 86.2 | 85.8 | 85.1 | 83.8 | 86.0 | 85.6 | 84.9 | 87.3 | 87.3 | 88.0 | | |
| [12] | A. schindleri | 82.9 | 85.1 | 84.2 | 83.6 | 83.3 | 85.3 | 84.7 | 87.1 | 87.1 | 87.1 | 90.9 | |
| [13] | A. johnsonii | 84.7 | 85.3 | 85.8 | 85.8 | 86.0 | 86.7 | 86.2 | 87.1 | 87.1 | 86.4 | 89.8 | 88.7 |
| [14] | genospecies 9 | 83.6 | 85.1 | 83.8 | 83.6 | 83.8 | 85.1 | 86.0 | 86.0 | 86.0 | 85.8 | 86.4 | 88.0 |
| [15] | A. lwoffii | 83.6 | 85.6 | 83.3 | 84.4 | 84.0 | 85.8 | 84.2 | 86.4 | 86.4 | 85.8 | 86.4 | 88.0 |
| [16] | A. gerneri | 81.8 | 80.0 | 82.0 | 81.6 | 80.9 | 82.4 | 81.6 | 87.3 | 87.3 | 86.7 | 84.0 | 83.3 |
| [17] | A. tandoii | 82.2 | 82.7 | 83.1 | 83.3 | 83.3 | 83.1 | 83.1 | 82.9 | 82.9 | 82.2 | 83.1 | 81.8 |
| [18] | A. towneri | 83.6 | 83.6 | 83.6 | 83.1 | 82.4 | 82.9 | 83.3 | 83.3 | 83.3 | 83.8 | 84.0 | 84.9 |
| [19] | A. haemolyticus | 83.3 | 83.1 | 84.4 | 81.3 | 82.4 | 82.7 | 82.0 | 84.7 | 84.7 | 83.8 | 81.8 | 81.8 |
| [20] | genospecies 6 | 82.0 | 82.0 | 82.0 | 82.0 | 82.0 | 83.8 | 82.2 | 81.8 | 81.8 | 81.8 | 81.3 | 80.7 |
| [21] | A. ursingii | 81.8 | 81.3 | 80.7 | 81.6 | 82.2 | 79.6 | 79.8 | 80.0 | 79.6 | 78.2 | 79.1 | 81.1 |
| [22] | A. grimonti | 80.9 | 81.6 | 81.6 | 82.2 | 82.2 | 83.6 | 83.1 | 80.2 | 80.2 | 81.6 | 78.2 | 80.7 |
| [23] | A. junii | 80.4 | 80.9 | 81.6 | 81.6 | 81.1 | 82.4 | 82.9 | 80.4 | 80.4 | 81.3 | 78.4 | 79.6 |
| [24] | A. radioresistense | 75.8 | 76.0 | 77.1 | 77.1 | 76.9 | 78.0 | 77.8 | 78.7 | 78.2 | 78.7 | 77.1 | 78.2 |

TABLE 8-continued

Comparison of similarity rates (%) of sequences (450 bp) of the partial sequences of rpoB region 2 in the different *Acinetobacter* species.

|  | | 13 | 14 | 15 | 16 | 17 | 18 | 19 | 20 | 21 | 22 | 23 |
|---|---|---|---|---|---|---|---|---|---|---|---|---|
| [1] | *A. calcoaceticus* | | | | | | | | | | | |
| [2] | genospecies 3 | | | | | | | | | | | |
| [3] | *A. baumannii* | | | | | | | | | | | |
| [4] | genospecies 13 | | | | | | | | | | | |
| [5] | *A. tjernbergiae* | | | | | | | | | | | |
| [6] | genospecies 16 | | | | | | | | | | | |
| [7] | *A. parvus* | | | | | | | | | | | |
| [8] | *A. baylyi* | | | | | | | | | | | |
| [9] | genospecies 11 | | | | | | | | | | | |
| [10] | genospecies 10 | | | | | | | | | | | |
| [11] | *A. bouvetii* | | | | | | | | | | | |
| [12] | *A. schindleri* | | | | | | | | | | | |
| [13] | *A. johnsonii* | | | | | | | | | | | |
| [14] | genospecies 9 | 86.0 | | | | | | | | | | |
| [15] | *A. lwoffii* | 86.7 | 95.1 | | | | | | | | | |
| [16] | *A. gerneri* | 83.6 | 82.2 | 82.4 | | | | | | | | |
| [17] | *A. tandoii* | 82.4 | 80.9 | 80.7 | 83.1 | | | | | | | |
| [18] | *A. towneri* | 83.8 | 85.1 | 85.1 | 85.3 | 88.7 | | | | | | |
| [19] | *A. haemolyticus* | 82.4 | 83.8 | 82.2 | 85.1 | 84.7 | 86.7 | | | | | |
| [20] | genospecies 6 | 81.8 | 81.3 | 81.8 | 84.7 | 83.8 | 84.7 | 87.3 | | | | |
| [21] | *A. ursingii* | 79.8 | 78.9 | 79.3 | 81.1 | 83.1 | 84.0 | 81.6 | 85.8 | | | |
| [22] | *A. grimonti* | 80.9 | 82.7 | 83.3 | 80.9 | 83.1 | 84.7 | 84.9 | 85.8 | 81.6 | | |
| [23] | *A. junii* | 80.7 | 80.9 | 81.8 | 81.3 | 83.6 | 84.2 | 85.6 | 86.0 | 80.9 | 98.0 | |
| [24] | *A. radioresistense* | 76.0 | 80.7 | 79.6 | 80.4 | 79.1 | 80.2 | 80.4 | 81.8 | 81.6 | 83.6 | 82.4 |

TABLE 9

Comparison of similarity rates (%) of sequences (350 bp) of the partial sequences of rpoB region 1 in the different *A. baumannii* strains.

| | Strains | 1 | 2 | 3 | 4 | 5 | 6 | 7 | 8 | 9 | 10 |
|---|---|---|---|---|---|---|---|---|---|---|---|
| [1] | 64.1 | | | | | | | | | | |
| [2] | 70.9 | 100.0 | | | | | | | | | |
| [3] | 70.33 | 100.0 | 100.0 | | | | | | | | |
| [4] | 105742 | 100.0 | 100.0 | 100.0 | | | | | | | |
| [5] | 53.79 | 100.0 | 100.0 | 100.0 | 100.0 | | | | | | |
| [6] | 70.8 | 99.4 | 99.4 | 99.4 | 99.4 | 99.4 | | | | | |
| [7] | 54.97 | 99.4 | 99.4 | 99.4 | 99.4 | 99.4 | 100.0 | | | | |
| [8] | 70.32 | 98.3 | 98.3 | 98.3 | 98.3 | 98.3 | 98.9 | 98.9 | | | |
| [9] | 70.34 | 98.3 | 98.3 | 98.3 | 98.3 | 98.3 | 98.9 | 98.9 | 100.0 | | |
| [10] | 68.38 | 98.3 | 98.3 | 98.3 | 98.3 | 98.3 | 98.9 | 98.9 | 99.4 | 99.4 | |
| [11] | 70.24 | 98.6 | 98.6 | 98.6 | 98.6 | 98.6 | 99.1 | 99.1 | 99.7 | 99.7 | 99.7 |
| [12] | 53.77 | 99.1 | 99.1 | 99.1 | 99.1 | 99.1 | 99.7 | 99.7 | 99.1 | 99.1 | 99.1 |
| [13] | 54.147 | 99.1 | 99.1 | 99.1 | 99.1 | 99.1 | 99.7 | 99.7 | 99.1 | 99.1 | 99.1 |
| [14] | 70.10 | 99.1 | 99.1 | 99.1 | 99.1 | 99.1 | 99.7 | 99.7 | 98.6 | 98.6 | 98.6 |
| [15] | 1072.1 | 98.9 | 98.9 | 98.9 | 98.9 | 98.9 | 99.4 | 99.4 | 98.3 | 98.3 | 98.3 |
| [16] | 70.21 | 99.1 | 99.1 | 99.1 | 99.1 | 99.1 | 99.7 | 99.7 | 98.6 | 98.6 | 98.6 |
| [17] | 70.28 | 98.9 | 98.9 | 98.9 | 98.9 | 98.9 | 99.4 | 99.4 | 98.3 | 98.3 | 98.3 |
| [18] | 70.35 | 98.9 | 98.9 | 98.9 | 98.9 | 98.9 | 99.4 | 99.4 | 98.3 | 98.3 | 98.3 |
| [19] | 70.22 | 99.1 | 99.1 | 99.1 | 99.1 | 99.1 | 99.7 | 99.7 | 98.6 | 98.6 | 98.6 |
| [20] | 103572 | 98.9 | 98.9 | 98.9 | 98.9 | 98.9 | 99.4 | 99.4 | 98.3 | 98.3 | 98.3 |
| [21] | 103655 | 95.4 | 95.4 | 95.4 | 95.4 | 95.4 | 95.4 | 95.4 | 94.9 | 94.9 | 94.9 |

| | Strains | 11 | 12 | 13 | 14 | 15 | 16 | 17 | 18 | 19 | 20 |
|---|---|---|---|---|---|---|---|---|---|---|---|
| [1] | 64.1 | | | | | | | | | | |
| [2] | 70.9 | | | | | | | | | | |
| [3] | 70.33 | | | | | | | | | | |
| [4] | 105742 | | | | | | | | | | |
| [5] | 53.79 | | | | | | | | | | |
| [6] | 70.8 | | | | | | | | | | |
| [7] | 54.97 | | | | | | | | | | |
| [8] | 70.32 | | | | | | | | | | |
| [9] | 70.34 | | | | | | | | | | |
| [10] | 68.38 | | | | | | | | | | |
| [11] | 70.24 | | | | | | | | | | |
| [12] | 53.77 | 99.4 | | | | | | | | | |
| [13] | 54.147 | 99.4 | 100.0 | | | | | | | | |
| [14] | 70.10 | 98.9 | 99.4 | 99.4 | | | | | | | |
| [15] | 1072.1 | 98.6 | 99.1 | 99.1 | 99.7 | | | | | | |
| [16] | 70.21 | 98.9 | 99.4 | 99.4 | 100.0 | 99.7 | | | | | |

TABLE 9-continued

Comparison of similarity rates (%) of sequences (350 bp) of the partial sequences of rpoB region 1 in the different *A. baumannii* strains.

| | | | | | | | | | | | |
|---|---|---|---|---|---|---|---|---|---|---|---|
| [17] | 70.28 | 98.6 | 99.1 | 99.1 | 99.7 | 99.4 | 99.7 | | | | |
| [18] | 70.35 | 98.6 | 99.1 | 99.1 | 99.7 | 99.4 | 99.7 | 100.0 | | | |
| [19] | 70.22 | 98.9 | 99.4 | 99.4 | 99.4 | 99.1 | 99.4 | 99.7 | 99.7 | | |
| [20] | 103572 | 98.6 | 99.1 | 99.1 | 99.1 | 98.9 | 99.1 | 99.4 | 99.4 | 99.7 | |
| [21] | 103655 | 95.1 | 95.1 | 95.1 | 95.1 | 94.9 | 95.1 | 95.4 | 95.4 | 95.7 | 95.4 |

TABLE 10

Comparison of similarity rates (%) of sequences (450 bp) of the partial sequences of rpoB region 2 in different *A. baumannii* strains

| | Strains | 1 | 2 | 3 | 4 | 5 | 6 | 7 | 8 | 9 | 10 |
|---|---|---|---|---|---|---|---|---|---|---|---|
| [1] | 70.10 | | | | | | | | | | |
| [2] | 70.21 | 100.0 | | | | | | | | | |
| [3] | 1072.1 | 99.8 | 99.8 | | | | | | | | |
| [4] | 103572 | 99.8 | 99.8 | 100.0 | | | | | | | |
| [5] | 53.77 | 99.1 | 99.1 | 99.3 | 99.3 | | | | | | |
| [6] | 70.22 | 99.1 | 99.1 | 99.3 | 99.3 | 99.6 | | | | | |
| [7] | 70.32 | 99.3 | 99.3 | 99.6 | 99.6 | 99.3 | 99.3 | | | | |
| [8] | 70.34 | 99.3 | 99.3 | 99.6 | 99.6 | 99.3 | 99.3 | 100.0 | | | |
| [9] | 68.38 | 99.3 | 99.3 | 99.6 | 99.6 | 99.3 | 99.3 | 100.0 | 100.0 | | |
| [10] | 54.147 | 99.3 | 99.3 | 99.6 | 99.6 | 99.3 | 99.3 | 100.0 | 100.0 | 100.0 | |
| [11] | 53.79 | 99.1 | 99.1 | 99.3 | 99.3 | 99.1 | 99.6 | 99.8 | 99.8 | 99.8 | 99.8 |
| [12] | 70.9 | 98.9 | 98.9 | 99.1 | 99.1 | 98.9 | 99.3 | 99.6 | 99.6 | 99.6 | 99.6 |
| [13] | 64.1 | 99.1 | 99.1 | 99.3 | 99.3 | 99.1 | 99.6 | 99.8 | 99.8 | 99.8 | 99.8 |
| [14] | 70.33 | 99.1 | 99.1 | 99.3 | 99.3 | 99.1 | 99.6 | 99.8 | 99.8 | 99.8 | 99.8 |
| [15] | 105742 | 99.1 | 99.1 | 99.3 | 99.3 | 99.1 | 99.6 | 99.8 | 99.8 | 99.8 | 99.8 |
| [16] | 54.97 | 99.1 | 99.1 | 99.3 | 99.3 | 99.1 | 99.1 | 99.8 | 99.8 | 99.8 | 99.8 |
| [17] | 70.8 | 99.1 | 99.1 | 99.3 | 99.3 | 98.7 | 98.7 | 99.3 | 99.3 | 99.3 | 99.3 |
| [18] | 70.24 | 99.6 | 99.6 | 99.8 | 99.8 | 99.1 | 99.1 | 99.8 | 99.8 | 99.8 | 99.8 |
| [19] | 70.35 | 99.6 | 99.6 | 99.8 | 99.8 | 99.6 | 99.6 | 99.8 | 99.8 | 99.8 | 99.8 |
| [20] | 70.28 | 99.6 | 99.6 | 99.8 | 99.8 | 99.1 | 99.1 | 99.3 | 99.3 | 99.3 | 99.3 |
| [21] | 103655 | 94.0 | 94.0 | 94.2 | 94.2 | 94.2 | 94.2 | 93.8 | 93.8 | 93.8 | 93.8 |

| | Strains | 11 | 12 | 13 | 14 | 15 | 16 | 17 | 18 | 19 | 20 |
|---|---|---|---|---|---|---|---|---|---|---|---|
| [1] | 70.10 | | | | | | | | | | |
| [2] | 70.21 | | | | | | | | | | |
| [3] | 1072.1 | | | | | | | | | | |
| [4] | 103572 | | | | | | | | | | |
| [5] | 53.77 | | | | | | | | | | |
| [6] | 70.22 | | | | | | | | | | |
| [7] | 70.32 | | | | | | | | | | |
| [8] | 70.34 | | | | | | | | | | |
| [9] | 68.38 | | | | | | | | | | |
| [10] | 54.147 | | | | | | | | | | |
| [11] | 53.79 | | | | | | | | | | |
| [12] | 70.9 | 99.8 | | | | | | | | | |
| [13] | 64.1 | 100.0 | 99.8 | | | | | | | | |
| [14] | 70.33 | 100.0 | 99.8 | 100.0 | | | | | | | |
| [15] | 105742 | 100.0 | 99.8 | 100.0 | 100.0 | | | | | | |
| [16] | 54.97 | 99.6 | 99.3 | 99.6 | 99.6 | 99.6 | | | | | |
| [17] | 70.8 | 99.1 | 98.9 | 99.1 | 99.1 | 99.1 | 99.6 | | | | |
| [18] | 70.24 | 99.6 | 99.3 | 99.6 | 99.6 | 99.6 | 99.6 | 99.6 | | | |
| [19] | 70.35 | 99.6 | 99.3 | 99.6 | 99.6 | 99.6 | 99.6 | 99.1 | 99.6 | | |
| [20] | 70.28 | 99.1 | 98.9 | 99.1 | 99.1 | 99.1 | 99.1 | 99.1 | 99.6 | 99.6 | |
| [21] | 103655 | 93.8 | 93.6 | 93.8 | 93.8 | 93.8 | 93.6 | 93.6 | 94.0 | 94.0 | 94.4 |

TABLE 11

Comparison of similarity rates (%) of the sequences of intergenic spacer rp/L-rpoB in different *A. baumannii* strains

| | Strains | 1 | 2 | 3 | 4 | 5 | 6 | 7 | 8 | 9 | 10 |
|---|---|---|---|---|---|---|---|---|---|---|---|
| [1] | 70.8 | | | | | | | | | | |
| [2] | 70.33 | 99.7 | | | | | | | | | |
| [3] | 68.38 | 100.0 | 99.7 | | | | | | | | |
| [4] | 105742 | 100.0 | 99.7 | 100.0 | | | | | | | |
| [5] | 64.1 | 100.0 | 99.7 | 100.0 | 100.0 | | | | | | |
| [6] | 103572 | 100.0 | 99.7 | 100.0 | 100.0 | 100.0 | | | | | |

TABLE 11-continued

Comparison of similarity rates (%) of the sequences of intergenic spacer rp/L-rpoB in different *A. baumannii* strains

| | Strains | 1 | 2 | 3 | 4 | 5 | 6 | 7 | 8 | 9 | 10 |
|---|---|---|---|---|---|---|---|---|---|---|---|
| [7] | 54.147 | 100.0 | 99.7 | 100.0 | 100.0 | 100.0 | 100.0 | | | | |
| [8] | 70.35 | 100.0 | 99.7 | 100.0 | 100.0 | 100.0 | 100.0 | 100.0 | | | |
| [9] | 70.32 | 100.0 | 99.7 | 100.0 | 100.0 | 100.0 | 100.0 | 100.0 | 100.0 | | |
| [10] | 70.28 | 100.0 | 99.7 | 100.0 | 100.0 | 100.0 | 100.0 | 100.0 | 100.0 | 100.0 | |
| [11] | 70.24 | 100.0 | 99.7 | 100.0 | 100.0 | 100.0 | 100.0 | 100.0 | 100.0 | 100.0 | 100.0 |
| [12] | 70.22 | 100.0 | 99.7 | 100.0 | 100.0 | 100.0 | 100.0 | 100.0 | 100.0 | 100.0 | 100.0 |
| [13] | 70.21 | 100.0 | 99.7 | 100.0 | 100.0 | 100.0 | 100.0 | 100.0 | 100.0 | 100.0 | 100.0 |
| [14] | 70.10 | 100.0 | 99.7 | 100.0 | 100.0 | 100.0 | 100.0 | 100.0 | 100.0 | 100.0 | 100.0 |
| [15] | 54.97 | 100.0 | 99.7 | 100.0 | 100.0 | 100.0 | 100.0 | 100.0 | 100.0 | 100.0 | 100.0 |
| [16] | 53.79 | 100.0 | 99.7 | 100.0 | 100.0 | 100.0 | 100.0 | 100.0 | 100.0 | 100.0 | 100.0 |
| [17] | 53.77 | 100.0 | 99.7 | 100.0 | 100.0 | 100.0 | 100.0 | 100.0 | 100.0 | 100.0 | 100.0 |
| [18] | 70.9 | 100.0 | 99.7 | 100.0 | 100.0 | 100.0 | 100.0 | 100.0 | 100.0 | 100.0 | 100.0 |
| [19] | 70.34 | 100.0 | 99.7 | 100.0 | 100.0 | 100.0 | 100.0 | 100.0 | 100.0 | 100.0 | 100.0 |
| [20] | 1072.1 | 99.3 | 99.0 | 99.3 | 99.3 | 99.3 | 99.3 | 99.3 | 99.3 | 99.3 | 99.3 |
| [21] | 103655 | 96.7 | 96.4 | 96.7 | 96.7 | 96.7 | 96.7 | 96.7 | 96.7 | 96.7 | 96.7 |

| | Strains | 11 | 12 | 13 | 14 | 15 | 16 | 17 | 18 | 19 | 20 |
|---|---|---|---|---|---|---|---|---|---|---|---|
| [1] | 70.8 | | | | | | | | | | |
| [2] | 70.33 | | | | | | | | | | |
| [3] | 68.38 | | | | | | | | | | |
| [4] | 105742 | | | | | | | | | | |
| [5] | 64.1 | | | | | | | | | | |
| [6] | 103572 | | | | | | | | | | |
| [7] | 54.147 | | | | | | | | | | |
| [8] | 70.35 | | | | | | | | | | |
| [9] | 70.32 | | | | | | | | | | |
| [10] | 70.28 | | | | | | | | | | |
| [11] | 70.24 | | | | | | | | | | |
| [12] | 70.22 | 100.0 | | | | | | | | | |
| [13] | 70.21 | 100.0 | 100.0 | | | | | | | | |
| [14] | 70.10 | 100.0 | 100.0 | 100.0 | | | | | | | |
| [15] | 54.97 | 100.0 | 100.0 | 100.0 | 100.0 | | | | | | |
| [16] | 53.79 | 100.0 | 100.0 | 100.0 | 100.0 | 100.0 | | | | | |
| [17] | 53.77 | 100.0 | 100.0 | 100.0 | 100.0 | 100.0 | 100.0 | | | | |
| [18] | 70.9 | 100.0 | 100.0 | 100.0 | 100.0 | 100.0 | 100.0 | 100.0 | | | |
| [19] | 70.34 | 100.0 | 100.0 | 100.0 | 100.0 | 100.0 | 100.0 | 100.0 | 100.0 | | |
| [20] | 1072.1 | 99.3 | 99.3 | 99.3 | 99.3 | 99.3 | 99.3 | 99.3 | 99.3 | 99.3 | |
| [21] | 103655 | 96.7 | 96.7 | 96.7 | 96.7 | 96.7 | 96.7 | 96.7 | 96.7 | 96.7 | 96.4 |

TABLE 12

Comparison of similarity rates (%) of sequences (301-310 bp) of the intergenic spacer rpoB-rpoC in different *A. baumannii* strains.

| | Strains | 1 | 2 | 3 | 4 | 5 | 6 | 7 | 8 | 9 | 10 |
|---|---|---|---|---|---|---|---|---|---|---|---|
| [1] | 54.97 | | | | | | | | | | |
| [2] | 103655 | 98.8 | | | | | | | | | |
| [3] | 70.10 | 100.0 | 98.8 | | | | | | | | |
| [4] | 70.24 | 100.0 | 98.8 | 100.0 | | | | | | | |
| [5] | 70.33 | 100.0 | 98.8 | 100.0 | 100.0 | | | | | | |
| [6] | 70.34 | 100.0 | 98.8 | 100.0 | 100.0 | 100.0 | | | | | |
| [7] | 70.35 | 100.0 | 98.8 | 100.0 | 100.0 | 100.0 | 100.0 | | | | |
| [8] | 1072.1 | 100.0 | 98.8 | 100.0 | 100.0 | 100.0 | 100.0 | 100.0 | | | |
| [9] | 103572 | 100.0 | 98.8 | 100 | 100.0 | 100.0 | 100.0 | 100.0 | 100.0 | | |
| [10] | 105742 | 100.0 | 98.8 | 100.0 | 100.0 | 100.0 | 100.0 | 100.0 | 100.0 | 100.0 | |
| [11] | 70.32 | 100.0 | 98.8 | 100.0 | 100.0 | 100.0 | 100.0 | 100.0 | 100.0 | 100.0 | 100.0 |
| [12] | 70.28 | 100.0 | 98.8 | 100.0 | 100.0 | 100.0 | 100.0 | 100.0 | 100.0 | 100.0 | 100.0 |
| [13] | 70.22 | 100.0 | 98.8 | 100.0 | 100.0 | 100.0 | 100.0 | 100.0 | 100.0 | 100.0 | 100.0 |
| [14] | 70.21 | 100.0 | 98.8 | 100.0 | 100.0 | 100.0 | 100.0 | 100.0 | 100.0 | 100.0 | 100.0 |
| [15] | 70.9 | 100.0 | 98.8 | 100.0 | 100.0 | 100.0 | 100.0 | 100.0 | 100.0 | 100.0 | 100.0 |
| [16] | 70.8 | 100.0 | 98.8 | 100.0 | 100.0 | 100.0 | 100.0 | 100.0 | 100.0 | 100.0 | 100.0 |
| [17] | 68.38 | 100.0 | 98.8 | 100.0 | 100.0 | 100.0 | 100.0 | 100.0 | 100.0 | 100.0 | 100.0 |
| [18] | 64.1 | 100.0 | 98.8 | 100.0 | 100.0 | 100.0 | 100.0 | 100.0 | 100.0 | 100.0 | 100.0 |
| [19] | 54.147 | 100.0 | 98.8 | 100.0 | 100.0 | 100.0 | 100.0 | 100.0 | 100.0 | 100.0 | 100.0 |
| [20] | 53.79 | 100.0 | 98.8 | 100.0 | 100.0 | 100.0 | 100.0 | 100.0 | 100.0 | 100.0 | 100.0 |
| [21] | 53.77 | 98.8 | 97.7 | 98.8 | 98.8 | 98.8 | 98.8 | 98.8 | 98.8 | 98.8 | 98.8 |

| | Strains | 11 | 12 | 13 | 14 | 15 | 16 | 17 | 18 | 19 | 20 |
|---|---|---|---|---|---|---|---|---|---|---|---|
| [1] | 54.97 | | | | | | | | | | |
| [2] | 103655 | | | | | | | | | | |
| [3] | 70.10 | | | | | | | | | | |

TABLE 12-continued

Comparison of similarity rates (%) of sequences (301-310 bp) of the intergenic spacer rpoB-rpoC in different *A. baumannii* strains.

| | | | | | | | | | | |
|---|---|---|---|---|---|---|---|---|---|---|
| [4] | 70.24 | | | | | | | | | |
| [5] | 70.33 | | | | | | | | | |
| [6] | 70.34 | | | | | | | | | |
| [7] | 70.35 | | | | | | | | | |
| [8] | 1072.1 | | | | | | | | | |
| [9] | 103572 | | | | | | | | | |
| [10] | 105742 | | | | | | | | | |
| [11] | 70.32 | | | | | | | | | |
| [12] | 70.28 | 100.0 | | | | | | | | |
| [13] | 70.22 | 100.0 | 100.0 | | | | | | | |
| [14] | 70.21 | 100.0 | 100.0 | 100.0 | | | | | | |
| [15] | 70.9 | 100.0 | 100.0 | 100.0 | 100.0 | | | | | |
| [16] | 70.8 | 100.0 | 100.0 | 100.0 | 100.0 | 100.0 | | | | |
| [17] | 68.38 | 100.0 | 100.0 | 100.0 | 100.0 | 100.0 | 100.0 | | | |
| [18] | 64.1 | 100.0 | 100.0 | 100.0 | 100.0 | 100.0 | 100.0 | 100.0 | | |
| [19] | 54.147 | 100.0 | 100.0 | 100.0 | 100.0 | 100.0 | 100.0 | 100.0 | 100.0 | |
| [20] | 53.79 | 100.0 | 100.0 | 100.0 | 100.0 | 100.0 | 100.0 | 100.0 | 100.0 | 100.0 |
| [21] | 53.77 | 98.8 | 98.8 | 98.8 | 98.8 | 98.8 | 98.8 | 98.8 | 98.8 | 98.8 | 98.8 |

BIBLIOGRAPHICAL REFERENCES

1. Bouvet P J, Jeanjean S. Delineation of new proteolytic espèce génomique in the genus *Acinetobacter*. Res Microbiol. 1989 May-June; 140(4-5):291-9.
2. Bouvet, P. J. M., and Grimont, P. A. D. Taxonomy of the genus *Acinetobacter* with the recognition of *Acinetobacter baumannii* sp. nov., *Acinetobacter haemolyticus* sp. nov., *Acinetobacter johnsonii* sp. nov., and *Acinetobacter junii* sp. nov. and amended descriptions of *Acinetobacter calcoaceticus* and *Acinetobacter lwoffii*. Int. J. Syst. Bacteriol., 1986, 36, 228-240.
3. Carr E L, Kampfer P, Patel B K, Gurtler V, Seviour R J. Seven novel species of *Acinetobacter* isolated from activated sludge. Int J Syst Evol Microbiol. 2003 July; 53(Pt 4):953-63.
4. Felseinstein 1989 1989. PHYLIPphylogeny inference package (version 3.2). Cladistics 5:164-166.
5. Gerner-Smidt P, Tjernberg I, Ursing J. Reliability of phenotypic tests for identification of *Acinetobacter* species. J Clin Microbiol. 1991 February; 29(2):277-82.
6. Gerner-Smidt P. Ribotyping of the *Acinetobacter* calcoaceticus-Acinetobacter baumannii complex. J Clin Microbiol. 1992 October; 30(10):2680-5.
7. Ibrahim A, Gerner-Smidt P, Liesack W. Phylogenetic relationship of the twenty-one DNA groups of the genus *Acinetobacter* as revealed by 16S ribosomal DNA sequence analysis. Int J Syst Bacteriol. 1997 July; 47(3):837-41.
8. Khamis A, Colson P, Raoult D, Scola B L. Usefulness of rpoB gene sequencing for identification of *Afipia* and *Bosea* species, including a strategy for choosing discriminative partial sequences. Appl Environ Microbiol. 2003 November; 69(11):6740-9.
9. Krawczyk B, Lewandowski K, Kur J. Comparative studies of the *Acinetobacter* genus and the species identification method based on the recA sequences. Mol Cell Probes. 2002 February; 16(1):1-11.
10. Nemec A, De Baere T, Tjernberg I, Vaneechoutte M, van der Reijden T J, Dijkshoorn L. *Acinetobacter ursingii* sp. nov. and *Acinetobacter schindleri* sp. nov., isolated from human clinical specimens. Int J Syst Evol Microbiol. 2001 September; 51(Pt 5):1891-9
11. Nemec A, Dijkshoorn L, Cleenwerck I, De Baere T, Janssens D, Van Der Reijden T J, Jezek P, Vaneechoutte M. *Acinetobacter parvus* sp. nov., a small-colony-forming species isolated from human clinical specimens. Int J Syst Evol Microbiol. 2003 September; 53(Pt 5):1563-7.
12. Ochman and Wilson A C. R Evolution in bacteria: evidence for a universal substitution rate in cellular genomes. J Mol Evol. 1987; 26:74-86.
13. Stackebrandt, E., and B. M. Goebel. 1994. Taxonomic note: a place for DNA-DNA reassociation and 16S rRNA sequence analysis in the present species definition in bacteriology. Int. J. Syst. Bacteriol. 44:846-849.
14. Rainey, F. A., E. Lang, and E. Stackebrandt. 1994. The phylogenetic structure of the genus *Acinetobacter*. FEMS Microbiol. Lett. 124:349-353.
15. Tjernberg I, Ursing J. Clinical strains of *Acinetobacter* classified by DNA-DNA hybridization. APMIS. 1989 July; 97(7):595-605.
16. Towner K J. Clinical importance and antibiotic resistance of *Acinetobacter* spp. Proceedings of a symposium held on 4-5 Nov. 1996 at Eilat, Israel. J Med Microbiol. 1997 September; 46(9):721-46.
17. Van Dessel H, Dijkshoorn L, Van Der Reijden T, Bakker N, Paauw A, Van Den Broek P, Verhoef J, Brisse S. Identification of a new geographically widespread multiresistant *Acinetobacter baumannii* clone from European hospitals. Res Microbiol. 2004 March; 155(2):105-12.
18. Thompson, J. D., D. G. Higgins, and T. J. Gibson. 1994. CLUSTAL W: improving the sensitivity of progressive multiple sequence alignment through sequence weighting, position-specific gap penalties and weight matrix choice. Nucleic Acids Res. 22:4673-4680
19. Yamamoto, S., and S. Harayama. 1996. Phylogenetic analysis of *Acinetobacter* strains based on the nucleotide sequences of gyrB genes and on the amino acid sequences of their products. Int. J. Syst. Bacteriol. 46:506-511.
20. Yamamoto, S., and S. Harayama. 1998. Phylogenetic relationships of *Pseudomonas putida* strains deduced from the nucleotide sequences of gyrB, rpoD and 16S rRNA genes. Int. J. Syst. Bacteriol. 48:813-819.
21. Yamamoto, S., P. J. Bouvet, and S. Harayama. 1999. Phylogenetic structures of the genus *Acinetobacter* based on gyrB sequences: comparison with the grouping by DNA-DNA hybridization. Int. J. Syst. Bacteriol. 49:87-95.

The invention claimed is:

1. A mixture of oligonucleotides comprising:
   (a) an equimolar mixture of each different oligonucleotide defined by a first single sequence consisting of at least 18 consecutive nucleotides of a nucleotide sequence set forth in SEQ ID NOS: 1-5 and 8,
   where:
     D represents A, G, or T,
     Y represents C or T,
     B represents C, G, or T,
     R represents A or G, and
     M represents A or C; or
   (b) an equimolar mixture of the full-length complementary sequences of the different oligonucleotides set forth in (a).

2. The mixture of oligonucleotides according to claim 1, wherein the first single sequence consists of the full-length sequence set forth in SEQ ID NO: 1.

3. A combination of primers comprising:
   a 5' primer comprising the mixture of oligonucleotides according to claim 1, wherein the first single sequence consists of at least 18 consecutive nucleotides of the nucleotide sequence set forth in SEQ ID NO: 1; and
   a 3' primer comprising a mixture of oligonucleotides selected from the group consisting of:
     (i) an equimolar mixture of each different oligonucleotide defined by a second single sequence consisting of at least 12 consecutive nucleotides of SEQ ID NO:2, where M represents A or C, R represents A or G, and Y represents C or T; and
     (ii) an equimolar mixture of the full-length complementary sequences of the different oligonucleotides set forth in (i).

4. A method for determining whether a bacterium belonging to the *Acinetobacter* genus is present in a sample, the method comprising:

(1) contacting the sample with the combination of primers according to claim 3;
   (2) amplifying the nucleic acids present in the sample by an enzymatic polymerization reaction; and
   (3) determining the presence of amplification product, wherein the presence of amplification product indicates the presence of a bacterium belonging to the *Acinetobacter* genus in the sample.

5. The method according to claim 4, further comprising:
   (4) determining the presence or absence in the sample of at least one *Acinetobacter* species selected from the group consisting of *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A. schindleri*, *A. ursingii*, *A. baylyi*, *A. bouvetii*, *A. gerneri*, *A. grimontii*, *A. tandoii*, *A. tjernbergiae*, *A. towneri*, and *A. parvus*, respectively comprising the rpoB sequences set forth in SEQ ID NOS: 9-32, by carrying out the following steps comprising:
   (4a) sequencing the amplification product, and
   (4b) comparing the sequence of the amplification product obtained in (4a) with at least one sequence selected from the group consisting of SEQ ID NOS: 33-56, which describe portions of the rpoB gene specific to, respectively, *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A schindleri, A. ursingii, A. baylyi, A. bouvetii, A. gerneri, A. grimontii, A. tandoii, A. tjernbergiae, A. towneri,* and *A. parvus.*

6. The method according to claim 4, further comprising:
(4) determining the presence or absence in the sample of at least one *Acinetobacter* species selected from the group consisting of *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A. schindleri, A. ursingii, A. baylyi, A. bouvetii, A. gerneri, A. grimontii, A. tandoii, A. tjernbergiae, A. towneri,* and *A. parvus,* respectively comprising the rpoB sequences set forth in SEQ ID NOS: 9-32, by contacting the amplification product with at least one species probe consisting of an rpoB gene fragment,
wherein formation of a hybridization complex between the species probe and the amplification product is indicative of the presence in the sample of the *Acinetobacter* species corresponding to the species probe, and the absence of a hybridization complex indicates that the species of *Acinetobacter* corresponding to the species probe is not present in the sample.

7. A method for detecting whether a species of *Acinetobacter* selected from the group consisting of: *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A schindleri, A. ursingii, A. baylyi, A. bouvetii, A. gerneri, A. grimontii, A. tandoii, A. tjernbergiae, A. towneri,* and *A. parvus,* respectively comprising the rpoB sequences set forth in SEQ ID NOS: 9-32, is present in a sample, comprising:
(1) contacting the sample with the combination of primers according to claim 3 to obtain a first amplification product; and
(2) identifying the *Acinetobacter* species from which the first amplification product was obtained by:
sequencing the first amplification product and comparing the sequence of the first amplification product to SEQ ID NOS: 33-56, which describe portions of the rpoB gene specific to, respectively, *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A schindleri, A. ursingii, A. baylyi, A. bouvetii, A. gerneri, A. grimontii, A. tandoii, A. tjernbergiae, A. towneri,* and *A. parvus*; or
contacting the first amplification product with a species probe consisting of one of SEQ ID NOS: 33-56, which describe portions of the rpoB gene specific to, respectively, *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A schindleri, A. ursingii, A. baylyi, A. bouvetii, A. gerneri, A. grimontii, A. tandoii, A. tjernbergiae, A. towneri,* and *A. parvus,* wherein formation of a hybridization complex between the species probe and the first amplification product is indicative of the presence in the sample of the species of *Acinetobacter* corresponding to the species probe and the absence of a hybridization complex indicates that the species of *Acinetobacter* corresponding to the species probe is not present in the sample; and
if the presence of *A. grimontii* or *A. junii,* respectively comprising the rpoB sequences set forth in SEQ ID NO: 28 and SEQ ID NO: 13, is determined, the following steps (3) and (4) are carried out:
(3) obtaining a second amplification product by contacting the sample with:
a 5' primer comprising a mixture of each different oligonucleotide defined by a third single sequence consisting of at least 12 consecutive nucleotides of the nucleotide sequence set forth in SEQ ID NO: 3, or the complementary sequences thereof, where R represents A or G, and B represents C, G, or T; and
a 3' primer comprising a mixture of each different oligonucleotide defined by a fourth single sequence consisting of at least 12 consecutive nucleotides of the nucleotide sequence set forth in SEQ ID NO: 4, or the complementary sequences thereof, where R represents A or G, B represents C, G, or T, and Y represents C or T; and
(4) determining whether the second amplification product obtained in (3) corresponds to any of the sequences set forth in SEQ ID NOS: 77-100; or
if the presence of *A. baylii* or genomic species 11, respectively comprising the rpoB the sequences set forth in SEQ ID NO: 25 and SEQ ID NO: 19 is determined, the following steps (5) and (6) are carried out:
(5) obtaining a second amplification product by contacting the sample with:
a 5' primer comprising at least 12 consecutive nucleotides of the nucleotide sequence set forth in SEQ ID NO: 7, or the complementary sequence thereof; and a 3' primer comprising a mixture of each different oligonucleotide defined by a third single sequence consisting of at least 12 consecutive nucleotides of the nucleotide sequence set forth in SEQ ID NO: 8, or the complementary sequences thereof, where R represents A or G; and
(6) determining whether the second amplification product obtained in (5) corresponds to any of the sequences set forth in SEQ ID NOS: 165-188.

8. The combination of primers according to claim 3, wherein the second single sequence consists of at least 18 consecutive nucleotides of the sequence set forth in SEQ ID NO: 2.

9. A method for detecting whether a species of *Acinetobacter* selected from the group consisting of: *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A. schindleri, A. ursingii, A. baylyi, A. bouvetii, A. gerneri, A. grimontii, A. tandoii, A. tjernbergiae,*

*A. towneri*, and *A. parvus*, respectively comprising the rpoB sequences set forth in SEQ ID NOS: 9-32, is present in a sample, comprising:

(1) contacting the sample with the combination of primers according to claim 3 to obtain a first amplification product; and (2) identifying the species from which the first amplification product was obtained by:

sequencing the first amplification product and comparing the sequence of the first amplification product to SEQ ID NOS: 33-56, which describe portions of the rpoB gene specific to, respectively, *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A schindleri*, *A. ursingii*, *A. baylyi*, *A. bouvetii*, *A. gerneri*, *A. grimontii*, *A. tandoii*, *A. tjernbergiae*, *A. towneri*, and *A. parvus*; or contacting the first amplification product with a species probe consisting of one of SEQ ID NOS: 33-56, which describe portions of the rpoB gene specific to, respectively, *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A schindleri*, *A. ursingii*, *A. baylyi*, *A. bouvetii*, *A. gerneri*, *A. grimontii*, *A. tandoii*, *A. tjernbergiae*, *A. towneri*, and *A. parvus*, wherein formation of a hybridization complex between the species probe and the first amplification product is indicative of the presence in the sample of the species of *Acinetobacter* corresponding to the species probe and the absence of a hybridization complex indicates that the species of *Acinetobacter* corresponding to the species probe is not present in the sample; and carrying out at least a second amplification wherein the following steps (3) and (4) are carried out:

(3) obtaining a second amplification product by contacting the sample with 5' and 3' primers selected from the group consisting of:

(i) a 5' primer comprising a mixture of each different oligonucleotide defined by a third single sequence consisting of at least 12 consecutive nucleotides of the nucleotide sequence set forth in SEQ ID NO: 3, or the complementary sequences thereof, where R represents A or G, and B represents C, G, or T; and a 3' primer comprising a mixture of each different oligonucleotide defined by a fourth single sequence consisting of at least 12 consecutive nucleotides of the nucleotide sequence set forth in SEQ ID NO: 4, or the complementary sequences thereof, where R represents A or G, B represents C, G, or T, and Y represents C or T;

(ii) a 5' primer comprising a mixture of each different oligonucleotide defined by a third single sequence consisting of at least 12 consecutive nucleotides of the nucleotide sequence set forth in SEQ ID NO: 5, or the complementary sequences thereof, where D represents A, G, or T, M represents A or C, and R represents A or G; and a 3' primer comprising at least 12 consecutive nucleotides of the nucleotide sequence set forth in SEQ ID NO: 6, or the complementary sequence thereof; and (iii) a 5' primer comprising at least 12 consecutive nucleotides of the nucleotide sequence set forth in SEQ ID NO: 7, or the complementary sequence thereof; and a 3' primer comprising a mixture of each different oligonucleotide defined by a third single sequence consisting of at least 12 consecutive nucleotides of the nucleotide sequence set forth in SEQ ID NO: 8, or the complementary sequences thereof, where R represents A or G; and (4) determining whether the second amplification product obtained in (3) corresponds to any of the sequences set forth in:

SEQ ID NOS: 77-100, if the 5' and 3' primers corresponding to SEQ ID NOS: 3 and 4 are selected in (3);

SEQ ID NOS: 121-144, if the 5' and 3' primers corresponding to SEQ ID NOS: 5 and 6 are selected in (3); or SEQ ID NOS: 165-188, if the 5' and 3' primers corresponding to SEQ ID NOS: 7 and 8 are selected in (3).

10. A method for detecting whether a species of *Acinetobacter* selected from the group consisting of: *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A. schindleri*, *A. ursingii*, *A. baylyi*, *A. bouvetii*, *A. gerneri*, *A. grimontii*, *A. tandoii*, *A. tjernbergiae*, *A. towneri*, and *A. parvus*, respectively comprising the rpoB sequences set forth in SEQ ID NOS: 9-32, is present in a sample, comprising:

(1) contacting the sample with the combination of primers according to claim 3 to obtain a first amplification product; and (2) identifying the species from which the first amplification product was obtained by:

sequencing the first amplification product and comparing the sequence of the first amplification product to SEQ ID NOS: 33-56, which describe portions of the rpoB gene specific to, respectively, *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A schindleri*, *A. ursingii*, *A. baylyi*, *A. bouvetii*, *A. gerneri*, *A. grimontii*, *A. tandoii*, *A. tjernbergiae*, *A. towneri*, and *A. parvus*; or contacting the first amplification product with a species probe consisting of one of SEQ ID NOS: 33-56, which describe portions of the rpoB gene specific to, respectively, *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A schindleri*, *A. ursingii*, *A. baylyi*, *A. bouvetii*, *A. gerneri*, *A. grimontii*, *A. tandoii*, *A. tjernbergiae*, *A. towneri*, and *A. parvus*, wherein formation of a hybridization complex between the species probe and the first amplification product is indicative of the presence in the sample of the species of *Acinetobacter* corresponding to the species probe and the absence of a hybridization complex indicates that the species of *Acinetobacter* corresponding to the species probe is not present in the sample; and if the presence of *A. baylii* or genomic species 11, respectively comprising the rpoB sequences set forth in SEQ ID NO: 25 and SEQ ID NO: 19 is determined, the following steps (3) and (4) are carried out:

(3) obtaining a second amplification product by contacting the sample with:
  a 5' primer comprising at least 12 consecutive nucleotides of the nucleotide sequence set forth in SEQ ID NO: 7, or the complementary sequence thereof; and
  a 3' primer comprising a mixture of each different oligonucleotide defined by a third single sequence consisting of at least 12 consecutive nucleotides of the nucleotide sequence set forth in SEQ ID NO: 8, or the complementary sequences thereof, where R represents A or G; and (4) determining whether the second amplification product obtained in (3) corresponds to any of the sequences set forth in SEQ ID NOS: 165-188.

11. A method for detecting whether a species of *Acinetobacter* selected from the group consisting of: *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A. schindleri, A. ursingii, A. baylyi, A. bouvetii, A. gerneri, A. grimontii, A. tandoii, A. tjernbergiae, A. towneri*, and *A. parvus*, respectively comprising the rpoB sequences set forth in SEQ ID NOS: 9-32, is present in a sample, comprising:

(1) obtaining a first amplification product by contacting the sample with the combination of primers according to claim 8, wherein the first single sequence consists of the full-length sequence set forth in SEQ ID NO: 1 and the second single sequence consists of the full-length sequence set forth in SEQ ID NO: 2; and (2) identifying the species from which the first amplification product was obtained by:

sequencing the first amplification product and comparing the sequence of the first amplification product to SEQ ID NOS: 33-56, which describe portions of the rpoB gene specific to, respectively, *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A schindleri, A. ursingii, A. baylyi, A. bouvetii, A. gerneri, A. grimontii, A. tandoii, A. tjernbergiae, A. towneri*, and *A. parvus*; or contacting the first amplification product with a species probe consisting of one of SEQ ID NOS: 33-56, which describe portions of the rpoB gene specific to, respectively, *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A schindleri, A. ursingii, A. baylyi, A. bouvetii, A. gerneri, A. grimontii, A. tandoii, A. tjernbergiae, A. towneri*, and *A. parvus*, wherein formation of a hybridization complex between the species probe and the first amplification product is indicative of the presence in the sample of the species of *Acinetobacter* corresponding to the species probe and the absence of a hybridization complex indicates that the species of *Acinetobacter* corresponding to the species probe is not present in the sample; and if the presence of *A. grimontii* or *A. junii*, respectively comprising the rpoB the sequences set forth in SEQ ID NO: 28 and SEQ ID NO: 13 is determined, the following steps (3) and (4) are carried out:

(3) obtaining a second amplification product by contacting the sample with:
  a 5' primer comprising a mixture of each different oligonucleotide defined by a third single sequence consisting of the full-length sequence set forth in SEQ ID NO: 3, or the complementary sequences thereof, where R represents A or G, and B represents C, G, or T; and
  a 3' primer comprising a mixture of each different oligonucleotide defined by a fourth single sequence consisting of the full-length sequence set forth in SEQ ID NO: 4, or the complementary sequences thereof, where R represents A or G, B represents C, G, or T, and Y represents C or T; and (4) determining whether the second amplification product obtained in (3) corresponds to any of the sequences set forth in SEQ ID NOS: 77-100; or if the presence of *A. baylii* or genomic species 11, respectively comprising the rpoB sequences set forth in SEQ ID NO: 25 or SEQ ID NO: 19 is determined, the following steps (5) and (6) are carried out:

(5) obtaining a second amplification product by contacting the sample with:
  a 5' primer consisting of the full-length sequence set forth in SEQ ID NO: 7, or the complementary sequence thereof; and
  a 3' primer comprising a mixture of each different oligonucleotide defined by a third single sequence consisting of the full-length sequence set forth in SEQ ID NO: 8, or the complementary sequences thereof, where R represents A or G; and (6) determining whether the second amplification product obtained in (5) corresponds to any of the sequences set forth in SEQ ID NOS: 165-188.

12. A method for detecting whether a species of *Acinetobacter* selected from the group consisting of: *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A. schindleri, A. ursingii, A. baylyi, A. bouvetii, A. gerneri, A. grimontii, A. tandoii, A. tjernbergiae, A. towneri*, and *A. parvus*, respectively comprising the rpoB sequences set forth in SEQ ID NOS: 9-32, is present in a sample, comprising:

(1) obtaining a first amplification product by contacting the sample with the combination of primers according to claim 8, wherein the first single sequence consists of the full-length sequence set forth in SEQ ID NO: 1 and the second single sequence consists of the full-length sequence set forth in SEQ ID NO:2; and
(2) identifying the species from which the first amplification product was obtained by:
sequencing the first amplification product and comparing the sequence of the first amplification product to SEQ ID NOS: 33-56, which describe portions of the rpoB gene specific to, respectively, *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A schindleri, A. ursingii, A. baylyi, A. bouvetii, A. gerneri, A. grimontii, A. tandoii, A. tjernbergiae, A. towneri*, and *A. parvus*; or
contacting the first amplification product with a species probe consisting of one of SEQ ID NOS: 33-56, which describe portions of the rpoB gene specific to, respectively, *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A schindleri, A. ursingii, A. baylyi, A. bouvetii, A. gerneri, A. grimontii, A. tandoii, A. tjernbergiae, A. towneri*, and *A. parvus*, wherein formation of a hybridization complex between the species probe and the first amplification product is indicative of the presence in the sample of the species of *Acinetobacter* corresponding to the species probe and the absence of a hybridization complex indicates that the species of *Acinetobacter* corresponding to the species probe is not present in the sample; and
carrying out at least a second amplification wherein the following steps (3) and (4) are carried out:
(3) obtaining a second amplification product by contacting the sample with 5' and 3' primers selected from the group consisting of:
  (i) a 5' primer comprising a mixture of each different oligonucleotide defined by a third single sequence consisting of the full-length sequence set forth in SEQ ID NO: 3, or the complementary sequences thereof, where R represents A or G, and B represents C, G, or T; and
  a 3' primer comprising a mixture of each different oligonucleotide defined by a fourth single sequence consisting of the full-length sequence set forth in SEQ ID NO: 4, or the complementary sequences thereof, where R represents A or G, B represents C, G, or T, and Y represents C or T;
  (ii) a 5' primer comprising a mixture of each different oligonucleotide defined by a third single sequence consisting of the full-length sequence set forth in SEQ ID NO: 5, or the complementary sequences thereof, where D represents A, G, or T, M represents A or C, and R represents A or G; and
  a 3' primer consisting of the full-length sequence set forth in SEQ ID NO: 6, or the complementary sequence thereof; and
  (iii) a 5' primer consisting of the full-length sequence set forth in SEQ ID NO: 7, or the complementary sequence thereof; and
  a 3' primer comprising a mixture of each different oligonucleotide defined by a third single sequence consisting of the full-length sequence set forth in SEQ ID NO: 8, or the complementary sequences thereof, where R represents A or G; and
(4) determining whether the second amplification product obtained in (3) corresponds to any of the sequences set forth in:
  SEQ ID NOS: 77-100, if the 5' and 3' primers corresponding to SEQ ID NOS: 3 and 4 are selected in (3);
  SEQ ID NOS: 121-144, if the 5' and 3' primers corresponding to SEQ ID NOS: 5 and 6 are selected in (3); or
  SEQ ID NOS: 165-188, if the 5' and 3' primers corresponding to SEQ ID NOS: 7 and 8 are selected in (3).

13. A method for detecting whether a species of *Acinetobacter* selected from the group consisting of: *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A. schindleri, A. ursingii, A. baylyi, A. bouvetii, A. gerneri, A. grimontii, A. tandoii, A. tjernbergiae, A. towneri*, and *A. parvus*, respectively comprising the rpoB sequences set forth in SEQ ID NOS: 9-32, is present in a sample, comprising:
(1) obtaining a first amplification product by contacting the sample with the combination of primers according to claim 8, wherein the first single sequence consists of the full-length sequence set forth in SEQ ID NO: 1 and the second single sequence consists of the full-length sequence set forth in SEQ ID NO:2; and
(2) identifying the species from which the first amplification product was obtained by:
sequencing the first amplification product and comparing the sequence of the first amplification product to SEQ ID NOS: 33-56, which describe portions of the rpoB gene specific to, respectively, *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A schindleri, A. ursingii, A. baylyi, A. bouvetii, A. gerneri, A. grimontii, A. tandoii, A. tjernbergiae, A. towneri*, and *A. parvus*; or
contacting the first amplification product with a species probe consisting of one of SEQ ID NOS: 33-56, which describe portions of the rpoB gene specific to, respectively, *A. calcoaceticus* (genomic species 1), *A. baumannii* (genomic species 2), genomic species 3, *A. haemolyticus* (genomic species 4), *A. junii* (genomic species 5), genomic species 6, *A. johnsonii* (genomic species 7), *A. lwoffii* (genomic species 8), genomic species 9, genomic species 10, genomic species 11, *A. radioresistens* (genomic species 12), genomic species 13, genomic species 16, *A schindleri, A. ursingii, A. baylyi, A. bouvetii, A. gerneri, A. grimontii, A. tandoii, A. tjernbergiae, A. towneri*, and *A. parvus*, wherein formation of a hybridization complex between the species probe and the first amplification product is indicative of the presence in the sample of the species of *Acinetobacter* corresponding to the species probe and the absence of a hybridization complex indicates that the species of *Acinetobacter* corresponding to the species probe is not present in the sample; and if the presence of *A. baylii* or genomic species 11, respectively comprising the rpoB sequences set forth in SEQ ID NO: 28 or SEQ ID NO: 19 is determined, the following steps (3) and (4) are carried out:

(3) obtaining a second amplification product by contacting the sample with:
- a 5' primer consisting of the full-length sequence set forth in SEQ ID NO: 7, or the complementary sequence thereof; and
- a 3' primer comprising a mixture of each different oligonucleotide defined by a third single sequence consisting of the full-length sequence set forth in SEQ ID NO: 8, or the complementary sequences thereof, where R represents A or G; and (4) determining whether the second amplification product obtained in (3) corresponds to any of the sequences set forth in SEQ ID NOS: 165-188.

14. A combination of primers, comprising:
a first pair of primers comprising the combination of primers set forth in claim 8; and
a second pair of primers selected from the group consisting of:
   (i) a 5' primer comprising an equimolar mixture of each different oligonucleotide defined by a third single sequence consisting of at least 18 consecutive nucleotides of the nucleotide sequence set forth in SEQ ID NO: 3, or the complementary sequences thereof, where R represents A or G, and B represents C, G, or T; and
   a 3' primer comprising an equimolar mixture of each different oligonucleotide defined by a fourth single sequence consisting of at least 18 consecutive nucleotides of the nucleotide sequence set forth in SEQ ID NO: 4, or the complementary sequences thereof, where R represents A or G, B represents C, G, or T, and Y represents C or T,
   (ii) a 5' primer comprising an equimolar mixture of each different oligonucleotide defined by a third single sequence consisting of at least 18 consecutive nucleotides of the nucleotide sequence set forth in SEQ ID NO:5, or the complementary sequences thereof, where D represents A, G, or T, M represents A or C, and R represents A or G; and
   a 3' primer comprising at least 18 consecutive nucleotides of the nucleotide sequence set forth in SEQ ID NO: 6, or the complementary sequence thereof; and
   (iii) a 5' primer comprising at least 18 consecutive nucleotides of the nucleotide sequence set forth in SEQ ID NO: 7, or the complementary sequence thereof; and
   a 3' primer comprising an equimolar mixture of each different oligonucleotide defined by a third single sequence consisting of at least 18 consecutive nucleotides of the nucleotide sequence set forth in SEQ ID NO: 8, or the complementary sequences thereof, where R represents A or G.

15. The mixture of oligonucleotides according to claim 1, wherein the first single sequence consists of the full-length sequence set forth in SEQ ID NO: 2.

16. The mixture of oligonucleotides according to claim 1, wherein the first single sequence consists of the full-length sequence set forth in SEQ ID NO: 3.

17. The mixture of oligonucleotides according to claim 1, wherein the first single sequence consists of the full-length sequence set forth in SEQ ID NO: 4.

18. The mixture of oligonucleotides according to claim 1, wherein the first single sequence consists of the full-length sequence set forth in SEQ ID NO: 5.

19. The mixture of oligonucleotides according to claim 1, wherein the first single sequence consists of the full-length sequence set forth in SEQ ID NO: 8.

20. A combination of primers comprising:
a 5' primer comprising the mixture of oligonucleotides according to claim 1, wherein the first single sequence consists of at least 18 consecutive nucleotides of the nucleotide sequence set forth in SEQ ID NO: 3; and
a 3' primer comprising a mixture of oligonucleotides selected from the group consisting of:
   (i) an equimolar mixture of each different oligonucleotide defined by a second single sequence consisting of at least 12 consecutive nucleotides of SEQ ID NO:4, where:
      B represents C, G, or T,
      R represents A or G, and
      Y represents C or T; and
   (ii) an equimolar mixture of the full-length complementary sequences of the different oligonucleotides set forth in (i).

21. A combination of primers comprising:
a 5' primer comprising the mixture of oligonucleotides according to claim 1, wherein the first single sequence consists of at least 18 consecutive nucleotides of the nucleotide sequence set forth in SEQ ID NO: 5; and
a 3' primer consisting of:
   at least 12 consecutive nucleotides of SEQ ID NO: 6; or
   the full-length complementary sequence of at least 12 consecutive nucleotides of SEQ ID NO: 6.

22. A combination of primers comprising:
a 3' primer comprising the mixture of oligonucleotides according to claim 1, wherein the first single sequence consists of at least 18 consecutive nucleotides of the nucleotide sequence set forth in SEQ ID NO: 8; and
a 5' primer consisting of:
   at least 12 consecutive nucleotides of SEQ ID NO: 7; or
   the full-length complementary sequence of at least 12 consecutive nucleotides of SEQ ID NO:7.

* * * * *